United States Patent
Chang et al.

(10) Patent No.: US 9,513,294 B2
(45) Date of Patent: Dec. 6, 2016

(54) MEGASTOKES AMINO-TRIAZOLYL-BODIPY COMPOUNDS AND APPLICATIONS TO LIVE NEURON STAINING AND HUMAN SERUM ALBUMIN FA1 DRUG SITE PROBING

(71) Applicants: National University of Singapore, Singapore (SG); Agency For Science, Technology and Research, Singapore (SG)

(72) Inventors: Young-Tae Chang, Singapore (SG); Jun Cheng Er, Singapore (SG); Cheryl Kit Mun Leong, Singapore (SG); Seong Wook Yun, Singapore (SG); Marc Vendrell Escobar, Edinburgh (GB); Mui Kee Tang, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/648,309

(22) PCT Filed: Dec. 26, 2013

(86) PCT No.: PCT/SG2013/000550
§ 371 (c)(1),
(2) Date: May 29, 2015

(87) PCT Pub. No.: WO2014/104975
PCT Pub. Date: Jul. 3, 2014

(65) Prior Publication Data
US 2015/0309040 A1    Oct. 29, 2015

Related U.S. Application Data

(60) Provisional application No. 61/745,916, filed on Dec. 26, 2012.

(51) Int. Cl.
| | |
|---|---|
| G01N 33/58 | (2006.01) |
| C09B 57/00 | (2006.01) |
| C09B 23/01 | (2006.01) |
| C09B 23/04 | (2006.01) |
| C07F 5/02 | (2006.01) |
| G01N 21/64 | (2006.01) |
| G01N 33/50 | (2006.01) |
| A61K 49/00 | (2006.01) |

(52) U.S. Cl.
CPC ......... *G01N 33/582* (2013.01); *A61K 49/0021* (2013.01); *C07F 5/022* (2013.01); *C09B 23/0008* (2013.01); *C09B 23/04* (2013.01); *C09B 57/00* (2013.01); *G01N 21/6428* (2013.01); *G01N 33/5005* (2013.01); *G01N 33/5058* (2013.01); *G01N 2333/765* (2013.01); *G01N 2458/30* (2013.01)

(58) Field of Classification Search
CPC ........................... C07F 5/022; G01N 33/582
USPC ......................................................... 544/1
See application file for complete search history.

(56) References Cited

U.S. PATENT DOCUMENTS

| 5,804,395 A | 9/1998 | Schade et al. |
| 5,854,216 A | 12/1998 | Gaudreau |
| 7,968,306 B2 | 6/2011 | Tsao et al. |
| 2012/0171665 A1 | 7/2012 | Keillor et al. |

FOREIGN PATENT DOCUMENTS

| CN | 101059507 | 10/2007 |
| KR | 20100101882 | 9/2010 |
| KR | 20120030351 | 3/2012 |
| WO | WO 2009/070234 A2 | 6/2009 |
| WO | WO 2012/071012 A2 | 5/2012 |
| WO | WO 2012/118444 A1 | 9/2012 |
| WO | WO 2012/173575 A1 | 12/2012 |

OTHER PUBLICATIONS

Ahn, Y-H., et al., Selective Human Serum Albumin Sensor from the Screening of a Fluorescent Rosamine Library, *J Comb. Chem.* 2008, 10, 376-380.

Alarcon, E., et al., "Photophysics and photochemistry of dyes bound to human serum albumin are determined by the dye localization", *Photochem.Photobiol. Sci.* 2010, 9, 93-102.

Appleyard, S.M., "Lighting up Neuronal Pathways: The Development of a Novel Transgenic Rat that Identifies Fos-Activated Neurons Using a Red Fluorescent Protein", *Endocrinology* 2009, 150(12): 5199-5201.

Baker, G.A., et al., "Effect of Fluorescent Probe Structure on the Dynamics at Cysteine-34 Within Bovine Serum Albumin: Evidence for Probe-Dependent Modulation of the Cybotactic Region", *Biopolymers* (2001), 59, 502-511.

Baldridge, A., et al., "Recapture of GFP Chromophore Fluorescence in Protein Host", *ASC Comb. Sci.* (2011), 13, 214-217.

Banerjee, M., et al., "Interaction of Merocyanine 540 with serum albumins: Photophysical and binding studies", *J.J. Photobiol.* (2011), 12, 1011-1344.

Banuelos, J., et al., "New 8-Amino-BODIPY Derivatives: Surpassing Laser Dyes at Blue-Edge Wavelengths", *Chem. Eur. J.* (2011), 17, 7261-7270.

Basken, N.E., et al., "Pharmacokinetics, Pharmacodynamics and Drug Metabolism", *J. Pharm. Sci.* (2009), 98, 2170-2179.

(Continued)

*Primary Examiner* — Kahsay Habte
(74) *Attorney, Agent, or Firm* — Hamilton, Brook, Smith & Reynolds, P.C.

(57) ABSTRACT

A library of novel amino-triazolyl-BODIPY compounds is described. Particular compounds of the library serve as selective fluorescent probes for human serum albumin (HSA) and for live primary neurons. The fluorescent probe for HSA binds uniquely and specifically to the fatty acid site 1 of HSA, and thus proves a valuable and unique probe for drugs that bind to such a site on HSA. Methods of synthesis for the library compounds are also described.

19 Claims, 19 Drawing Sheets

(56) References Cited

OTHER PUBLICATIONS

Basken, N.E., Green, M.A., "Cu(II) Bis(thiosemicarbazone) Radiopharmaceutical Binding to Serum ALbumin: Further Definition of Species-Dependence and Associated Substituent Effects", Nucl. Med. Biol. (2009), 36(5): 495-504.
Bernhard, C., et al., "First bodipy-DOTA derivatives as probes for bimodal imaging", Chem. Commun. (2010), 46, 8267-8269.
Bhattacharya, A., et al., "Crystallographic Analysis Reveals Common Modes of Binding of Medium and Long-chain Fatty Acids to Human Serum Albumin", J. Mol. Biol. (2000), 303, 721-732.
Bozdemir, O., et al., "Selective Manipulation of ICT and PET Processes in Styryl-Bodipy Derivatives: Applications in Molecular Logic and Fluorescence Sensing of Metal Ions", J. Am. Chem. Soc. (2010), 132, 8029-8036.
Brewer, G.J., "Isolation and culture of adult rat hippocampal neurons", journal of Neuroscience Methods (1997), 71, 143-155.
Buyukcakir, O., et al., "Tetrastyryl-Bodipy Dyes: Convenient Syntheses and Characterization of Elusive Near IR Fluorophores", Am. Chem. Soc. (2009), 11(20): 4644-4647.
Chen, X., et al., "Facile, sensitive and selective fluorescence turn-on detection of HAS/BSA in aqueous solution utilizing 2,4-dihydroxyl-3-iodo salicylaldehyde azine", Talanta (2010), 80, 1952-1958.
Coskun, A., et al., "Effective PET and ICT Switching of Boradiazaindacene Emission: A Unimolecular, Emission-Mode, Molecular Half-Subtractor with Reconfigurable Logic Gates", Am. Chem. Soc. (2005), 7(23): 5187-5189.
Cui, F., et al., "Fluorescent investigation of the interactions between N-(p-chlorophenyl)-N-(1-naphthyl) thiourea and serum albumin: Synchronous fluorescence determination of serum albumin", Analytica Chimica Acta (2006), 571, 175-183.
Curry, S., "Lessons from the Crystallographic Analysis of Small Molecule Binding of Human Serum Albumin", Drug Metab. Pharmacokinet. (2009), 24(4): 342-357.
Curry, S., "Plasma albumin as a fatty acid carrier", Advances in Molecular and Cell Biology (2004), 33, 29-46.
Curry, S., et al., "Crystal structure of human serum albumin complexed with fatty acid reveals an asymmetric distribution of binding sites", Natural Structural Biology (1998), 5(9): 827.
Curry, S., et al., "Fatty acid binding to human serum albumin: new insights from crystallographic studies", Biochimica et Biophysica Acta (1999), 1441, 131-140.
Deepa, S., Mishra, A.K., "Fluorescence spectroscopic study of serum albumin-bromadiolone interaction: fluorimetric determinationof bromadiolone", (2005), 38, 556-563.
DeFelipe, J., "From the Connectome to the Synaptome: An Epic Love Story", Science 330 (2010), 1198.
Ding, F., "Characterization of Alizarin Red S Binding sites and structural changes on human serum albumin: A biophysical study", Journal of Hazardous Materials (2011), 186, 352-359.
Duff, K., Suleman, F., "Transgenic mouse models of Alzheimer's disease: How useful have they been for therapeutic development?", Briefings in Functional Genomics and Proteomics (2004), 3, 47-59.
Er, J., et al., "MegaStokes BODIPY-triazoles as environmentally sensitive turn-on fluorescent dyes", Chem. Sci. (2013), 4, 2168-2176.
Fanali, G., et al., "Human serum albumin: From bench to bedside", Molecular Aspects of Medicine (2012), 33, 209-290.
Ghuman, J., et al., "Structural Basis of the Drug-binding Specificity of Human Serum Albumin", J. Mol. Biol. (2005), 353, 38-52.
Han, J., et al., "3- and 5-Functionalized BODIPYs via the Liebeskind-Srogl reaction", Org. Biomol. Chem. (2009), 7, 34-36.
Hendricks, J.A., et al., "Synthesis of [18F]BODIPY: Bifunctional Reporter for Hybrid Optical/Positron Emission Tomography Imaging", Angew. Chem. Int. Ed. (2012), 51, 4603-4606.
Honig, M.G., Hume, R.I., "DiI and DiO: versatile fluorescent dyes for neuronal laballing and pathway tracing", TINS (1989), 12(9): 333-341.

Huang, C.Y., "Determination of Binding Stoichiometry by the Continuous Variation Method: The Job Plot", Methods in Enzymology (1982), 87, 509.
International Search Report and Written Opinion from PCT/SG2013/000550, entitled Megastokes Amino-Triazolyl-Bodipy Compounds and Applications to Live Neuron Staining and Human Serum Albumin FA1 Drug Site Probing, date of mailing Feb. 11, 2014.
Kessler, M.A., et al., "Albumin Blue 580 Fluorescence Assay for Albumin", Analytical Biochemistry (1997), 248, 180-182.
Kessler, M.A., et al., "Microalbuminuria and borderline-increased albumin excretion determined with a centrifugal analyzer and the Albumin Blue 580 fluorescence assay", Clinical Chemistry (1997), 43(6): 996-1002.
Kobbert, C., et al., "Current concepts in neuroanatomical tracing", Progress in Neurobiology (2000), 62, 327-351.
Komatsu, T., et al., "Development of 2,6-carboxy-substituted boron dipyrromethene (BODIPY) as a novel scaffold of ratiometric fluorescent probes for live cell imaging", Chem. Comm. (2009), 7015-7017.
Lavis, D.L., et al., "Bright Ideas for Chemical Biology", ACS Chemical Biology (2008), 3(3): 142.
Lee J., et al., "Synthesis of a BODIPY Library and Its Application to the Development of Live Cell Glucagon Imaging Probe", J. Am. Chem. Soc. (2009), 131, 10077-10082.
Leen, V., et al., "Direct functionalization of BODIPY dyes by oxidative nucleophilic hydrogen substitution at the 3- or 3,5-positions", Chem. Comm. (2010), 46, 4908-4910.
Li, L., et al., "Synthesis and Spectral Properties of Functionalized, Water-Soluble BODIPY Derivatives", J. Org. Chem. (2008), 73, 1963-1970.
Li, L., et al., "Functionalization of the 4,4-difluoro-4-bora-3a, 4a-diaza-s-indacene (BODIPY) core", Bioorganic & Medicinal Chemistry Letters (2008), 18, 3112-3116.
Lima, J.J., et al., "Species-Dependent Binding of Disopyramide Enantiomers", Drug Metabolism and Disposition (1988), 16(4): 563.
Loudet, A., Burgess, K., "BODIPY Dyes and Their Derivatives: Synthesis and Spectroscopic Properties", Chem. Rev. (2007), 107, 4891-4932.
Lu, T., et al., "Determination of non-protein cysteine in human serum by a designed BODIPY-based fluorescent probe", Talanta (2011), 83, 1050-1056.
Martin, A., et al., "Near IR emitting BODIPY fluorophores with mega-stokes shifts", Chem. Commun. (2012), 48, 5617-5619.
Mathias, C.J., et al., "Species-Dependent Binding of Copper(II) Bis(Thiosemicarbazone) Radiopharmaceuticals to Serum Albumin", J. Nucl. Med. (1995), 36, 1451-1455.
Meldal, M., et al., "Cu-Catalyzed Azide—Alkyne Cycloaddition", Chem. Rev. (2008), 108, 2952-3015.
Moreno, F., et al., "Interaction of Acrylodan with Human Serum Albumin. A Fluorescence Spectroscopic Study", Photochemistry and Photobiology (1999), 70(5): 695-700.
Moreno, F., et al., "The Fluorescent Probe Prodan Characterizes the Warfarin Binding Site on Human Serum Albumin", Photochemistry and Photobiology (1999), 69(1): 8-15.
Notification Concerning Transmittal of International Preliminary Report on Patentability for International Application No. PCT/SG2013/000550, entitled: Megastokes Amino-Triazolyl-Bodipy Compounds and Applications to Live Neuron Staining and Human Serum Albumin FA1 Drug Site Probing, date of mailing Jul. 9, 2015.
Okano, H., et al., "Isolation and transplantation of dopraminergic neurons and neural stem cells", Parkinsonism and Related Disorders (2009), 9, 23-28.
Park, K.K., et al., "Novel 7-(dimethylamino)fluorine-based fluorescent probes and their binding to human serum albumin", Org. Biomol. Chem. (2009), 7, 4225-4232.
Park, K.K., et al., "Solvent and pH Effects on the Fluorescence of 7-(Dimethylomino)-2-Fluorenesulfonate", J. Fluoresc (2007), 17, 361-369.

(56) References Cited

OTHER PUBLICATIONS

Petitpas, I., et al., "Crystal Structures of Human Serum Albumin Complexed with Monounsaturated and Polyunsaturated Fatty Acids", *J. Mol. Biol.* (2001), 314, 955-960.

Petitpas, I., et al., "Structural basis of albumin-thyroxine interactions and familial dysalbuminemic hyperthyroxinemia", *PNAS* (2003), 100(11): 6440-6445.

Pistolozzi, M., Bertucci, C., "Species-Dependent Stereoselective Drug Binding to Albumin: A Circular Dichroism Study", *Chirality* (2008), 20, 552-558.

Qi, Z., et al., "Probing the binding of morin to human serum albumin by optical spectroscopy", *Journal of Pharmaceutical and Biomedical Analysis* (2008), 46, 699-706.

Qian, X., et al., "Chemical Communications", *RSC Publishing* (2010), 46(35): 6393-6612.

Qin, W., et al., "3,5-Dianilino Substituted Difluoroboron Dipyrromethene: Synthesis, Spectroscopy, Photophysics, Crystal Structure, Electrochemistry, and Quantum-Chemical Calculations", *J. Phys. Chem. C* (2009), 113, 11731-11740.

Qin, W., et al., "Boron Dipyrromethene Analogs with Phenyl, Styryl, and Ethynylphenyl Substituents: Synthesis, Photophysics, Electrochemistry, and Quantum-Chemical Calculations", *J. Phys. Chem. A* (2007), 111, 8588-8597.

Qin, W., et al., "Synthesis, Spectroscopy, Crystal Structure, Electrochemistry, and Quantum Chemical and Molecular Dynamics Calculations of a 3-Anilino Difluoroborn Dipyrromethene Dye", *J. Phys. Chem. A* (2009), 113, 439-447.

Rohacova, J., et al., "Dansyl Labeling to Modulate the Relative Affinity of Bile Acids for the Binding Sites of Human Serum Albumin", *J. Phys. Chem. B* (2011), 115, 10518-10524.

Rohand, T., et al., "Functionalisation of fluorescent BODIPY dyes by nucleophilic substitution", *Chem. Commun.* (2006), 266-268.

Rohand, T., et al., "Photophysics of 3,5-diphenoxy substituted BODIPY dyes in solution", *Photochem. Photobiol. Sci.* (2007), 6, 1061-1066.

Rowe, D.J.F., et al., "Microalbuminuria in diabetes mellitus: review and recommendations for the measurement of albumin in urine", *Ann. Clin. Biochem.* (1990), 27, 297-312.

Ryan, A., et al., "Structural basis of binding of fluorescent, site-specific dansylated amino acids to human serum albumin", *Journal of Structural Biology* (2011), 174, 84-91.

Scrafton, D.K., et al., "Click-fluors: Modular Fluorescent Saccharide Sensors Based on a 1,2,3-Triazole Ring", *J. Org. Chem.* (2008), 73, 2871-2874.

Sengupta, B., et al., "Binding of Quercetin with human Serum Albumin: A Critical Spectroscopic Study", *Biopolymers* (2003), 72, 427-434.

Simard, J.R., et al., "Locating high affinity fatty acid-binding sites on albumin by x-ray crystallography and NMR spectroscopy", *National Academy of Sciences of the USA* (2005), 102(50): 17958-17963.

Simard, J.R., et al., "Locating high-affinity fatty acid-binding sites on albumin by x-ray crystallography and NMH spectroscopy", *PNAS* (2005), 102(50): 17958-17963.

Sivakumar, K., et al., "A Fluorogenic 1,3-Dipolar Cycloaddition Reaction of 3-Azidocoumarins and Acetylenes", *Organic Letters* (2004), 6(24): 4603-4606.

Smith, N.W., et al., "Triazole-containing BODIPY dyes as novel fluorescent probes for soluble oligomers of amyloid A1-42 peptide", *Biochem. and Biophys. Research Commun.* (2010), 391, 1455-1458.

Subramanyam, R., et al., "Novel binding studies of human serum albumin with trans-feruloyl maslinic acid", *Journal of Photochemistry and Photobiology B* (2009), 95, 81-88.

Sudlow, G., et al., "Further Characterization of Specific Drug Binding Sites on Human Serum Albumin", *Molecular Pharmacology* (2010), 12, 1052-1061.

Sudlow, G., et al., "The Characterization of Two Specific Drug Binding Sites on Human Serum Albumin", *Molecular Pharmacology* (1975), 11, 824-832.

Sugio, S., et al., "Crystal structure of human serum albumin at 2.5 A resolution", *Protein Engineering* (1999), 12(6): 439-446.

Sun, Y., et al., "Interactions between 4-(2-dimethylaminoethyloxy)-N-octadecyl-1, 8-naphthalimide and serum albumins: Investigation by spectroscopic approach", *Journal of Luminescence* (2012), 132, 879-886.

Sunahara, H., et al., "Design and Synthesis of a Library of BODIPY-Based Environmental Polarity Sensors Utilizing Photoinduced Electron-Transfer-Controled Fluorescence On/Off Switching", *J. Am. Chem. Soc.* (2007), 129, 5597-5604.

Takehara, K., "Binding Properties of Hydrophobic Molecules to Human Serum Albumin Studied by Fluorescence Titration", *The Japan Society for Analytical Chemistry* (2009), 25, 115.

Temelli, B., Unaleroglu, C., "Synthesis of meso-tetraphenyl porphyrins via condensation of dipyrromethanes with N-tosyl imines", *Tetrahedron* (2009), 65, 2043-2050.

Ulrich, G., et al., "The Chemistry of Fluorescent Bodipy Dyes: Versatility Unsurpassed", *Angew. Chem. Int. Ed.* (2008), 47, 1184-1201.

Umezawa K., et al., "Bright, Color-Tunable Fluorescent Dyes in the Visible-Near-Infrared Region", *J. Am. Chem. Soc.* (2008), 130, 1550-1551.

Vendrell, M., et al., "Combinatorial Strategies in Fluorescent Probe Development", *Chem. Rev.* (2012), 112, 4391-4420.

Vendrell, M., et al., "Solid-phase synthesis of BODIPY dyes and development of an immunoglobulin fluorescent sensor", *Chem. Commun.* (2011), 47, 8424-8426.

Verbelen, B., et al., "Direct palladium-catalysed C-H arylation of BODIPY dyes at the 3- and 3,5-positions", *Chem. Commun.* (2012), 48, 9129-9131.

Wang, C., et al., "Tuning the optical properties of BODIPY dye through Cu(I) catalyzed azide-alkyne cycloaddition (CuAAC) reaction", *Chem. Sci. China* (2012), 55(1): 125-130.

Wang, Y., et al., "A fluorescent fatty acid probe, DAUDA, selectively displaces two myristates bound in human serum albumin", *Protein Science* (2011), 20, 2095-2101.

Wardell, M., "The Atomic Structure of Human Methemalbumin at 1.9 A", *Biochem. and Biophys. Research Commun.* (2002), 291, 813-819.

Wilton, D.C., "The fatty acid analogue 11-(dansylamino)undecanoic acid is a fluorescent probe for the bilirubin-binding sites of albumin and not for the high-affinity fatty acid-binding sites", *Biochem. J.* (1990), 270, 163-166.

Yu, C., et al., "Isoindole-BODIPY Dyes as Red to Near-Infrared Fluorophores", *Chem. Eur. J.* ( 2012), 18, 6437-6442.

Yun, S.W., et al., "Neural stem cell specific fluorescent chemical probe binding to FABP7", *PNAS* (2012), 109(26): 10214-10217.

Zhang, G., et al., "Fluorescence spectrometric studies on the binding of puerarin to human serum albumin using warfarin, ibuprofen and digitoxin as site markers with the aid of chemometrics", *Journal of Luminescence* (2011), 131, 2716-2724.

Zhu, L., et al., "A new drug binding subsite on human serum albumin and drug-drug interaction studied by X-ray crystallography", *The Journal of Structural Biology* (2008), 162, 40-49.

Zsila, F., "Subdomain IB Is the Third Major Drug Binding Region of Human Serum Albumin: Toward the Three-Sites Model", *Mol. Pharmaceutics* (2013), 10, 1668-1682.

Zunszain, P.A., et al., "Crystal structural analysis of human serum albumin complexed with hemin and fatty acid", *BMC Structural Biology* (2003), 3(6): 1-9.

MEGASTOKES AMINO-TRIAZOLYL-BODIPY COMPOUNDS AND APPLICATIONS TO LIVE NEURON STAINING AND HUMAN SERUM ALBUMIN FA1 DRUG SITE PROBING

RELATED APPLICATION

This application is the U.S. National Stage of International Application No. PCT/SG2013/000550, filed Dec. 26, 2013, which designates the U.S., published in English, and claims the benefit of U.S. Provisional Application No. 61/745,916, filed Dec. 26, 2012. The entire teachings of the above applications are incorporated herein by reference.

BACKGROUND OF THE INVENTION

The need for understanding essential recognition events in chemistry and biology has directed considerable efforts toward the development of chemical probes. Fluorescent probes are attractive and versatile tools for both analytical sensing and optical imaging because of their high sensitivity, fast response time, and technical simplicity. However, the mechanisms that regulate the interaction between fluorescent probes and their targets are often poorly understood; hence, the ability to predict structural requirements and to design new probes using theoretical calculations is limited. Combinatorial approaches have recently boosted the generation and optimization of fluorescent probes, especially for complex scientific problems that remain indefinite at the molecular recognition level. The development of combinatorial strategies for derivatizing known fluorescent scaffolds with commercially available building blocks using conventional synthetic procedures would enable access to a broader scope of fluorescent probes.

The development of fluorescent and molecular imaging probes based on the BODIPY scaffold has been widely exploited due to its outstanding fluorescent properties (e.g. high photostability, extinction coefficients and quantum yields, tunable excitation and emission spectra) (1-7) and facile conversion into probes for Positron Emission Tomography (PET) imaging (8,9). Most methods to derivatize the 4,4-difluoro-4-bora-3a,4a-diaza-s-indacene (BODIPY) scaffold involve solution-phase chemistry, which often requires tedious purification steps (10). Efforts to derivatize BODIPY on solid-phase have been hampered by its lability in both acidic and basic conditions (11).

There is a need to develop methods to rapidly achieve new compound libraries based on useful fluorescent scaffolds, such as the BODIPY-based scaffold. Moreover, within these libraries, there is a need to develop selective and specific probes for various analytes with critical biological functions.

SUMMARY OF THE INVENTION

The present invention is based the discovery of selective fluorescent probes for detection of biological analyte human serum albumin, and the related discovery of fluorescent probes that are selective for the visualization of live neurons. Accordingly, in one embodiment, the invention is a novel class of amino-triazolyl BODIPY compounds. The compounds of the present invention are rapidly synthesized through high-throughput synthetic methods and contain three moieties that may be derivatized. The present invention also relates to methods of synthesis of the amino-triazolyl BODIPY compounds. Specifically, both solid-phase and solution-phase synthetic methods are described.

In another embodiment, the present invention is a fluorescent probe for human serum albumin. In yet another embodiment, the invention is a fluorescent dye for selective staining of primary neurons. The present invention further relates to methods for the detection of human serum albumin in a sample of biological fluid. In some embodiments, the measure of fluorescence intensity is proportional to the concentration of human serum albumin. Also described herein are methods for visualizing live neurons, which may be used in in vitro or in vivo applications.

BRIEF DESCRIPTION OF THE DRAWINGS

The foregoing will be apparent from the following more particular description of example embodiments of the invention, as illustrated in the accompanying drawings.

FIG. 7a shows fluorescence emission response of BDC-9 (10 µM) upon interaction with serial dilutions of the respective albumins (from $1.2 \times 10^{-4}$ to 4 mg/mL); $\lambda_{exc.}$: 460 nm, $\lambda_{em.}$: 575 nm; values are represented as means and error bars as standard deviations (n=3). FIG. 7b is a photographic image of BDC-9 (10 µM) mixed with respective albumins. Irradiation with a handheld UV lamp at 365 nm.

DETAILED DESCRIPTION OF THE INVENTION

Figure 1:
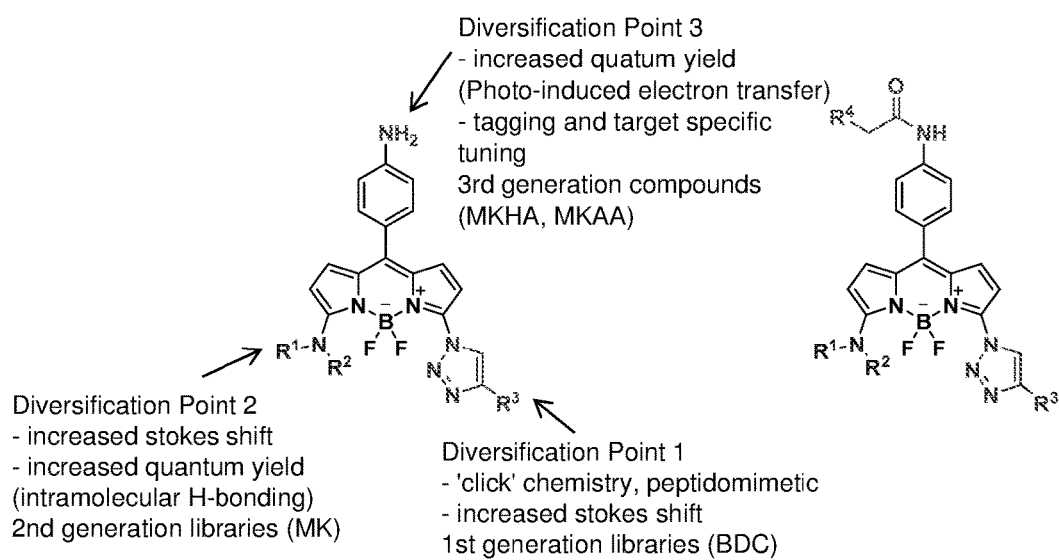
FIG. 1 shows the BODIPY-based BDC and MK library designs, and also points out the relationships between structure and spectral properties.
Figure 2:
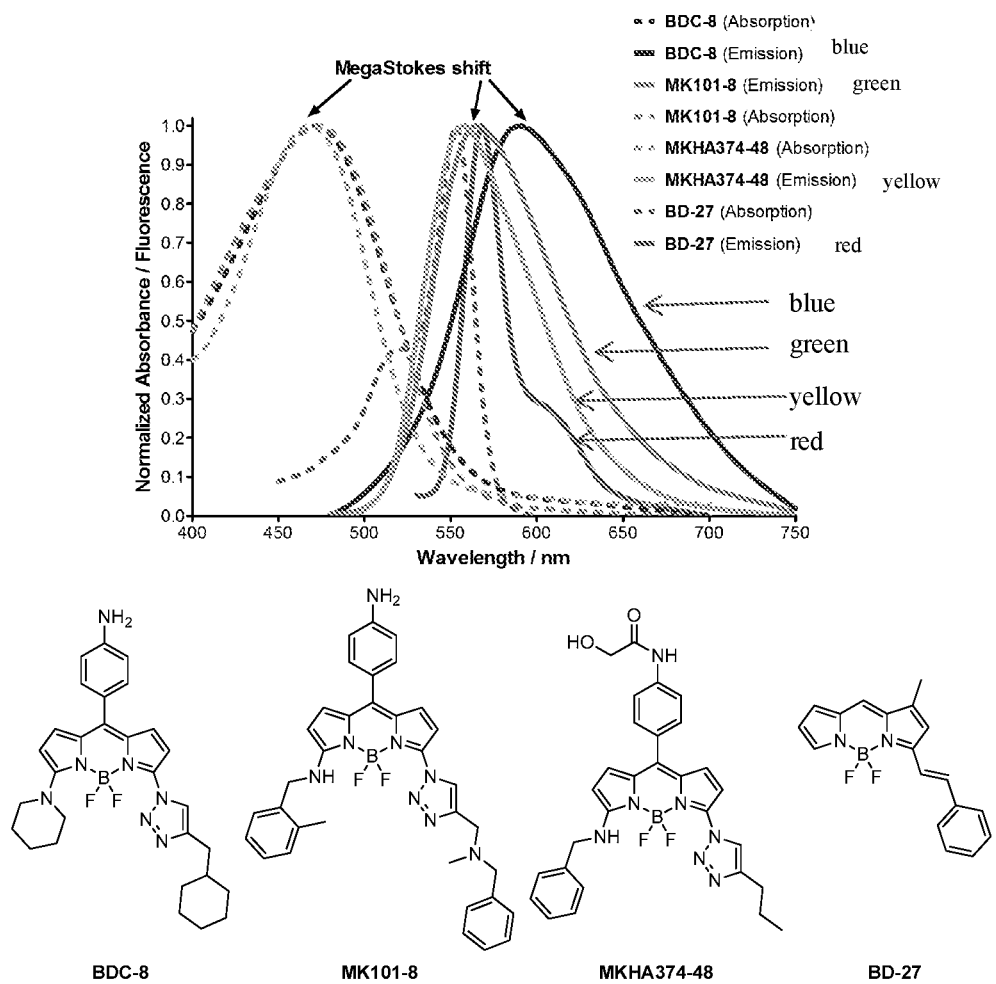
FIG. 2 shows normalized absorbance and fluorescence emission spectra of representative amino-triazolyl-BODIPYs. BDC-8 (Blue): absorbance $\lambda_{max}$=473 nm, emission $\lambda_{max}$=585 nm; MK101-8 (Green): absorbance $\lambda_{max}$=474 nm, emission $\lambda_{max}$=563 nm; MKHA374-48 (Yellow): absorbance $\lambda_{max}$=468 nm, $\lambda_{em}$=557 nm. The corresponding spectra of a reported BODIPY (BD-27; Red) are also included for comparison: absorbance $\lambda_{max}$=551 nm, emission $\lambda_{max}$=568 nm. The structures of BDC-8, MK101-8, MKHA374-48 and BD-27 are also depicted.

A description of example embodiments of the invention follows.

A novel class of triazole-derivatized 4,4-difluoro-4-bora-3a,4a-diaza-s-indacene (BODIPY) compounds is disclosed. This class of compounds includes two novel fluorescent probes, including a human serum albumin (HSA) probe that is the first to independently bind to fatty acid site 1, and also including a neuronal cell probe that stains specifically and uniquely primary neurons.

Library Design—MegaStokes Amino-Triazolyl-BODIPY Compounds

The first solid-phase BODIPY library employing Knoevenagel reactions and mildly acidic cleavage conditions that preserved the integrity of the fluorophore was recently reported (12). The present invention relates to an alternative solid-phase combinatorial derivatization strategy employing Copper-Catalyzed Azide-Alkyne Cycloaddition (CuAAC) to prepare the first library of amino-triazolyl-BODIPY compounds (BDC and MK) and their corresponding acetyl (AC), chloroacetyl (CA) and hydroxyacetyl (HA) derivatives (13). Notably, the introduction of a triazole moiety paired with an amino substituent at the positions 3 and 5 of the BODIPY core rendered fluorescent compounds with very large Stokes shifts (from 74 to 160 nm). MegaStokes dyes, which minimize the overlap between their excitation and emission spectra, offer an increased sensitivity over other fluorophores and an exceptional potential as sensors for in vitro applications. While other fluorescent structures (e.g. coumarin, styryl) have been modified to increase their Stokes shifts, compounds of the BDC and MK libraries disclosed herein represent the first systematic generation of Mega-Stokes dyes based on the BODIPY scaffold. Furthermore, these amino-triazolyl-BODIPY compounds displayed sensitivity to environmental changes. Identified herein are compounds that behave as environmentally-sensitive fluorescent turn-on sensors. The inherent fluorescence of such BODIPY core structures is recovered at specific environments.

Design, Synthesis and Photophysical Properties

CuAAC is highly favored for combinatorial purposes due to its high efficiency, robustness and its success with mild reaction conditions (13,14). The resulting triazole ring is chemically stable and, at certain positions within a fluorescent core, can modulate the spectral wavelengths of the resulting fluorescent derivatives (15,16). A survey of the literature revealed that the incorporation of electron-donating and withdrawing groups at positions 3 and 5 of the BODIPY scaffold can effectively alter its Stokes shifts (17-19). Based on these reports, a trifunctional BODIPY aniline (4, Scheme 1) was designed for the synthesis of the BODIPY library. This scaffold possesses three points for diversification—two electrophilic sites at positions 3 and 5, which can be modified, for example, via CuAAC and nucleophilic substitution respectively (20-24), and one aniline site at the meso position, which can be modified by acetylation.

Two methods for synthesizing Amino-Triazolyl BODIPY compounds were developed, namely, the solid-phase method and the solution phase method. The solution-phase method allows for production of the BODIPY compound on a larger scale, while the solid-phase method provides a practical route to large library of compounds. Both methods are detailed below.

Solid-Phase Synthesis

The solid-phase method allows for the rapid synthesis of a large library of Amino-Triazolyl BODIPY compounds on small scale. The aniline function on 4 enabled loading of the scaffold onto chlorotrityl chloride polystyrene (CTC-PS) resin. Subsequent cleavage under weakly acidic conditions preserves the integrity of the fluorophore (Scheme 1) (12). In certain embodiments, other chlorinated or brominated solid support scaffolds may be used.

In an example embodiment, the synthesis of 4 consisted of four steps with an overall yield of 37%. 1 was readily prepared from p-nitrobenzaldehyde and pyrrole following reported methods (25,26). Chlorination with N-chlorosuccinimide (NCS) followed by oxidation with 2,3-dichloro-5,6-dicyano-1,4-benzoquinone (DDQ) afforded 2, which was subsequently treated with $BF_3.OEt_2$ to obtain the highly stable BODIPY analogue 3 (26,27). Reduction with activated iron rendered 4 in quantitative yields. The aniline was then loaded onto CTC-PS resin using standard coupling conditions. Treatment with sodium azide generated a di-substituted azide intermediate upon which diversity was introduced, first by mono-substitution with the amine building blocks (Scheme 3) and subsequently by the CuAAC with the alkyne building blocks (Scheme 4). Final cleavage with 0.5% trifluoroacetic acid (TFA) in $CH_2Cl_2$ yielded the corresponding amino-triazolyl-BODIPY compounds of the BDC and MK libraries with average purities of 95% in minimum purification steps. These compounds possess a free aniline which can be further acetylated with acid chloride building blocks for added functionality, generating corresponding acetyl (AC), chloroacetyl (CA), acetoxyacetyl (AA) and hydroxyacetyl (HA) derivatives (Scheme 5). In certain embodiments, a CA tag is useful for protein labeling, while a HA tag coupled to some MK compounds possess a specific fluorescence response to primary neurons. In certain embodiments, an AA tag, and other similar derivatives, can be a useful hydrophobic HA precursor with improved permeability into intact live cells. Subsequent hydrolysis by cellular esterases liberates the active HA compound.

Scheme 1. Solid-Phase Synthesis of Amino-Triazolyl BODIPY Compounds.

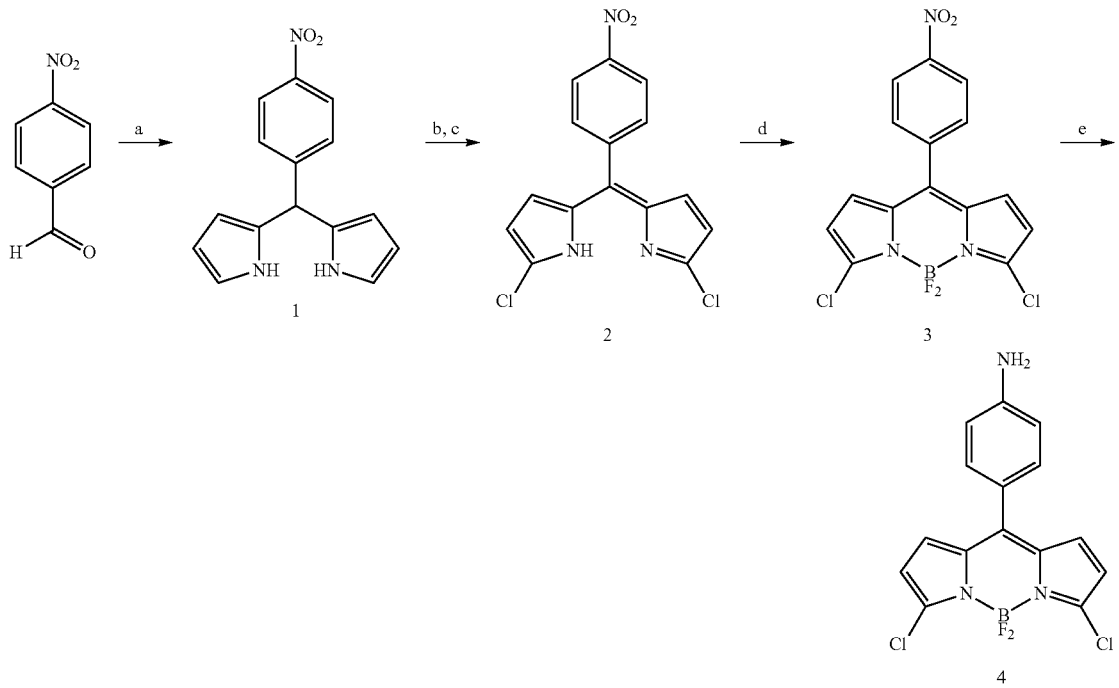

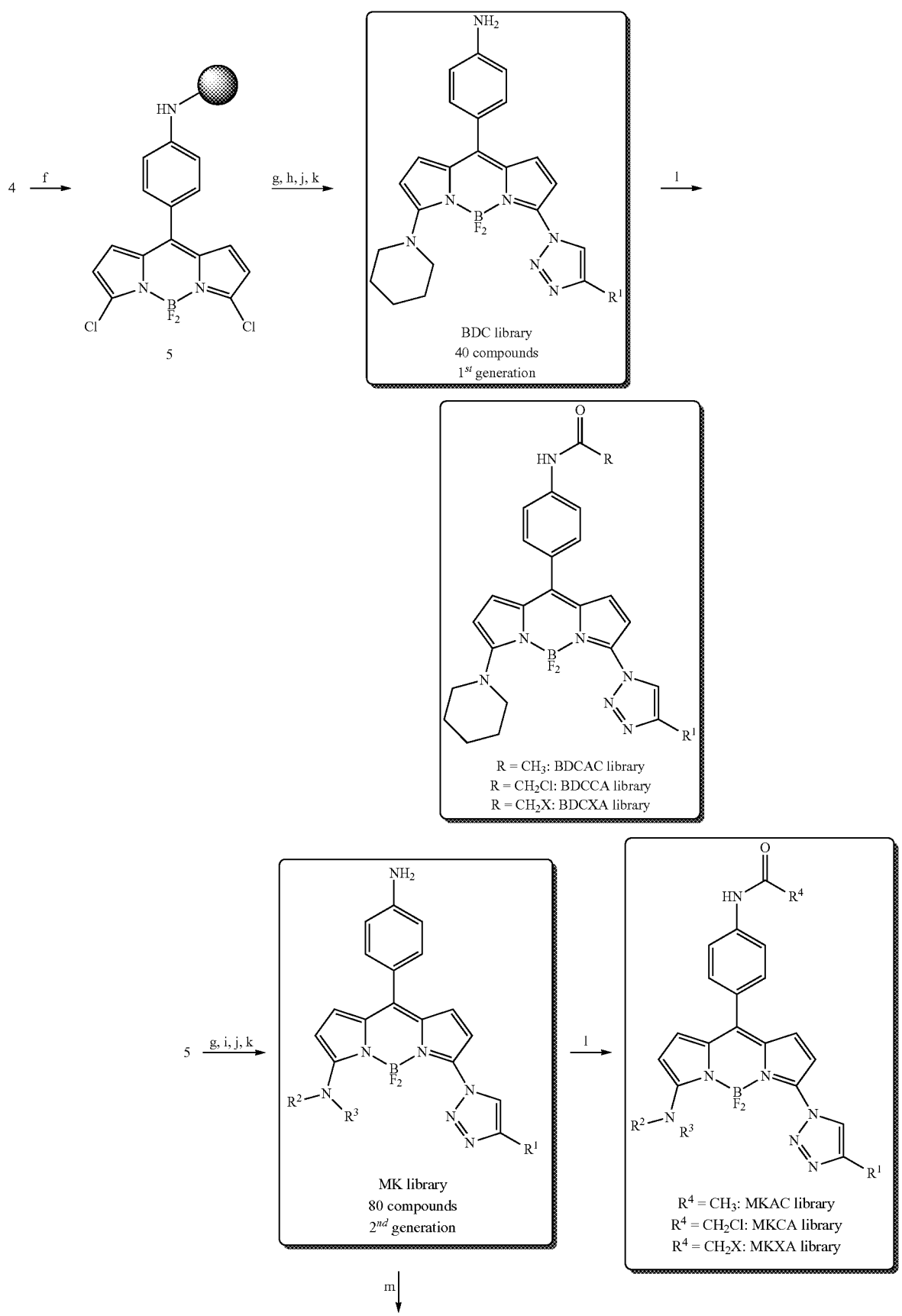

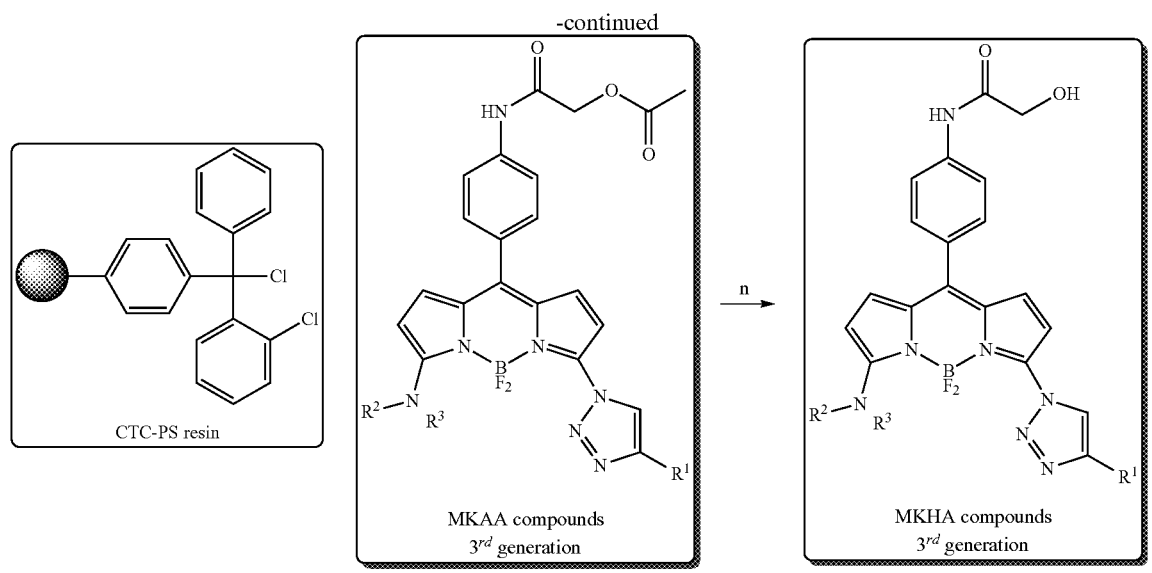

Reagents and conditions: (a) pyrrole, TFA, rt, 3 h; (b) NCS, dry THF, -78° C. to rt, 3 h; (c) DDQ, dry CH$_2$Cl$_2$, rt, 1 h; (d) BF$_3$OEt$_2$, dry CH$_2$Cl$_2$, rt, 2 h; (e) activated Fe, CH$_3$OH:CH$_3$COOH (10:1), reflux, 15 min; (f) CTC-PS resin, DIEA, CH$_2$Cl$_2$/DMF, rt, 24 h; (g) NaN$_3$, DMF, rt, 30 min; (h) DMF:piperidine (4:1), rt, 45 min; (i) DMF:R$^2$R$^3$NH (4:1), rt, 1 h; (j) R$^1$—C≡CH, CuI, ascorbic acid, rt, 30 min; (k) 0.5% TFA in CH$_2$Cl$_2$; (l) R$^4$COCl, sat. NaHCO$_3$, rt, 10 min; (m) CH$_3$COOCH$_2$COCl, sat. NaHCO$_3$, rt, 10 min; (n) K$_2$CO$_3$, MeOH, H$_2$O, rt, 1 h. The dark sphere in compound 5 represents chlorotrityl polystyrene resin.

Solution Phase Synthesis

In alternate embodiments, a solution phase method to generate the BDC and MK compounds is used for large-scale synthesis of the dyes (Scheme 2). In an example embodiment, compounds 1, 2 and 3 were synthesized as described in the solid-phase method. The amino and triazolyl functions were subsequently added to 3. Compound 3 was first treated with approximately 2.2 equivalents of sodium azide in dimethylformamide (DMF) solvent to generate a di-substituted azide intermediate. This was immediately followed by nucleophilic substitution with 1 equivalent of the respective amine building block (Scheme 3) without purification. Upon reaction completion, the DMF was removed, and the crude mixture re-dissolved in tert-butanol solvent before performing CuAAC with the appropriate alkyne building block (Scheme 4). Final reduction of the nitrobenzene moiety with activated iron revealed the corresponding BDC and MK compounds, which are optionally further acetylated using the steps described in solid-phase synthesis to generate corresponding acetyl (AC), chloroacetyl (CA), acetoxyacetyl (AA) and hydroxyacetyl (HA) derivatives (Scheme 5)

Scheme 2. Solution Phase Synthesis of Amino-Triazolyl BODIPY Compounds.

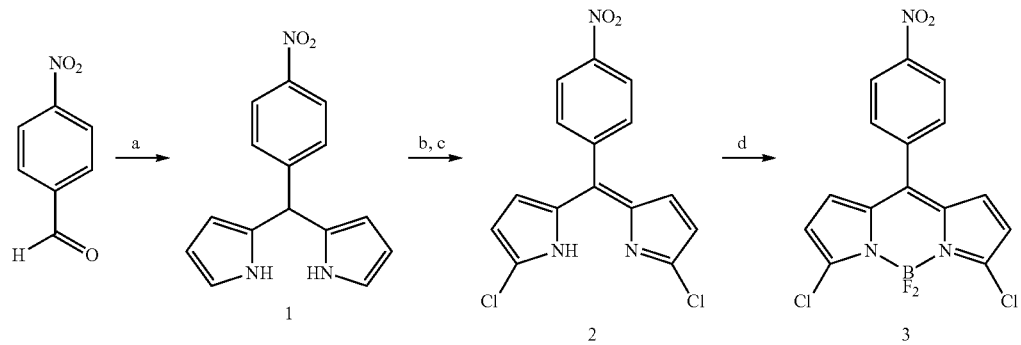

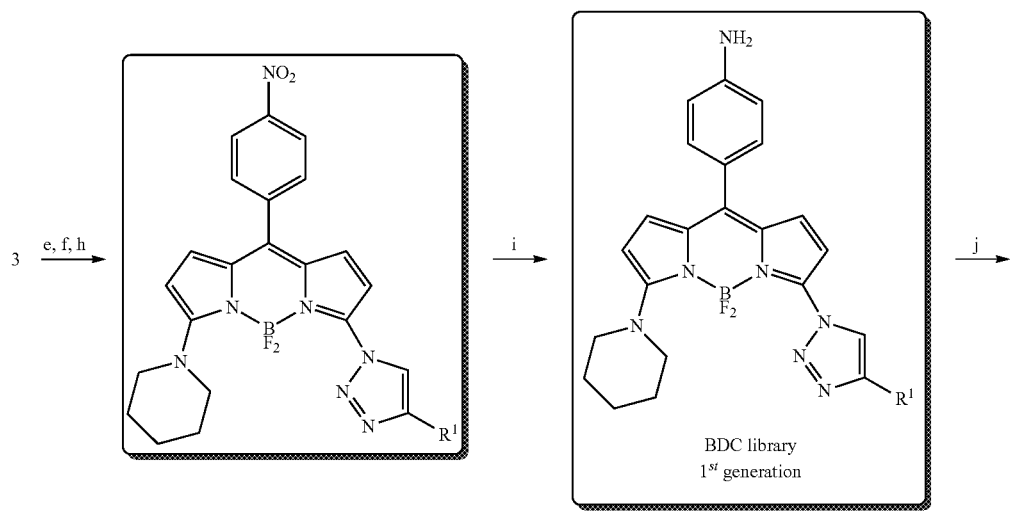
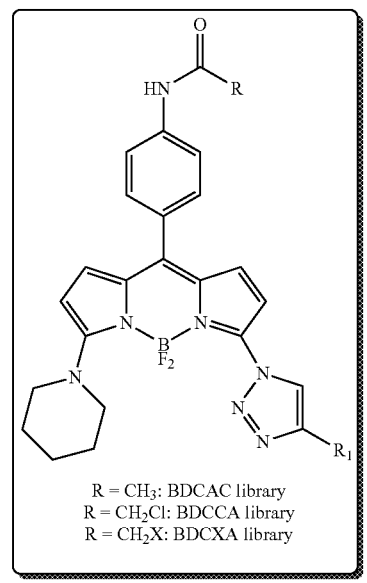
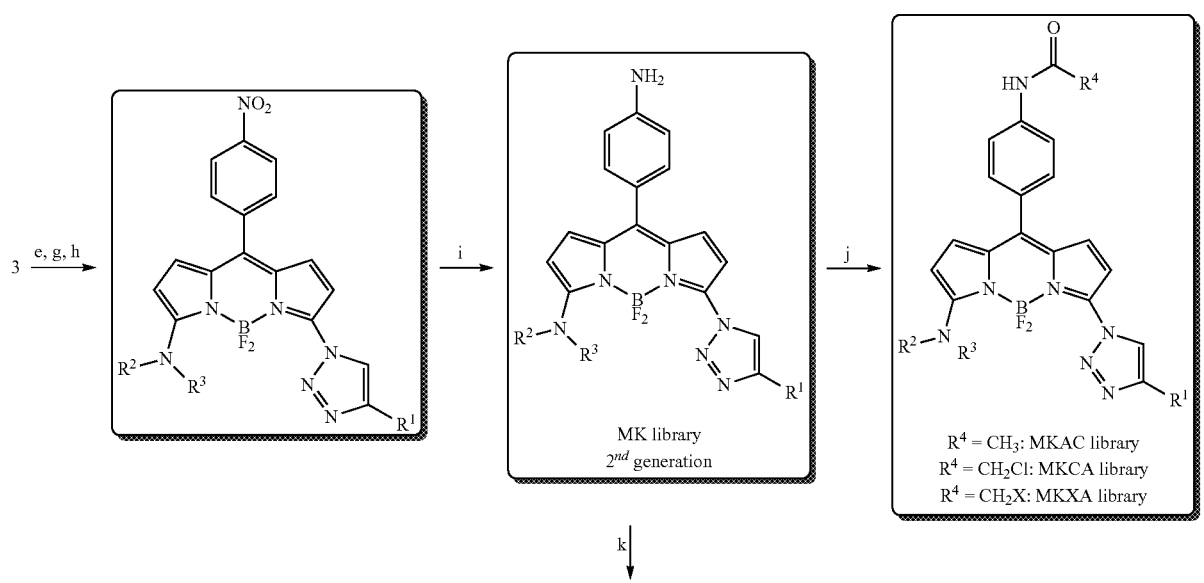

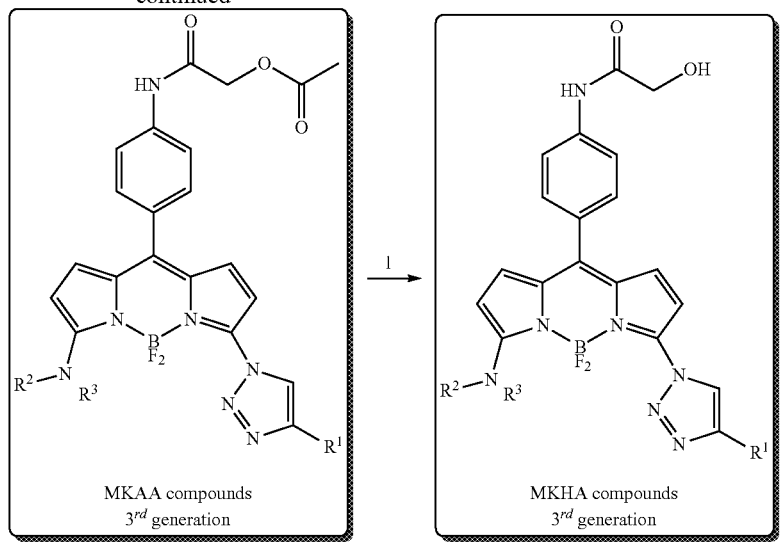

Reagents and conditions: (a) pyrrole, TFA, rt, 3 h; (b) NCS, dry THF, -78° C. to rt, 3 h; (c) DDQ, dry CH$_2$Cl$_2$, rt, 1 h; (d) BF$_3$OEt$_2$, dry CH$_2$Cl$_2$, rt, 2 h; (e) NaN$_3$ (2.2 equiv.) DMF, rt, 30 min; (f) piperidine (1 equiv.), DMF, rt; (g) R$^2$R$^3$NH (1 equiv), DMF, rt, 1 h; (h) R$^1$—C≡CH, CuI, ascorbic acid, tBuOH, rt; (i) activated Fe, CH$_3$OH:CH$_3$COOH (10:1), reflux; (j) R$^4$COCl, sat. NaHCO$_3$, rt, 10 min; (k) CH$_3$COOCH$_2$COCl, sat. NaHCO$_3$, rt, 10 min; (l) K$_2$CO$_3$, MeOH, H$_2$O, rt, 1 h.

In certain embodiments, the amine building blocks of the present invention include primary and secondary amines, for example HNR$_x$R$_y$, wherein R$_x$ and R$_y$ are each independently H, (C$_1$-C$_{10}$)alkyl, (C$_6$-C$_{10}$)aryl(C$_0$-C$_6$)alkyl, (C$_3$-C$_{10}$) heteroaryl, (C$_3$-C$_8$)cycloalkyl, (C$_2$-C$_{10}$)alkynyl or (C$_2$-C$_{10}$) alkenyl, each of which is optionally substituted with 1-5 substituents, each at any position, and each selected from (C$_1$-C$_6$)alkyl, (C$_1$-C$_6$)alkoxy, NH$_2$, —NH(C$_1$-C$_6$ alkyl), —NH(CO)(C$_1$-C$_6$ alkyl), —NH(CO)(C$_1$-C$_6$ haloalkyl), —NH(CO)(C$_1$-C$_6$ alkoxy), —NH(CO)(C$_1$-C$_6$ haloalkoxy), —NH(CO)(C$_2$-C$_6$ alkenyl), —Si(C$_1$-C$_6$ alkyl), —SO$_2$(C$_1$-C$_6$ alkyl), —SH, —B(OH)$_2$,-OTosyl, —CO(C$_1$-C$_6$ alkoxyl), —COH, —COOH, —CO(C$_1$-C$_6$ alkyl) or halogen. In preferred embodiments, the substituent does not have a hydroxyl group present. In alternate embodiments, the R$_x$ and R$_y$ substituents may be taken together to form a ring, such that the ring comprises a cyclic amino group such as piperidine and pyrrolidine, and may include heteroatoms such as in morpholine. The cyclic amino group is optionally substituted by 1-5 substituents selected from halogen or (C$_1$-C$_6$)alkyl, or is optionally fused together with another ring system, for example an aromatic ring system. The substitution can be present at any of the ortho, meta, or para positions of an aromatic ring system. In certain other embodiments, the amine building block includes a benzyl amine, which is optionally substituted at any one or more positions by a substituent, each independently selected from H, (C$_1$-C$_6$)alkyl, (C$_1$-C$_6$)alkoxy, NH$_2$, —NH(C$_1$-C$_6$ alkyl), —NH(CO)(C$_1$-C$_6$ alkyl), —NH(CO)(C$_1$-C$_6$ haloalkyl), —NH(CO)(C$_1$-C$_6$ alkoxy), —NH(CO)(C$_1$-C$_6$ haloalkoxy), —NH(CO)(C$_2$-C$_6$ alkenyl), —Si(C$_1$-C$_6$ alkyl), —SO$_2$(C$_1$-C$_6$ alkyl), —SH, —B(OH)$_2$, —OTosyl, —CO(C$_1$-C$_6$ alkoxyl), —COH, —COOH, —CO(C$_1$-C$_6$ alkyl) or halogen. In alternate embodiments, the amine building block is amino benzene, wherein the benzene ring is optionally substituted at any one or more positions by a substituent, each independently selected from H, (C$_1$-C$_6$)alkyl, (C$_1$-C$_6$)alkoxy, NH$_2$, —NH(C$_1$-C$_6$ alkyl), —NH(CO)(C$_1$-C$_6$ alkyl), —NH(CO)(C$_1$-C$_6$ haloalkyl), —NH(CO)(C$_1$-C$_6$ alkoxy), —NH(CO)(C$_1$-C$_6$ haloalkoxy), —NH(CO)(C$_2$-C$_6$ alkenyl), —Si (C$_1$-C$_6$ alkyl), —SO$_2$(C$_1$-C$_6$ alkyl), —SH, —B(OH)$_2$, —OTosyl, —CO(C$_1$-C$_6$ alkoxyl), —COH, —COOH, —CO (C$_1$-C$_6$ alkyl) or halogen. Certain example embodiments of amine building blocks that may be used in the invention are shown in Scheme 3.

Scheme 3. Amine Building blocks for the BDC and MK libraries.

BDC and MK Libraries - Example Amine Building Blocks

M20
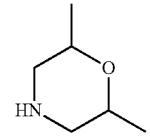

M66
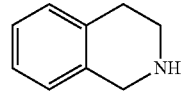

M101
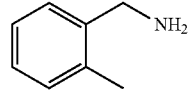

M103
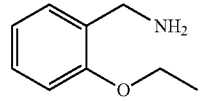

M181
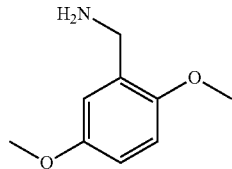

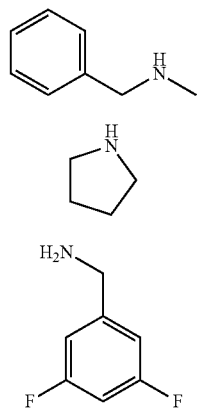

M195

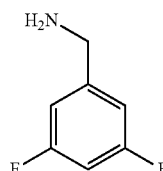

M215

M412

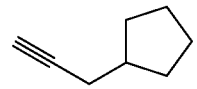

K7

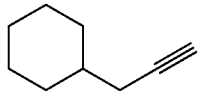

K8

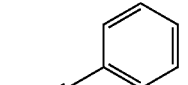

K9

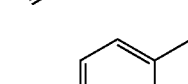

K10

In certain embodiments of the invention, the alkyne building block is a compound of the formula $R^1$—C≡CH, where $R^1$ is selected from $(C_1-C_{10})$alkyl, $(C_3-C_8)$cycloalkyl, $(C_6-C_{10})$aryl, $(C_2-C_{10})$alkenyl, $(C_2-C_{10})$alkynyl, or $(C_3-C_{10})$ heteroaryl, further wherein $R^1$ is optionally substituted at any position with 1-5 substituents selected from $(C_1-C_{10})$ alkyl, $(C_2-C_{10})$alkenyl, $(C_2-C_{10})$alkynyl, $(C_3-C_8)$cycloalkyl, $(C_1-C_6)$alkoxy, $(C_6-C_{10})$aryloxy, $(C_6-C_{10})$aryl, amino, —NH(CO)($C_1-C_6$ alkyl), —NH(CO)($C_2-C_6$ alkenyl), —NH(CO)($C_2-C_6$ alkynyl), —NH(CO)($C_1-C_6$ haloalkyl), halo, $OCF_3$, $CF_3$, hydroxyl, or a halogen radioisotope. Certain example embodiments of alkyne building blocks that may be used in the present invention are shown in Scheme 4.

<u>Scheme 4. Alkyne building blocks for the BDC and MK libraries.</u>

BDC and MK libraries - Example Alkyne Building Blocks

K1

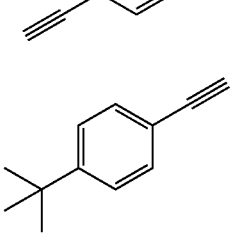

K11

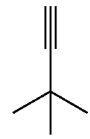

K2

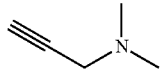

K3

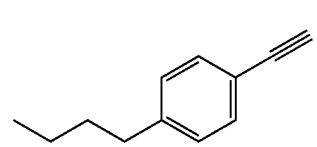

K12

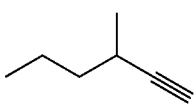

K4

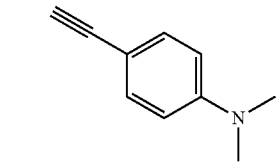

K13

K5

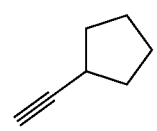

K6

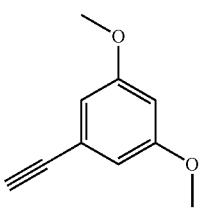

K14

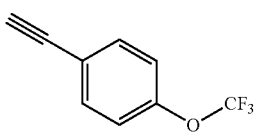

K15

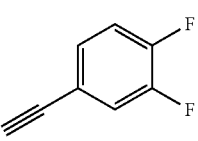

K16

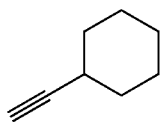

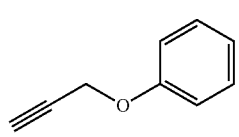

K17

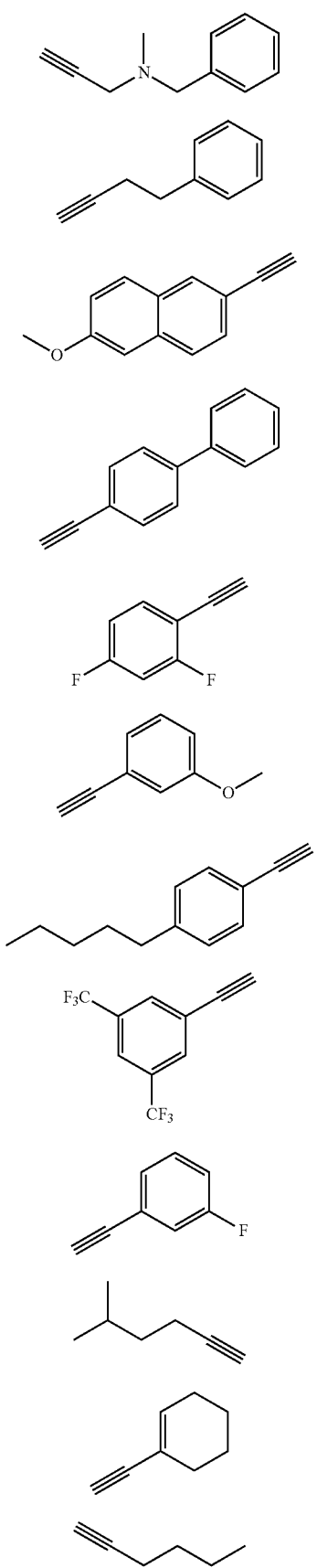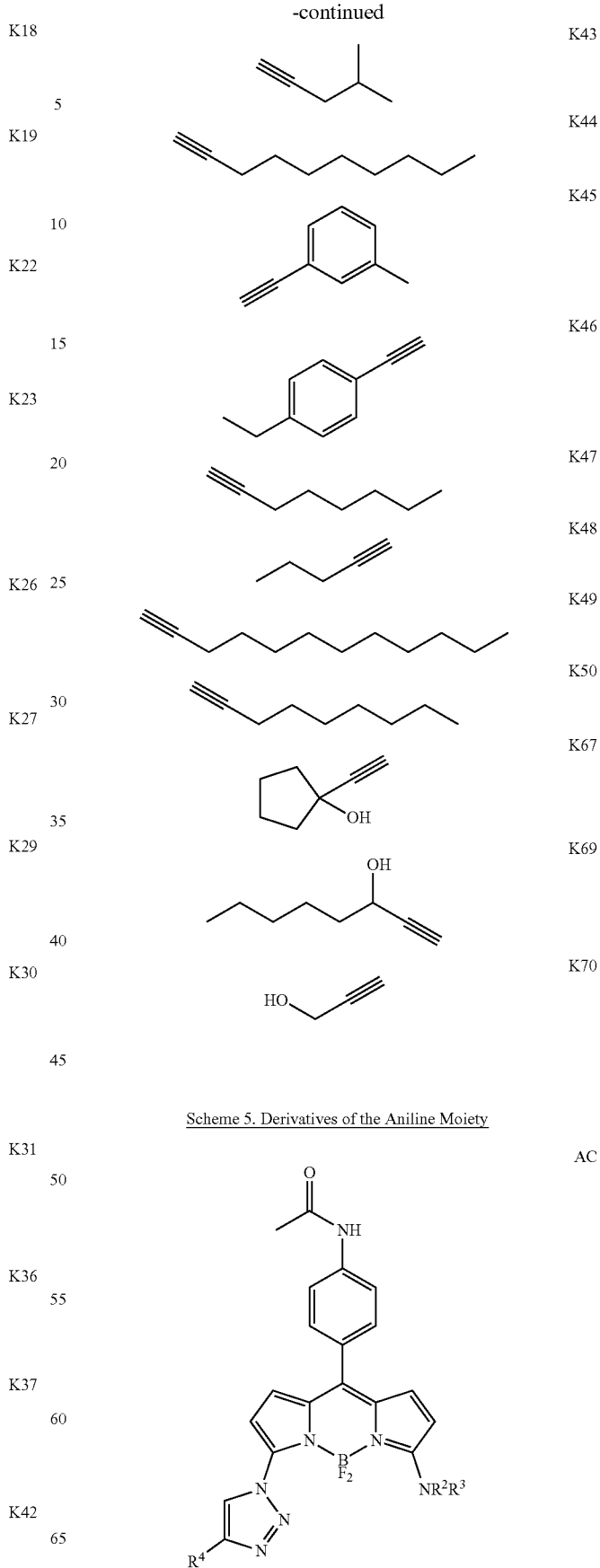
Scheme 5. Derivatives of the Aniline Moiety

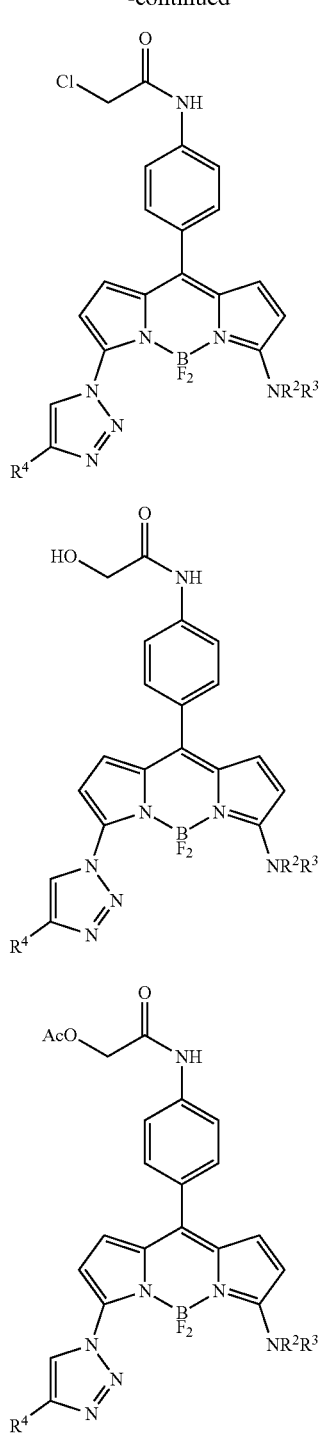

In certain embodiments of the invention, the acid chloride building block has the structure of the formula $R^4COCl$, wherein $R^4$ is $CO(C_1-C_6)$alkyl, which is optionally substituted with 1-3 additional substituents at any position, the substituents independently selected from halogen, hydroxyl, —$NH_2$, NH-acetyl, or O-acetyl. Preferred embodiments of acid chloride include the following substitutions. When $R^4$ is methyl, an AC derivative is formed (e.g., BDCAC or MKAC). When $R^4$ is $CH_2Cl$, a CA derivative is formed. Similarly, when $R^4$ is $CH_2X$, an XA derivative is formed. AA derivatives include compounds in which $R^4$ is $CH_2OAc$, and HA derivatives include $R^4$ equal to $CH_2OH$.

Photophysical Properties

Many of the amino-triazolyl-BODIPY compounds of the present invention exhibited similar absorbance wavelength maxima (Table 1), whereas their emission maxima spanned across a much broader range. Notably, the spectral properties of MegaStokes BODIPY dyes can be fine-tuned with different alkyne building blocks. In some embodiments, electron-rich alkynes (e.g. 4-ethynyl-N,N-dimethylaniline) generate compounds with longer absorption wavelengths than alkynes containing electron-withdrawing groups (e.g. 4-(trifluoromethoxy)phenylacetylene). While BDC and MK compounds exhibited low quantum yields due to photoinduced electron transfer (PeT) effect (28,29), the acetylation of the aniline group partially recovered their fluorescence emission with an average 7-fold fluorescence increase. On the other hand, MK compounds derived from primary amine building blocks displayed an additional 4 to 7-fold increase in fluorescence quantum yields. Without being bound to theory, it is believed that this phenomenon is a result of an intramolecular hydrogen bond formed between the free NH and BODIPY-fluorine, which reduces the conformational flexibility of structure and hence, increases fluorescence (30). These properties affirm the ability of the BDC and MK compounds of the present invention to behave as fluorescent turn-on sensors with potentially tunable quantum yields.

TABLE 1

Spectral properties of amino-triazolyl-BODIPY compounds.

| Library | $\lambda_{abs}$ range/nm | $\lambda_{em}$ range/nm | Average Quantum Yield ($\phi$) |
|---|---|---|---|
| BDC | 466-478 | 547-616 | 0.002 |
| BDCAC | 459-469 | 537-619 | 0.014 |
| BDCCA | 458-468 | 537-627 | 0.012 |
| MK | 470-481 | 560-596 | 1° amines: 0.012 |
|  |  |  | 2° amines: 0.003 |
| MKAC | 461-470 | 558-590 | 1° amines: 0.19 |
|  |  |  | 2° amines: 0.026 |
| MKCA | 459-470 | 558-587 | 1° amines: 0.29 |
|  |  |  | 2° amines: 0.040 |
| MKHA/MKAA | 468-470 | 556-560 | 0.31 |

Amino-Triazolyl BODIPY Compounds as Fluorescent Molecular Rotors

The Amino-triazolyl BODIPY compounds of the present invention have freely rotatable motifs at positions 3 and 5 of the BODIPY core. In certain embodiments, specific environments restrict the rotation of these motifs. These environments include interacting with a suitable analyte. Restriction of the rotation results in a turn-on fluorescence response. The molecular rotor characteristics of the amino-triazolyl BODIPY compounds are validated in Example 2, via fluorescence analysis of the spectra of BDC-9 in different Solvents of similar polarities, which cover a range of viscosities.

A Unique Probe for Human Serum Albumin

Human serum albumin (HSA) is the most abundant protein in the human blood plasma. With a circulating concentration of about 0.6 mM, HSA plays a major role in maintaining osmotic pressure and physiological pH (31). Albuminuria—the loss of HSA in urine is a well-established cardiovascular risk marker and an indication of liver and renal disease (32,33). More importantly, this incredibly plastic protein is the major transporter for a wide array of essential ligands including hormones, fatty acids and drug molecules. Consequently, efforts have been made to develop sensitive and site specific fluorescent probes that can be used for detecting and quantifying HSA in biofluids and identifying binding sites of drugs.

HSA consists of nine binding sites (34-38), amongst which fatty acid (FA) sites 1, 3 and 4 (Sudlow Site II), 5, 6 and 7 (Sudlow Site I) are known to have affinity for drug compounds (31,39-44). Therefore, there is great need to designing fluorescent probes applicable for simple competition assays to identify drug binding sites. Probes have successfully been developed for FA sites 3, 4, 6 and 7 (45-61). However, fluorescent probes for the remaining sites are lacking. The different sites of HSA have different physical properties and have important roles in the pharmacokinetics of drugs. Therefore, identifying the HSA binding site or sites of drugs is crucial. Fluorescent compounds that bind specifically to the different HSA sites can be a convenient tool for probing the binding site of drugs using simple competition assays. There is a need to develop selective fluorescent probes with a binding affinity for fatty acid 1 or 5 of HSA.

The amino-triazolyl-BODIPY compounds of the present invention are especially useful as fluorescent probes for biological analytes such as human serum albumin. Specifically, compounds of Formula (I) exhibit selectivity for HSA, wherein Formula (I) is:

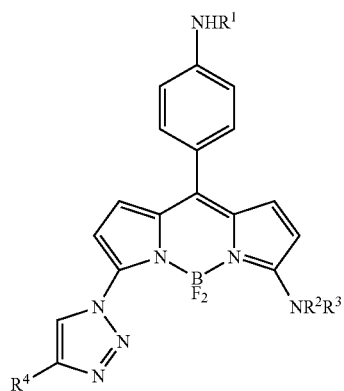

(I)

wherein:

$R^1$ is H or $CO(C_1-C_6)$alkyl, wherein $CO(C_1-C_6)$alkyl is optionally substituted at any position with 1-3 substituents selected from halogen, hydroxyl, O-acetyl, NH-acetyl, or —$NH_2$;

$R^2$ and $R^3$ are each, independently, H, $(C_1-C_{10})$alkyl, $(C_6-C_{10})$aryl$(C_0-C_6)$alkyl, $(C_3-C_{10})$heteroaryl, $(C_3-C_8)$cycloalkyl, $(C_2-C_{10})$alkynyl or $(C_2-C_{10})$alkenyl, wherein $R^2$ and $R^3$ are optionally substituted at any position with 1-5 substituents selected from $(C_1-C_6)$alkyl, $(C_1-C_6)$alkoxy, $NH_2$, —$NH(C_1-C_6$ alkyl), —$NH(CO)(C_1-C_6$ alkyl), —$NH(CO)(C_1-C_6$ haloalkyl), —$NH(CO)(C_1-C_6$ alkoxy), —$NH(CO)(C_1-C_6$ haloalkoxy), —$NH(CO)(C_2-C_6$ alkenyl), —$Si(C_1-C_6$ alkyl), —$SO_2(C_1-C_6$ alkyl), —SH, —$B(OH)_2$, —OTosyl, —$CO(C_1-C_6$ alkoxyl), —COH, —COOH, —$CO(C_1-C_6$ alkyl) or halogen;

or $R^2$ and $R^3$ are taken together to form a ring, wherein the ring is optionally substituted with 1-5 additional substituents selected from halogen or $(C_1-C_6)$alkyl; and $R^4$ is $(C_1-C_{10})$alkyl, $(C_3-C_8)$cycloalkyl, $(C_6-C_{10})$aryl, $(C_2-C_{10})$alkynyl, $(C_2-C_{10})$alkynyl, or $(C_3-C_{10})$heteroaryl, further wherein $R^4$ is optionally substituted at any position with 1-5 substituents selected from $(C_1-C_{10})$alkyl, $(C_2-C_{10})$alkenyl, $(C_2-C_{10})$alkynyl, $(C_3-C_8)$cycloalkyl, $(C_1-C_6)$alkoxy, $(C_6-C_{10})$aryloxy, $(C_6-C_{10})$aryl, amino, —$NH(CO)(C_1-C_6$ alkyl), —$NH(CO)(C_2-C_6$ alkenyl), —$NH(CO)(C_2-C_6$ alkynyl), —$NH(CO)(C_1-C_6$ haloalkyl), halo, $OCF_3$, $CF_3$, hydroxyl, or a halogen radioisotope.

In more particular embodiments, the compound of Formula (II) is selective for the FA1 site of HSA:

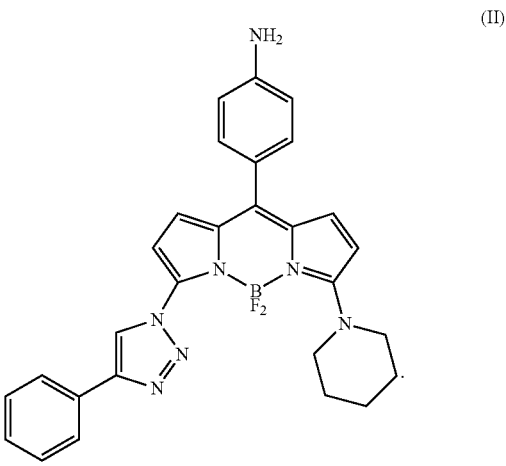

(II)

In certain embodiments, the invention is a fluorescent probe for human serum albumin (HSA), comprising a compound of Formula (II).

In other embodiments, the invention is a method for detecting human serum albumin (HSA) in a sample of a biological fluid, comprising contacting a sample of biological fluid thought to contain HSA with a compound of Formula (I) to form an incubation media;

incubating the incubation media under conditions sufficient to form an incubated mixture; and analyzing the mixture of by fluorescence microscopy, wherein an increase in the fluorescence signal of the mixture relative to the fluorescence signal of the compound of Formula (I) not in the presence of a sample containing HSA is indicative of the presence of HSA.

In some embodiments of the method to detect HSA, a measure of intensity of the fluorescence signal is proportional to the concentration of the HSA present in the sample. In certain embodiments, the compound of Formula (I) has the structure of Formula (II). "Incubating", as used herein, can mean mixing, either by mechanical means, or else by diffusion. Incubating can further comprise maintaining a temperature profile. In certain embodiments, a compound of Formula (I) has a baseline fluorescence. Therefore, in an analytical method to determine the presence of HSA, a change in fluorescence, for example an increase in fluorescence signal or a shift in emission maxima, relative to the baseline fluorescence of Formula (I), is indicative of the target analyte. Methods of visualizing a live neuron include fluorescence microscopy. Fluorescence microscopy methods for measuring a fluorescence signal of a compound of Formula (I) include general fluorescence microscopy, confocal, two-photon, and superresolution (e.g. STORM) microscopy.

X-ray crystallographic studies of HSA have found that the FA1 site is an important drug binding site. Compared to existing fluorescent probes, the amino-triazolyl BODIPY compounds of the present invention can be used for the direct probing of drugs that bind to the HSA FA1 site using simple binding competition assays. Upon binding to HSA, the fluorescent dye exhibits very high fluorescence. Drugs having an affinity to the FA1 site compete with the fluorescent dye for site binding. Hence, in another embodiment of the invention, the present invention includes a method for assessing drug binding to the FA1 site of HSA, the methods comprising monitoring the decrease in dye fluorescence. The methods also provide a measure of the drug's binding strength.

A Unique Probe for Primary Neurons

Elucidating the complex neuronal networks that govern neural function have long been a subject of interest to neuroscientists who believed that human thought could be deciphered by mapping the tangle of neuron connections within the brain (82). As such numerous neuron labeling methods have also evolved to enable the visualization of these complex cells. These include the Golgi method, Nissl staining as well as calcium dyes such as Fura and DiI (83). However, most established neuron labeling dyes work best on fixed tissue preparations or are not selective for neurons but rather depend on retrograde labeling or manual injection to achieve the desired effect in live cells (84). Apart from those mentioned above, there are no chemical dyes to date that are capable of specifically labeling live neurons in their in vitro or in vivo settings.

The availability of a neuron compound negates the need for antibody and transgenic animal use. This is especially useful in the case of neurons because most neuronal markers are intracellular (e.g. β-III-tubulin, MAP2. NeuN) and hence require cell permeabilization (and hence cell death). A wide range of fluorescent protein expressing neuron mouse models are available, however the expression of fluorescent proteins is not consistent throughout animal development (e.g. time needed for activation of cre-recombinase in the Thy1 transgenic mouse line) (85). Thus there are windows of neuronal development which are still difficult to study, with each possibly requiring different neuronal models for the best fluorescent protein expression. Also, incorporation of fluorescent protein expression may possibly interfere with cell function thus making it difficult to draw functional conclusions from these transgenic models (86).

The absence of good neuronal markers for cell isolation is also an issue (87). Neurons are generally difficult to isolate and culture. They are most viable and open to in vitro culture at embryonic and post-natal stages, likely due to increased plasticity at an early developmental stage although it has been established that adult neurons too can be isolated for in vitro culture given the appropriate culture and isolation conditions (88). The use of lentiviral transfection has also become a popular method for selectively labeling neuronal populations of interest (89). Current methods of neuron labeling involved antibody labeling, which compromises the viability of the cells or transgenic modification for fluorescent protein expression, which may affect the native function of the cells. A majority of neuron labeling dyes that are on the market lack neuronal specificity but rather rely on retrograde labeling or microinjection to achieve neuron labeling. However, these methods are time consuming and often suffer from low labeling efficiency. There remains a need for a fluorescent dye that is able to label live neurons, enabling a wide range of cell tracking and isolation applications without the restrictions imposed by some of the previously mentioned methodologies.

The amino-triazolyl-BODIPY compounds of the present invention are especially useful as fluorescent probes for primary neurons. The compounds disclosed herein achieve live neuron specific labeling over other neural cells. This can be applied generically to all neuronal cell preparations regardless of genetic background and results in a stable fluorescent signal which is useful for many applications. Specifically, compounds of Formula (I) exhibit selectivity for staining live neurons, wherein Formula (I) is:

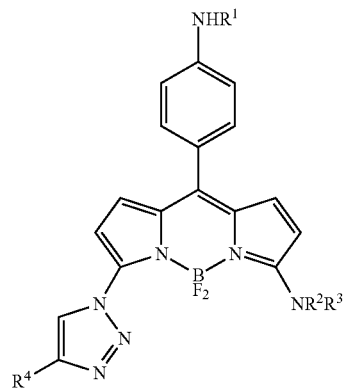

wherein:

$R^1$ is H or $CO(C_1-C_6)$alkyl, wherein $CO(C_1-C_6)$alkyl is optionally substituted at any position with 1-3 substituents selected from halogen, hydroxyl, O-acetyl, NH-acetyl, or $-NH_2$;

$R^2$ and $R^3$ are each, independently, H, $(C_1-C_{10})$alkyl, $(C_6-C_{10})$aryl$(C_0-C_6)$alkyl, $(C_3-C_{10})$heteroaryl, $(C_3-C_8)$cycloalkyl, $(C_2-C_{10})$alkynyl or $(C_2-C_{10})$alkenyl, wherein $R^2$ and $R^3$ are optionally substituted at any position with 1-5 substituents selected from $(C_1-C_6)$alkyl, $(C_1-C_6)$alkoxy, $NH_2$, $-NH(C_1-C_6$ alkyl), $-NH(CO)(C_1-C_6$ alkyl), $-NH(CO)(C_1-C_6$ haloalkyl), $-NH(CO)(C_1-C_6$ alkoxy), $-NH(CO)(C_1-C_6$ haloalkoxy), $-NH(CO)(C_2-C_6$ alkenyl), $-Si(C_1-C_6$ alkyl), $-SO_2(C_1-C_6$ alkyl), $-SH$, $-B(OH)_2$, $-OTosyl$, $-CO(C_1-C_6$ alkoxyl), $-COH$, $-COOH$, $-CO(C_1-C_6$ alkyl) or halogen;

or $R^2$ and $R^3$ are taken together to form a ring, wherein the ring is optionally substituted with 1-5 additional substituents selected from halogen or $(C_1-C_6)$alkyl; and $R^4$ is $(C_1-C_{10})$alkyl, $(C_3-C_8)$cycloalkyl, $(C_6-C_{10})$aryl, $(C_2-C_{10})$alkenyl, $(C_2-C_{10})$alkynyl, or $(C_3-C_{10})$heteroaryl, further wherein $R^4$ is optionally substituted at any position with 1-5 substituents selected from $(C_1-C_{10})$alkyl, $(C_2-C_{10})$alkenyl, $(C_2-C_{10})$alkynyl, $(C_3-C_8)$cycloalkyl, $(C_1-C_6)$alkoxy, $(C_6-C_{10})$aryloxy, $(C_6-C_{10})$aryl, amino, $-NH(CO)(C_1-C_6$ alkyl), $-NH(CO)(C_2-C_6$ alkenyl), $-NH(CO)(C_2-C_6$ alkynyl), $-NH(CO)(C_1-C_6$ haloalkyl), halo, $OCF_3$, $CF_3$, hydroxyl, or a halogen radioisotope.

In more particular embodiments, the compound of Formula (III) is selective for staining live neurons:

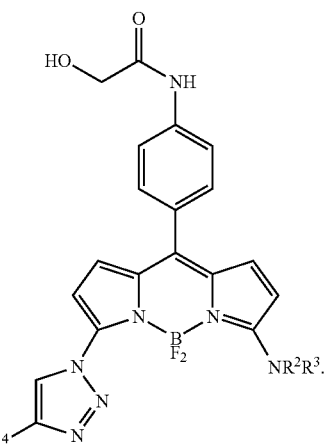

wherein:

$R^2$, $R^3$, and $R^4$ are defined as in Formula (I).

In other particular embodiments, the compound of Formula (XIV) is selective for staining live neurons:

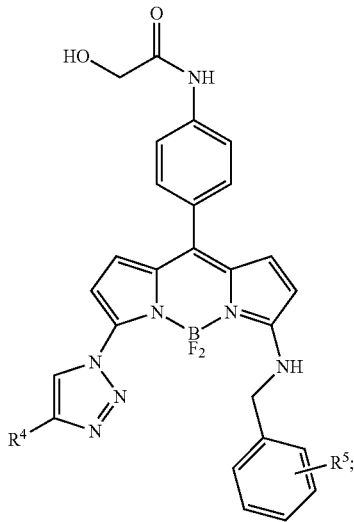

wherein:

$R^4$ is $(C_1-C_{10})$alkyl, $(C_3-C_8)$cycloakyl, $(C_6-C_{10})$aryl, $(C_2-C_{10})$alkenyl, $(C_2-C_{10})$alkynyl, or $(C_3-C_{10})$heteroaryl, further wherein $R^4$ is optionally substituted at any position with 1-5 substituents selected from $(C_1-C_{10})$alkyl, $(C_2-C_{10})$alkenyl, $(C_2-C_{10})$alkynyl, $(C_3-C_8)$cycloalkyl, $(C_1-C_6)$alkoxy, $(C_6-C_{10})$aryloxy, $(C_6-C_{10})$aryl, amino, —NH(CO)($C_1-C_6$ alkyl), —NH(CO)($C_2-C_6$ alkenyl), —NH(CO)($C_2-C_6$ alkynyl), —NH(CO)($C_1-C_6$ haloalkyl), halo, $OCF_3$, $CF_3$, hydroxyl, or a halogen radioisotope; and $R^5$ is present at any position with 1-5 substituents selected from H, $(C_1-C_6)$alkyl, $(C_1-C_6)$alkoxy, $NH_2$, —NH($C_1-C_6$ alkyl), —NH(CO)($C_1-C_6$ alkyl), —NH(CO)($C_1-C_6$ haloalkyl), —NH(CO)($C_1-C_6$ alkoxy), —NH(CO)($C_1-C_6$ haloalkoxy), —NH(CO)($C_2-C_6$ alkenyl), —Si($C_1-C_6$ alkyl), —$SO_2$($C_1-C_6$ alkyl), —SH, —B(OH)$_2$, —OTosyl, —CO($C_1-C_6$ alkoxyl), —COH, —COOH, —CO($C_1-C_6$ alkyl) or halogen.

In yet another particular embodiment, the selective stain for live neurons is a compound of Formula (V):

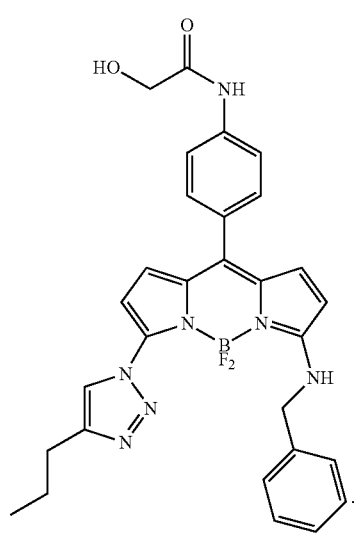

In some embodiments, the invention is a fluorescent dye for the specific staining of live neurons. In certain embodiments, the dye is a compound of formula (XV):

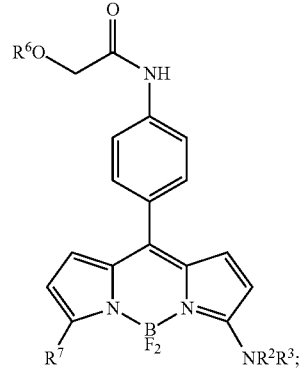

wherein:

$R^2$ and $R^3$ are each, independently, H, $(C_1-C_{10})$alkyl, $(C_6-C_{10})$aryl($C_0-C_6$)alkyl, $(C_3-C_{10})$heteroaryl, $(C_3-C_8)$cycloalkyl, $(C_2-C_{10})$alkynyl or $(C_2-C_{10})$alkenyl;

wherein $(C_1-C_{10})$alkyl, $(C_6-C_{10})$aryl($C_0-C_6$)alkyl, $(C_3-C_{10})$heteroaryl, $(C_3-C_8)$cycloalkyl, $(C_2-C_{10})$alkynyl and $(C_2-C_{10})$alkenyl are optionally substituted at any position with 1-5 substituents selected from $(C_1-C_6)$alkyl, $(C_1-C_6)$alkoxy, $NH_2$, —NH($C_1-C_6$ alkyl), —NH(CO)($C_1-C_6$ alkyl), —NH(CO)($C_1-C_6$ haloalkyl), —NH(CO)($C_1-C_6$ alkoxy), —NH(CO)($C_1-C_6$ haloalkoxy), —NH(CO)($C_2-C_6$ alkenyl), —Si($C_1-C_6$ alkyl), —$SO_2$($C_1-C_6$ alkyl), —SH, —B(OH)$_2$, —OTosyl, —CO($C_1-C_6$ alkoxyl), —COH, —COOH, —CO($C_1-C_6$ alkyl) or halogen;

or $R^2$ and $R^3$ are taken together to form a ring, wherein the ring is optionally substituted with 1-5 additional substituents selected from halogen or $(C_1-C_6)$alkyl;

$R^6$ is H or $CO(CH_3)$; and $R^7$ is $(C_1-C_{10})$alkyl, $(C_3-C_8)$cycloalkyl, $(C_6-C_{10})$aryl, $(C_2-C_{10})$alkenyl, $(C_2-C_{10})$alkynyl, or $(C_3-C_{10})$heteroaryl, further wherein $R^4$ is optionally substituted at any position with 1-5 substituents selected from $(C_1-C_{10})$alkyl, $(C_2-C_{10})$alkenyl, $(C_2-C_{10})$alkynyl, $(C_3-C_8)$cycloalkyl, $(C_1-C_6)$alkoxy, $(C_6-C_{10})$aryloxy, $(C_6-C_{10})$aryl, amino, —NH(CO)($C_1-C_6$ alkyl), —NH(CO)($C_2-C_6$ alkenyl), —NH(CO)($C_2-C_6$ alkynyl), —NH(CO)($C_1-C_6$ haloalkyl), halo, $OCF_3$, $CF_3$, hydroxyl, or a halogen radioisotope.

In other embodiments, the invention is a method for visualizing live neurons in a cell culture, comprising: contacting a cell culture with a compound of Formula (I) to form an incubation media, incubating the incubation media of under conditions sufficient to stain the live neurons and visualizing the stained live neurons with fluorescence microscopy.

In certain embodiments, the method utilizes a compound of Formula (I) having the structure of Formula (XIV) or (V). In certain embodiments, the method is used in an in vitro application. In certain other embodiments, the method is used in an in vivo application. "Incubating", as used herein, can mean mixing, either by mechanical means, or else by diffusion. Incubating can further comprise maintaining a temperature profile. Methods of visualizing a live neuron include fluorescence microscopy. In certain other embodiments, for example for compounds containing $^{18}$F, positron Emission Tomography (PET) techniques may be used. Fluorescence microscopy includes general fluorescence microscopy, confocal, two-photon, and superresolution (e.g. STORM) microscopy.

In certain embodiments, the neuron dyes of the present invention monitor neuron viability, development and dendrite formation in in vitro cultures/assays of neural cells. The dyes disclosed herein can also be combined with other fluorescent cell labels to investigate cellular interactions. The dyes may also be applied to brain slices and in vivo for neuron imaging by two photon or whole animal imaging. Neuron dyes may have applications in disease models such as Rett or Parkinson's, where they can be used to monitor the degeneration of neurons in disease pathogenesis.

Definitions

"Alkyl" means a saturated aliphatic branched or straight-chain monovalent hydrocarbon radicals, typically $C_1$-$C_{10}$, preferably $C_1$-$C_6$. "($C_1$-$C_6$) alkyl" means a radical having from 1-6 carbon atoms in a linear or branched arrangement. "($C_1$-$C_6$)alkyl" includes methyl, ethyl, propyl, butyl, tert-butyl, pentyl and hexyl.

"Alkylene" means a saturated aliphatic straight-chain divalent hydrocarbon radical. Thus, "($C_1$-$C_6$)alkylene" means a divalent saturated aliphatic radical having from 1-6 carbon atoms in a linear arrangement. "($C_1$-$C_6$)alkylene" includes methylene, ethylene, propylene, butylene, pentylene and hexylene.

"Heterocycle" means a saturated or partially unsaturated (3-7 membered) monocyclic heterocyclic ring containing one nitrogen atom and optionally 1 additional heteroatom independently selected from N, O or S. When one heteroatom is S, it can be optionally mono- or di-oxygenated (i.e., —S(O)— or —S(O)$_2$—). Examples of monocyclic heterocycle include, but not limited to, azetidine, pyrrolidine, piperidine, piperazine, hexahydropyrimidine, tetrahydrofuran, tetrahydropyran, morpholine, thiomorpholine, thiomorpholine-1,1-dioxide, tetrahydro-2H-1,2-thiazine, tetrahydro-2H-1,2-thiazine-1,1-dioxide, isothiazolidine, or isothiazolidine 1,1-dioxide.

"Cycloalkyl" means saturated aliphatic cyclic hydrocarbon ring. Thus, "$C_3$-$C_8$ cycloalkyl" means (3-8 membered) saturated aliphatic cyclic hydrocarbon ring. $C_3$-$C_8$ cycloalkyl includes, but is not limited to cyclopropyl, cyclobutyl, cyclopentyl, cyclohexyl, cycloheptyl, and cyclooctyl. Preferably, cycloalkyl is $C_1$-$C_6$ cycloalkyl.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkyl is as defined above. Alkoxy is preferably O($C_1$-$C_6$)alkyl and includes methoxy, ethoxy, propoxy, butoxy, pentoxy and hexoxy.

"Cycloalkoxy" means an cycloalkyl-O— group wherein the cycloalkyl is as defined above. Exemplary ($C_3$-$C_7$) cycloalkyloxy groups include cyclopropoxy, cyclobutoxy, cyclopentoxy, cyclohexoxy and cycloheptoxy.

"Hetero" refers to the replacement of at least one carbon atom member in a ring system with at least one heteroatom selected from N, S, and O. A hetero ring system may have 1 or 2 carbon atom members replaced by a heteroatom.

"Halogen" and "halo" are interchangeably used herein and each refers to fluorine, chlorine, bromine, or iodine.

"Cyano" means —C≡N.

"Nitro" means —NO$_2$.

As used herein, an amino group may be a primary (—NH$_2$), secondary (—NHR$_x$), or tertiary (—NR$_x$R$_y$), wherein R$_x$ and R$_y$ may be any alkyl, aryl, heterocyclyl, cycloalkyl or alkenylene, each optionally and independently substituted with one or more substituents described above. The R$_x$ and R$_y$ substituents may be taken together to form a "ring", wherein the "ring", as used herein, is cyclic amino groups such as piperidine and pyrrolidine, and may include heteroatoms such as in morpholine.

The terms "haloalkyl", "halocycloalkyl" and "haloalkoxy" mean alkyl, cycloalkyl, or alkoxy, as the case may be, substituted with one or more halogen atoms. The term "halogen" means F, Cl, Br or I. Preferably the halogen in a haloalkyl or haloalkoxy is F.

The term "acyl group" means —C(O)B*, wherein B* is an optionally substituted alkyl group or aryl group (e.g., optionally substituted phenyl).

An "alkylene group" is represented by —[CH$_2$]$_z$—, wherein z is a positive integer, preferably from one to eight, more preferably from one to four.

An "alkenylene group" is an alkylene in which at least a pair of adjacent methylenes are replaced with —CH═CH—.

The term "($C_6$-$C_{16}$)aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-16 ring atoms. A "substituted aryl group" is substituted at any one or more substitutable ring atom. The term "$C_6$-$C_{16}$ aryl" as used herein means a monocyclic, bicyclic or tricyclic carbocyclic ring system containing from 6 to 16 carbon atoms and includes phenyl (Ph), naphthyl, anthracenyl, 1,2-dihydronaphthyl, 1,2,3,4-tetrahydronaphthyl, fluorenyl, indanyl, indenyl and the like. The ($C_6$-$C_{10}$)aryl($C_1$-$C_6$)alkyl group connects to the rest of the molecule through the ($C_1$-$C_6$)alkyl portion of the ($C_6$-$C_{10}$)aryl($C_1$-$C_6$)alkyl group.

The term benzyl (Bn) refers to —CH$_2$Ph.

The term "heteroaryl", "heteroaromatic", "heteroaryl ring", "heteroaryl group" and "heteroaromatic group", used alone or as part of a larger moiety as in "heteroarylalkyl" or "heteroarylalkoxy", refers to aromatic ring groups having five to fourteen total ring atoms selected from carbon and at least one (typically 1-4, more typically 1 or 2) heteroatoms (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 total atoms of which, unless otherwise specified, one, two, three, four or five are heteroatoms independently selected, from N, NH, N($C_{1-6}$ alkyl), O and S. ($C_3$-$C_{10}$)heteroaryl includes furyl, thiophenyl, pyridinyl, pyrrolyl, imidazolyl, and in preferred embodiments of the invention, heteroaryl is ($C_3$-$C_{10}$)heteroaryl.

The term "2-4 member polycyclyl" is a cyclic compound with 2-4 hydrocarbon loop or ring structures (e.g., benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these.

The term "Alkenyl" means a straight or branched hydrocarbon radical including at least one double bond. The ($C_6$-$C_{10}$)aryl($C_2$-$C_6$)alkenyl group connects to the remainder of the molecule through the ($C_2$-$C_6$)alkenyl portion of ($C_6$-$C_{10}$)aryl($C_2$-$C_6$)alkenyl. Similarly, the term "alkynyl" means a straight or branched hydrocarbon radical including at least one carbon-carbon triple bond.

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

A solid support resin is used in solid phase synthesis. One such example is a "CT-PS resin". Specifically, it is 2-chlorotrityl-polystyrene.

A "cellular extract" is lysed cells from which insoluble matter has been removed via centrifugation.

A "tissue section" is a portion of tissue suitable for analysis. A tissue section can refer to a single tissue section or a plurality of tissue sections.

A "biological fluid" is a liquid or gas of biological origin. In the present application, a biological fluid can include blood, blood plasma, urine, saliva, and mucous.

As used herein, "spectroscopy" encompasses any method by which matter reacts with radiated energy. This includes, but is in no way limited to, microscopy, fluorescence microscopy, UV/Vis spectrometry, and flow cytometry.

As used herein, a "chemical reactive moiety" refers to a low molecular weight, nonprotein compound that can be incorporated into a structure or compound, such as a fluorophore, that is useful for detection of a biological analyte. In preferred embodiments of the invention, the chemical reactive moiety is covalently bound to the fluorophore, either through an atom in its own structure, or a covalently bound chemical linking group. A key feature of a chemical reactive moiety for use with the present invention is its ability to bind a biological analyte. In a preferred embodiment, a chemical reactive moiety is selective for binding a certain biological analyte. Examples of such chemical reactive moieties include acryloyl groups, haloacetyl groups, N-hydroxy succinimide esters, imidoesters, pentafluorophenyl esters, hydroxymethyl phosphines, maleimides, pyridyldisulfides, thiosulfonates, vinylsulfones, hydrazides, alkoxyamines, aryl azides, benzophenones, and isocyanates. In preferred embodiments, the chemical reactive moiety is biotin, which binds avidin for detection, or a diazirine moiety, which works as a photoreactive crosslinker. Illumination by UV light (360 nm) generates a carbene from the diazirine which then reacts to form covalent bonds with nearby nucleophiles present in the biological analyte.

EXAMPLES

Example 1

Synthesis of BDC and MK BODIPY Compounds

Materials

All commercially available reagents, solvents and proteins were purchased from Sigma Aldrich, Alfa Aesar, Fluka, Merck or Acros, and used as received unless otherwise stated. $CH_2Cl_2$ (Fisher Scientific, analytical grade) was freshly distilled from $P_2O_5$ under nitrogen. Anhydrous THF was purchased from Alfa Aesar and used without further purification. Phosphate buffer was prepared following a modified recipe of Dulbecco's PBS buffer (lx): 0.2 g $KH_2PO_4$, 2.17 g $Na_2HPO_4.7H_2O$, 1000 mL MilliQ™ $H_2O$, pH 7.3.

Analysis $^1$H-NMR, $^{19}$F-NMR and $^{13}$C-NMR spectra were recorded on Bruker ACF300 (300 MHz), DPX300 (300 MHz) and AMX500 (500 MHz) spectrometers. High resolution mass spectra (ESI) were obtained on a Finnigan/MAT 95XL-T spectrometer. Spectroscopic and quantum yield data were measured on a SpectraMax M2 spectrophotometer (Molecular Devices). Data analysis was performed using GraphPrism 5.0. Analytical characterization was performed on a HPLC-MS (Agilent-1200 series) with a DAD detector and a single quadrupole mass spectrometer (6130 series) with an ESI probe. Analytical HPLC method: eluents, A: $H_2O$ (0.1% HCOOH), B: $CH_3CN$ (0.1% HCOOH), gradient 5% B to 95% B (10 min). Reverse-phase Phenomenex $C_{18}$ Luna column (4.6×50 mm$^2$, 3.5 m particle size), flow rate: 1 mL/min.

Quantum Yield Measurements

Quantum yields were calculated by measuring the integrated emission area of the fluorescent spectra and comparing to the area measured for Acridine Yellow in EtOH when excited at 460 nm ($\Phi_{fluorescence}^{AcridineYellow}$=0.47). Quantum yields for the amino-triazolyl-BODIPYs were calculated using the equation below, where F represents the area of fluorescent emission, η is the refractive index of the solvent, and Abs is absorbance at the excitation wavelength selected for standards and samples. Emission was integrated between 510 and 700 nm.

$$\Phi_{fluorescence}^{sample} = \Phi_{fluorescence}^{reference} \left(\frac{F^{sample}}{F^{reference}}\right)\left(\frac{\eta^{sample}}{\eta^{reference}}\right)\left(\frac{Abs^{reference}}{Abs^{sample}}\right)$$

Synthesis

General Procedure for the Preparation of BDC and MK Library Compounds on Solid Phase:

2-chlorotrityl chloride resin (220 mg, 0.275 mmol) was swollen in $CH_2Cl_2$ (3.0 mL) for 15 min. A solution of 4 (30 mg, 0.085 mmol) and DIEA (200 μL, 1.15 mmol) in DMF:$CH_2Cl_2$ (1:1, 2 mL) was added to the resin suspension and shaken at rt for 24 h, after which the resin was capped with MeOH (0.4 mL, 1.8 mL/g resin) and DIEA (100 μL) for 12 h. The resin was filtered, washed with DMF (4×10 mL) and CH$_2$Cl$_2$ (4×10 mL) and dried. The loaded resin was resuspended in CH$_2$Cl$_2$ and shaken at rt for 15 minutes and washed with DMF. A suspension of NaN$_3$ (50 mg, 0.77 mmol) in DMF (3.0 mL) was added and the reaction mixture further shaken at rt for 30 min. After washing with DMF (4×10 mL), a solution of DMF:piperidine (4:1) (4.0 mL) was added and the reaction was shaken for 45 minutes. The alkyne (0.854 mmol), CuI (65 mg, 0.34 mmol) and ascorbic acid (60 mg, 34 mmol) were subsequently added and the reaction mixture shaken for another 30 min. The resin was filtered, washed with DMF (4×10 mL) and CH$_2$Cl$_2$ (4×10 mL), following which cleavage was performed with 0.5% TFA in CH$_2$Cl$_2$ (3×15 mL, 10 min each). The organic extracts were recovered and concentrated in vacuo. The residue was purified by flash column chromatography on silica gel (eluent: CH$_2$Cl$_2$ to CH$_2$Cl$_2$:MeOH (98:2) to afford the corresponding BDC and MK library compound as an orange solid (generally ca. 16 mg, 0.03 mmol, 70% yield). Tables 2 and 5 have specific chemical structures and detailed characterization data, including percent purity at 254 nm, calculated and experimentally determined mass, $\lambda_{max}$ for the absorption and emission spectra, and quantum yield ($\phi$).

General Procedure for the Preparation of BDC and MK Library Compounds in Solution Phase:

To a solution of 3 (100 mg, 0.26 mmol) in acetonitrile (1 mL) was added NaN$_3$ (34 mg, 0.52 mmol) and stirred for 30 min. The corresponding amine (0.26 mmol) was then added and the reaction stirred for an additional 1 h. The reaction mixture was evaporated in vacuo and re-dissolved in t-BuOH:THF:H$_2$O (4:1:1) (1 mL), following which the alkyne (0.26 mmol), CuI (50 mg, 0.26 mmol) and ascorbic acid (46 mg, 0.26 mmol) were added and stirred for 30 min. Organic solvents were evaporated in vacuo and the resulting residue diluted with water (20 mL) and extracted with DCM (20 mL×3). The combined organic extracts were concentrated in vacuo and purified by flash column chromatography on silica gel. The resulting residue was dissolved in EtOH (1 mL) and acetic acid (0.1 mL) and heated to 90° C. A suspension of iron powder (28 mg, 0.5 mmol) was activated in 1M HCl for 1 min, rinsed with absolute EtOH and added to the reaction mixture. Upon reaction completion, iron was removed and the solvent was evaporated in vacuo. The residue was diluted with CH$_2$Cl$_2$ (20 mL) and washed with with saturated NaHCO$_3$ (3×20 mL). The organic extract was washed with saturated brine and dried over anhydrous Na$_2$SO$_4$ and evaporated in vacuo to afford the corresponding BDC and MK library compound as an orange solid (generally ca. 35 mg, 0.06 mmol, 24% overall yield). Tables 2 and 5 have specific chemical structures and detailed characterization data.

General Procedure for the Preparation of BDCAC, BDCCA, MKAC and MKCA Library Compounds:

To a solution of the respective BDC and MK compounds (generally ca. 6 mg, 0.011 mmol) in CH$_2$Cl$_2$ (1.5 mL), 6 drops of saturated aqueous NaHCO$_3$ were added and cooled to 0° C. An acid chloride (generally ~10 μL, 0.11 mmol) was added in portions over 1 min and the resulting mixture was stirred at rt and monitored by analytical TLC. Upon reaction completion, the reaction was diluted with CH$_2$Cl$_2$ (15 mL), washed with water (2×15 mL), saturated NaHCO$_3$ (1×15 mL), saturated brine (1×15 mL) and dried over anhydrous Na$_2$SO$_4$. The organic extract was evaporated to afford the corresponding BDCAC, BDCCA, BDCXA, MKAC, MKCA or MKXA compounds as an orange solid (generally ca. 6 mg, >90% yield). Tables 3, 4, 6 and 7 have specific chemical structures and detailed characterization data.

General Procedure for the Preparation of MKHA Compounds:

To a solution of the respective MK compound (generally ca. 6 mg, 0.011 mmol) in CH$_2$Cl$_2$ (1.5 mL), 6 drops of saturated aqueous NaHCO$_3$ were added and cooled to 0° C. Acetoxylacetyl chloride (10 μL, 0.11 mmol) was added in portions over 1 min and the resulting mixture was stirred at rt and monitored by analytical TLC. Upon completion, CH$_2$Cl$_2$ was evaporated and the mixture re-dissolved in MeOH (1.5 mL). 6 drops of saturated aqueous Na$_2$CO$_3$ were added and the reaction mixture stirred at rt and monitored by analytical TLC. The reaction was diluted with CH$_2$Cl$_2$ (15 mL), washed with water (2×15 mL), saturated NaHCO$_3$ (1×15 mL), saturated brine (1×15 mL) and dried over anhydrous Na$_2$SO$_4$. The organic extract was evaporated to afford the corresponding MKHA compound as an orange solid (generally ca. 6 mg, >90% yield). Table 8 contains chemical structures and detailed characterization data.

Preparation Procedures for Specific Compounds and Characterization Data:

2,2'-((4-nitrophenyl)methylene)bis(1H-pyrrole) (1). To a solution of 4-nitrobenzaldehyde (1.0 g, 6.6 mmol) in pyrrole (10 mL, 144 mmol) was added TFA (0.51 mL, 0.66 mmol) and stirred at rt for 3 h. The mixture was concentrated in vacuo, and purified by flash column chromatography on silica gel (hexane: EtOAc, 4:1) to afford 1 as a bright yellow solid (1.63 g, 6.10 mmol, 92% yield). $^1$H NMR (300 MHz, CDCl$_3$): δ 8.17 (d, J=8.7 Hz, 2H), 7.99 (br. s, 2H), 7.36 (d, J=8.7 Hz, 2H), 7.99 (br. s, 2H), 6.75 (d, J=5.8 Hz, 2H), 6.18 (dd, J=5.8, 2.9 Hz, 2H), 5.87 (br. s, 2H), 5.58 (s, 1H); $^{13}$C NMR (125 MHz, CDCl$_3$): δ=144.7, 144.2, 132.2, 130.5, 123.8, 118.0, 108.5, 107.7, 45.9; MS (ESI): m/z [M+H]$^+$= 268.1.

1,1-Dichloro-5-(4-nitrophenyl)dipyrromethene (2). A solution of 1 (1.1 g, 4.1 mmol) in anhydrous THF (35 mL) was stirred under N$_2$ atmosphere at −78° C. for 15 min. N-chlorosuccinimide (1.4 g, 10.3 mmol) in anhydrous THF (35 mL) was added dropwise using a pressure equalizing funnel and the resulting mixture was stirred at rt for 3 h. Upon completion, 2,3-dichloro-5,6-dicyano-p-benzoquinone (1.12 g, 4.92 mmol) was added and the reaction mixture stirred at rt for an additional 2 h. THF was removed in vacuo and the resulting mixture was diluted with water (20 mL) and extracted with CH$_2$Cl$_2$ (3×70 mL). The combined organic extracts were washed with saturated brine, dried over anhydrous Na$_2$SO$_4$ and the solvents-removed in vacuo. The resulting residue was purified by flash column chromatography on silica gel (hexane: EtOAc, 10:1) to afford 2 as a dark orange solid (0.78 g, 2.3 mmol, 57% yield). $^1$H NMR (300 MHz, CDCl$_3$): δ=8.32 (d, J=4.3 Hz, 2H), 7.62 (d, J=4.3 Hz, 2H), 6.41 (d, J=2.1 Hz, 2H), 6.29 (d, J=2.1 Hz, 2H); $^{13}$C NMR (125 MHz, CDCl$_3$): δ=164.0, 147.1, 146.6, 146.1, 136.0, 130.8, 127.3, 123.8, 121.8, 116.3, 112.1, 32.7, 14.8; MS (ESI): m/z [M+H]$^+$=334.0.

3,5-Dichloro-8-(4'-nitrophenyl)-4,4-difluoro-4-bora-3a, 4a-diaza-s-indacence (3). To a solution of 2 (1.0 g, 2.97 mmol) in anhydrous CH$_2$Cl$_2$ (70 mL) was added N,N-diisopropylethylamine (3.1 mL, 17.8 mmol) stirred at 0° C. for 10 min. Boron trifluoride diethyl etherate (2.2 mL, 17.8 mmol) was added dropwise and the resulting mixture was stirred at rt for 2 h. Upon completion, solvents were removed in vacuo and the residue purified by flash column chromatography on silica gel (hexane:EtOAc:MeOH, 10:1:0.1) to afford 3 as a deep reddish-purple solid (0.81 g, 2.14 mmol, 72% yield). $^1$H NMR (300 MHz, CDCl$_3$): δ=8.39 (d, J=4.4 Hz, 2H), 7.69 (d, J=4.4 Hz, 2H), 6.75 (d, J=2.2 Hz, 2H), 6.48 (d, J=2.2 Hz, 2H); $^{13}$C NMR (125 MHz, CDCl$_3$): δ=162.4, 148.4, 147.1, 132.0, 125.3, 126.8, 124.5, 123.8, 127.3, 120.8, 114.9, 111.3; $^{19}$F NMR (282 MHz, CDCl$_3$): δ=−72.12 (q, J=30 Hz); MS (ESI): m/z [M+H]$^+$=382.9.

3,5-Dichloro-8-(4'-aminophenyl)-4,4-difluoro-4-bora-3a, 4a-diaza-s-indacence (4). A suspension of iron powder (1.46 g, 26.2 mmol) was activated in 1M HCl for 1 min, rinsed with absolute EtOH and used as such. A solution of 3 (500 mg, 1.3 mmol) in EtOH (80 mL) and acetic acid (8 mL) was added the activated iron and refluxed. The reaction mixture was monitored by TLC. Upon completion, iron was removed and the solvent was evaporated in vacuo. The residue was diluted with water and extracted with $CH_2Cl_2$ (3×70 mL). The combined organic extracts were washed with saturated $Na_2CO_3$, saturated brine, dried over anhydrous $Na_2SO_4$ and the solvents removed in vacuo. The residue was purified by flash column chromatography on silica gel (hexane:EtOAc:MeOH:$NH_3$: 6:3:1:0.05) to afford 4 as a dark red solid (197 mg, 0.56 mmol, 98% yield). $^1H$ NMR (300 MHz, $CDCl_3$): δ=7.33 (dt, J=8.5, 2.6 Hz, 2H), 6:92 (d, J=3.8 Hz, 2H), 6.76 (dt, J=8.5, 2.6 Hz, 2H), 6.42 (d, J=3.8 Hz, 2H), 4.11 (br. s, 2H); $^{13}C$ NMR (125 MHz, $CDCl_3$): δ=162.4, 147.6, 132.0, 128.7, 125.2, 26.9, 124.5, 120.8, 114.9, 111.3; $^{19}F$ NMR (282 MHz, $CDCl_3$): δ=−72.05 (q, J=25 Hz); HRMS ($C_{15}H_{11}BCl_2F_2N_3$): Calc. [M+H]$^+$: 352.0386. Found [M+H]$^+$: 352.0215.

10-(4-aminophenyl)-5,5-difluoro-7-(4-phenyl-1H-1,2,3-triazol-1-yl)-3-(piperidin-1-yl)-5H-dipyrrolo[1,2-c:2',1'-f][1,3,2]diazaborinin-4-ium-5-uide (BDC-9): Orange solid (17 mg, 0.032 mmol, 72% yield); $^1H$ NMR (500 MHz, $CDCl_3$): δ=8.56 (s, 1H), 7.94 (d, J=6.9 Hz, 2H), 7.45 (t, J=7.6, Hz, 2H), 7.35 (t, J=7.6 Hz, 1H), 7.27 (d, 8.2 Hz, 2H), 6.94 (d, J=5.7 Hz, 1H), 6.80 (d, J=8.2 Hz, 2H), 6.62 (d, J=3.8 Hz, 1H), 6.42 (d, J=3.8 Hz, 1H), 6.32 (d, J=5.1 Hz, 1H), 5.30 (s, 1H), 3.78-3.88 (m, 4H), 1.64-1.80 (m, 6H), 1.26 (br. s, 2H); $^{13}C$ NMR (75 MHz, $CDCl_3$): δ=162.2, 146.7, 136.0, 135.7, 134.9, 131.8, 131.3, 131.0, 130.8, 129.6, 128.7, 127.9, 126.0, 125.0, 122.4, 122.3, 116.9, 115.4, 115.0, 114.9, 109.7, 53.4, 52.0, 29.7, 26.3, 24.0; $^{19}F$ NMR (282 MHz, $CDCl_3$): δ=−55.82 (q, J=34 Hz); HRMS ($C_{28}H_{27}BF_2N_7$): Calc. [M+H]$^+$: 510.2384. Found [M+H]$^+$: 510.2399.

7-(benzylamino)-5,5-difluoro-10-(4-(2-hydroxyacetamido)phenyl)-3-(4-propyl-1H-1,2,3-triazol-1-yl)-5H-dipyrrolo[1,2-c:2',1'-][1,3,2]diazaborinin-4-ium-5-uide (MKHA374-48): Orange solid (15 mg, 0.027 mmol, 61% yield); $^1H$ NMR (500 MHz, $CDCl_3$): δ=8.91 (s, 1H), 8.15 (s, 1H), 7.71 (d, J=8.2 Hz, 2H), 7.33-7.39 (m, 5H), 7.27-7.30 (m, 3H), 6.95 (d, J=5.0 Hz, 1H), 6.74 (br. s, 1H), 6.38 (s, 2H), 6.20 (d, J=4.4 Hz, 1H), 4.60 (d, J=6.3 Hz, 2H), 4.30 (s, 2H), 2.80 (t, J=7.6 Hz, 2H), 1.80 (qt, J=7.6 Hz, 2H), 1.03 (t, J=7.6 Hz, 3H); $^{13}C$ NMR (125 MHz, $CDCl_3$): δ=170.8, 162.5, 139.0, 136.9, 136.1, 133.9, 132.4, 132.0, 131.8, 131.0, 129.2, 128.9, 128.4, 127.6, 126.8, 119.6, 119.0, 112.5, 109.5, 62.6, 48.4, 28.7, 22.4, 13.7; $^{19}F$ NMR (282 MHz, $CDCl_3$): δ=−68.29 (q, J=33 Hz); HRMS ($C_{29}H_{28}BF_2N_7O_2$): Calc. [M+H]$^+$: 556.2444. Found [M+H]$^+$: 556.2461.

TABLE 2

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-1 | 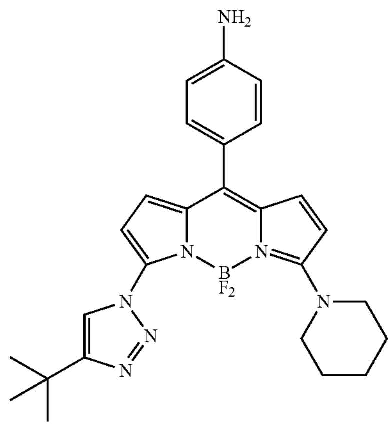 | 95% | 489.3 | 490.0 | 475 | 593 | 0.18 |
| BDC-2 | 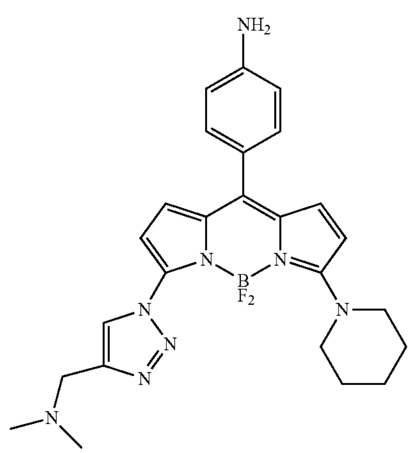 | 95% | 490.3 | 491.0 | 469 | 587 | 0.13 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-3 | 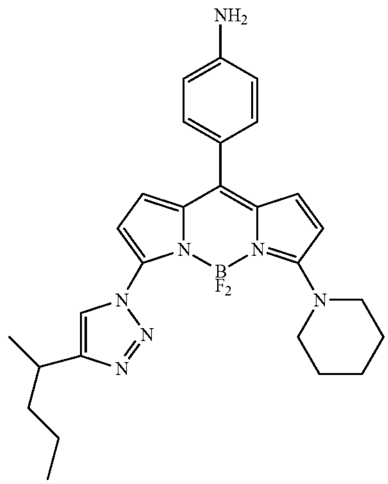 | 98% | 503.3 | 504.3 | 475 | 567 | 0.37 |
| BDC-4 | 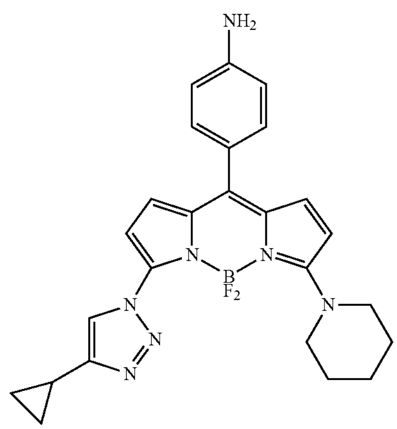 | 95% | 473.2 | 474.2 | 475 | 590 | 0.16 |
| BDC-5 | 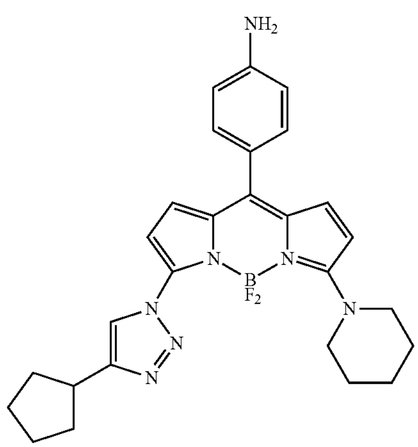 | 99% | 501.3 | 502.2 | 476 | 582 | 0.16 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-6 | 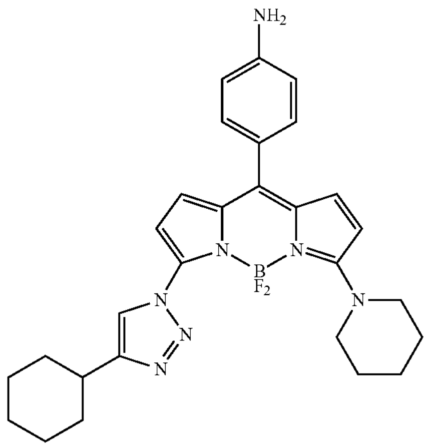 | 86% | 515.4 | 516.2 | 473 | 582 | 0.24 |
| BDC-7 | 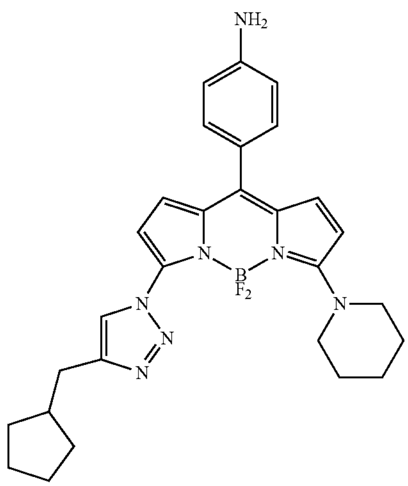 | 99% | 515.3 | 516.2 | 476 | 573 | 0.23 |
| BDC-8 | 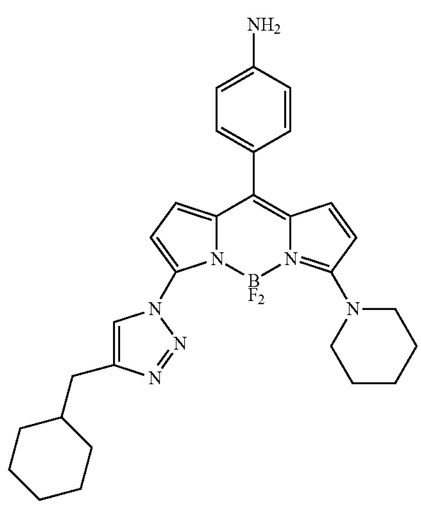 | 88% | 529.3 | 503.2 | 473 | 585 | 0.24 |

TABLE 2-continued
Chemical structures and characterization data for the BDC compound library.
| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-9 | 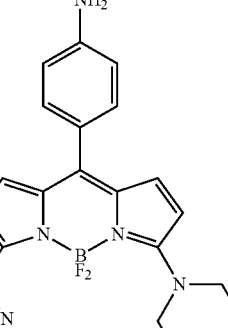 | 97% | 509.2 | 510.2 | 472 | 581 | 0.22 |
| BDC-10 | 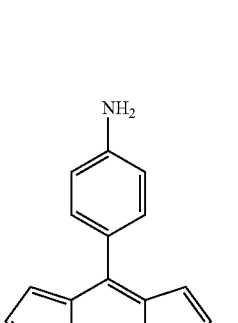 | 92% | 523.3 | 524.2 | 470 | 564 | 0.28 |
| BDC-11 | 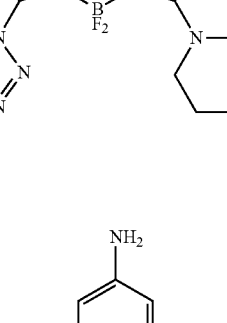 | 97% | 565.3 | 566.3 | 471 | 552 | 0.74 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-12 | 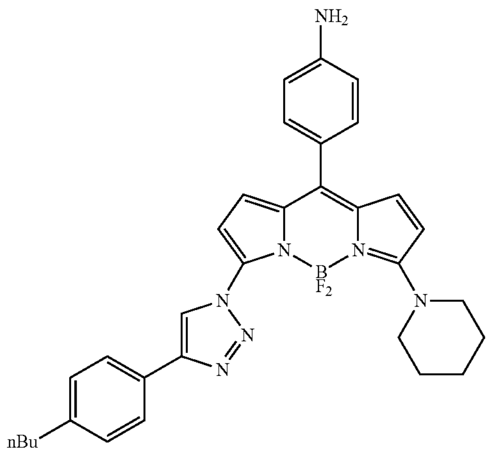 | 90% | 565.3 | 566.3 | 473 | 594 | 0.09 |
| BDC-13 | 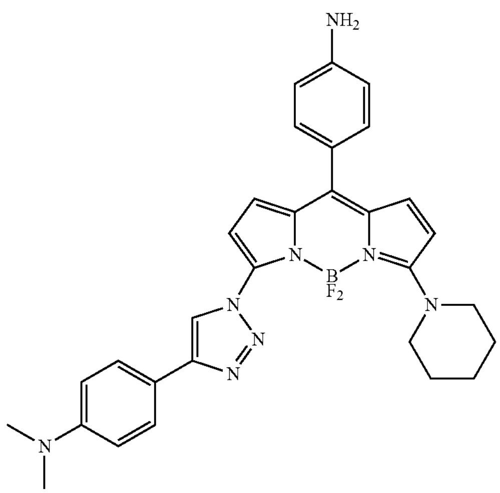 | 97% | 552.3 | 553.2 | 475 | 616 | 0.03 |
| BDC-14 | 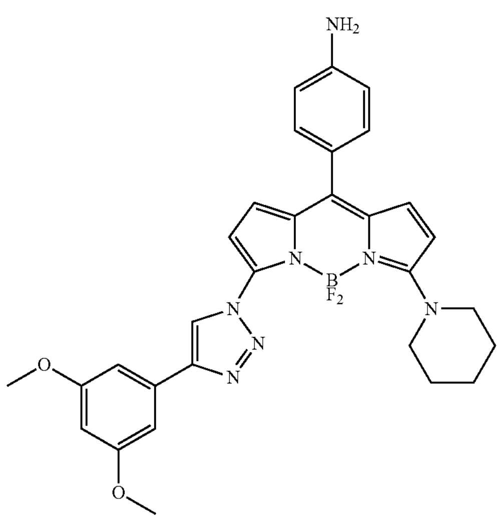 | 99% | 569.3 | 570.2 | 473 | 578 | 0.18 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-15 | 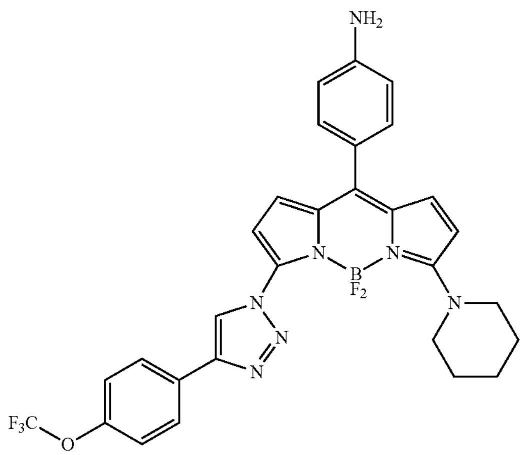 | 84% | 593.2 | 594.0 | 469 | 549 | 0.19 |
| BDC-16 | 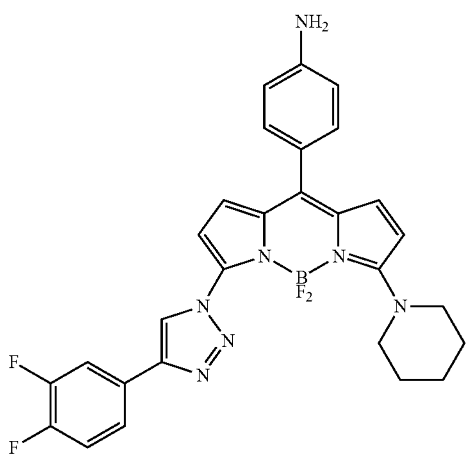 | 95% | 545.2 | 546.1 | 471 | 585 | 0.18 |
| BDC-17 | 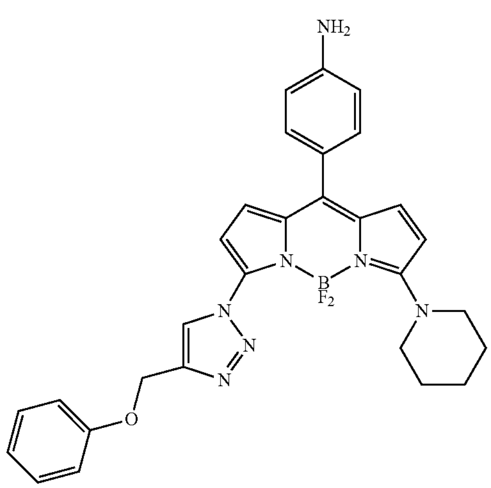 | 99% | 539.2 | 540.2 | 474 | 591 | 0.11 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-18 | 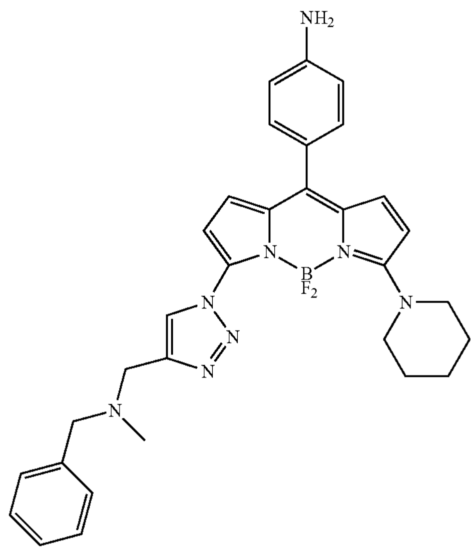 | 87% | 566.3 | 567.3 | 471 | 580 | 0.18 |
| BDC-19 | 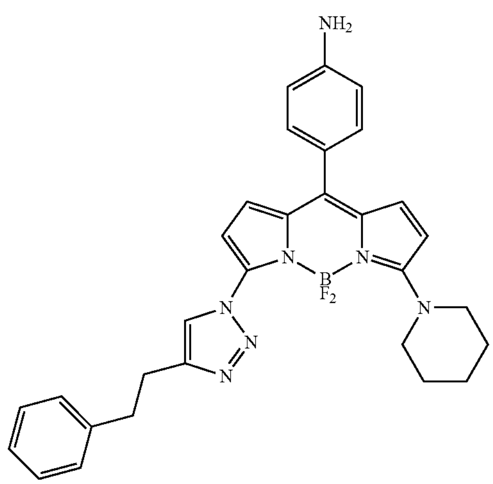 | 98% | 537.3 | 538.2 | 476 | 594 | 0.08 |
| BDC-22 | 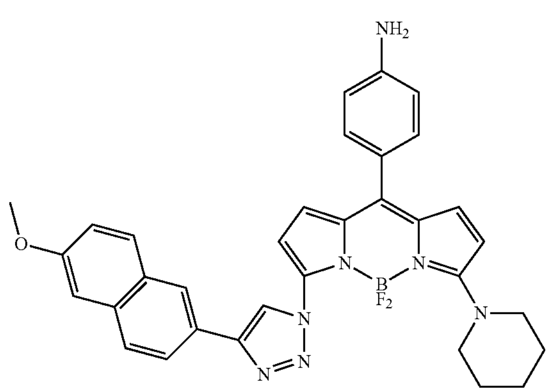 | 99% | 589.3 | 590.2 | 472 | 579 | 0.28 |

TABLE 2-continued
Chemical structures and characterization data for the BDC compound library.
| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-23 | 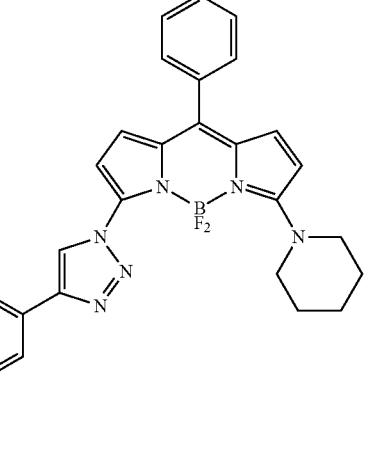 | 99% | 585.5 | 586.3 | 472 | 570 | 0.20 |
| BDC-26 | 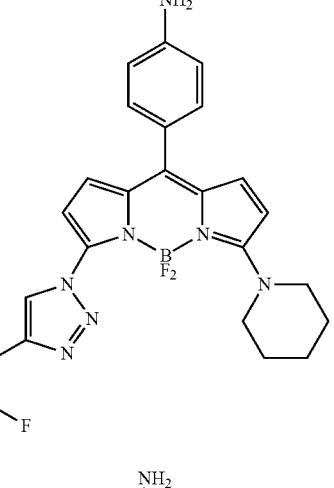 | 91% | 545.2 | 546.2 | 473 | 585 | 0.12 |
| BDC-27 | 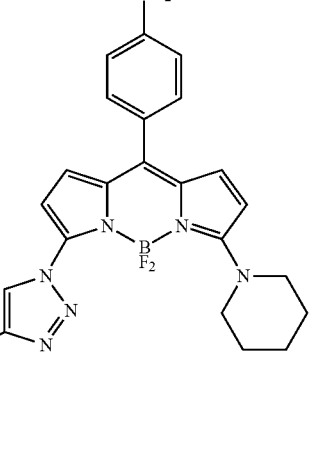 | 58% | 539.2 | 540.2 | 472 | 565 | 0.17 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-29 | 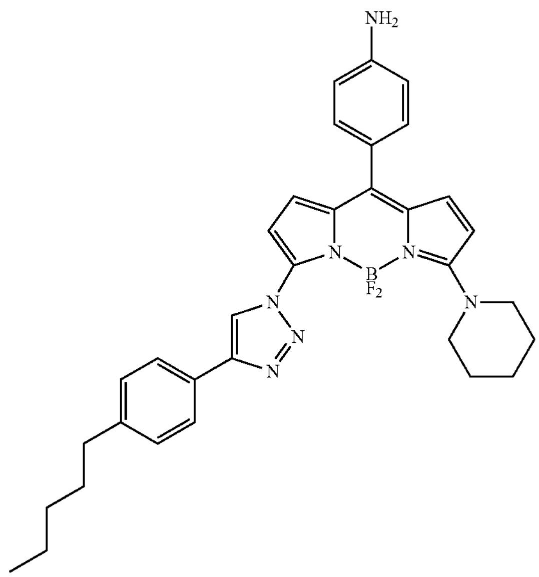 | 93% | 579.3 | 580.3 | 471 | 586 | 0.23 |
| BDC-30 | 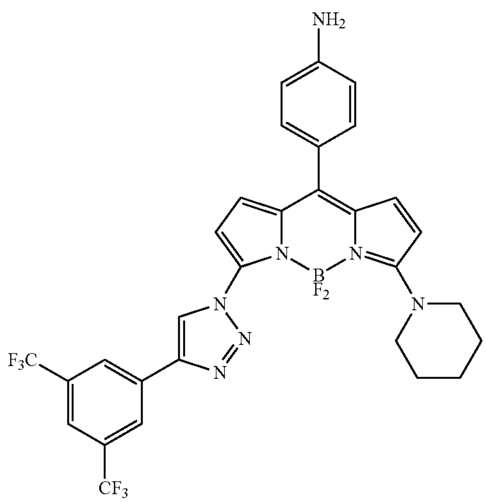 | 92% | 645.2 | 646.1 | 466 | 547 | 0.57 |
| BDC-31 | 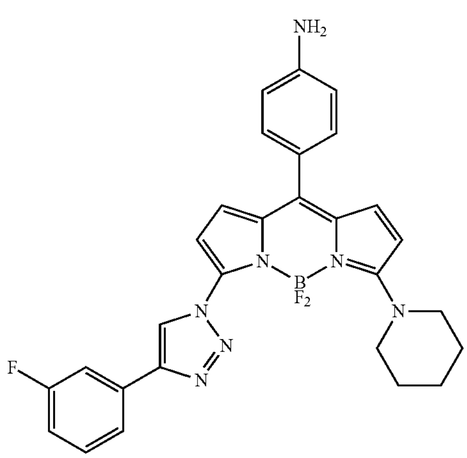 | 96% | 527.2 | 528.2 | 470 | 582 | 0.11 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-36 | 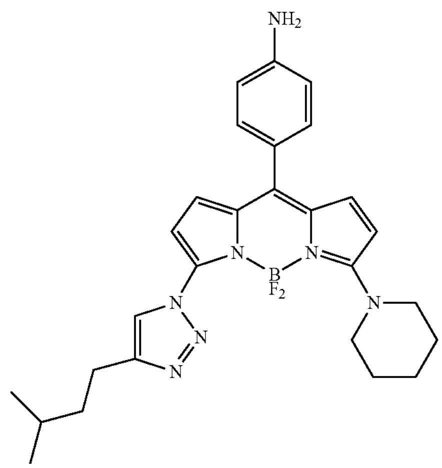 | 98% | 503.3 | 504.1 | 476 | 590 | 0.11 |
| BDC-37 | 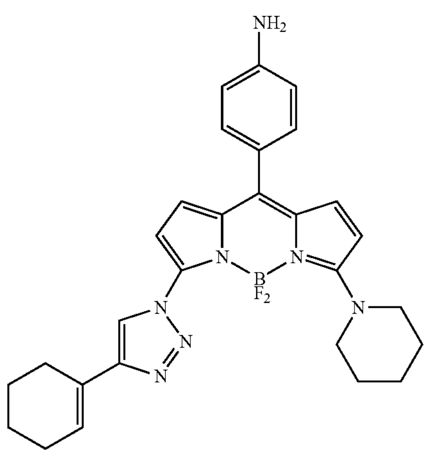 | 96% | 513.3 | 514.2 | 474 | 579 | 0.12 |
| BDC-42 | 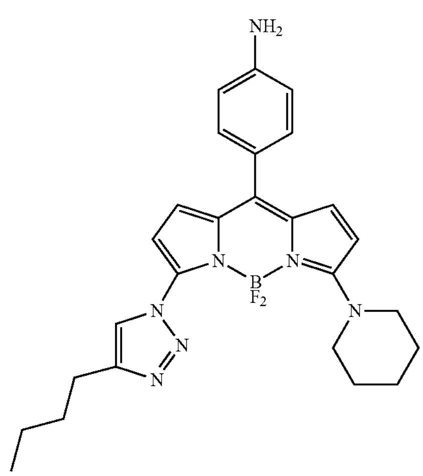 | 92% | 489.3 | 490.2 | 473 | 584 | 0.19 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-43 | 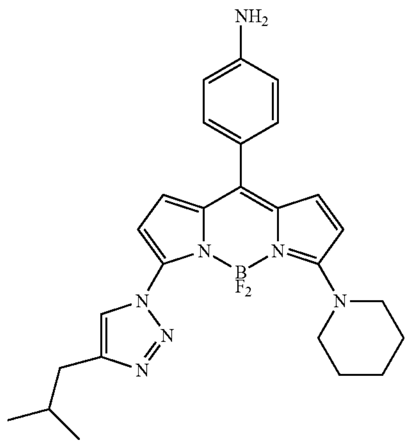 | 95% | 489.3 | 490.2 | 476 | 589 | 0.10 |
| BDC-44 | 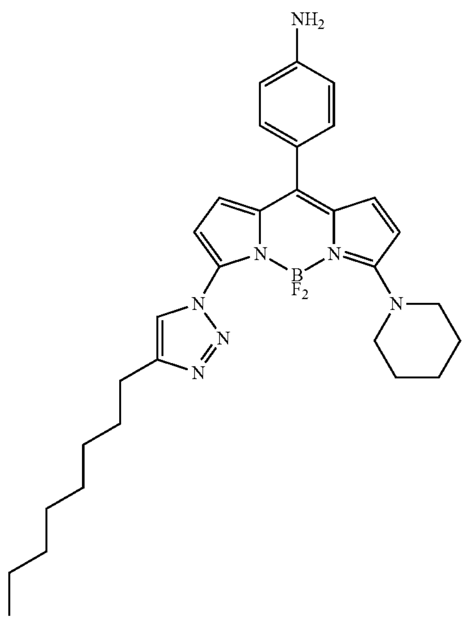 | 94% | 545.3 | 546.1 | 475 | 583 | 0.13 |
| BDC-45 | 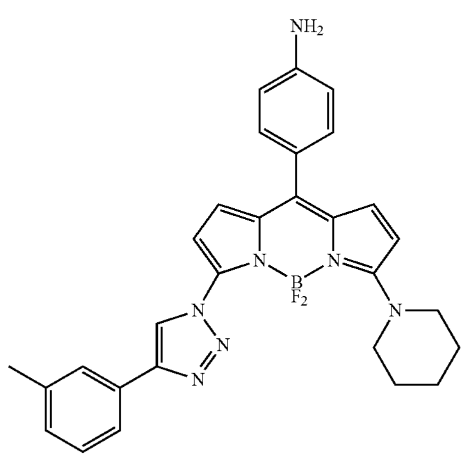 | 84% | 523.3 | 524.2 | 469 | 556 | 0.42 |

TABLE 2-continued

Chemical structures and characterization data for the BDC compound library.

| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-46 | 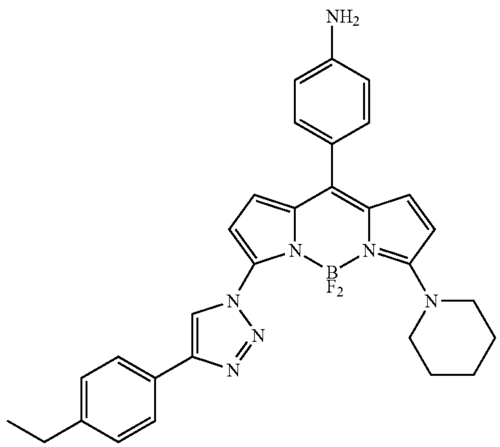 | 98% | 537.3 | 538.2 | 473 | 585 | 0.10 |
| BDC-47 | 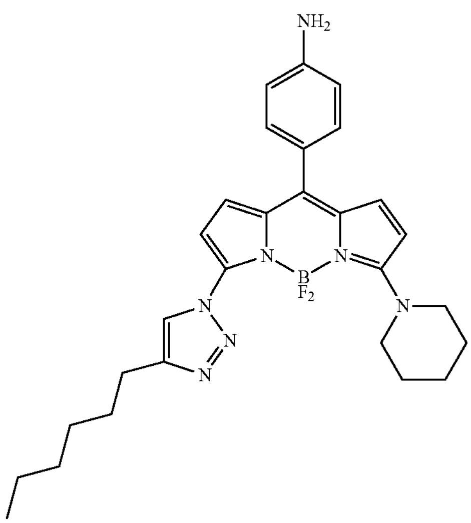 | 90% | 517.3 | 518.2 | 473 | 574 | 0.16 |
| BDC-48 | 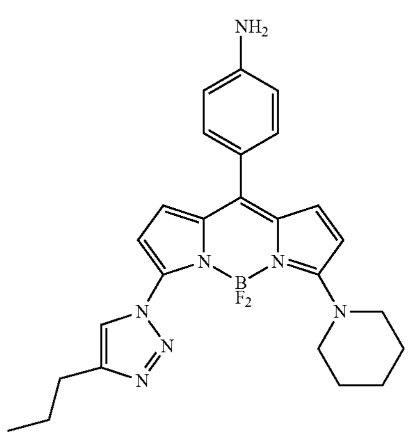 | 96% | 475.3 | 476.2 | 476 | 582 | 0.10 |

TABLE 2-continued
Chemical structures and characterization data for the BDC compound library.
| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-49 | 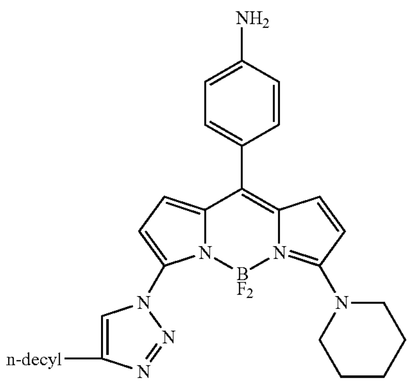 | 92% | 573.4 | 574.2 | 475 | 589 | 0.12 |
| BDC-50 | 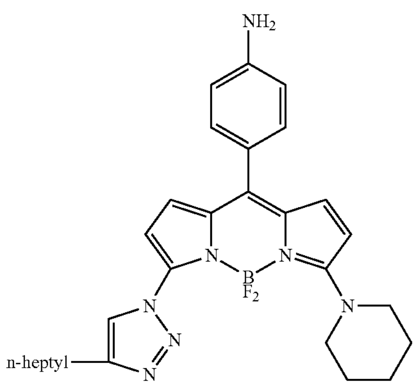 | 93% | 531.3 | 532.2 | 475 | 577 | 0.13 |
| BDC-67 | 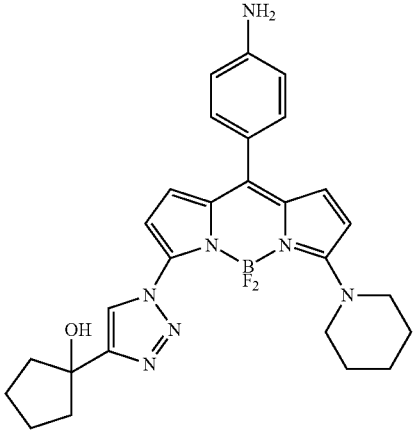 | 99% | 517.3 | 518.1 | 478 | 595 | 0.09 |

TABLE 2-continued
Chemical structures and characterization data for the BDC compound library.
| Code | Structure | purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDC-69 | 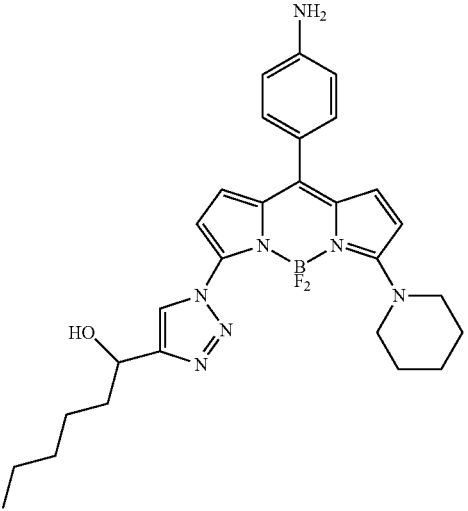 | 92% | 533.3 | 534.2 | 476 | 586 | 0.13 |
| BDC-70 | 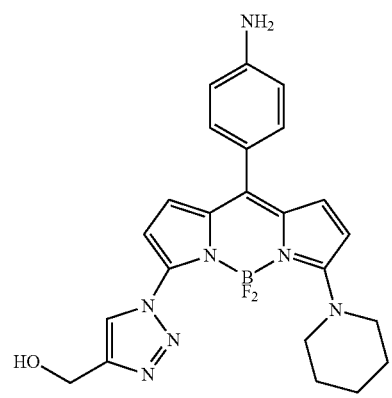 | 99% | 463.3 | 464.2 | 474 | 586 | 0.13 |

TABLE 3

Chemical structures and characterization data for the BDCAC compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-1 | 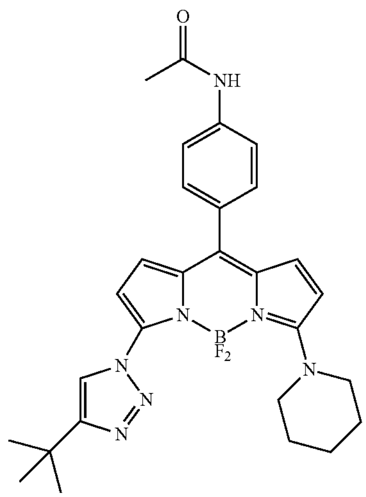 | 95% | 531.4 | 532.3 | 469 | 580 | 1.5 |
| BDCAC-2 | 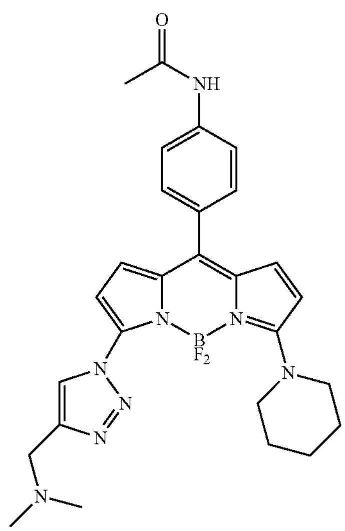 | 98% | 532.4 | 533.3 | 466 | 591 | 0.8 |
| BDCAC-3 | 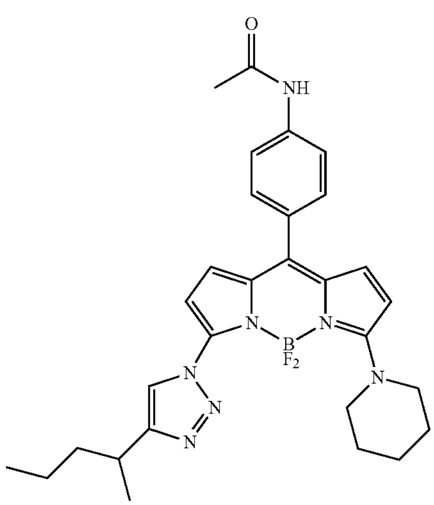 | 97% | 545.4 | 546.3 | 467 | 585 | 1.5 |

TABLE 3-continued

Chemical structures and characterization data for the BDCAC compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-4 | 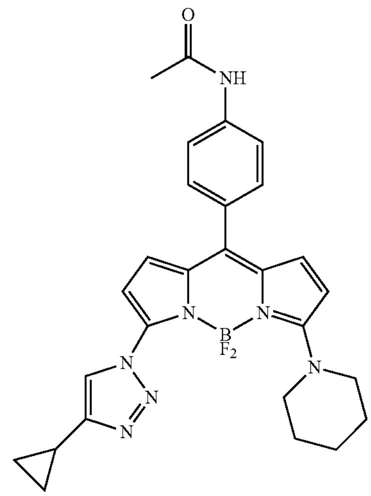 | 97% | 515.4 | 516.2 | 467 | 578 | 1.5 |
| BDCAC-5 | 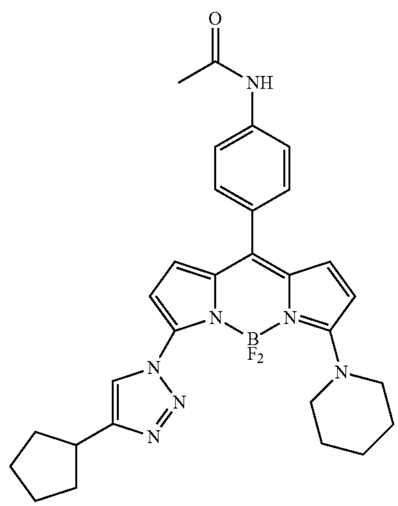 | 99% | 543.4 | 544.3 | 469 | 588 | 1.3 |
| BDCAC-6 | 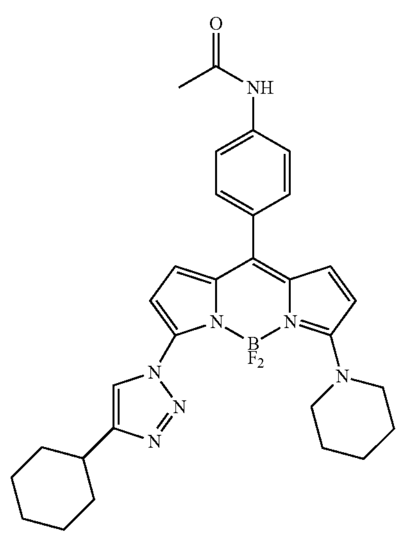 | 93% | 557.5 | 558.1 | 467 | 560 | 2.4 |

TABLE 3-continued

Chemical structures and characterization data for the BDCAC compound library.

| Code | Structure | Purity (254 nm) | m/z (calc.) | m/z (exper.) | $\lambda_{max}$ Absorp. (nm) | $\lambda_{max}$ Emission (nm) | ϕ (%) |
|---|---|---|---|---|---|---|---|
| BDCAC-7 | 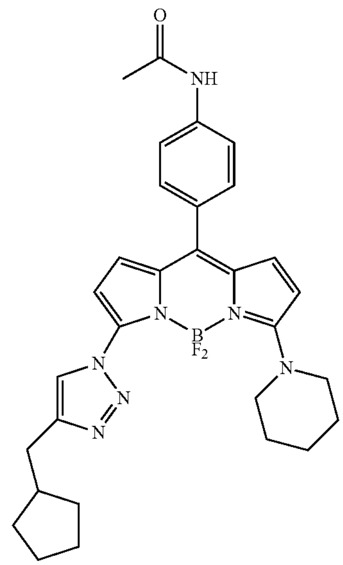 | 98% | 557.5 | 558.3 | 467 | 585 | 1.3 |
| BDCAC-8 | 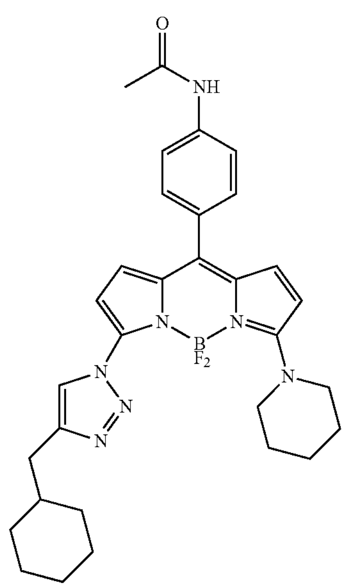 | 98% | 571.5 | 572.3 | 468 | 585 | 0.9 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| BDCAC-9 | 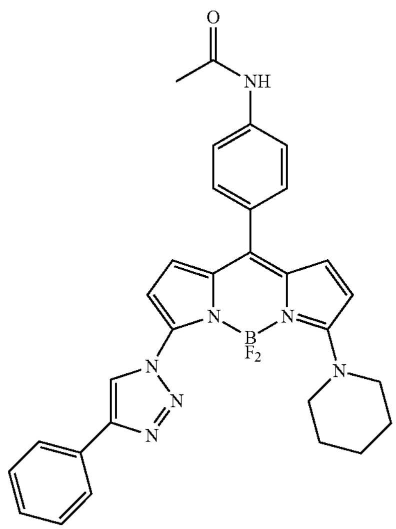 | 97% | 551.4 | 552.1 | 465 | 579 | 1.1 |
| BDCAC-10 | 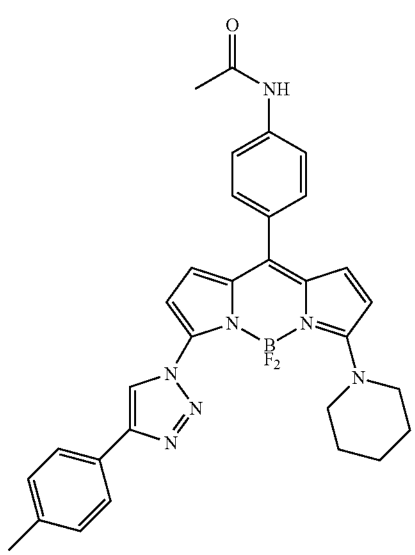 | 91% | 565.4 | 566.2 | 464 | 556 | 2.4 |

TABLE 3-continued

Chemical structures and characterization data for the BDCAC compound library.

| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| BDCAC-11 | 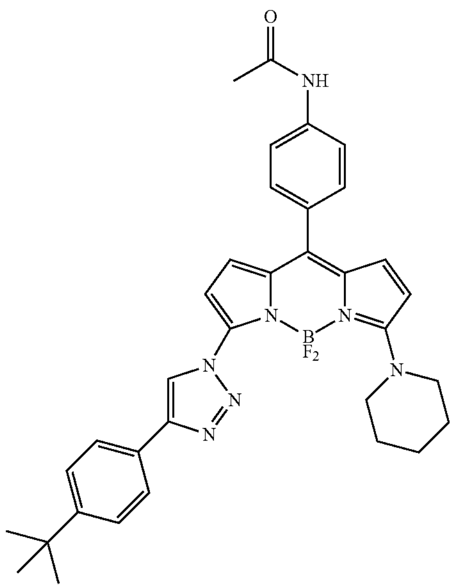 | 96% | 607.5 | 608.3 | 465 | 582 | 1.4 |
| BDCAC-12 | 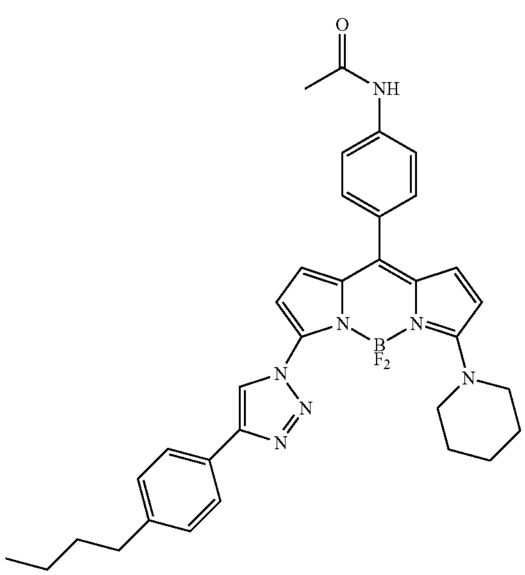 | 89% | 607.5 | 608.3 | 464 | 558 | 1.6 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-13 | 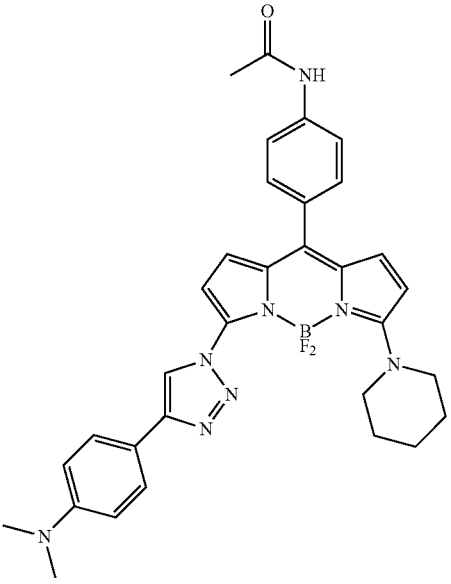 | 98% | 594.5 | 595.2 | 467 | 619 | 0.1 |
| BDCAC-14 | 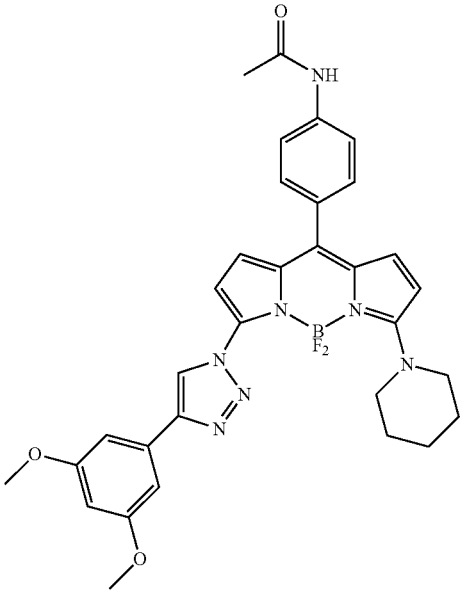 | 98% | 611.5 | 612.3 | 464 | 588 | 1.0 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-15 | 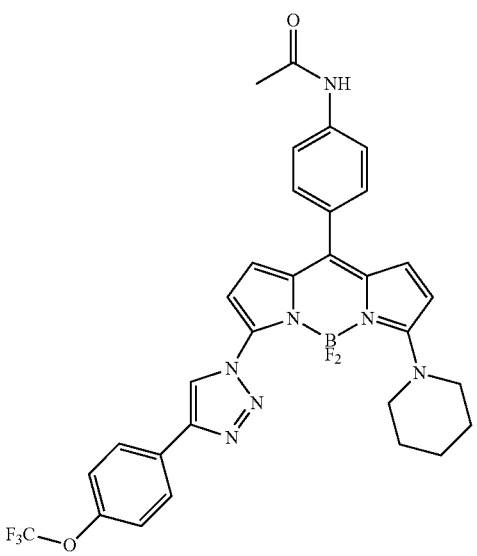 | 84% | 635.4 | 636.2 | 463 | 537 | 2.7 |
| BDCAC-16 | 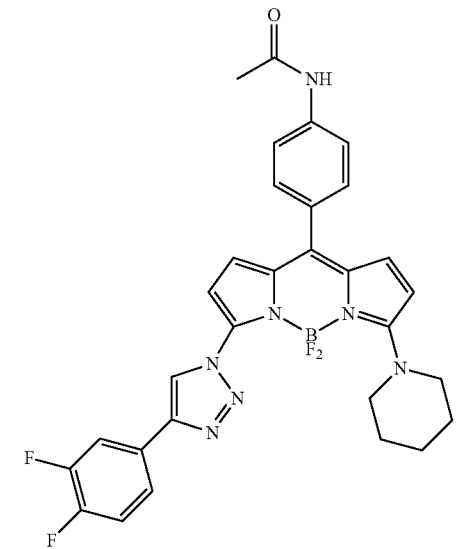 | 93% | 587.4 | 588.2 | 462 | 586 | 0.7 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| BDCAC-17 | 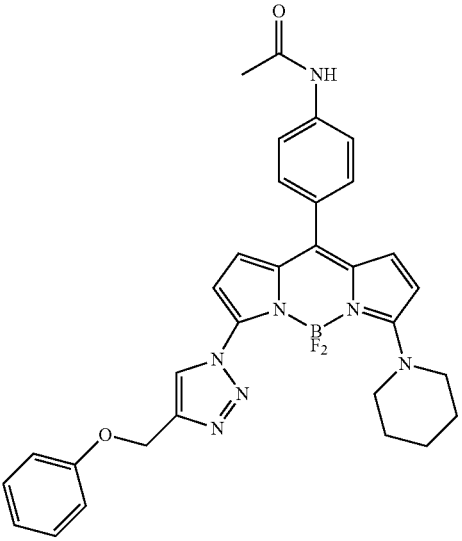 | 99% | 581.4 | 582.2 | 465 | 584 | 0.8 |
| BDCAC-18 | 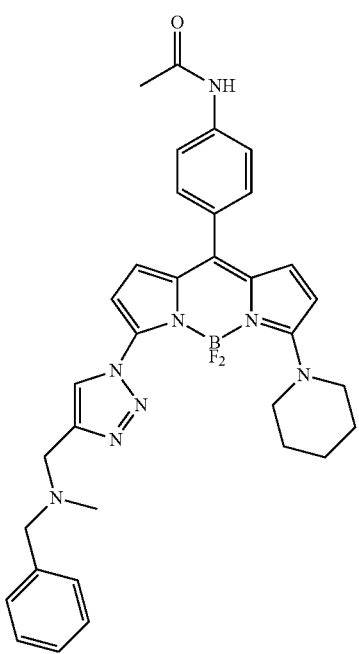 | 88% | 608.5 | 609.3 | 465 | 588 | 0.8 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-19 | 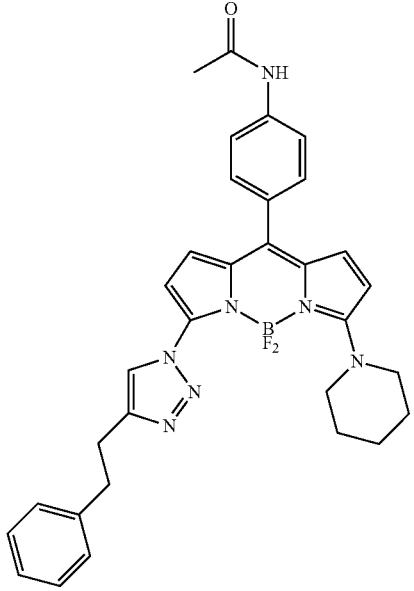 | 98% | 579.5 | 580.3 | 467 | 580 | 0.9 |
| BDCAC-22 | 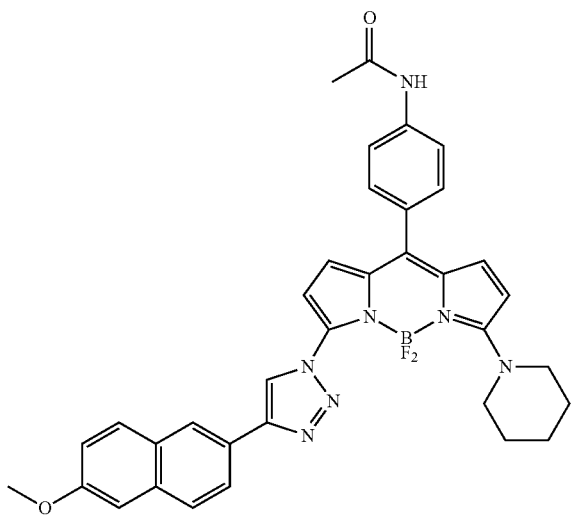 | 98% | 631.5 | 632.2 | 465 | 585 | 1.2 |

TABLE 3-continued

Chemical structures and characterization data for the BDCAC compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-23 | | 99% | 627.4 | 628.3 | 465 | 574 | 1.3 |
| BDCAC-26 | | 91% | 587.4 | 588.2 | 465 | 567 | 1.3 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-27 | 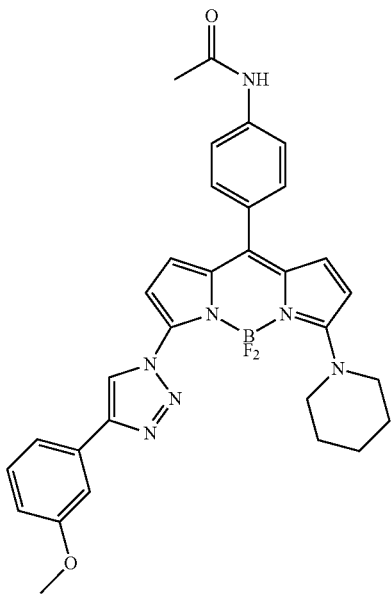 | 89% | 581.4 | 582.2 | 464 | 555 | 2.1 |
| BDCAC-29 | 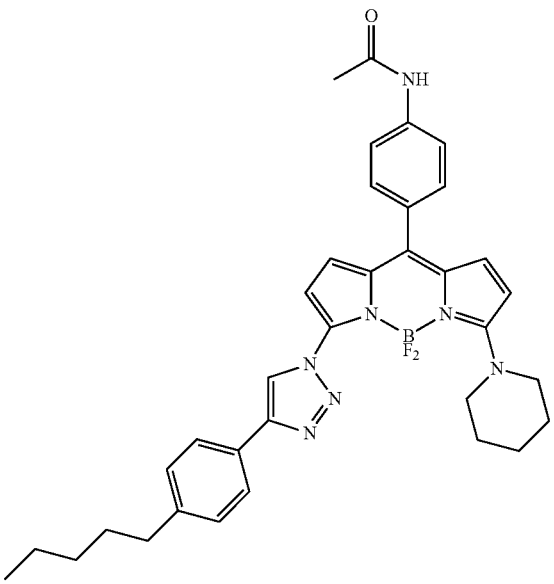 | 95% | 621.5 | 622.3 | 465 | 561 | 1.6 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-30 | 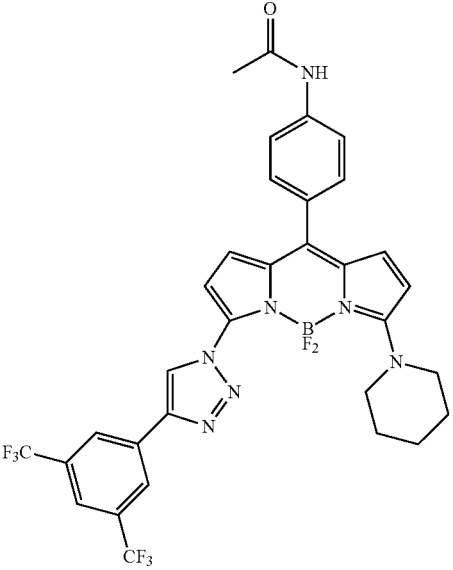 | 93% | 687.4 | 688.2 | 459 | 549 | 3.5 |
| BDCAC-31 | 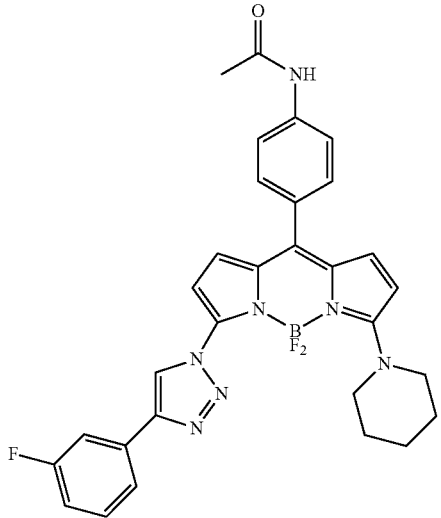 | 97% | 569.4 | 570.1 | 463 | 569 | 0.9 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | ϕ (%) |
|---|---|---|---|---|---|---|---|
| BDCAC-36 | 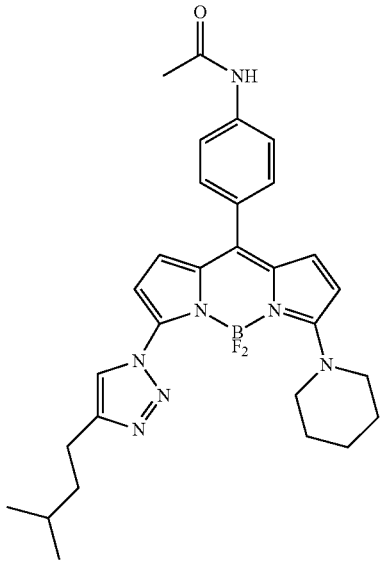 | 99% | 545.4 | 546.2 | 467 | 585 | 0.8 |
| BDCAC-37 | 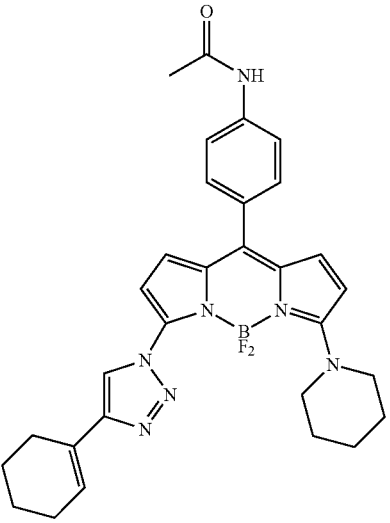 | 95% | 555.4 | 556.3 | 466 | 565 | 1.9 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-42 | 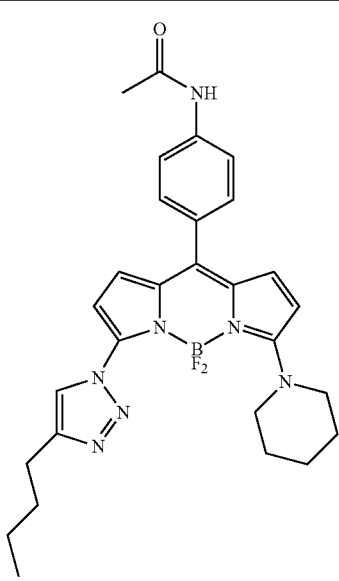 | 98% | 531.4 | 532.2 | 467 | 577 | 1.3 |
| BDCAC-43 | 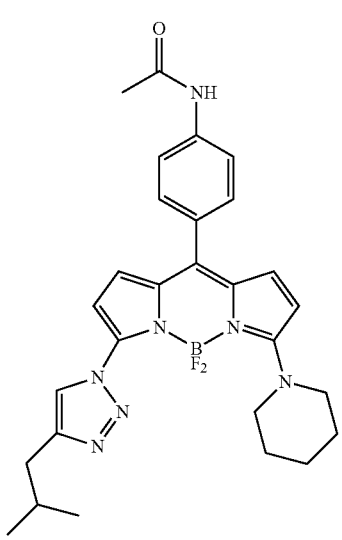 | 95% | 531.4 | 532.2 | 467 | 581 | 0.8 |

TABLE 3-continued

Chemical structures and characterization data for the BDCAC compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-44 | 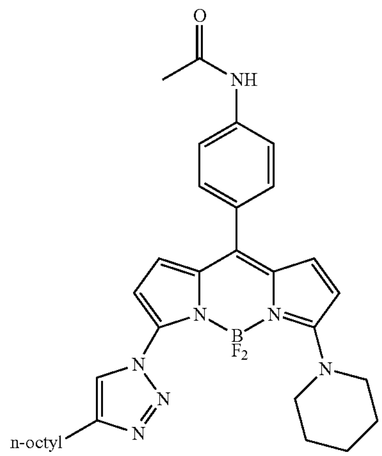 | 95% | 587.5 | 588.4 | 468 | 581 | 0.8 |
| BDCAC-45 | 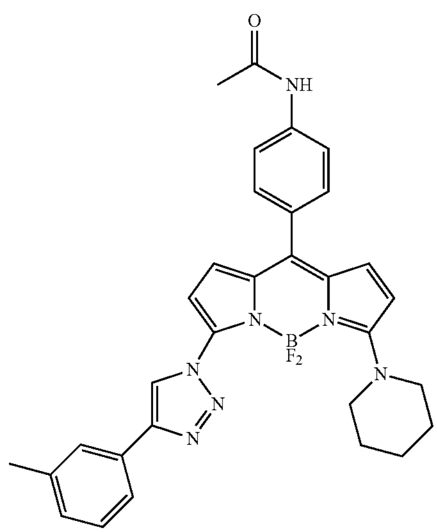 | 87% | 565.4 | 566.2 | 463 | 551 | 3.2 |
| BDCAC-46 | 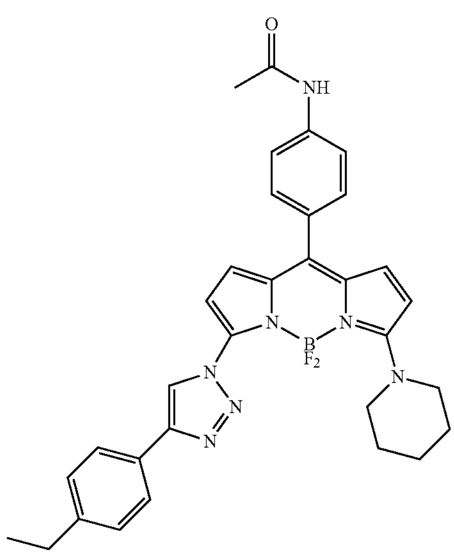 | 99% | 579.5 | 580.3 | 465 | 578 | 1.4 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-47 | 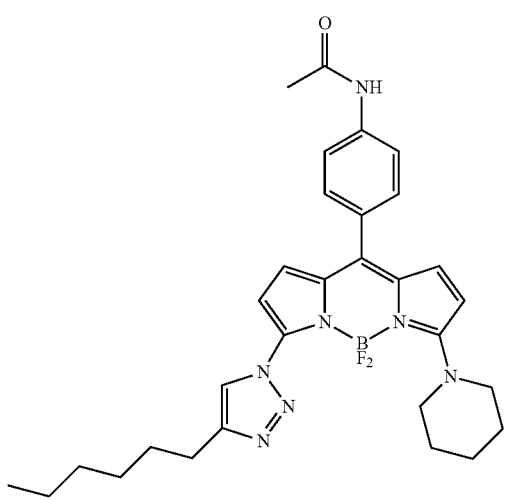 | 81% | 559.5 | 560.3 | 467 | 562 | 1.4 |
| BDCAC-48 | 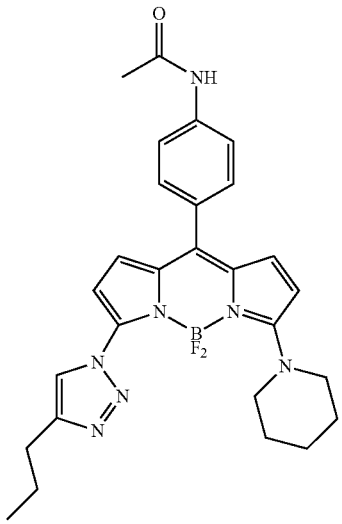 | 95% | 517.4 | 518.1 | 467 | 576 | 1.6 |
| BDCAC-49 | 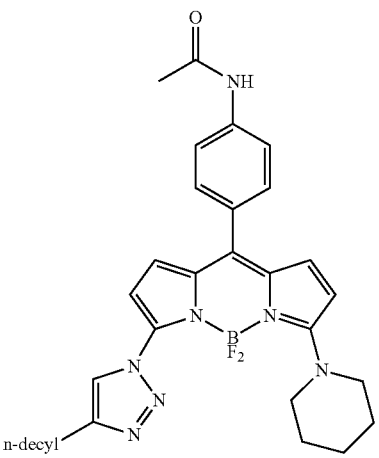 | 96% | 615.6 | 616.4 | 467 | 575 | 1.3 |

TABLE 3-continued

Chemical structures and characterization data for the BDCAC compound library.

| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| BDCAC-50 | 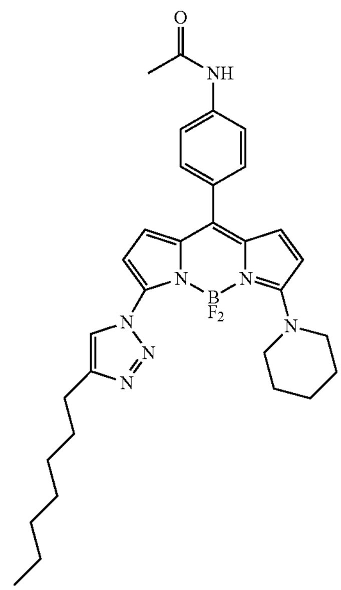 | 94% | 573.5 | 574.3 | 467 | 567 | 1.4 |
| BDCAC-67 | 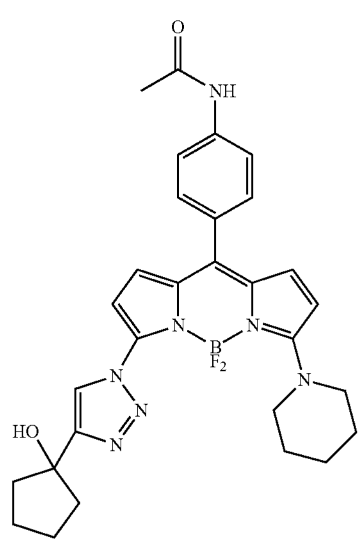 | 97% | 559.4 | 560.3 | 469 | 592 | 0.8 |

TABLE 3-continued
Chemical structures and characterization data for the BDCAC compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCAC-69 | 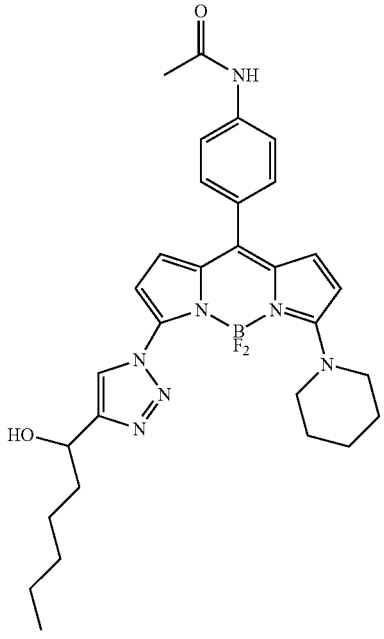 | 92% | 575.5 | 576.3 | 468 | 587 | 0.8 |
| BDCAC-70 | 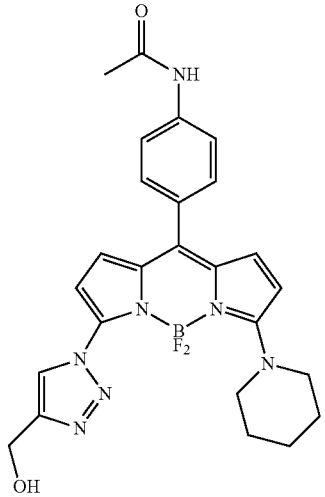 | 99% | 505.3 | 506.0 | 467 | 583 | 0.7 |

TABLE 4

Chemical structures and characterization data for the BDCCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-1 | 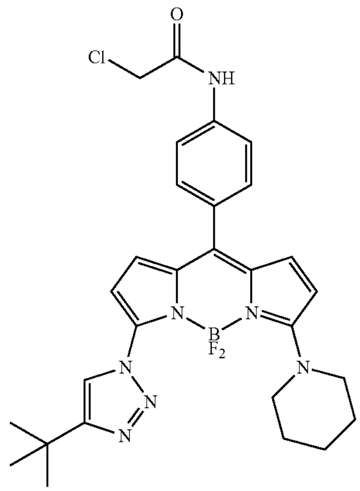 | 93% | 565.9 | 566.2 | 468 | 581 | 0.7 |
| BDCCA-2 | 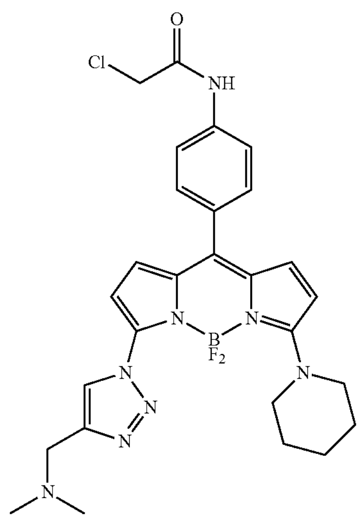 | 52% | 566.8 | 567.1 | 461 | 586 | 0.4 |
| BDCCA-3 | 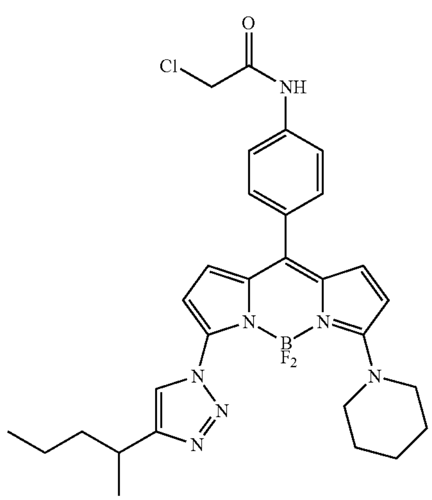 | 97% | 579.9 | 580.2 | 467 | 587 | 0.9 |

TABLE 4-continued

Chemical structures and characterization data for the BDCCA compound library.

| Code | Structure | Purity (254 nm) | m/z (calc.) | m/z (exper.) | $\lambda_{max}$ Absorp. (nm) | $\lambda_{max}$ Emission (nm) | ϕ (%) |
| --- | --- | --- | --- | --- | --- | --- | --- |
| BDCCA-4 | 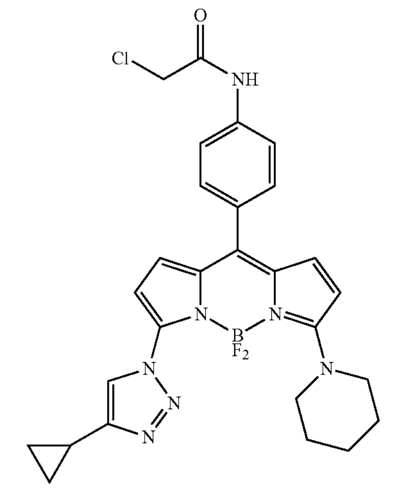 | 92% | 549.8 | 550.1 | 467 | 577 | 1.1 |
| BDCCA-5 | 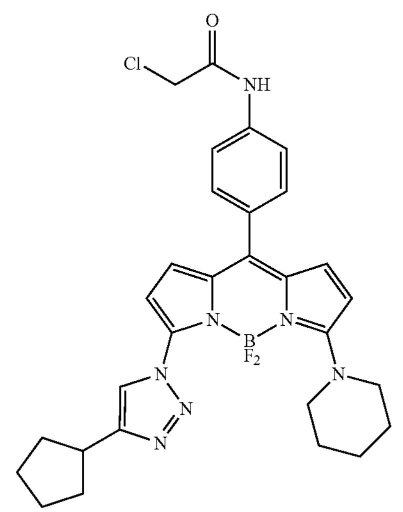 | 98% | 577.9 | 578.3 | 468 | 588 | 0.9 |
| BDCCA-6 | 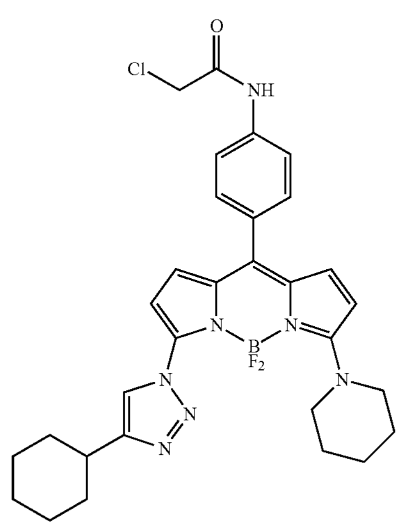 | 80% | 591.9 | 592.3 | 467 | 555 | 2.3 |

TABLE 4-continued

Chemical structures and characterization data for the BDCCA compound library.

| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| BDCCA-7 | 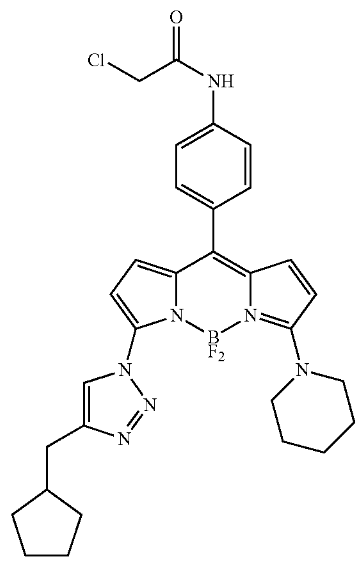 | 99% | 591.9 | 592.3 | 468 | 590 | 0.9 |
| BDCCA-8 | 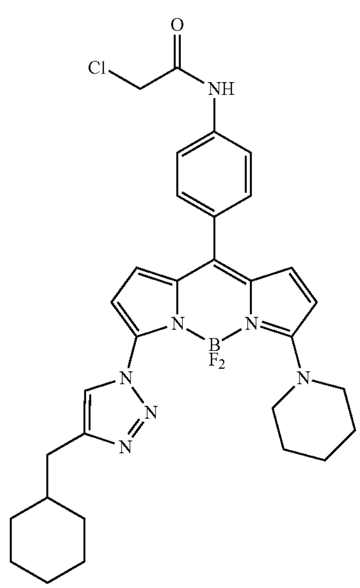 | 79% | 605.9 | 606.3 | 468 | 589 | 0.6 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-9 | 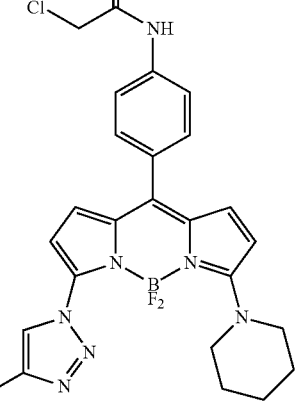 | 97% | 585.8 | 586.1 | 464 | 577 | 1.1 |
| BDCCA-10 | 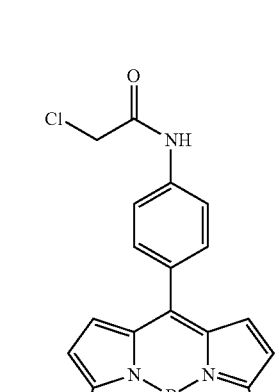 | 90% | 599.9 | 600.2 | 463 | 558 | 2.9 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-11 | 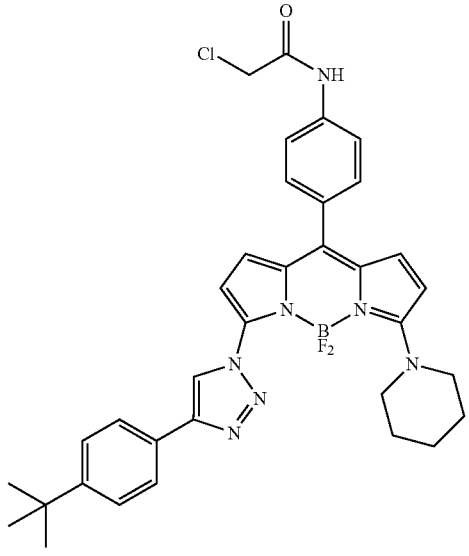 | 90% | 642.0 | 642.3 | 464 | 587 | 1.3 |
| BDCCA-12 | 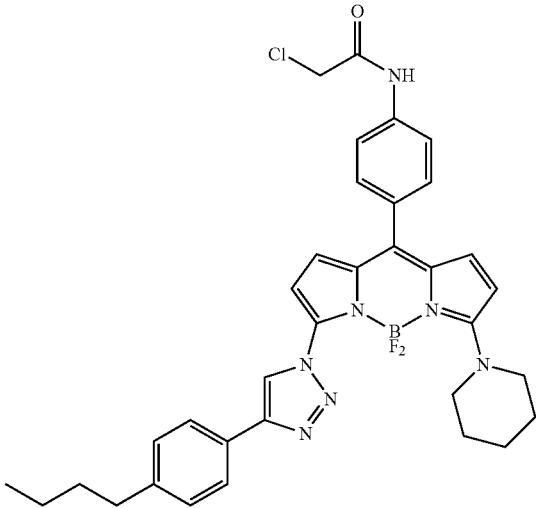 | 91% | 642.0 | 642.3 | 464 | 552 | 1.6 |

TABLE 4-continued

Chemical structures and characterization data for the BDCCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-13 | 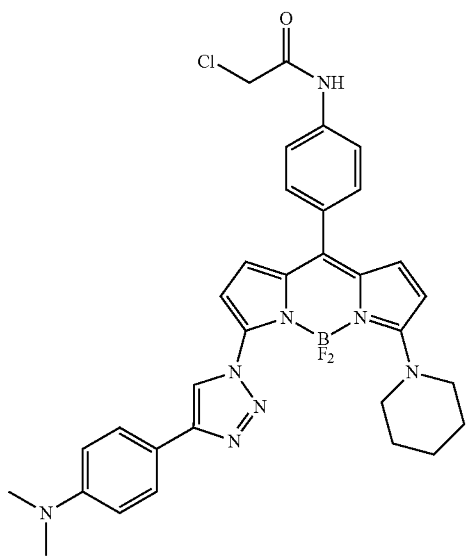 | 98% | 628.9 | 629.3 | 467 | 627 | 0.1 |
| BDCCA-14 | 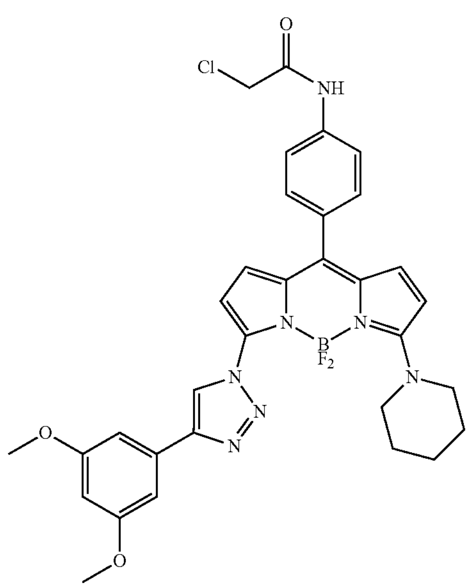 | 97% | 645.9 | 646.2 | 463 | 589 | 0.8 |

TABLE 4-continued
Chemical structures and characterization data for the BDCCA compound library.
| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| BDCCA-15 | 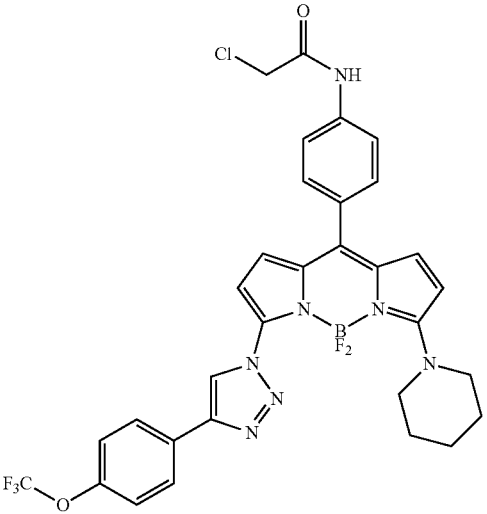 | 82% | 669.8 | 670.2 | 462 | 537 | 2.2 |
| BDCCA-16 | 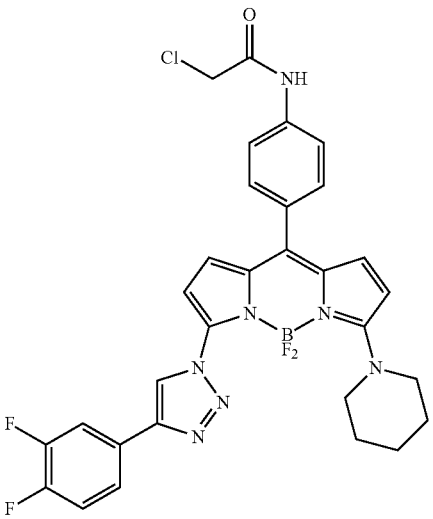 | 93% | 621.8 | 622.1 | 462 | 581 | 0.7 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-17 | 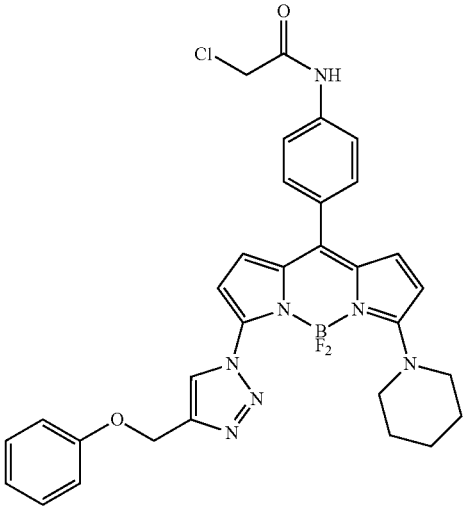 | 98% | 615.9 | 616.2 | 464 | 584 | 0.7 |
| BDCCA-18 | 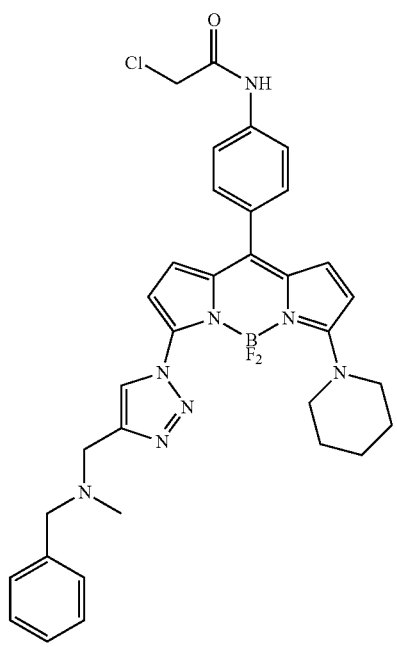 | 87% | 642.9 | 643.3 | 465 | 587 | 0.7 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-19 | 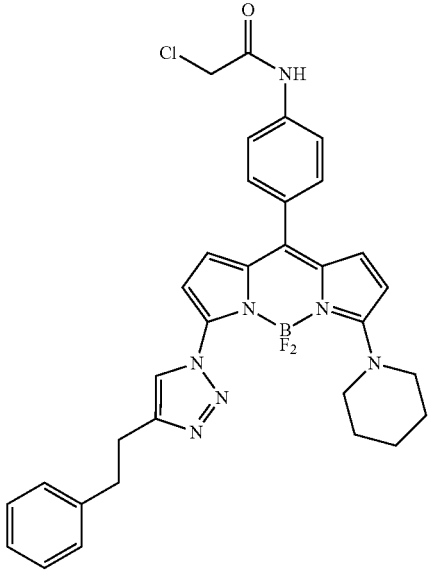 | 96% | 613.9 | 614.2 | 466 | 578 | 1.0 |
| BDCCA-22 | 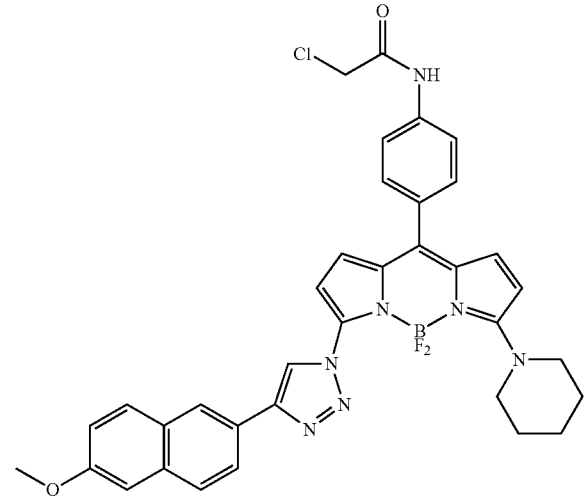 | 97% | 665.9 | 666.3 | 464 | 586 | 1.1 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| BDCCA-23 | 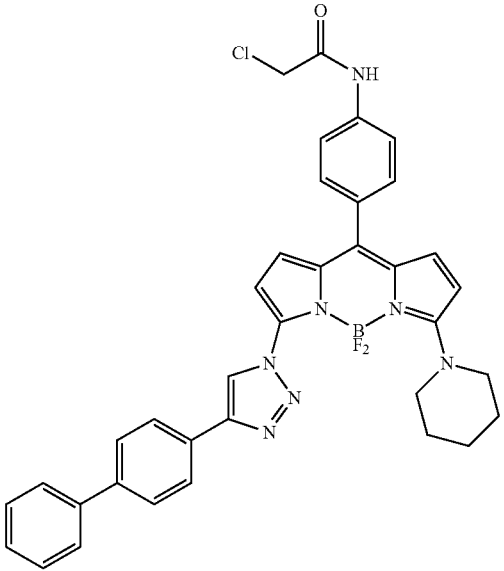 | 96% | 661.9 | 662.2 | 464 | 575 | 1.2 |
| BDCCA-26 | 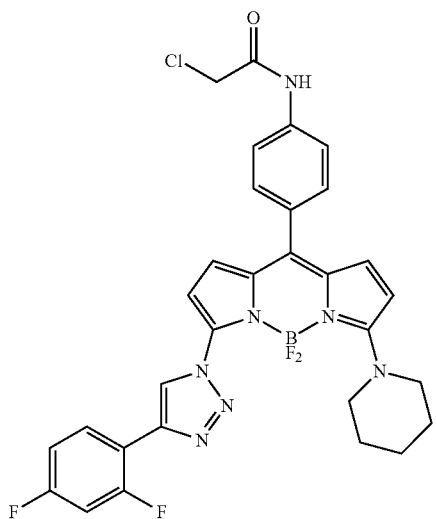 | 89% | 621.8 | 622.2 | 465 | 568 | 1.3 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-27 | 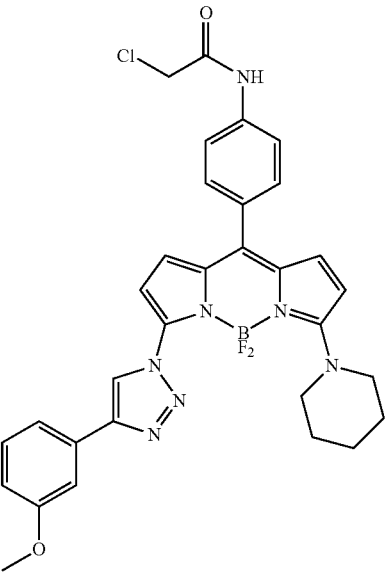 | 81% | 615.9 | 616.2 | 463 | 552 | 2.3 |
| BDCCA-29 | 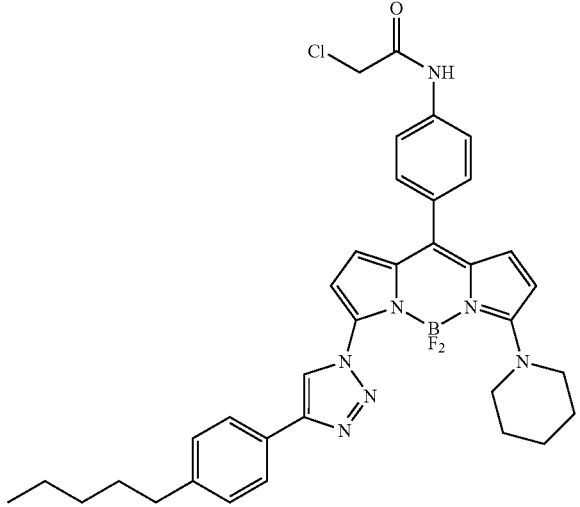 | 90% | 656.0 | 656.3 | 464 | 548 | 1.7 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-30 | 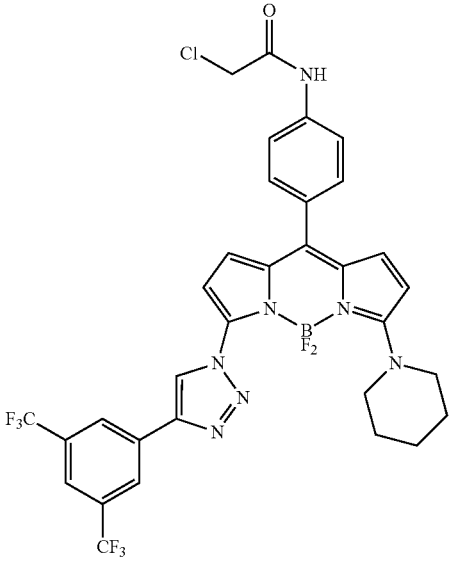 | 87% | 721.8 | 722.2 | 458 | 556 | 2.6 |
| BDCCA-31 | 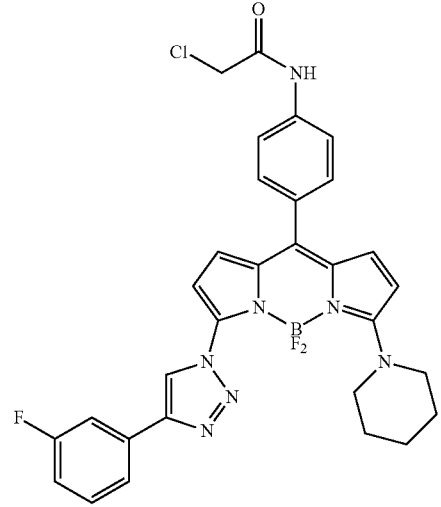 | 94% | 603.8 | 604.2 | 462 | 568 | 1.0 |

TABLE 4-continued

Chemical structures and characterization data for the BDCCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-36 | 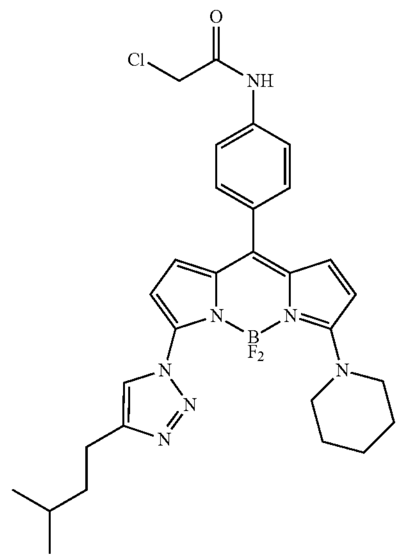 | 99% | 579.9 | 580.3 | 467 | 584 | 0.5 |
| BDCCA-37 | 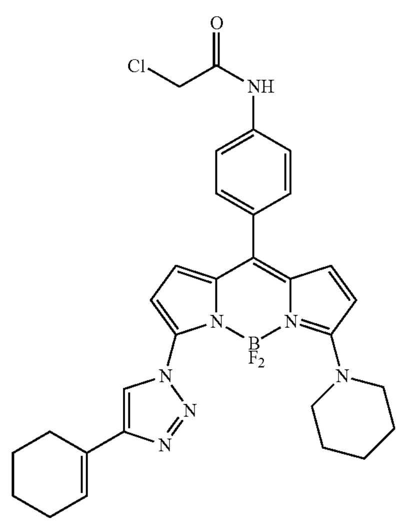 | 95% | 589.9 | 590.2 | 465 | 565 | 1.7 |

TABLE 4-continued

Chemical structures and characterization data for the BDCCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-42 | 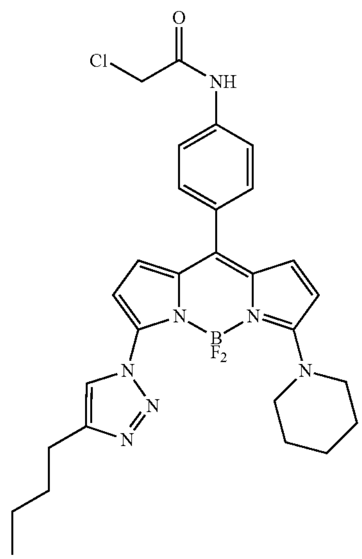 | 89% | 565.9 | 566.1 | 467 | 577 | 1.3 |
| BDCCA-43 | 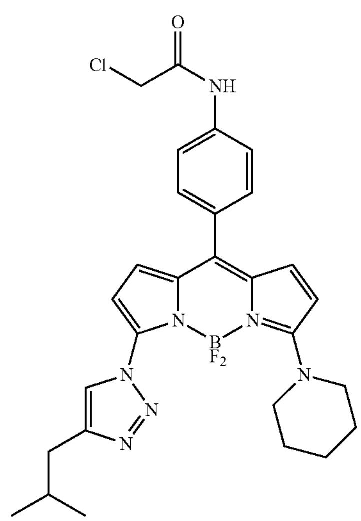 | 94% | 565.9 | 566.2 | 466 | 583 | 0.8 |
| BDCCA-44 | 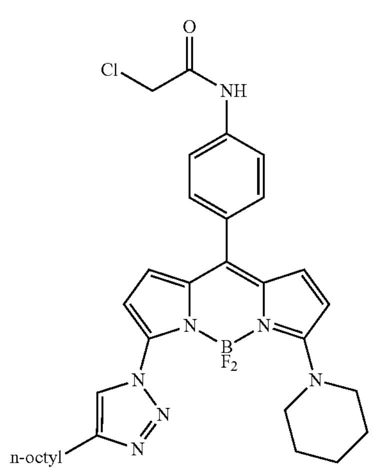 | 95% | 621.3 | 622.3 | 466 | 582 | 0.7 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-45 | 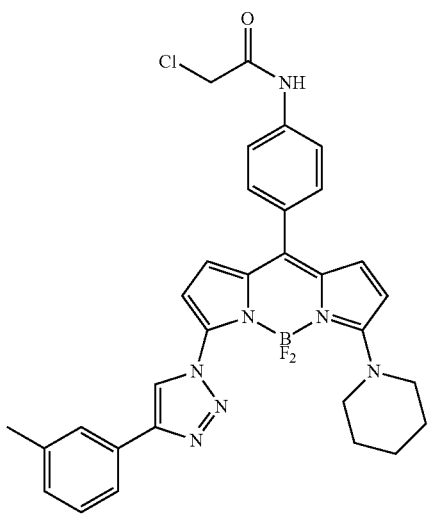 | 81% | 599.9 | 600.2 | 463 | 555 | 2.7 |
| BDCCA-46 | 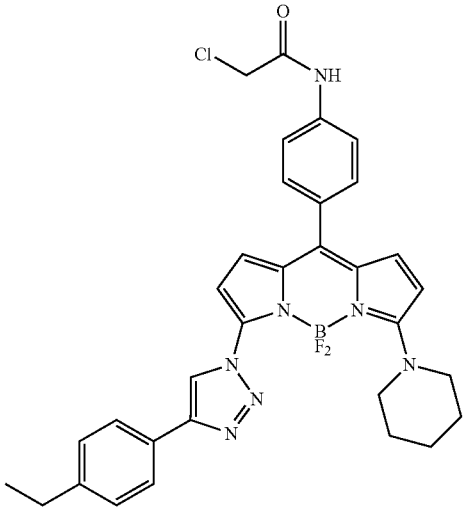 | 99% | 613.9 | 614.1 | 464 | 568 | 1.2 |
| BDCCA-47 | 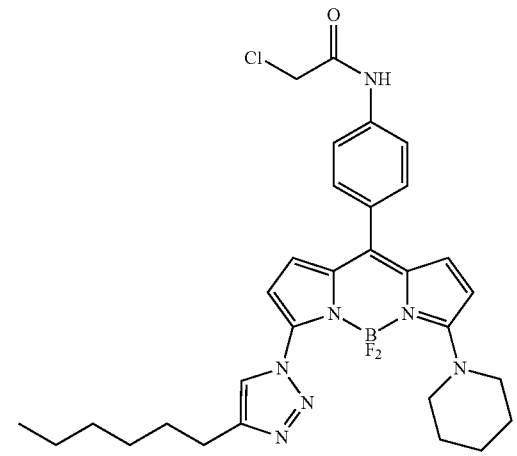 | 89% | 593.9 | 594.3 | 466 | 560 | 1.8 |

TABLE 4-continued

Chemical structures and characterization data for the BDCCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| BDCCA-48 | 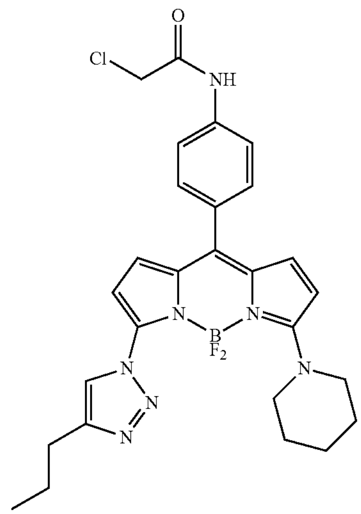 | 95% | 551.8 | 552.2 | 466 | 569 | 1.4 |
| BDCCA-49 | 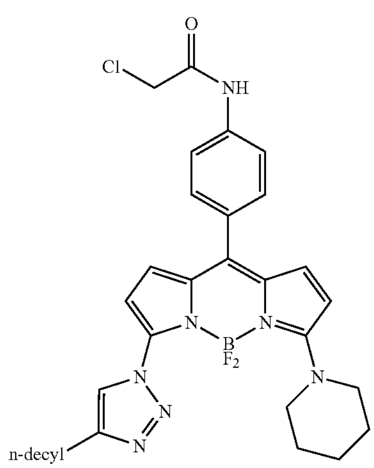 | 90% | 649.3 | 650.3 | 466 | 575 | 1.2 |

TABLE 4-continued
Chemical structures and characterization data for the BDCCA compound library.
| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| BDCCA-50 | 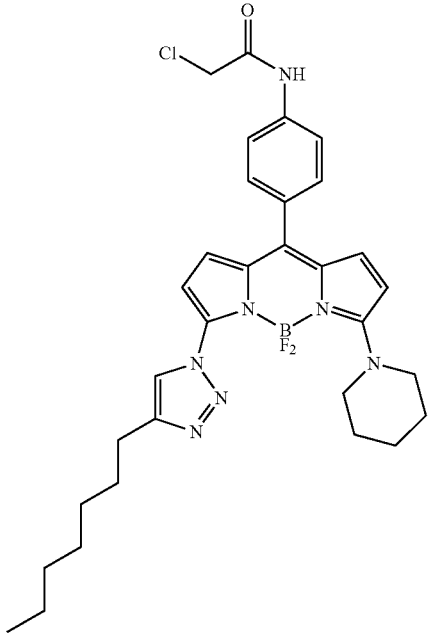 | 87% | 607.9 | 608.3 | 466 | 568 | 1.0 |
| BDCCA-67 | 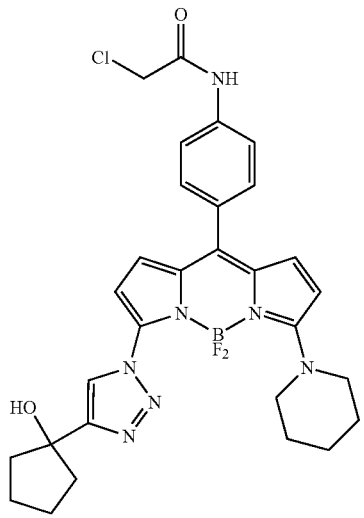 | 87% | 593.2 | 594.2 | 468 | 590 | 0.7 |

TABLE 4-continued
Chemical structures and characterization data for the BDCCA compound library.
| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| BDCCA-69 | 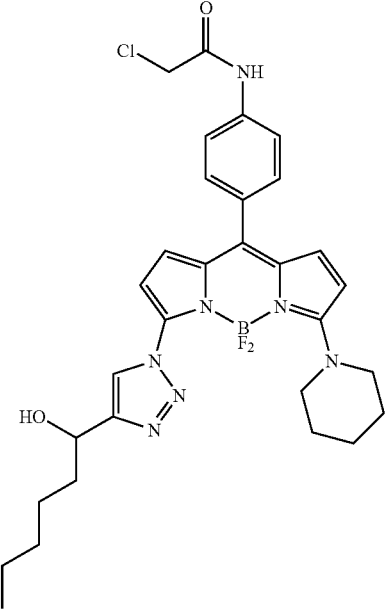 | 89% | 609.9 | 610.3 | 467 | 587 | 0.7 |
| BDCCA-70 | 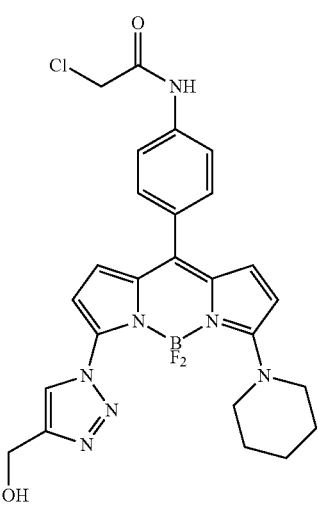 | 93% | 539.8 | 540.0 | 465 | 584 | 0.6 |

TABLE 5

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MK20-3 | 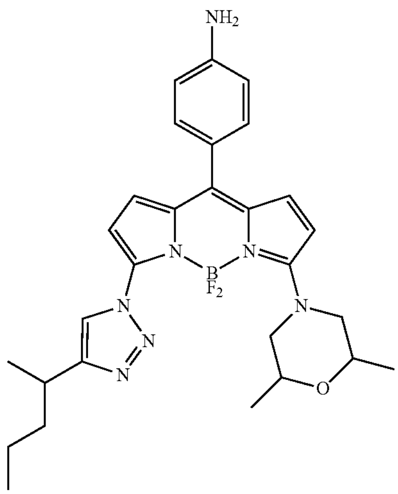 | 89% | 533.29 | 534.7 | 476 | 573 | 0.10 |
| MK20-4 | 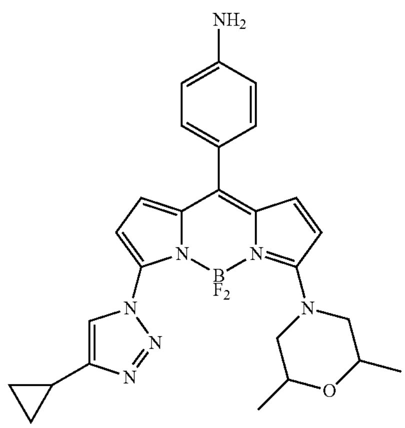 | 87% | 503.24 | 504.6 | 476 | 564 | 0.50 |
| MK20-5 | 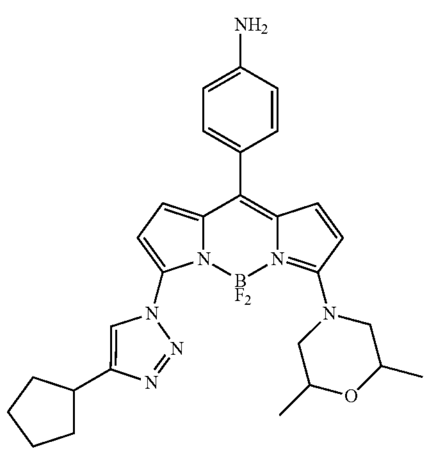 | 86% | 531.27 | 532.7 | 476 | 580 | 0.57 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MK20-8 | 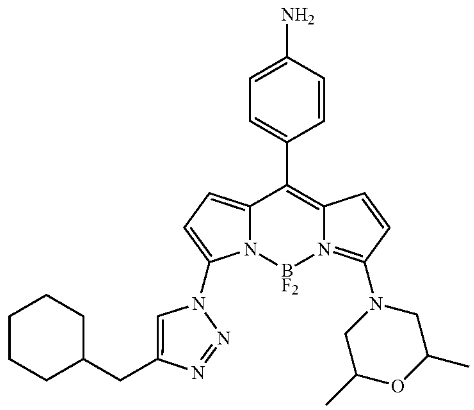 | 89% | 559.30 | 560.7 | 476 | 563 | 0.32 |
| MK20-18 | 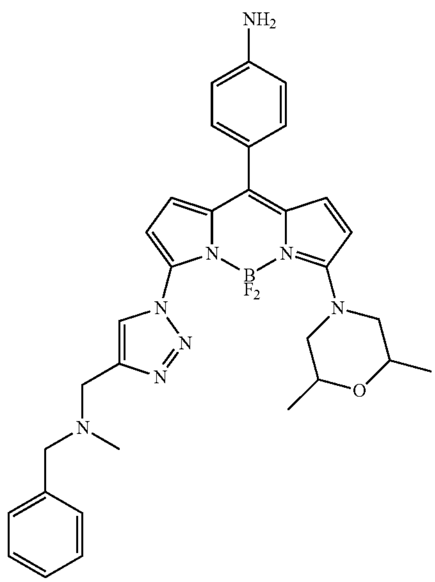 | 98% | 596.30 | 597.7 | 477 | 582 | 0.23 |
| MK20-19 | 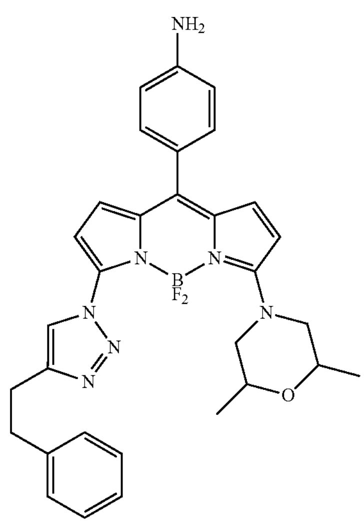 | 95% | 567.27 | 568.7 | 477 | 578 | 0.34 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MK20-43 | 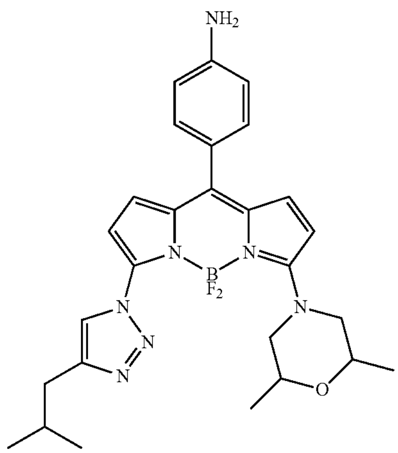 | 99% | 519.27 | 520.6 | 478 | 584 | 0.23 |
| MK20-48 | 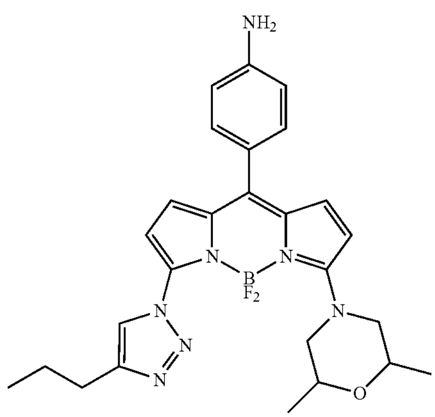 | 89% | 505.26 | 506.6 | 476 | 580 | 0.25 |
| MK20-69 | 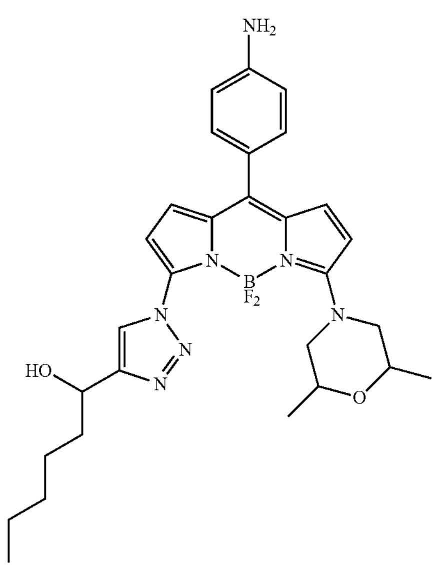 | 99% | 563.30 | 564.7 | 480 | 586 | 0.16 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK20-70 | 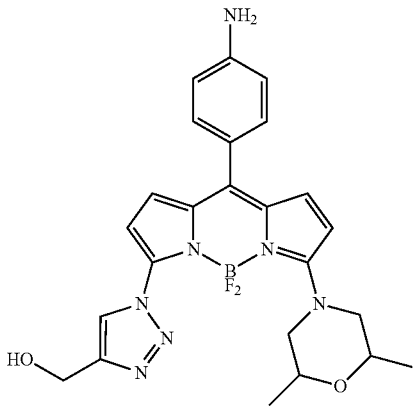 | 99% | 493.22 | 494.6 | 479 | 584 | 0.18 |
| MK66-3 | 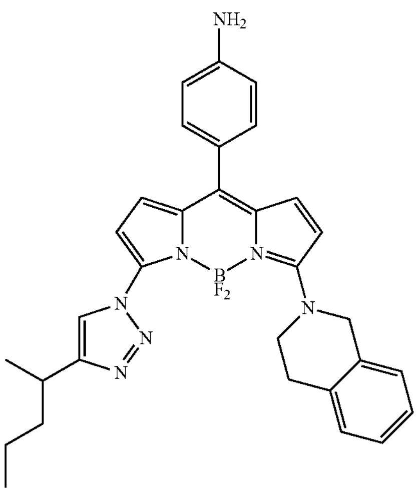 | 99% | 551.28 | 552.7 | 479 | 579 | 0.16 |
| MK66-4 | 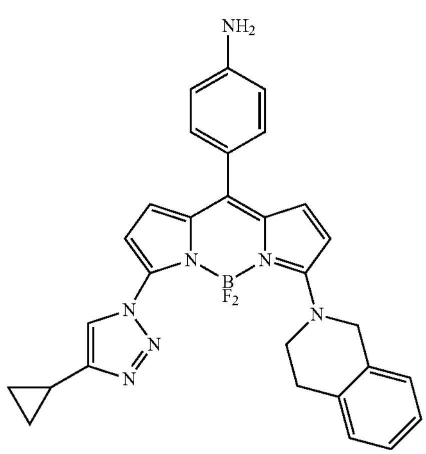 | 99% | 521.23 | 522.6 | 479 | 587 | 0.12 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK66-5 | 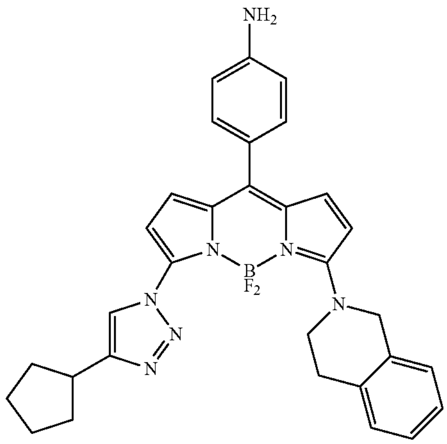 | 99% | 549.26 | 550.6 | 481 | 582 | 0.19 |
| MK66-8 | 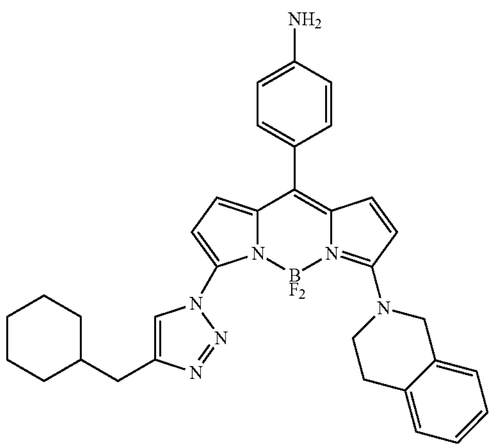 | 99% | 577.29 | 578.7 | 480 | 590 | 0.12 |
| MK66-18 | 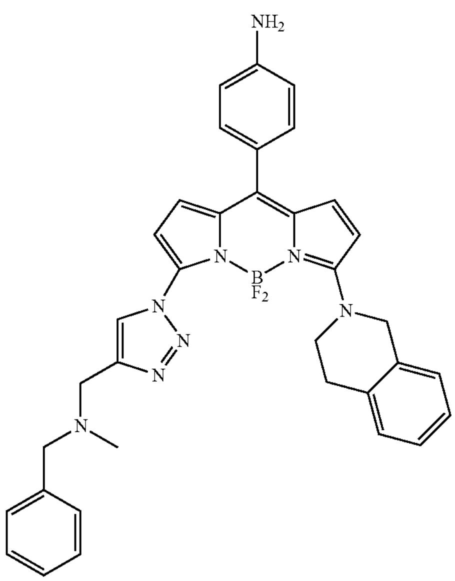 | 99% | 614.29 | 615.7 | 478 | 587 | 0.14 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK66-19 | | 99% | 585.26 | 586.7 | 480 | 585 | 0.13 |
| MK66-43 | | 99% | 537.26 | 538.6 | 480 | 582 | 0.14 |
| MK66-48 | | 99% | 523.25 | 524.6 | 480 | 581 | 0.12 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MK66-69 | 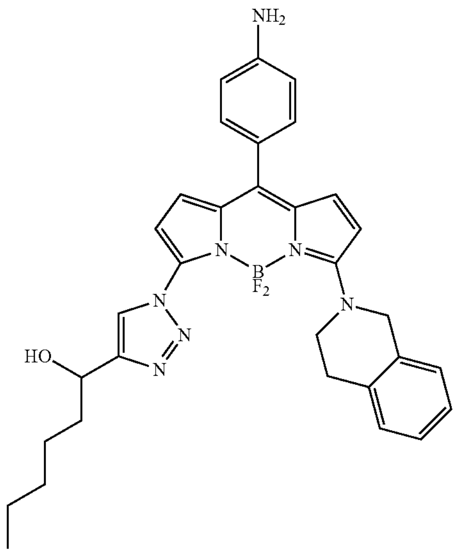 | 99% | 581.29 | 582.7 | 480 | 583 | 0.14 |
| MK66-70 | 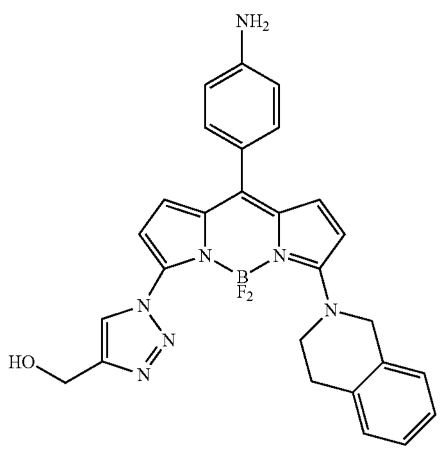 | 99% | 511.21 | 512.6 | 479 | 596 | 0.14 |
| MK101-3 | 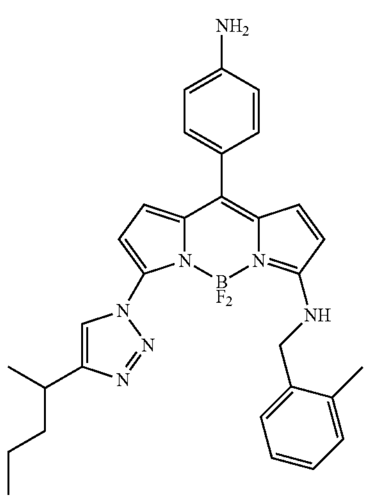 | 97% | 539.28 | 540.7 | 475 | 562 | 1.08 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK101-4 | 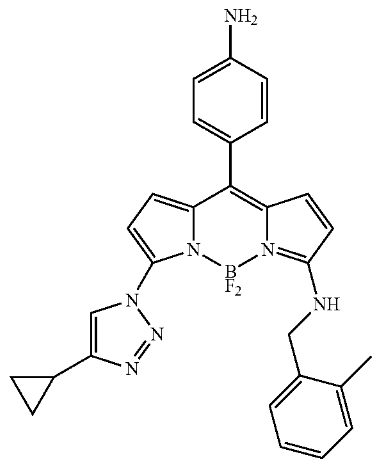 | 99% | 509.23 | 510.6 | 474 | 566 | 0.70 |
| MK101-5 | 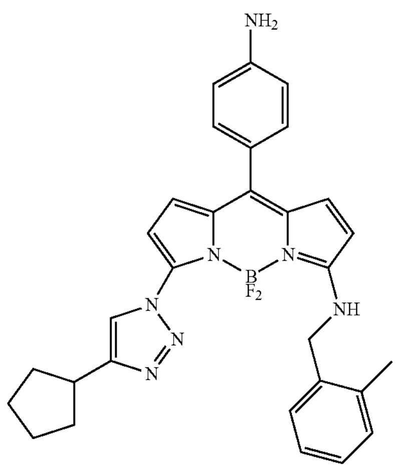 | 97% | 537.26 | 538.6 | 475 | 565 | 0.58 |
| MK101-8 | 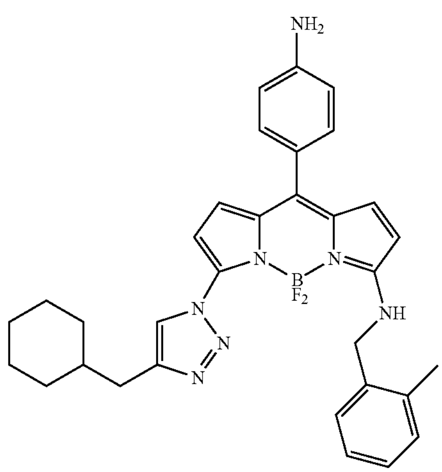 | 94% | 565.29 | 566.7 | 475 | 564 | 0.64 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MK101-18 | 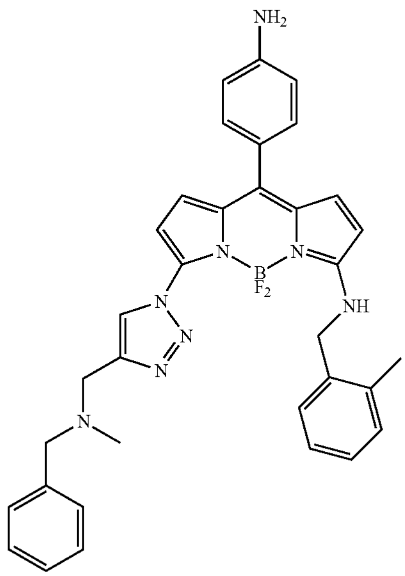 | 92% | 602.29 | 603.7 | 474 | 563 | 0.179 |
| MK101-19 | 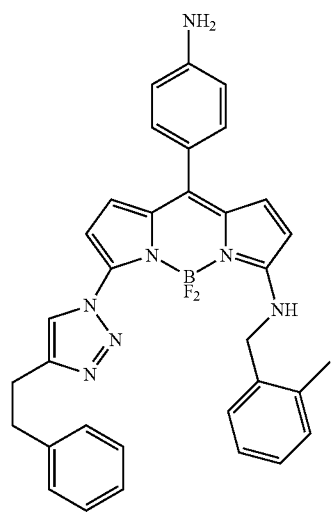 | 82% | 573.26 | 574.7 | 472 | 560 | 2.03 |
| MK101-43 | 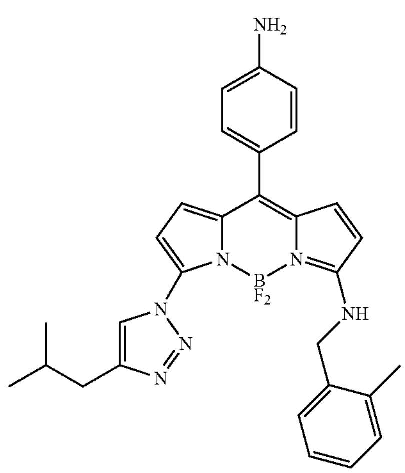 | 90% | 525.26 | 526.7 | 474 | 562 | 2.36 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK101-48 | 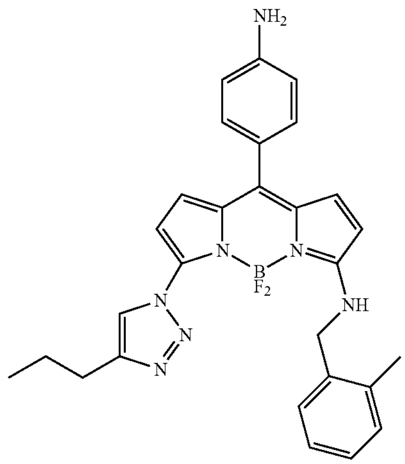 | 90% | 511.25 | 512.6 | 473 | 562 | 2.92 |
| MK101-69 | 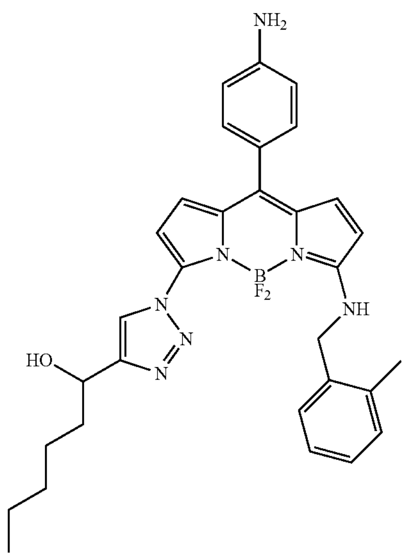 | 96% | 569.29 | 570.7 | 475 | 563 | 2.40 |
| MK101-70 | 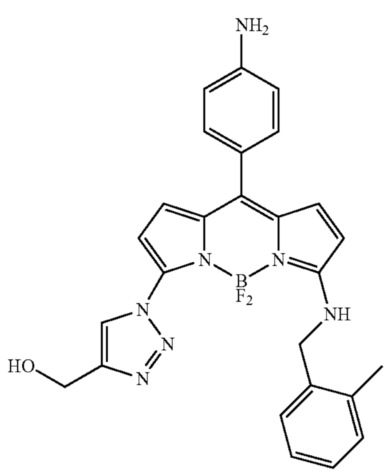 | 87% | 499.21 | 500.6 | 474 | 565 | 1.92 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK103-3 | 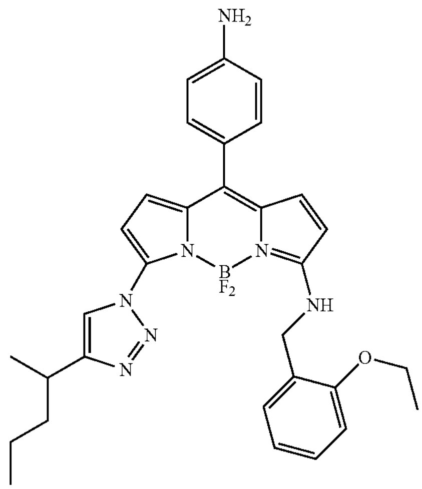 | 99% | 569.29 | 570.7 | 474 | 564 | 1.71 |
| MK103-4 | 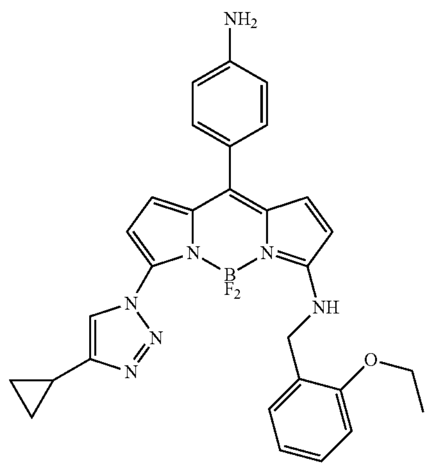 | 95% | 539.24 | 540.6 | 473 | 563 | 1.68 |
| MK103-5 | 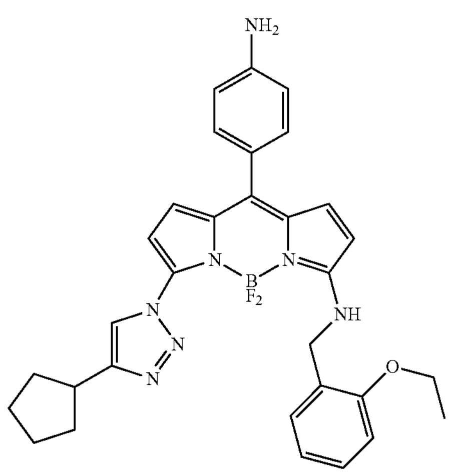 | 99% | 567.27 | 568.6 | 473 | 564 | 2.01 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK103-8 | | 98% | 595.30 | 596.7 | 473 | 563 | 1.64 |
| MK103-18 | | 95% | 632.30 | 633.7 | 473 | 565 | 1.19 |
| MK103-19 | | 95% | 603.27 | 604.7 | 472 | 568 | 1.96 |

US 9,513,294 B2
157                                                                                                      158
TABLE 5-continued
Chemical structures and characterization data for the MK compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK103-43 | 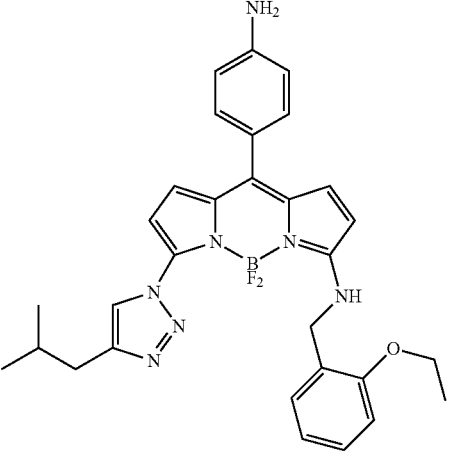 | 97% | 555.27 | 556.7 | 474 | 563 | 1.30 |
| MK103-48 | 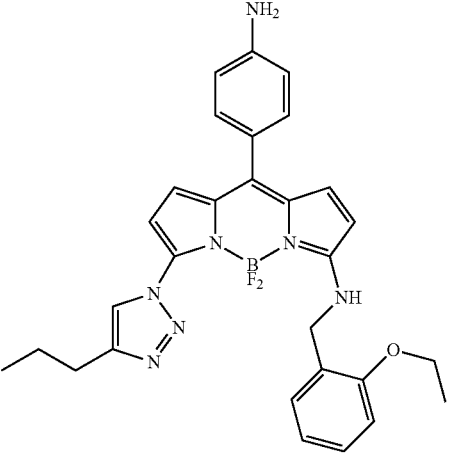 | 96% | 541.26 | 542.7 | 473 | 563 | 1.91 |
| MK103-69 | 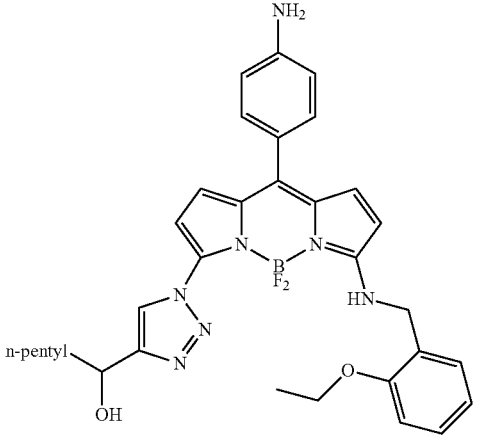 | 93% | 599.30 | 600.7 | 474 | 563 | 2.28 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK103-70 | 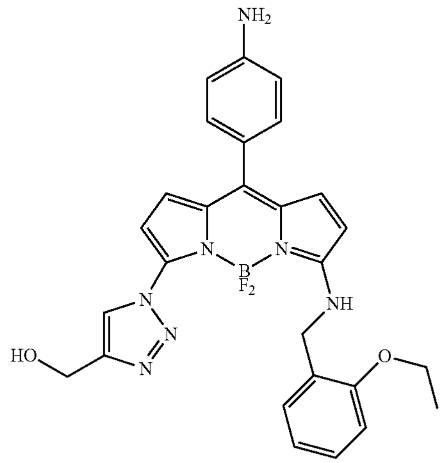 | 98% | 529.22 | 530.6 | 472 | 562 | 1.93 |
| MK181-3 | 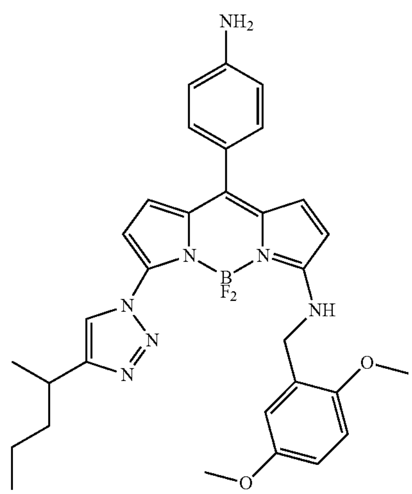 | 98% | 585.28 | 586.7 | 473 | 565 | 0.36 |
| MK181-4 | 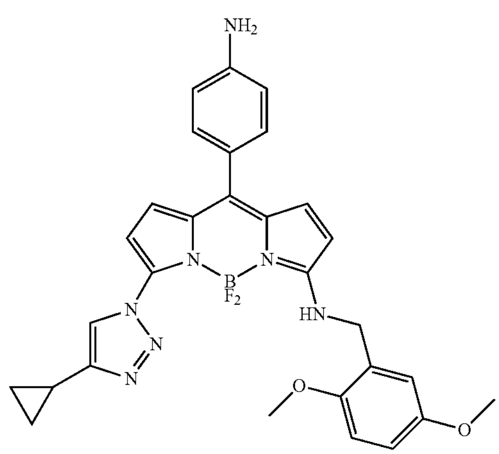 | 99% | 555.24 | 556.6 | 474 | 566 | 0.28 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK181-5 | 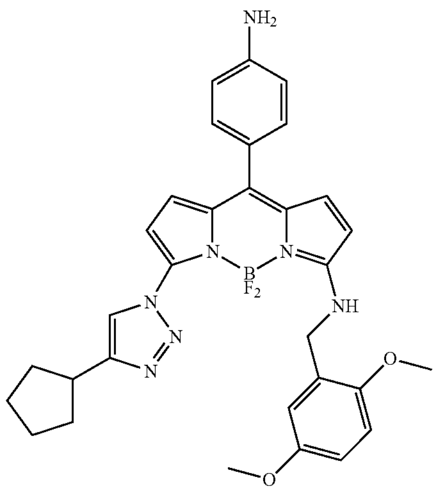 | 99% | 583.27 | 584.7 | 475 | 563 | 0.43 |
| MK181-8 | 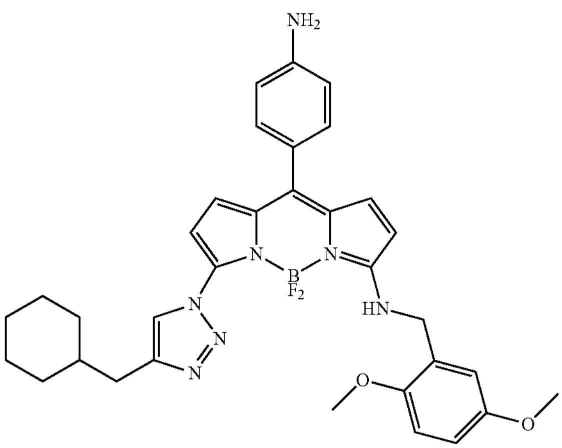 | 99% | 611.30 | 612.8 | 474 | 565 | 0.33 |
| MK181-18 | 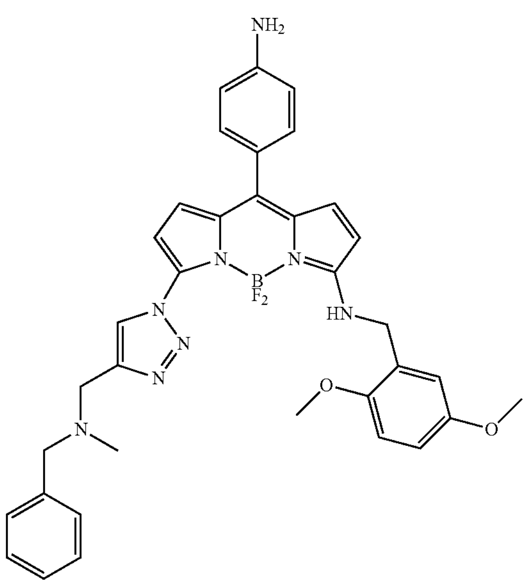 | 99% | 648.29 | 649.7 | 473 | 563 | 0.52 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK181-19 | 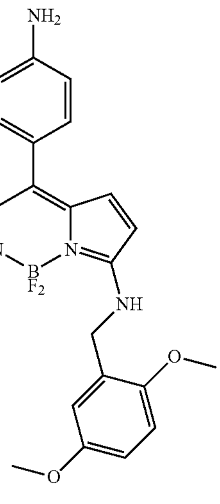 | 99% | 619.27 | 620.7 | 474 | 564 | 0.85 |
| MK181-43 | 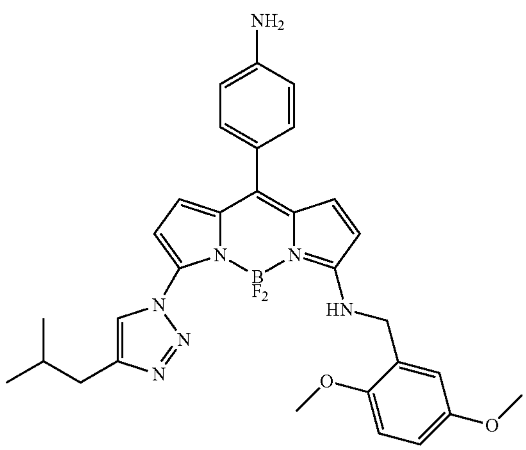 | 99% | 571.27 | 572.6 | 475 | 566 | 0.37 |
| MK181-48 | 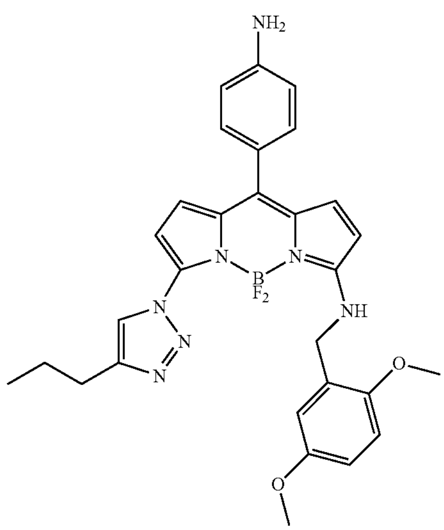 | 99% | 557.25 | 558.7 | 473 | 563 | 0.50 |

TABLE 5-continued
Chemical structures and characterization data for the MK compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK181-69 | 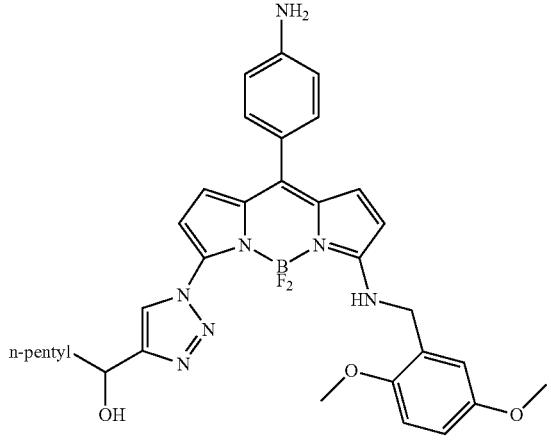 | 99% | 615.29 | 616.7 | 473 | 563 | 0.86 |
| MK181-70 | 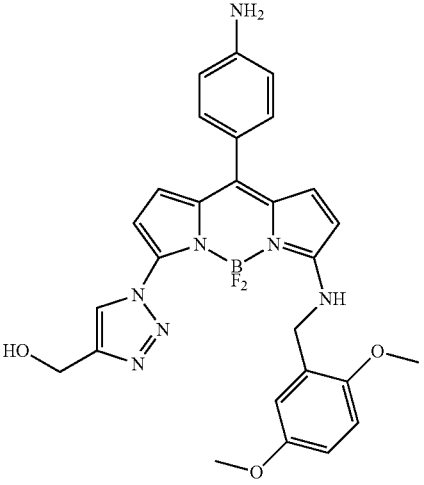 | 99% | 545.22 | 546.6 | 472 | 568 | 0.88 |
| MK195-3 | 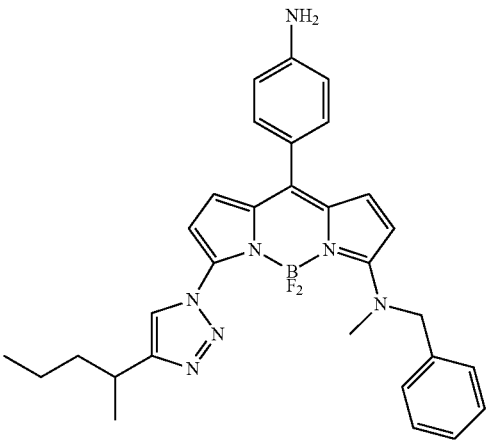 | 88% | 539.28 | 540.7 | 476 | 564 | 0.46 |

TABLE 5-continued
Chemical structures and characterization data for the MK compound library.
| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MK195-4 | 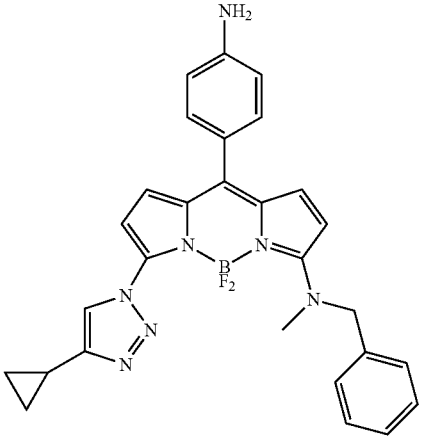 | 86% | 509.23 | 510.6 | 476 | 566 | 0.34 |
| MK195-5 | 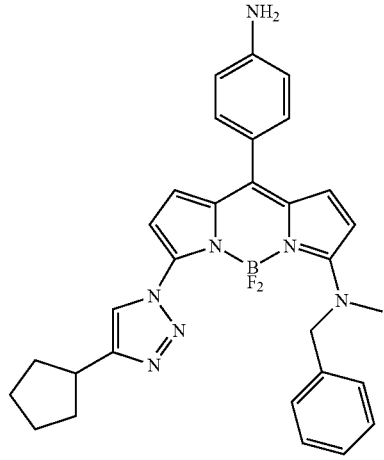 | 95% | 537.26 | 538.6 | 477 | 579 | 0.39 |
| MK195-8 | 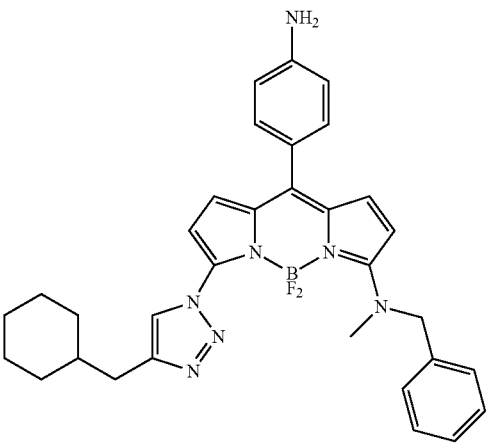 | 95% | 565.29 | 566.7 | 476 | 579 | 0.36 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK195-18 | 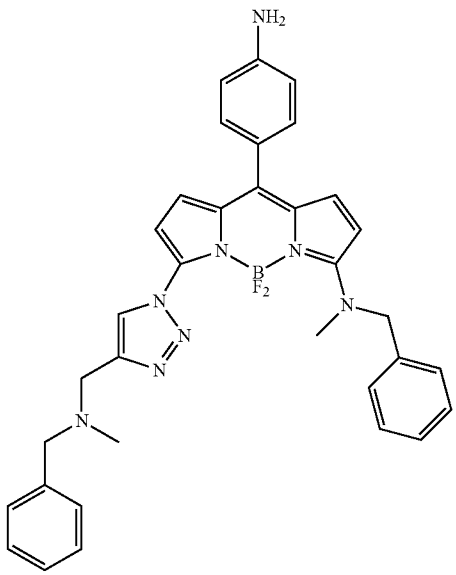 | 83% | 602.29 | 603.7 | 475 | 580 | 0.52 |
| MK195-19 | 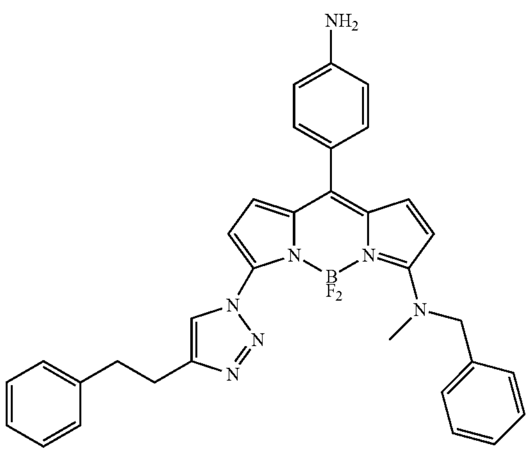 | 92% | 573.26 | 574.7 | 477 | 582 | 0.27 |
| MK195-43 | 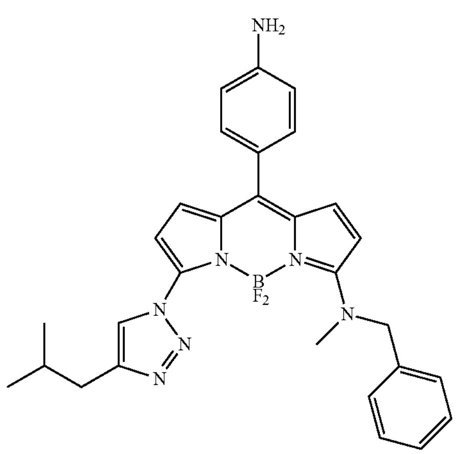 | 87% | 525.26 | 526.6 | 475 | 571 | 0.41 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK195-48 | 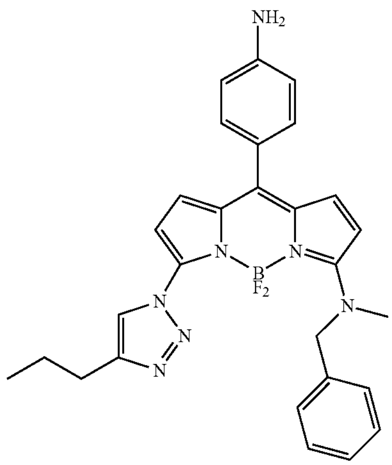 | 91% | 511.25 | 512.6 | 476 | 584 | 0.32 |
| MK195-69 | 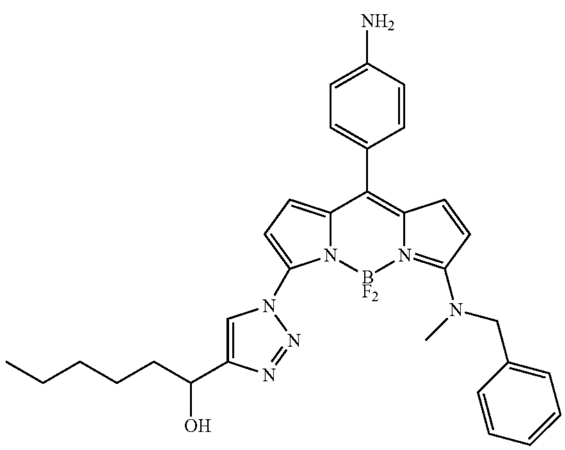 | 96% | 569.29 | 570.7 | 476 | 591 | 0.28 |
| MK195-70 | 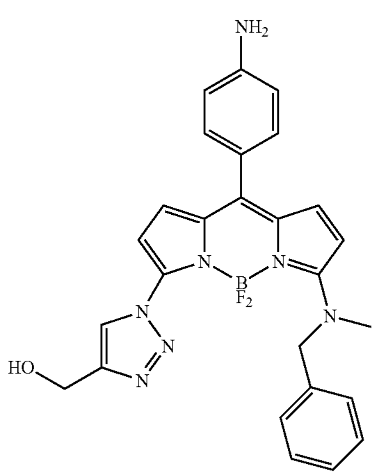 | 99% | 499.21 | 500.6 | 475 | 592 | 0.27 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK215-3 | | 98% | 489.26 | 490.6 | 471 | 567 | 0.26 |
| MK215-4 | | 99% | 459.22 | 460.6 | 470 | 576 | 0.29 |
| MK215-5 | | 98% | 487.25 | 488.6 | 471 | 568 | 0.53 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK215-8 | 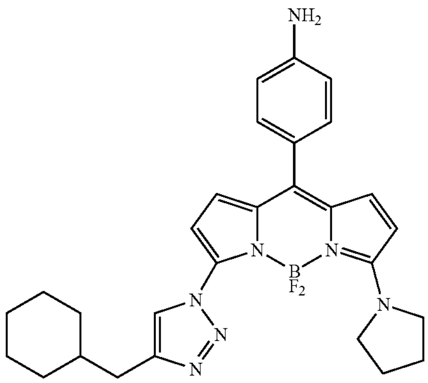 | 97% | 515.28 | 516.7 | 470 | 574 | 0.56 |
| MK215-18 | 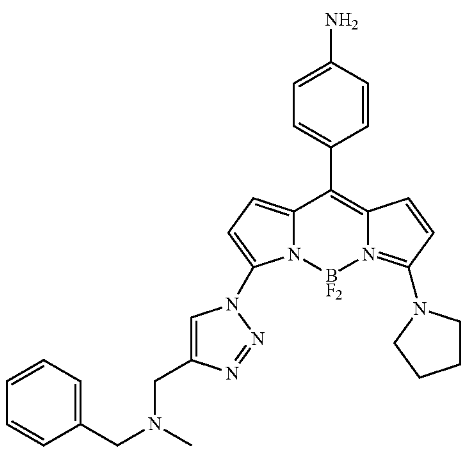 | 99% | 552.27 | 553.7 | 471 | 583 | 0.24 |
| MK215-19 | 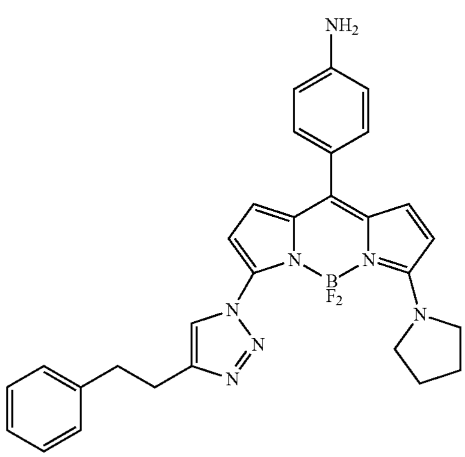 | 99% | 523.25 | 524.6 | 471 | 578 | 0.22 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK215-43 | 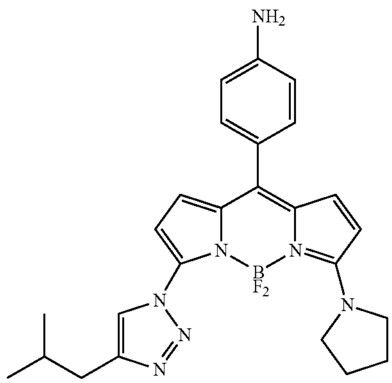 | 99% | 457.25 | 476.6 | 471 | 571 | 0.33 |
| MK215-48 | 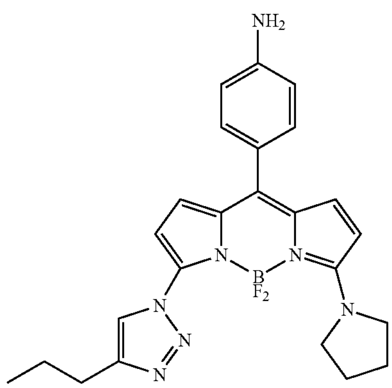 | 99% | 461.23 | 462.6 | 470 | 575 | 0.29 |
| MK215-69 | 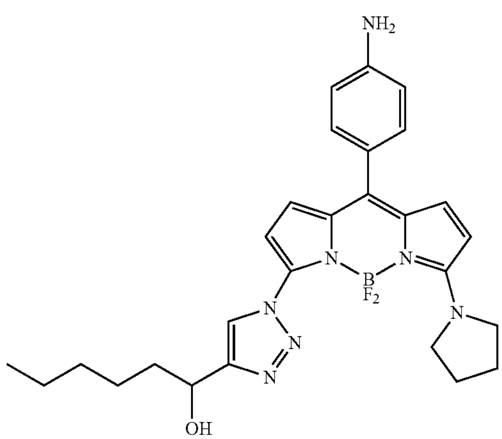 | 99% | 519.27 | 520.6 | 470 | 580 | 0.33 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK215-70 | 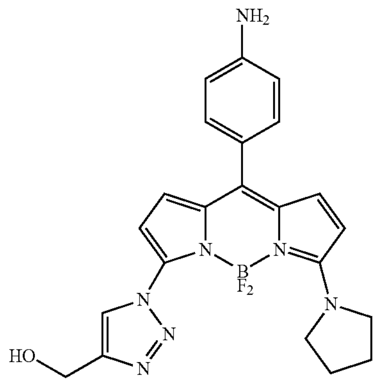 | 99% | 449.19 | 450.5 | 471 | 595 | 0.22 |
| MK412-3 | 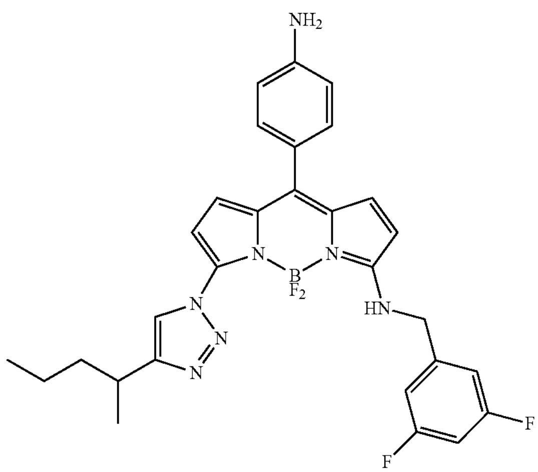 | 98% | 561.24 | 562.6 | 476 | 562 | 0.63 |
| MK412-4 | 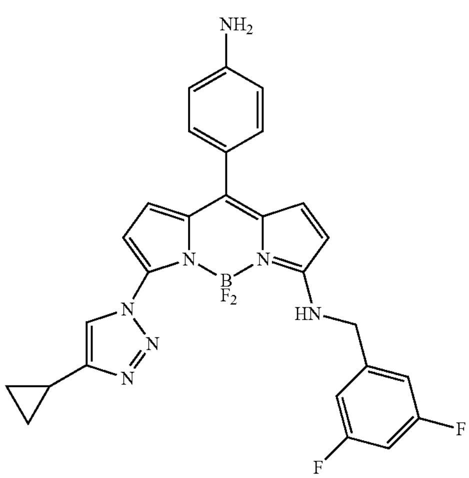 | 99% | 531.20 | 532.6 | 475 | 562 | 0.67 |

TABLE 5-continued
Chemical structures and characterization data for the MK compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK412-5 | 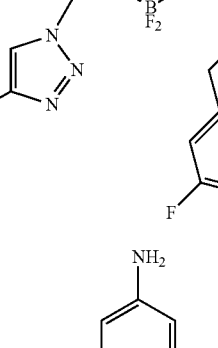 | 99% | 559.23 | 560.6 | 476 | 567 | 0.68 |
| MK412-8 | 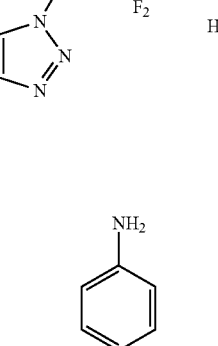 | 99% | 587.26 | 588.7 | 476 | 563 | 0.56 |
| MK412-18 | 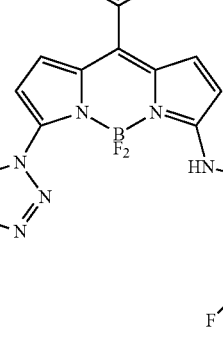 | 99% | 624.25 | 625.7 | 473 | 563 | 1.02 |

TABLE 5-continued

Chemical structures and characterization data for the MK compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK412-19 | 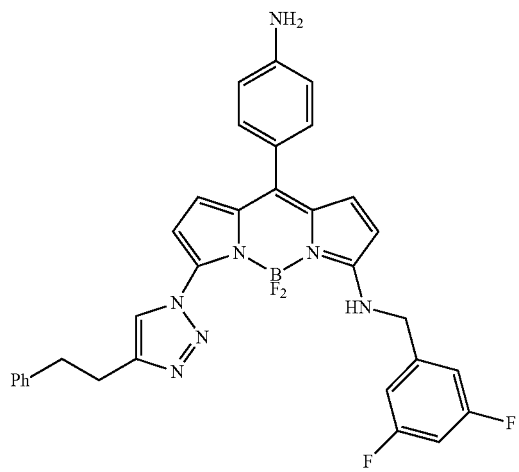 | 99% | 595.23 | 596.6 | 475 | 564 | 0.92 |
| MK412-43 | 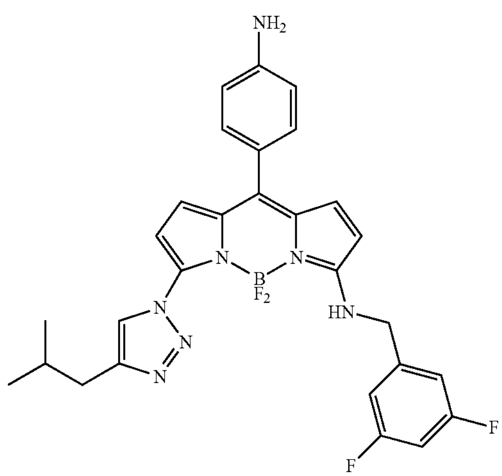 | 99% | 547.23 | 548.6 | 476 | 564 | 0.86 |
| MK412-48 | 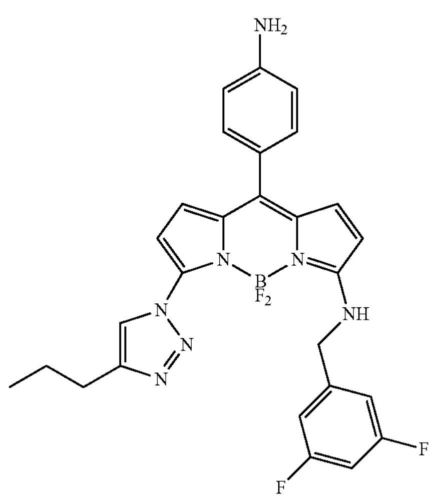 | 97% | 533.21 | 534.6 | 474 | 563 | 1.55 |

TABLE 5-continued
Chemical structures and characterization data for the MK compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MK412-69 | 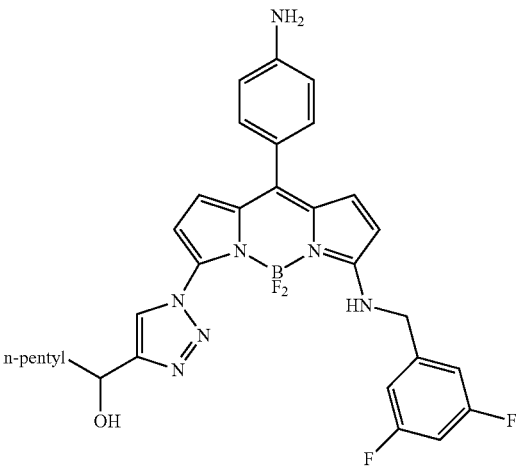 | 99% | 591.25 | 592.6 | 476 | 563 | 1.98 |
| MK412-70 | 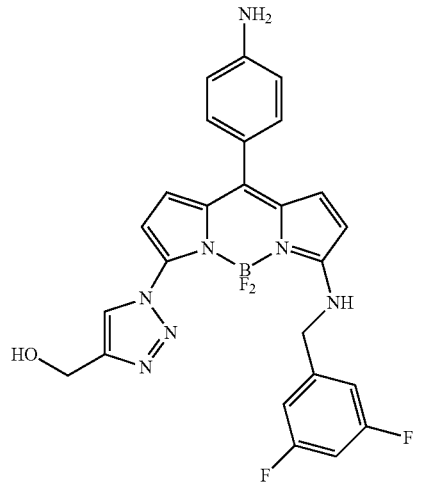 | 59% | 521.18 | 522.5 | 470 | 562 | 1.89 |

TABLE 6

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC20-3 | 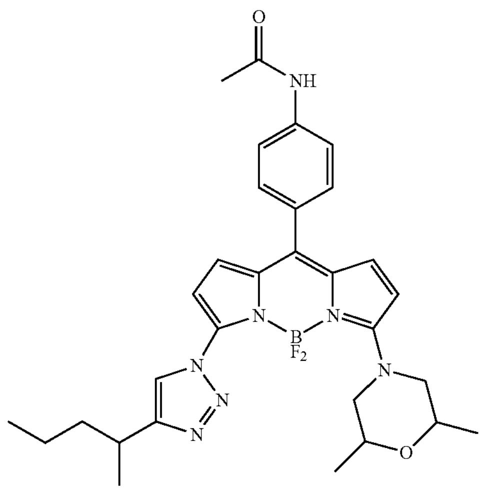 | 96% | 575.30 | 576.7 | 466 | 583 | 2.40 |
| MKAC20-4 | 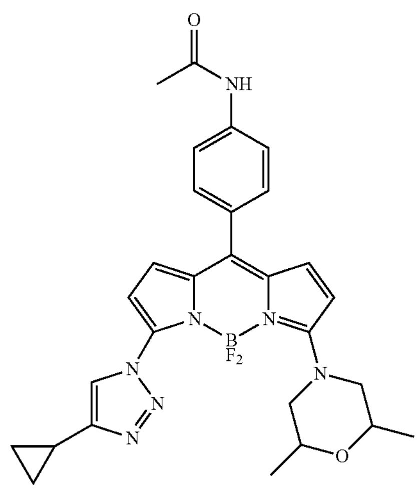 | 91% | 545.25 | 546.6 | 466 | 585 | 3.64 |
| MKAC20-5 | 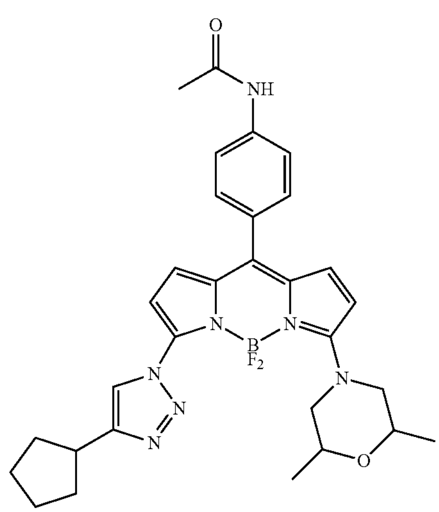 | 95% | 573.28 | 574.7 | 467 | 580 | 3.47 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
| --- | --- | --- | --- | --- | --- | --- | --- |
| MKAC20-8 | 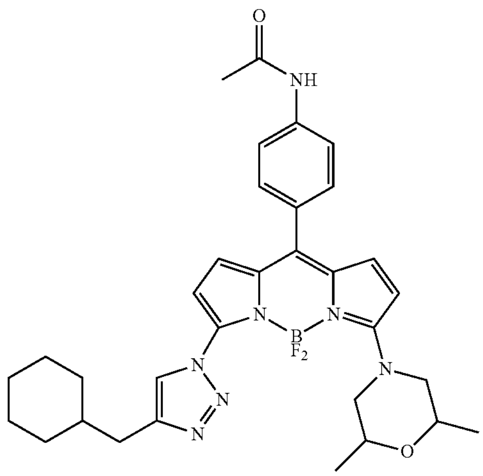 | 88% | 601.31 | 602.7 | 466 | 583 | 4.98 |
| MKAC20-18 | 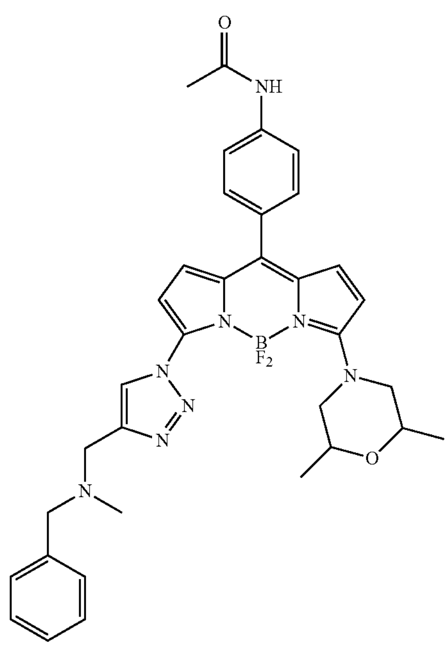 | 99% | 638.31 | 639.8 | 467 | 583 | 2.13 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC20-19 | 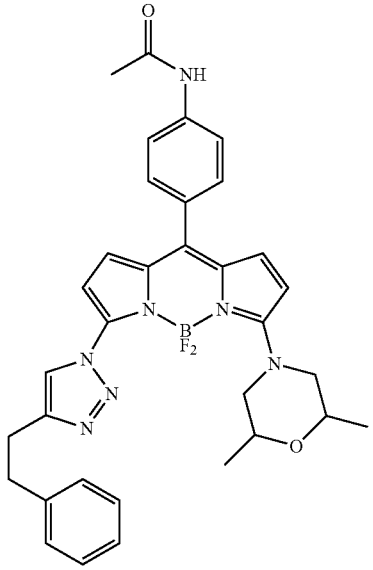 | 93% | 609.28 | 610.7 | 467 | 579 | 3.12 |
| MKAC20-43 | 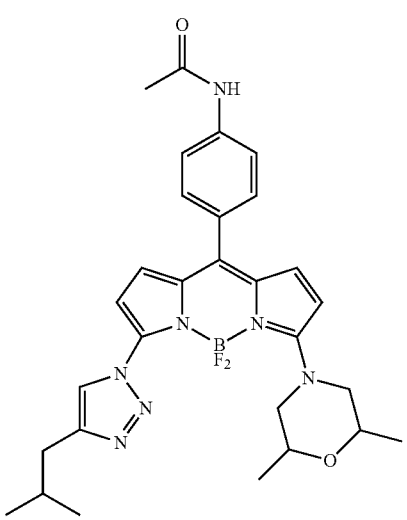 | 99% | 561.28 | 562.7 | 467 | 586 | 1.55 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC20-48 | 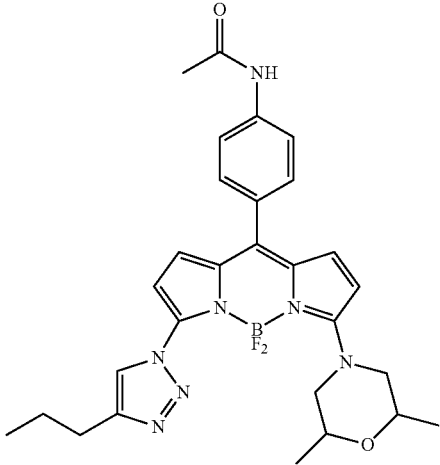 | 93% | 547.27 | 548.7 | 467 | 581 | 2.93 |
| MKAC20-69 | 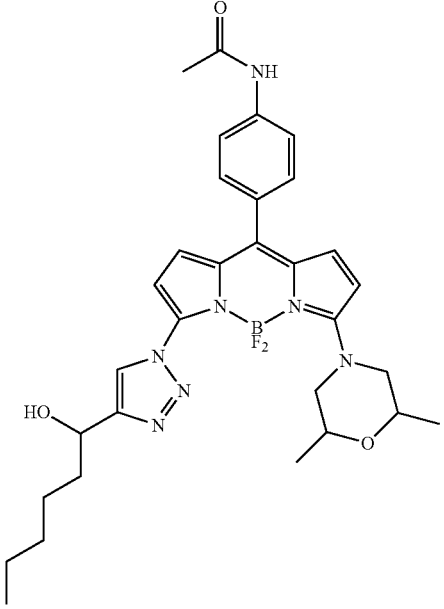 | 99% | 605.31 | 606.8 | 469 | 590 | 2.23 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC20-70 | 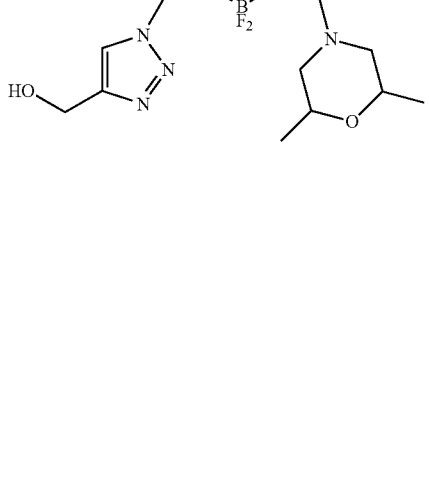 | 99% | 535.23 | 536.6 | 467 | 586 | 1.33 |
| MKAC66-3 | 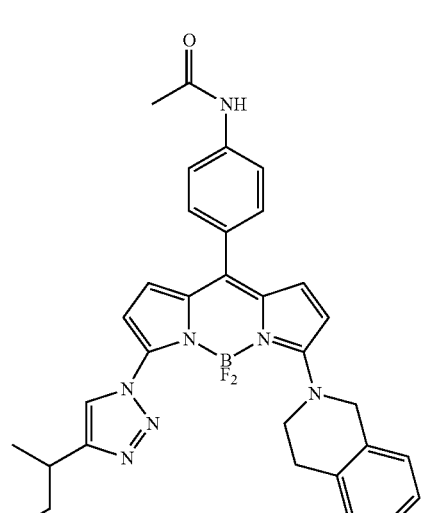 | 99% | 593.29 | 594.7 | 469 | 583 | 2.40 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC66-4 | 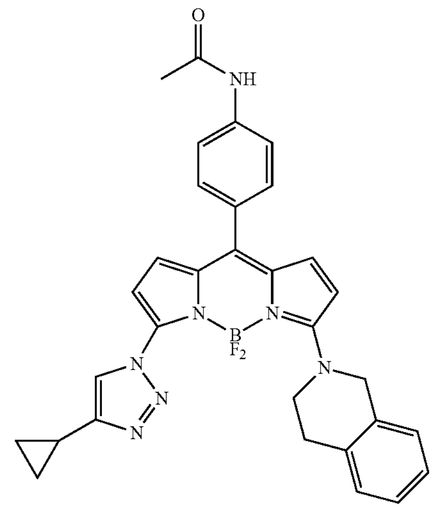 | 99% | 563.24 | 564.6 | 469 | 580 | 2.56 |
| MKAC66-5 | 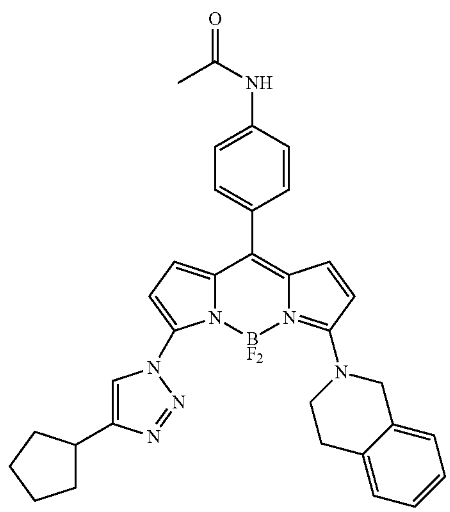 | 99% | 591.27 | 592.7 | 470 | 583 | 1.96 |
| MKAC66-8 | 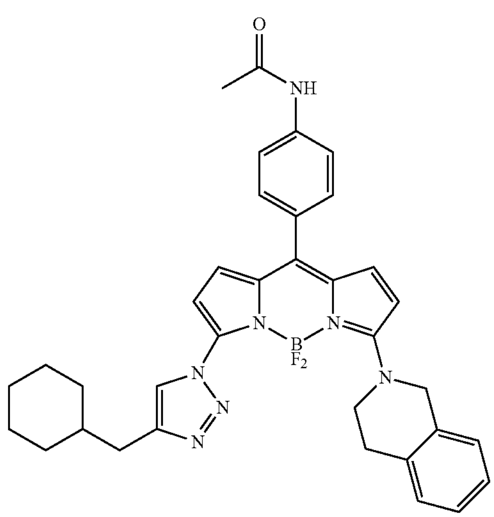 | 99% | 619.30 | 620.7 | 469 | 578 | 2.20 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC66-18 | 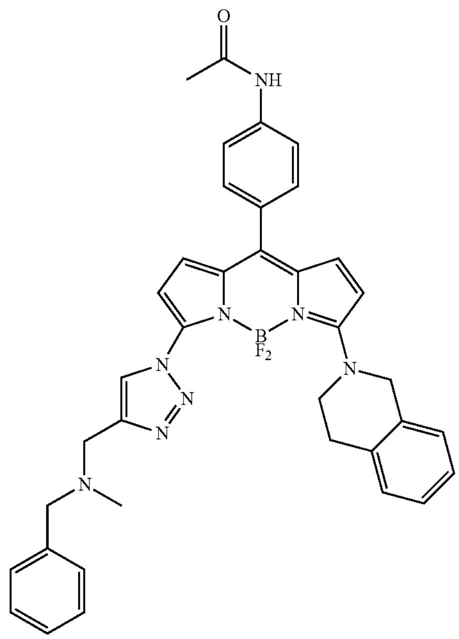 | 99% | 656.30 | 657.8 | 468 | 585 | 1.56 |
| MKAC66-19 | 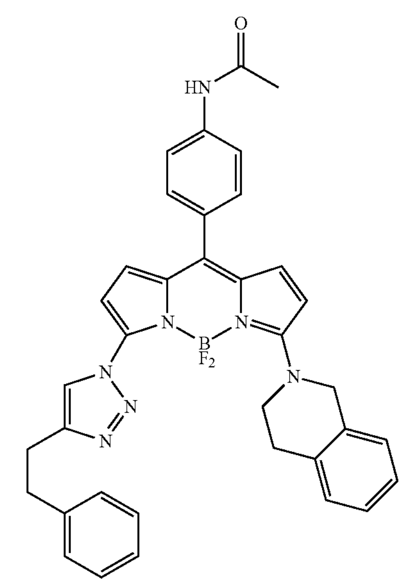 | 99% | 627.27 | 628.7 | 470 | 580 | 1.76 |

TABLE 6-continued
Chemical structures and characterization data for the MKAC compound library.
| Code | Structure | Purity (254 nm) | m/z Calculated | m/z Experimental | λ$_{max}$ Abs. (nm) | λ$_{max}$ Em. (nm) | φ (%) |
|---|---|---|---|---|---|---|---|
| MKAC66-43 | 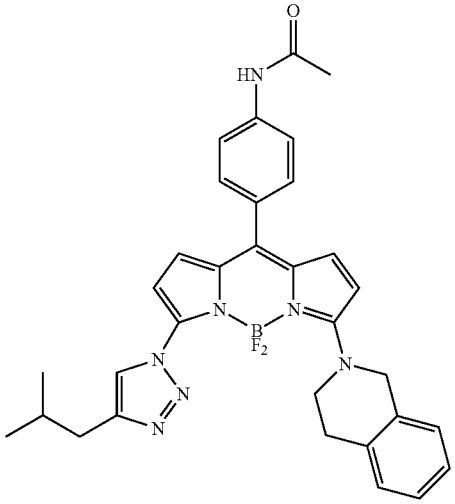 | 99% | 579.27 | 580.7 | 469 | 581 | 1.92 |
| MKAC66-48 | 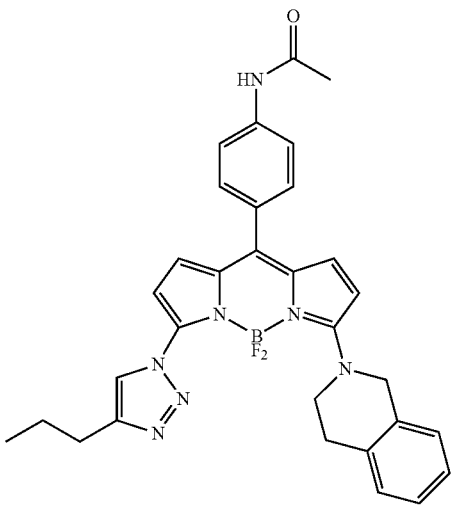 | 99% | 565.26 | 566.7 | 469 | 582 | 2.14 |

TABLE 6-continued
Chemical structures and characterization data for the MKAC compound library.
| Code | Structure | Purity (254 nm) | m/z Calculated | m/z Experimental | λ$_{max}$ Abs. (nm) | λ$_{max}$ Em. (nm) | φ (%) |
|---|---|---|---|---|---|---|---|
| MKAC66-69 | 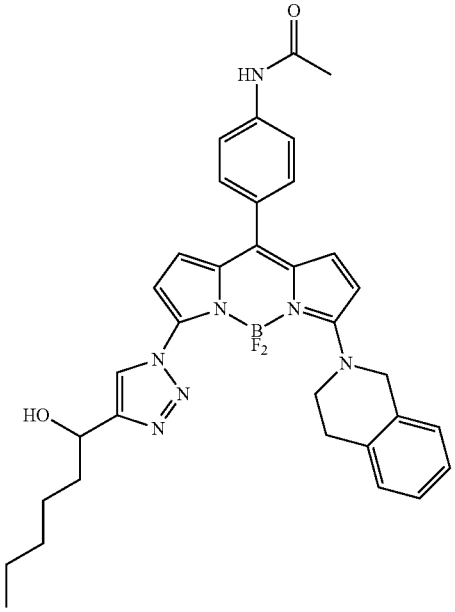 | 99% | 623.30 | 624.7 | 469 | 579 | 1.88 |
| MKAC66-70 | 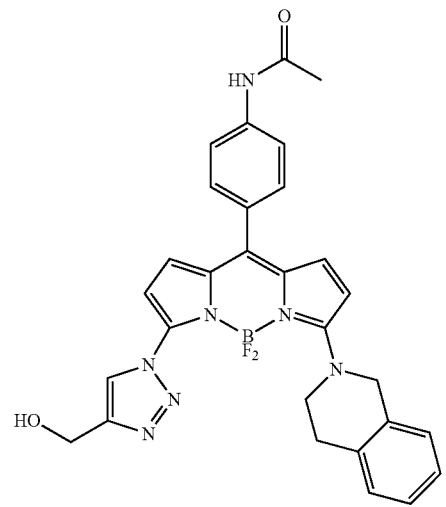 | 99% | 553.22 | 554.6 | 468 | 582 | 1.44 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKA101-3 | 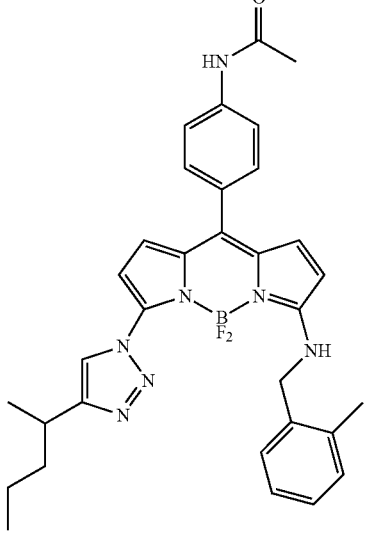 | 96% | 581.29 | 582.7 | 464 | 562 | 21.57 |
| MKAC101-4 | 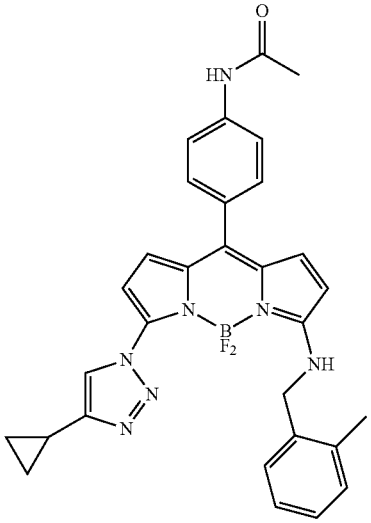 | 99% | 551.24 | 552.6 | 465 | 563 | 23.84 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC101-5 | 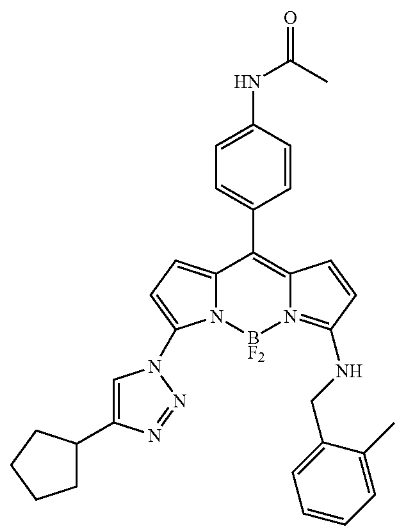 | 99% | 579.27 | 580.7 | 466 | 563 | 23.69 |
| MKAC101-8 | 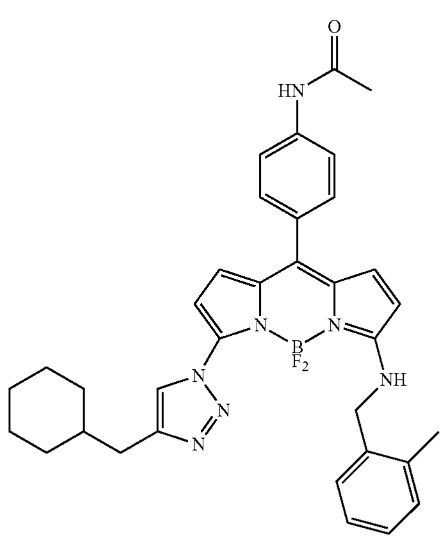 | 97% | 607.30 | 608.7 | 465 | 563 | 21.14 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC101-18 | 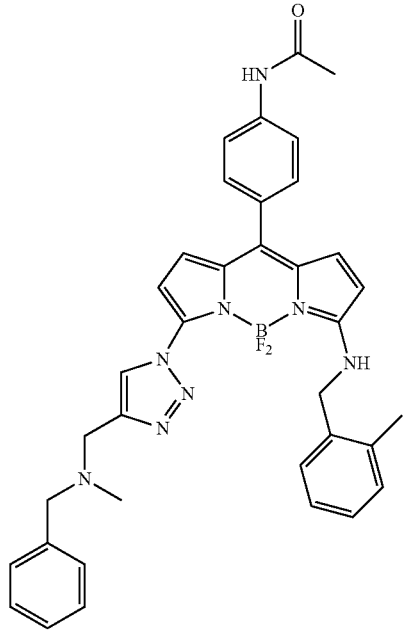 | 93% | 644.30 | 645.7 | 465 | 362 | 13.14 |
| MKAC101-19 | 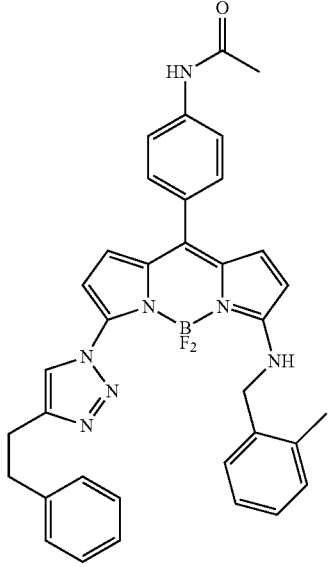 | 83% | 615.27 | 616.7 | 464 | 560 | 23.26 |

TABLE 6-continued
Chemical structures and characterization data for the MKAC compound library.
| Code | Structure | Purity (254 nm) | m/z Calculated | m/z Experimental | λ$_{max}$ Abs. (nm) | λ$_{max}$ Em. (nm) | φ (%) |
|---|---|---|---|---|---|---|---|
| MKAC101-43 | 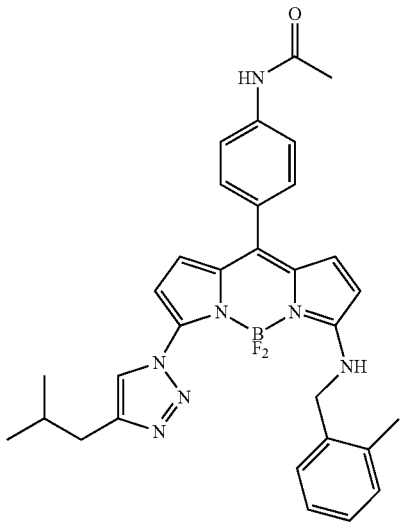 | 99% | 567.27 | 568.6 | 465 | 562 | 20.12 |
| MKAC101-48 | 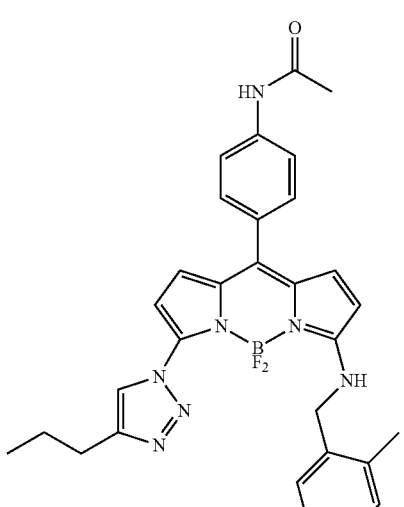 | 90% | 553.26 | 554.7 | 465 | 562 | 17.25 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC101-69 | 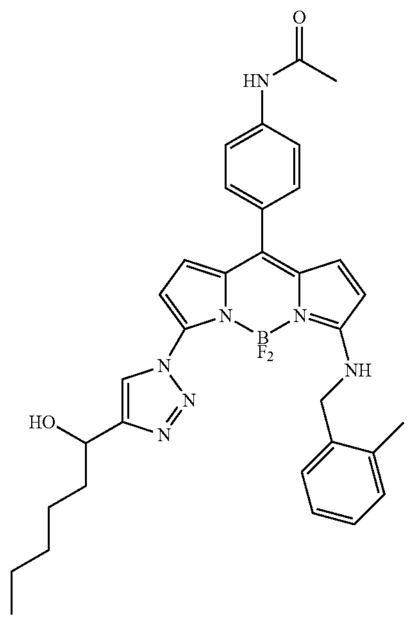 | 99% | 611.30 | 612.7 | 461 | 562 | 24.08 |
| MKAC101-70 | 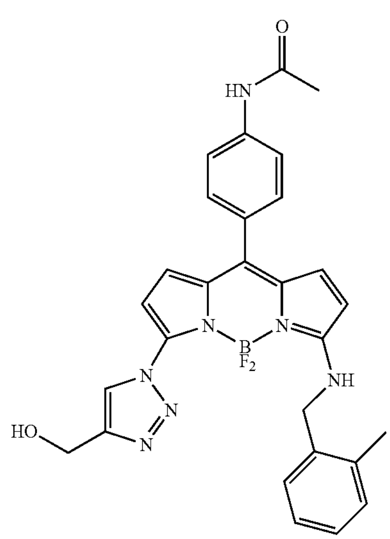 | 99% | 541.22 | 542.6 | 465 | 561 | 18.11 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC103-3 | 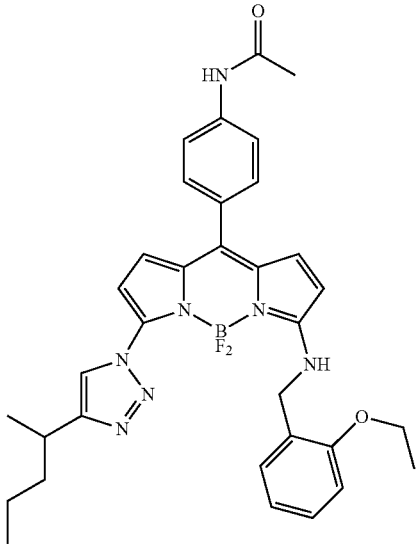 | 99% | 611.30 | 612.7 | 465 | 561 | 23.42 |
| MKAC103-4 | 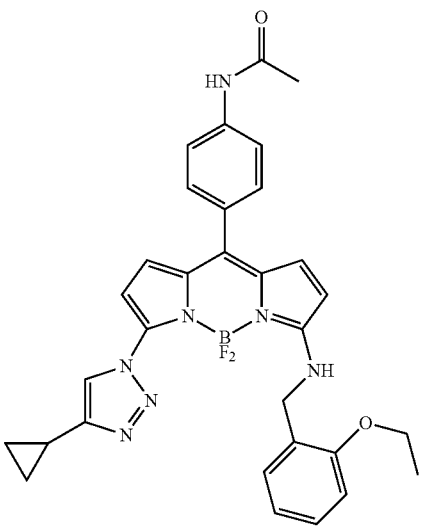 | 99% | 581.25 | 582.7 | 464 | 565 | 24.86 |

TABLE 6-continued
Chemical structures and characterization data for the MKAC compound library.
| Code | Structure | Purity (254 nm) | m/z Calculated | m/z Experimental | λ_max Abs. (nm) | λ_max Em. (nm) | φ (%) |
|---|---|---|---|---|---|---|---|
| MKAC103-5 | 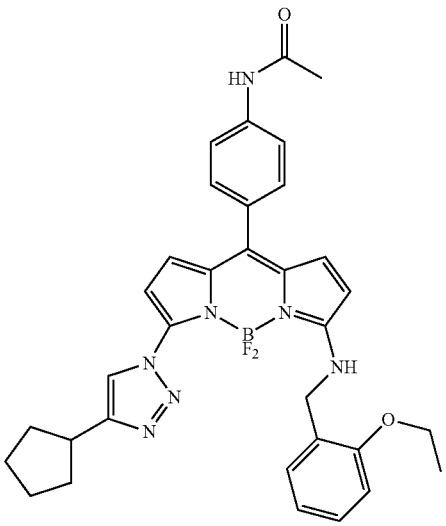 | 99% | 609.28 | 610.7 | 465 | 562 | 18.11 |
| MKAC103-8 | 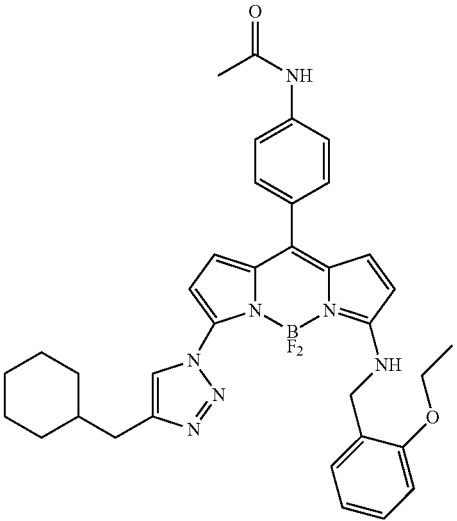 | 97% | 637.31 | 638.8 | 465 | 562 | 25.32 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | $\phi$ (%) |
|---|---|---|---|---|---|---|---|
| MKAC103-18 | 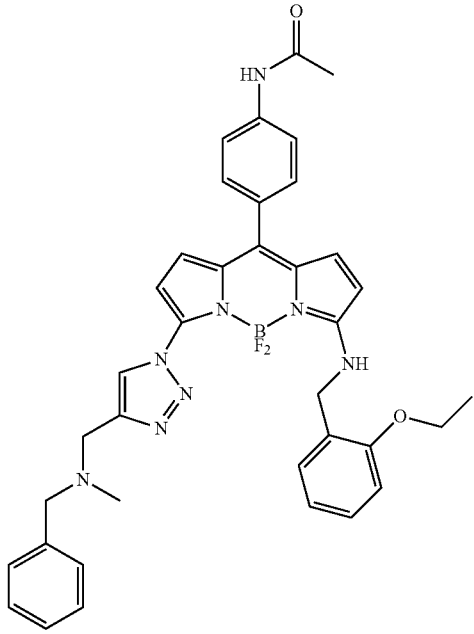 | 98% | 674.31 | 675.8 | 465 | 560 | 18.63 |
| MKAC103-19 | 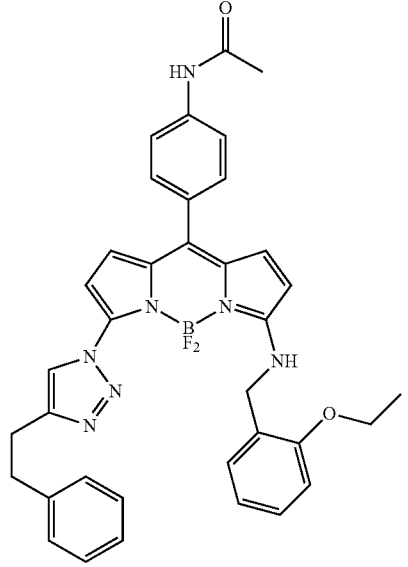 | 93% | 645.28 | 646.7 | 464 | 562 | 29.05 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC103-43 | 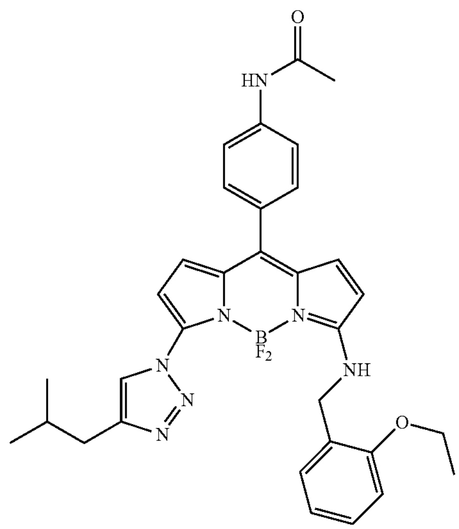 | 99% | 597.28 | 598.7 | 465 | 560 | 22.79 |
| MKAC103-48 | 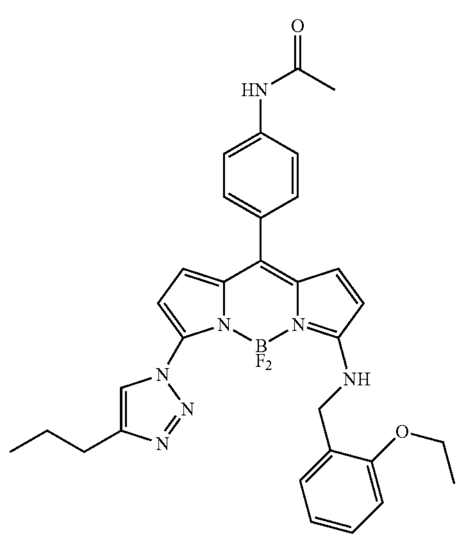 | 99% | 583.27 | 584.7 | 466 | 562 | 20.07 |

TABLE 6-continued
Chemical structures and characterization data for the MKAC compound library.
| Code | Structure | Purity (254 nm) | m/z Calculated | m/z Experimental | λ$_{max}$ Abs. (nm) | λ$_{max}$ Em. (nm) | φ (%) |
| --- | --- | --- | --- | --- | --- | --- | --- |
| MKAC103-69 | 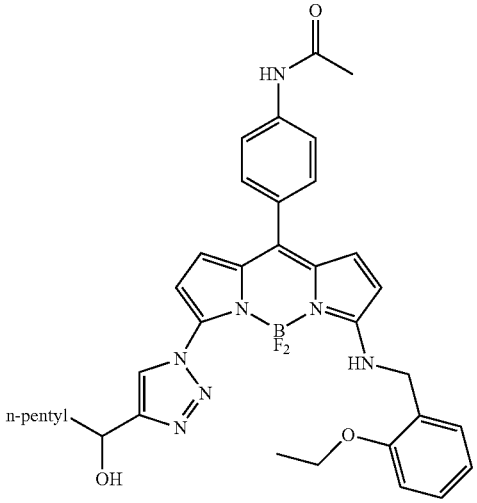 | 99% | 641.31 | 642.7 | 465 | 561 | 20.91 |
| MKAC103-70 | 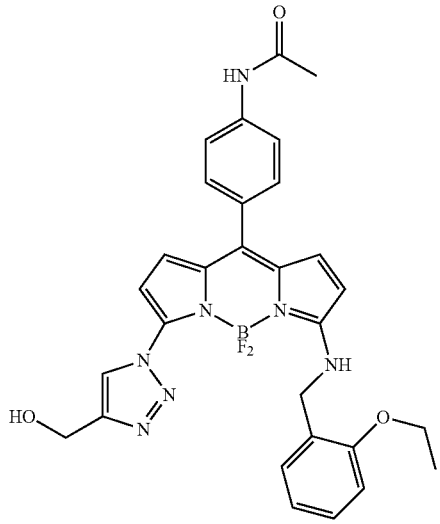 | 99% | 571.23 | 572.6 | 464 | 558 | 15.35 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
| --- | --- | --- | --- | --- | --- | --- | --- |
| MKAC181-3 | 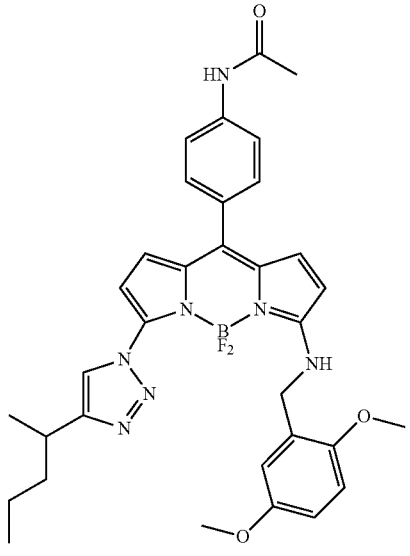 | 97% | 627.29 | 628.7 | 465 | 562 | 15.41 |
| MKAC181-4 | 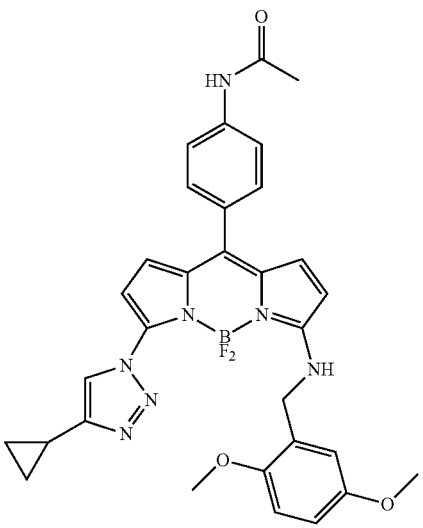 | 99% | 597.25 | 598.7 | 464 | 562 | 15.43 |

TABLE 6-continued
Chemical structures and characterization data for the MKAC compound library.
| Code | Structure | Purity (254 nm) | m/z Calculated | m/z Experimental | λ_max Abs. (nm) | λ_max Em. (nm) | φ (%) |
|---|---|---|---|---|---|---|---|
| MKAC181-5 | 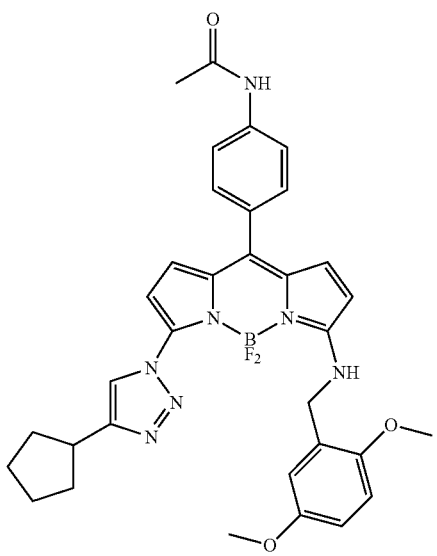 | 99% | 625.28 | 626.7 | 464 | 563 | 10.37 |
| MKAC181-8 | 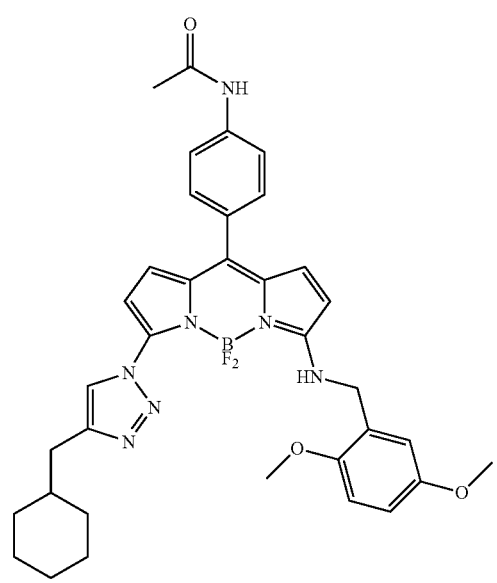 | 99% | 653.31 | 654.8 | 465 | 564 | 13.98 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
| --- | --- | --- | --- | --- | --- | --- | --- |
| MKAC181-18 | 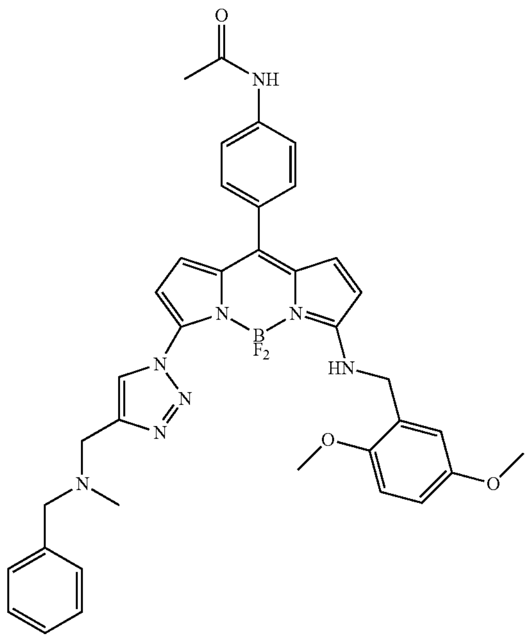 | 99% | 690.30 | 691.7 | 464 | 561 | 18.28 |
| MKAC181-19 | 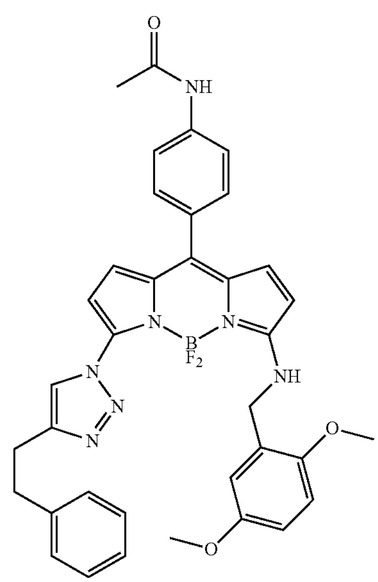 | 99% | 661.28 | 662.7 | 464 | 561 | 14.0 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC181-43 | 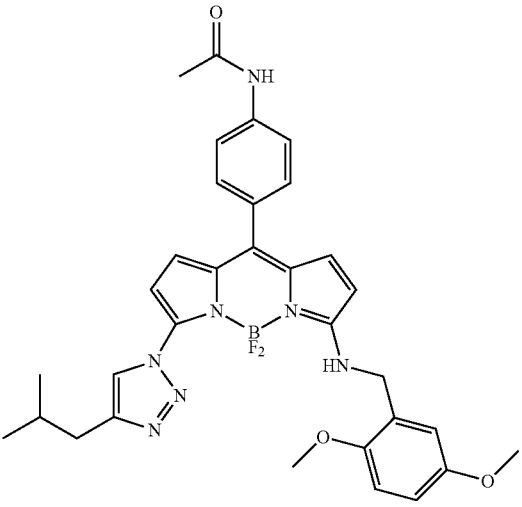 | 99% | 613.28 | 614.7 | 467 | 562 | 13.79 |
| MKAC181-48 | 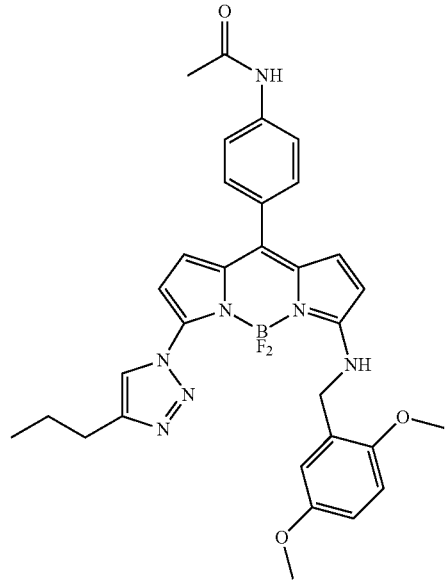 | 99% | 599.26 | 600.7 | 465 | 561 | 11.03 |

TABLE 6-continued
Chemical structures and characterization data for the MKAC compound library.
| Code | Structure | Purity (254 nm) | m/z Calculated | m/z Experimental | λ$_{max}$ Abs. (nm) | λ$_{max}$ Em. (nm) | φ (%) |
|---|---|---|---|---|---|---|---|
| MKAC181-69 | 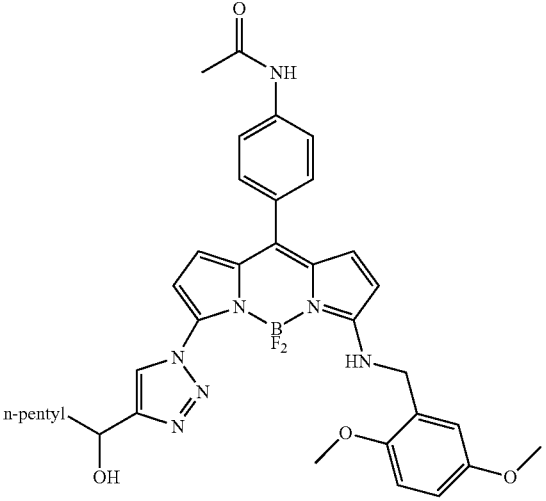 | 99% | 657.30 | 658.8 | 465 | 561 | 16.50 |
| MKAC181-70 | 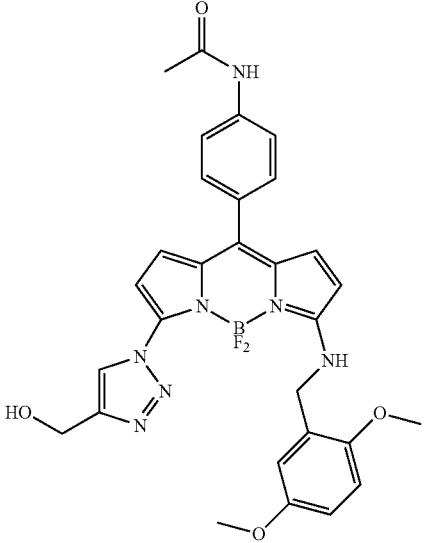 | 99% | 587.23 | 588.6 | 465 | 559 | 15.37 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
| --- | --- | --- | --- | --- | --- | --- | --- |
| MKAC195-3 | 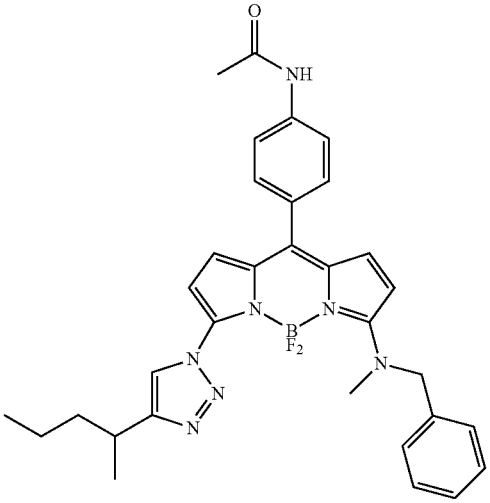 | 78% | 581.29 | 582.7 | 465 | 574 | 6.53 |
| MKAC195-4 | 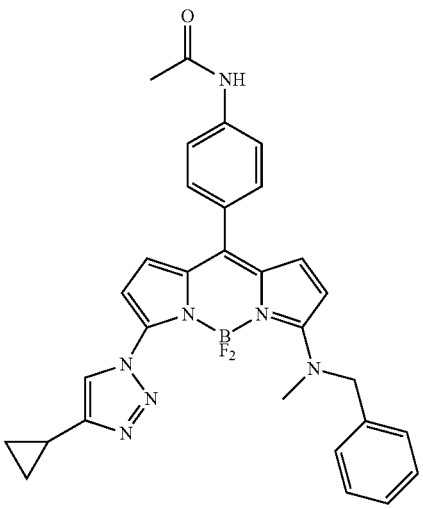 | 83% | 551.24 | 552.6 | 466 | 582 | 5.45 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC195-5 | 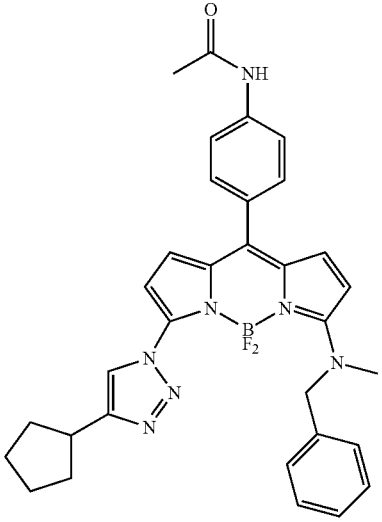 | 88% | 579.27 | 580.7 | 467 | 578 | 4.18 |
| MKAC195-8 | 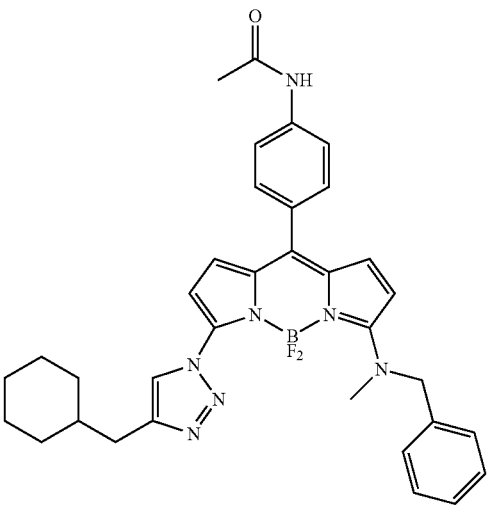 | 78% | 607.30 | 608.7 | 466 | 577 | 3.65 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC195-18 | 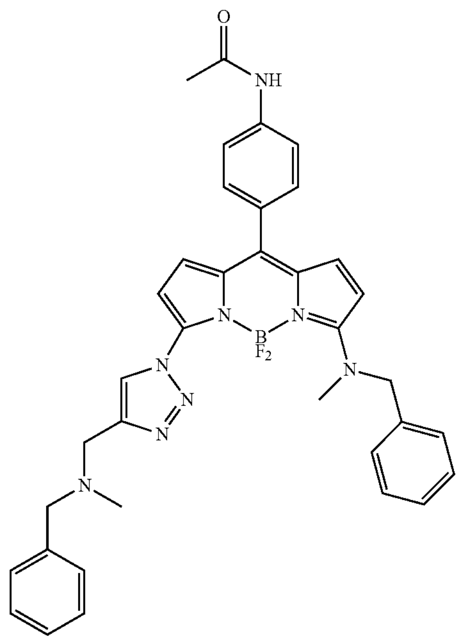 | 92% | 644.30 | 645.7 | 465 | 575 | 1.85 |
| MKAC195-19 | 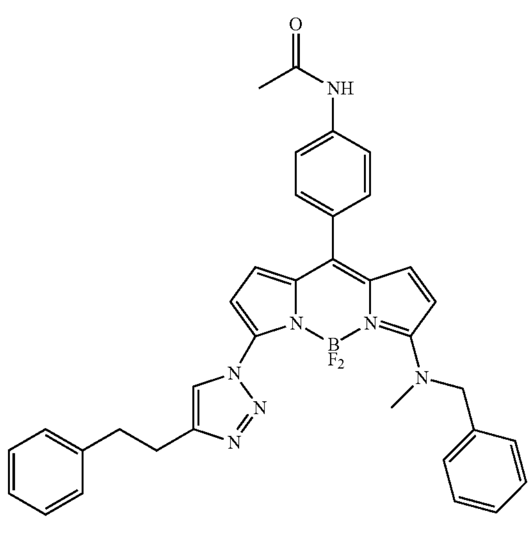 | 76% | 615.27 | 616.7 | 467 | 577 | 3.78 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC195-43 | 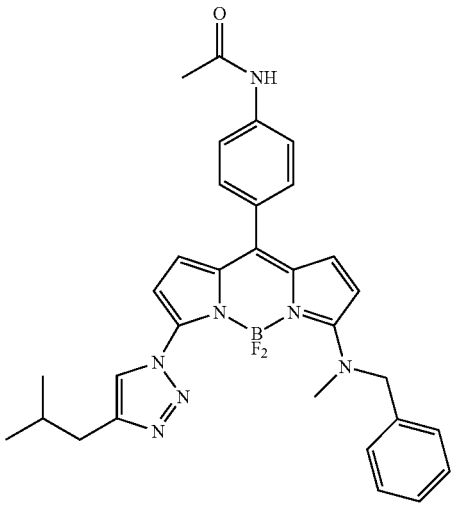 | 82% | 567.27 | 568.7 | 466 | 580 | 3.48 |
| MKAC195-48 | 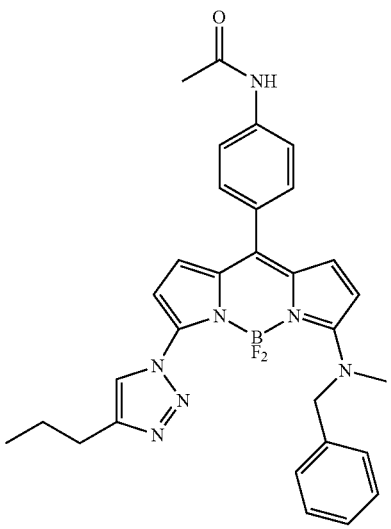 | 88% | 553.26 | 554.7 | 467 | 575 | 2.72 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC195-69 | 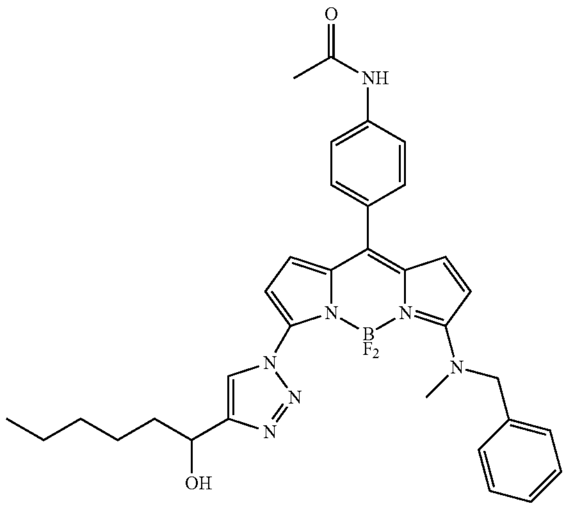 | 96% | 611.30 | 612.7 | 467 | 560 | 3.467 |
| MKAC195-70 | 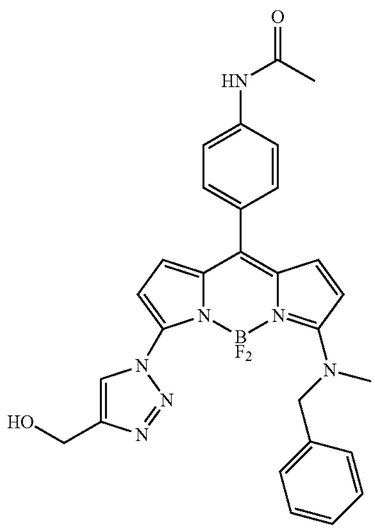 | 99% | 541.22 | 542.6 | 464 | 579 | 1.67 |
| MKAC215-3 | 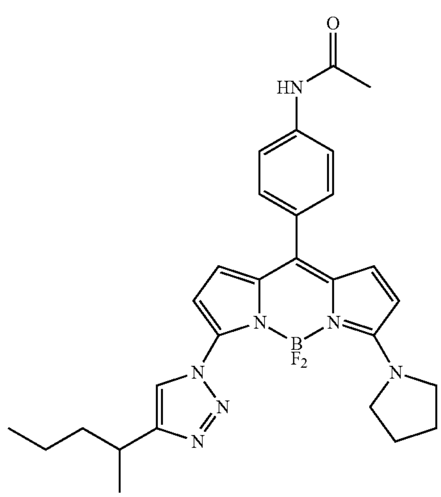 | 99% | 531.27 | 532.6 | 461 | 569 | 3.81 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC215-4 | 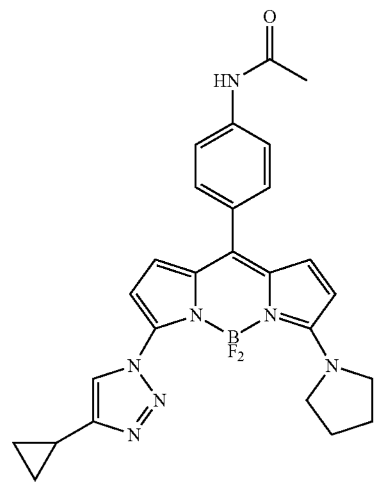 | 99% | 501.23 | 502.6 | 462 | 576 | 2.35 |
| MKAC215-5 | 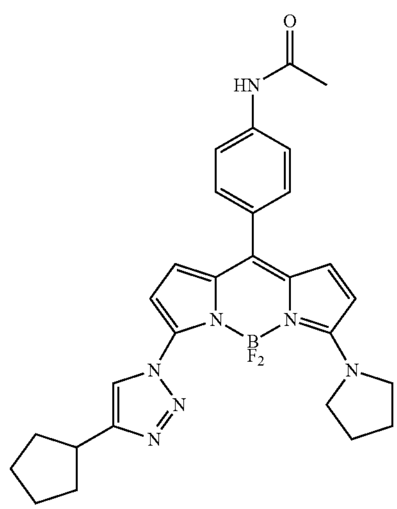 | 99% | 529.26 | 530.6 | 463 | 574 | 1.00 |
| MKAC215-8 | 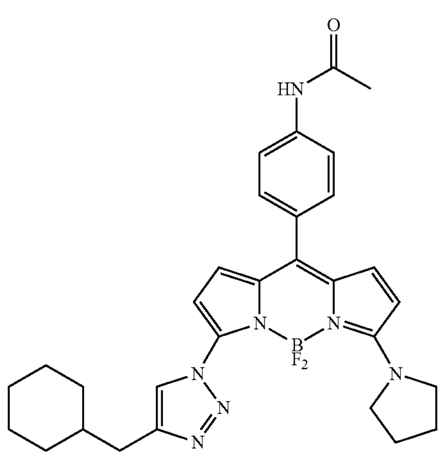 | 82% | 557.29 | 558.7 | 462 | 568 | 1.17 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC215-18 | 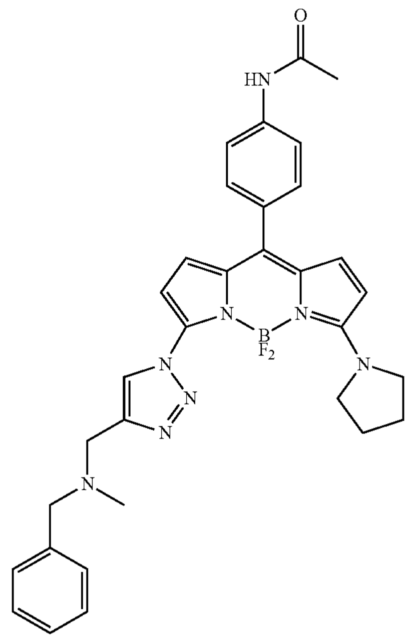 | 99% | 594.28 | 595.7 | 461 | 569 | 1.54 |
| MKAC215-19 | 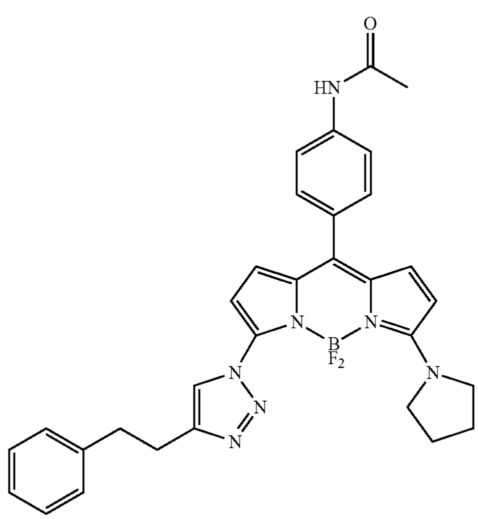 | 99% | 565.26 | 566.7 | 462 | 567 | 3.41 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC215-43 | 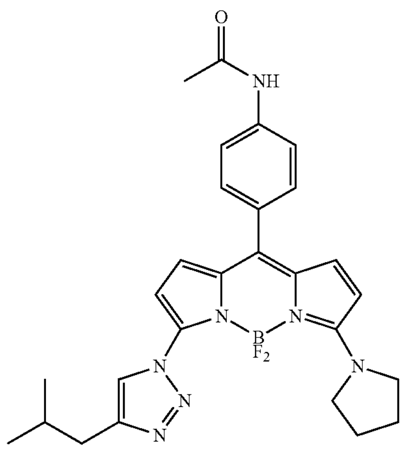 | 99% | 517.26 | 518.6 | 461 | 565 | 1.83 |
| MKAC215-48 | 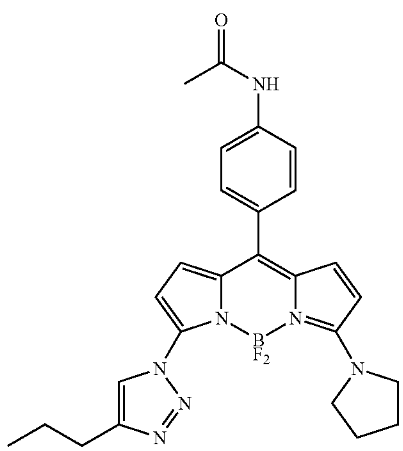 | 99% | 503.24 | 504.6 | 461 | 566 | 2.70 |
| MKAC215-69 | 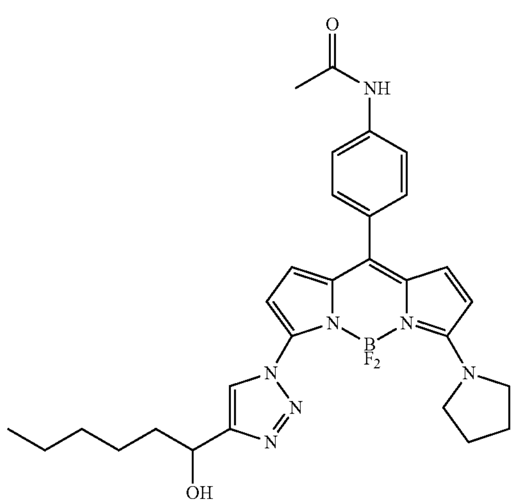 | 99% | 561.28 | 562.7 | 462 | 566 | 2.00 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC215-70 | | 93% | 491.21 | 492.6 | 461 | 574 | 1.11 |
| MKAC412-3 | | 99% | 603.25 | 604.7 | 466 | 561 | 27.73 |
| MKAC412-4 | | 99% | 573.21 | 574.6 | 466 | 562 | 26.84 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC412-5 | 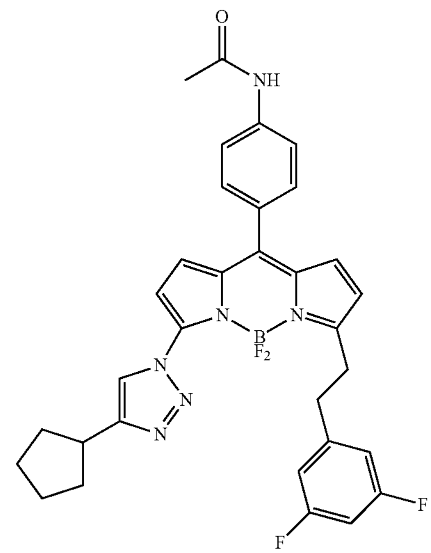 | 99% | 601.24 | 602.7 | 467 | 560 | 27.51 |
| MKAC412-8 | 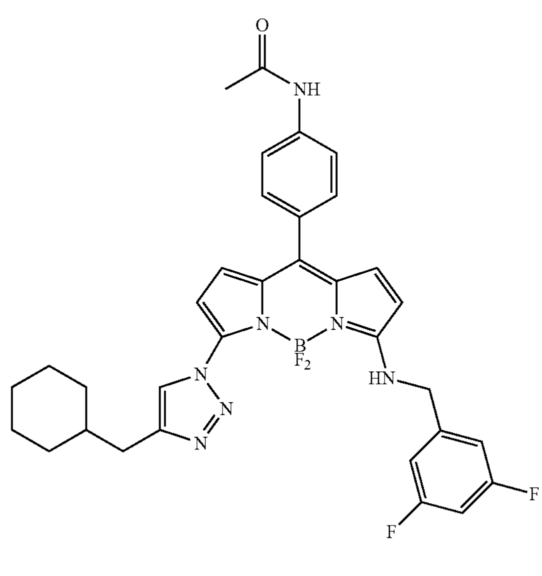 | 99% | 629.27 | 630.7 | 467 | 562 | 16.81 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC412-18 | 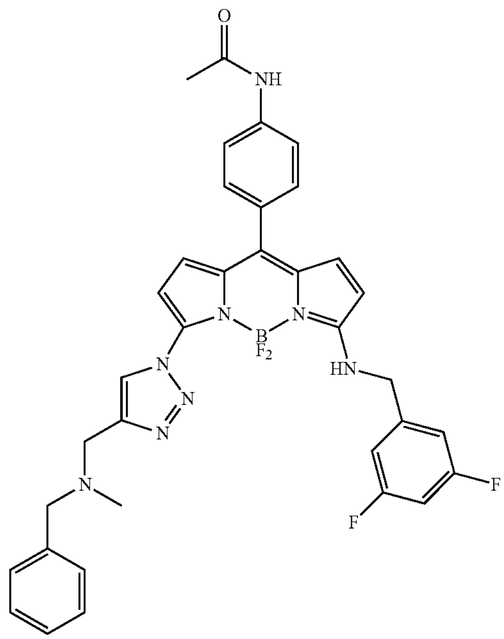 | 99% | 666.27 | 667.7 | 465 | 561 | 21.83 |
| MKAC412-19 | 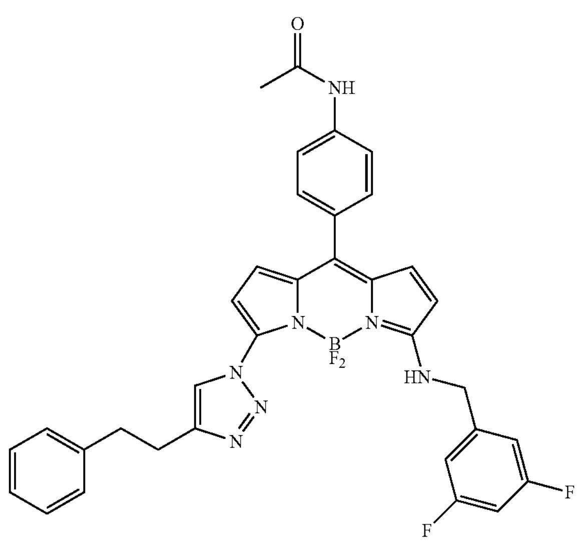 | 99% | 637.24 | 638.7 | 467 | 562 | 24.16 |

TABLE 6-continued
Chemical structures and characterization data for the MKAC compound library.
| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC412-43 | 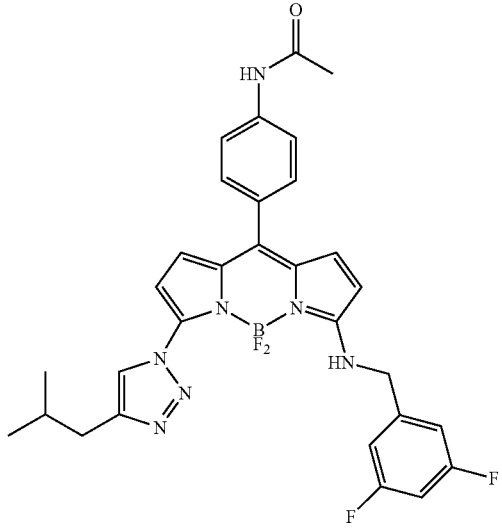 | 99% | 589.24 | 590.7 | 467 | 560 | 18.26 |
| MKAC412-48 | 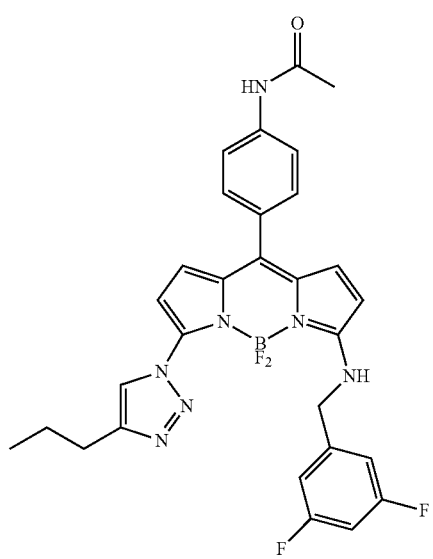 | 95% | 575.22 | 576.7 | 467 | 561 | 22.19 |

TABLE 6-continued

Chemical structures and characterization data for the MKAC compound library.

| Code | Structure | Purity (254 nm) | m/z Calculated | m/z Experimental | $\lambda_{max}$ Abs. (nm) | $\lambda_{max}$ Em. (nm) | φ (%) |
|---|---|---|---|---|---|---|---|
| MKAC412-69 | 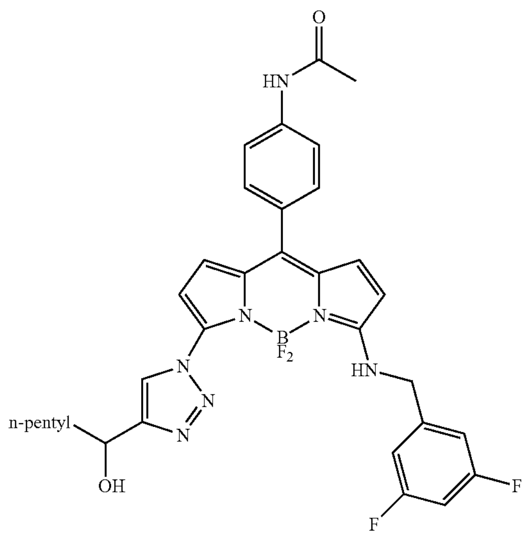 | 99% | 633.26 | 634.7 | 468 | 563 | 17.68 |
| MKAC412-70 | 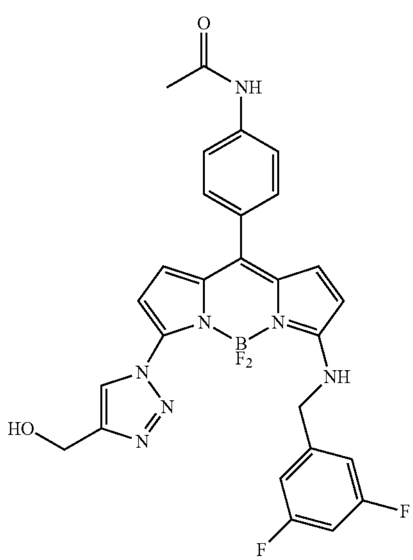 | 59% | 563.19 | 564.6 | 461 | 561 | 3.96 |

TABLE 7

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA20-3 | 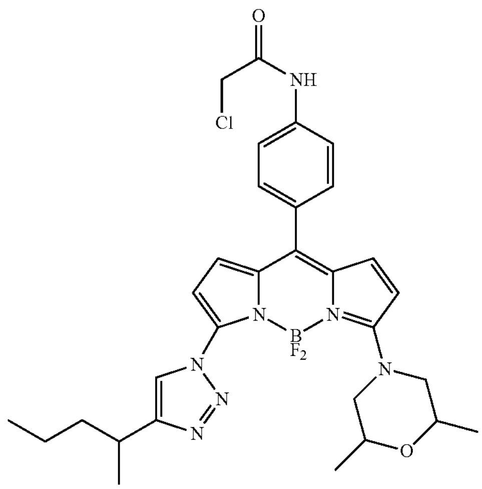 | 94% | 609.26 | 610.7 | 467 | 581 | 3.15 |
| MKCA20-4 | 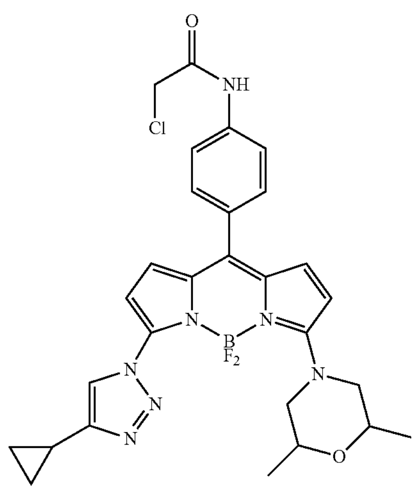 | 92% | 579.21 | 580.6 | 466 | 581 | 6.11 |
| MKCA20-5 | 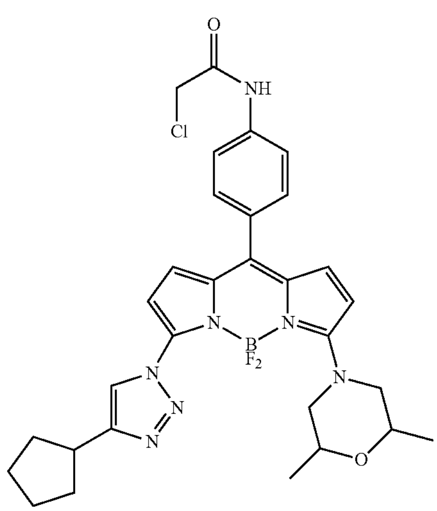 | 93% | 607.24 | 608.7 | 468 | 581 | 4.60 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA20-8 | 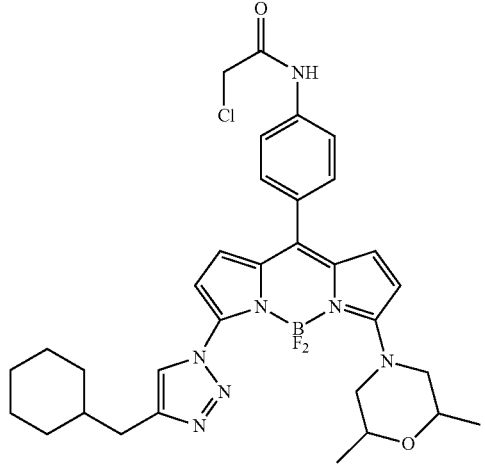 | 86% | 635.27 | 636.7 | 466 | 573 | 6.71 |
| MKCA20-18 | 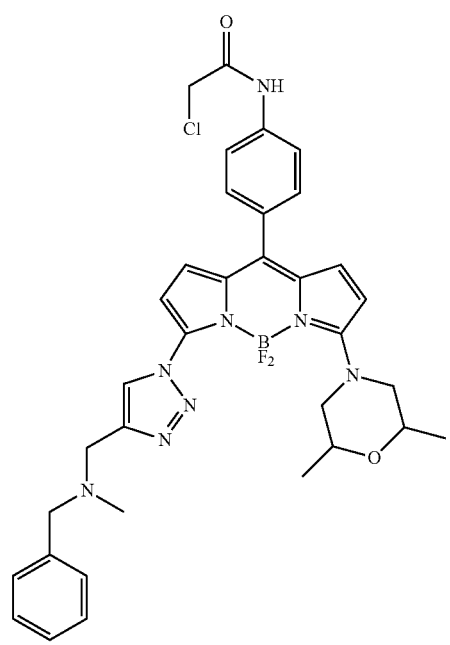 | 99% | 672.27 | 673.7 | 466 | 585 | 2.54 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| MKCA20-19 | 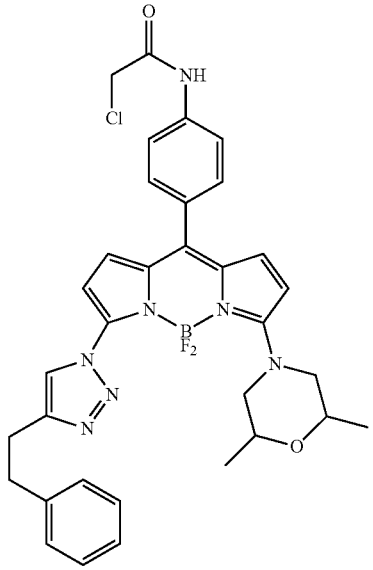 | 95% | 643.24 | 644.7 | 467 | 583 | 5.32 |
| MKCA20-43 | 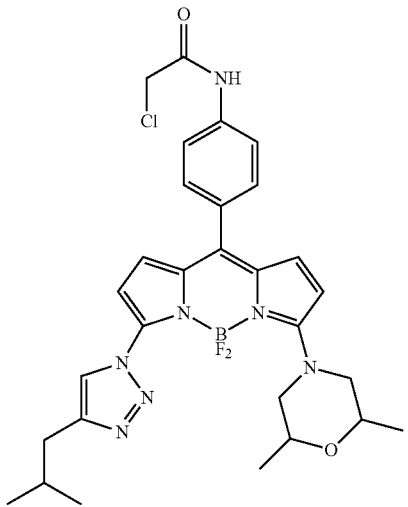 | 99% | 595.24 | 596.7 | 468 | 585 | 2.19 |

TABLE 7-continued
Chemical structures and characterization data for the MKCA compound library.
| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| MKCA20-48 | 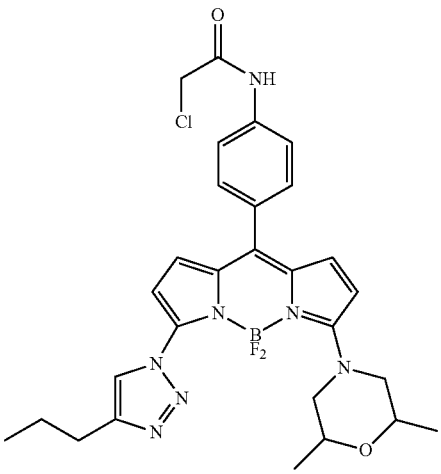 | 89% | 581.23 | 582.7 | 466 | 569 | 4.88 |
| MKCA20-69 | 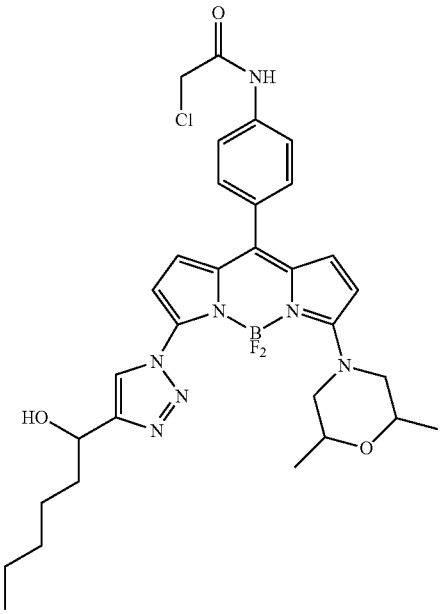 | 99% | 639.27 | 640.7 | 469 | 586 | 3.23 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA20-70 | 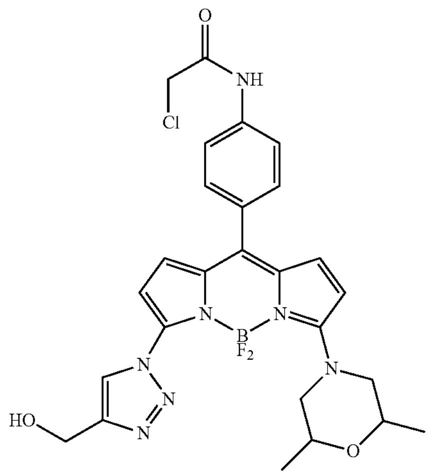 | 99% | 569.19 | 570.6 | 469 | 587 | 2.64 |
| MKCA66-3 | 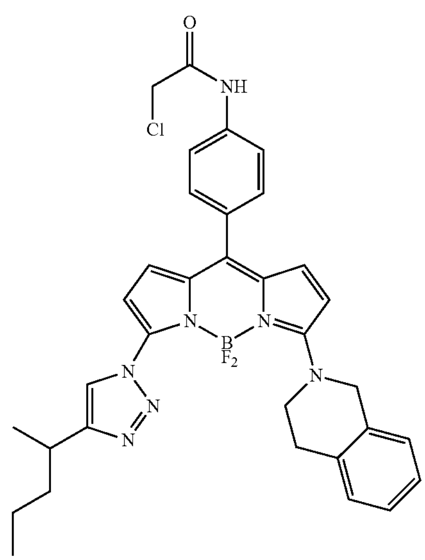 | 99% | 627.25 | 628.7 | 469 | 582 | 3.50 |

TABLE 7-continued

Chemical structures and characterization data for the MKCA compound library.

| Code | Structure | Purity (254 nm) | m/z (calc.) | m/z (exper.) | λ_max Absorp. (nm) | λ_max Emission (nm) | φ (%) |
|---|---|---|---|---|---|---|---|
| MKCA66-4 | 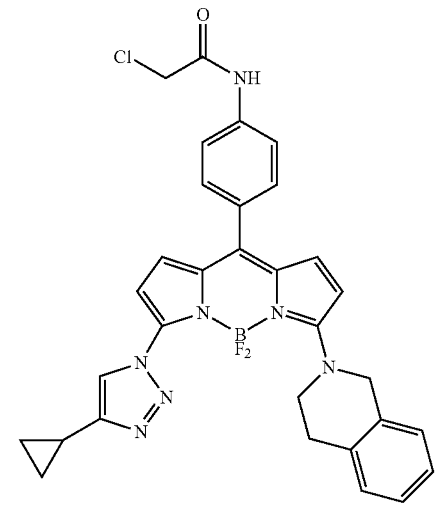 | 99% | 597.2 | 598.6 | 469 | 587 | 3.33 |
| MKCA66-5 | 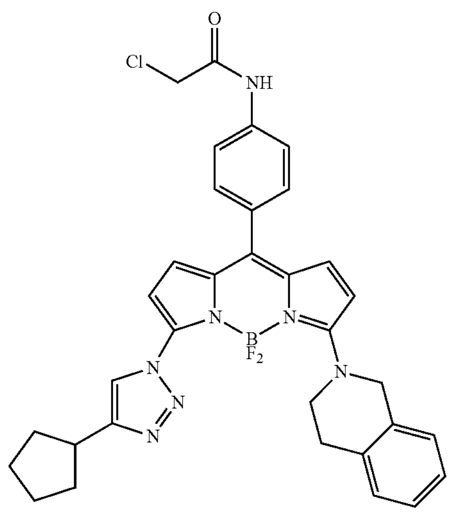 | 99% | 625.23 | 626.7 | 470 | 587 | 3.11 |
| MKCA66-8 | 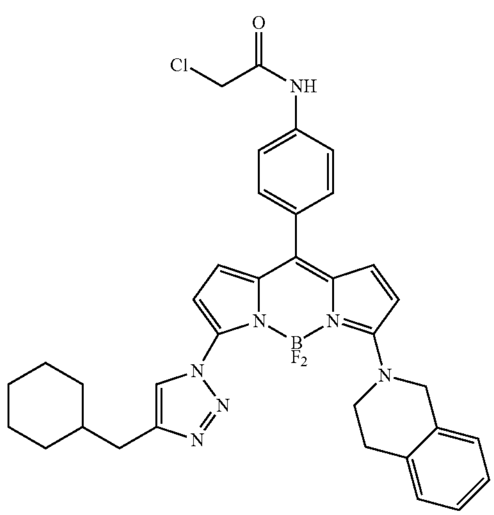 | 99% | 653.26 | 654.7 | 469 | 582 | 3.05 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MKCA66-18 | 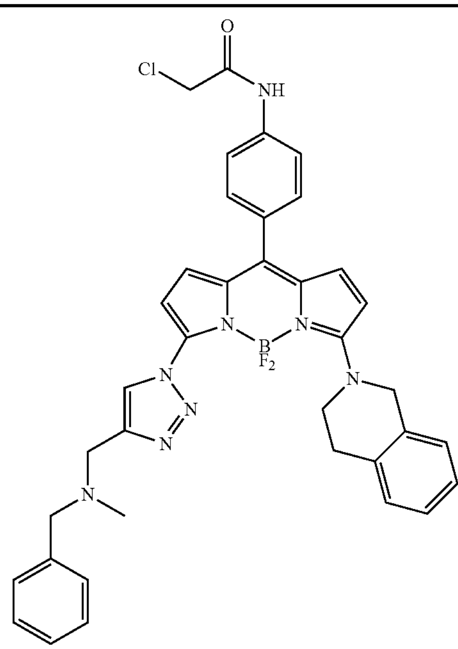 | 87% | 690.26 | 691.7 | 466 | 585 | 2.33 |
| MKCA66-19 | 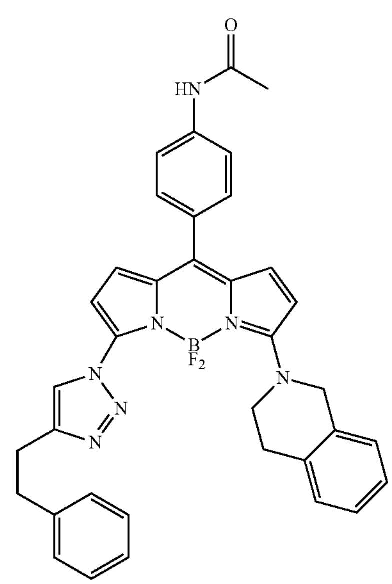 | 99% | 661.23 | 662.7 | 469 | 586 | 3.22 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA66-43 | 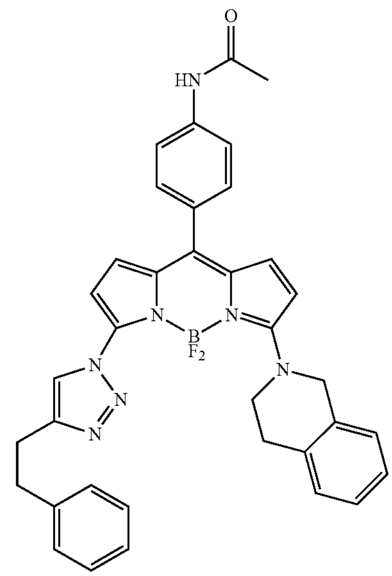 | 99% | 613.23 | 614.7 | 469 | 581 | 3.04 |
| MKCA66-48 | 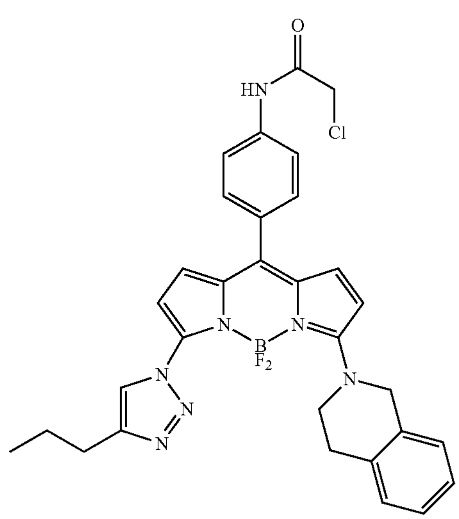 | 99% | 599.22 | 600.6 | 469 | 584 | 3.18 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA66-69 | 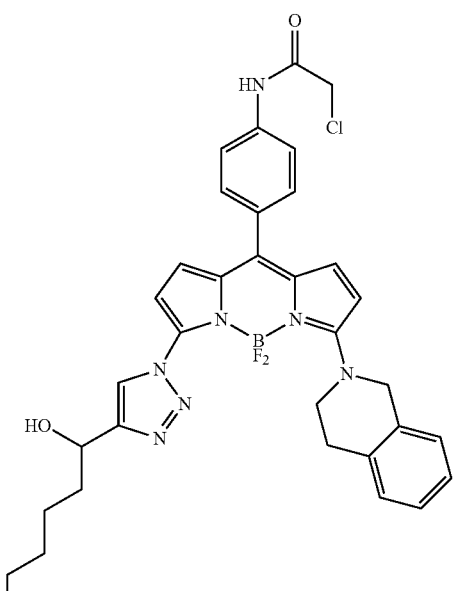 | 99% | 657.26 | 658.7 | 469 | 586 | 3.38 |
| MKCA66-70 | 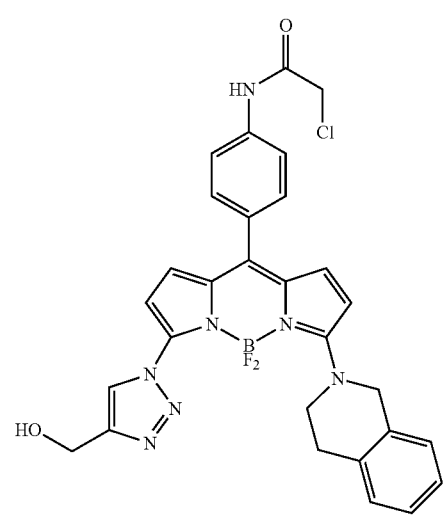 | 99% | 587.18 | 588.6 | 468 | 581 | 2.61 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA101-3 | 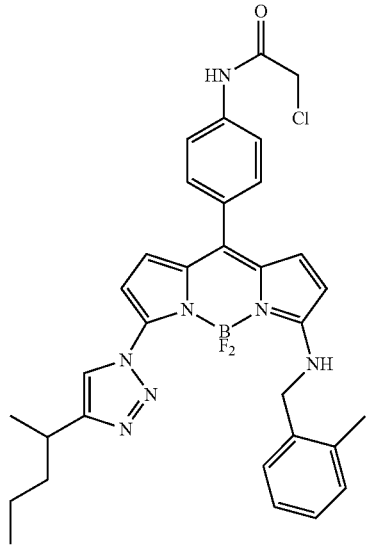 | 94% | 615.25 | 616.7 | 464 | 563 | 31.22 |
| MKCA101-4 | 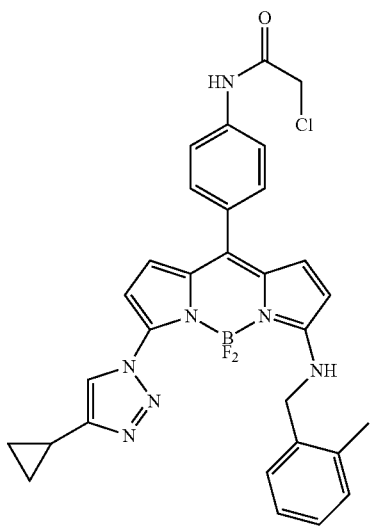 | 99% | 585.2 | 586.6 | 464 | 565 | 34.56 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA101-5 | 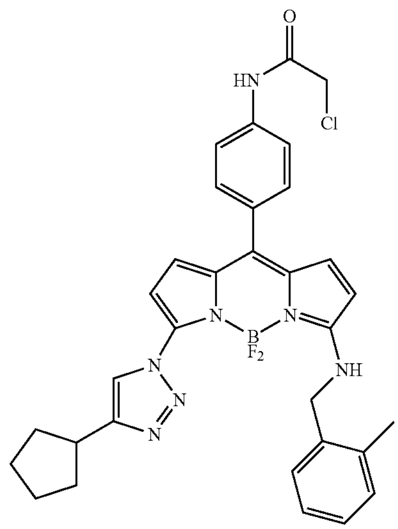 | 99% | 613.23 | 614.7 | 466 | 563 | 31.53 |
| MKCA101-8 | 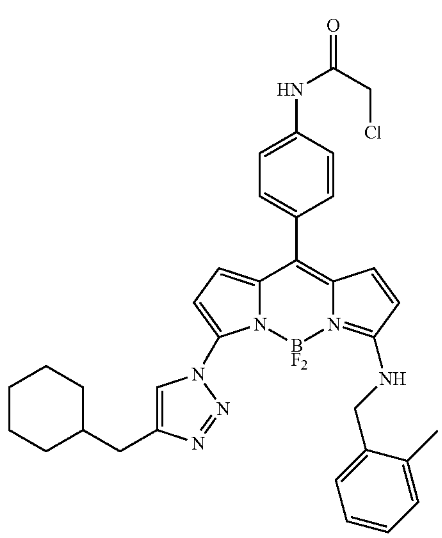 | 99% | 641.26 | 642.7 | 464 | 562 | 30.95 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA101-18 | 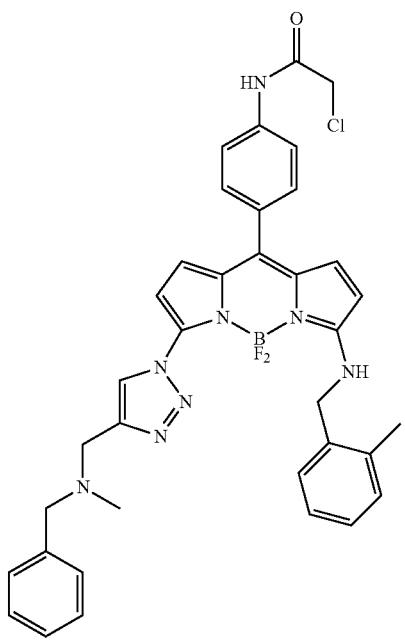 | 62% | 678.26 | 679.7 | 462 | 562 | 21.53 |
| MKCA101-19 | 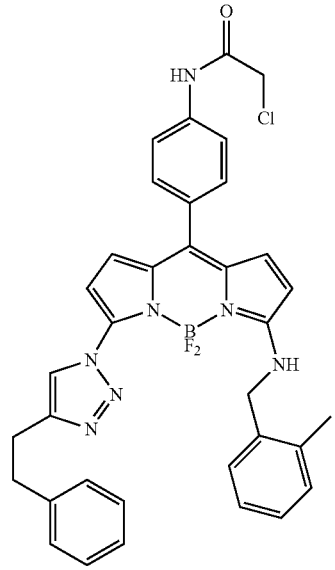 | 93% | 649.23 | 650.7 | 463 | 562 | 33.37 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA101-43 | 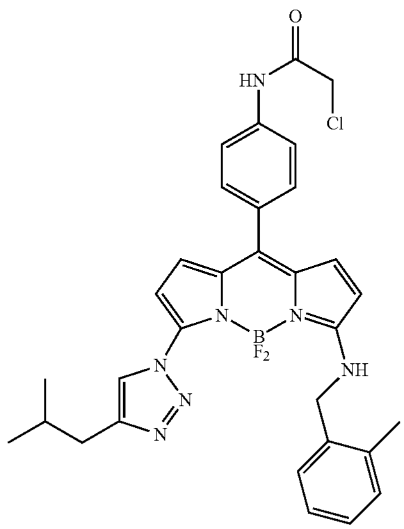 | 99% | 601.23 | 602.6 | 466 | 562 | 29.92 |
| MKCA101-48 | 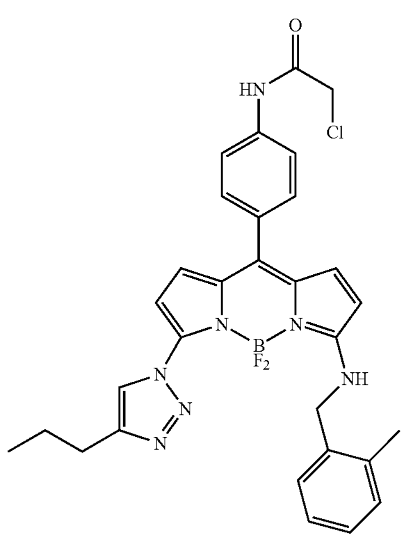 | 88% | 587.22 | 588.6 | 465 | 562 | 28.94 |

TABLE 7-continued

Chemical structures and characterization data for the MKCA compound library.

| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| MKCA101-69 | 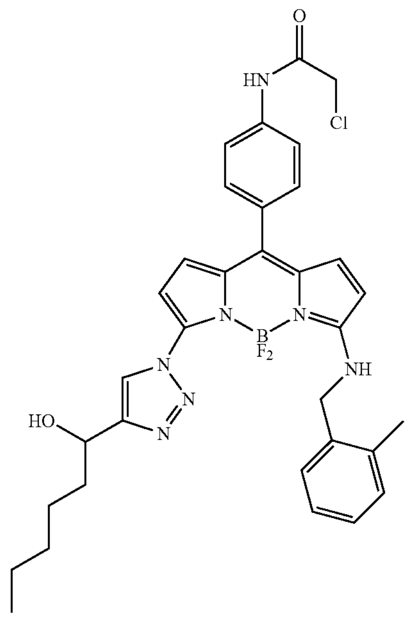 | 88% | 645.26 | 646.7 | 466 | 562 | 21.93 |
| MKCA101-70 | 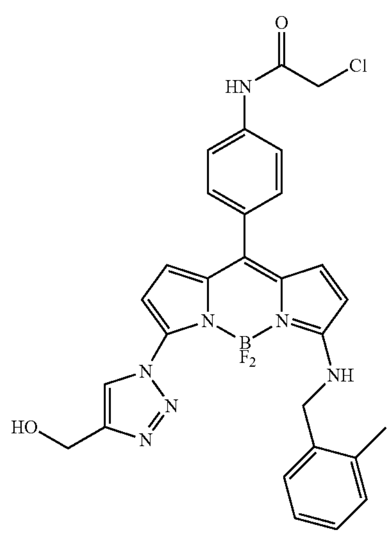 | 78% | 575.18 | 576.6 | 465 | 560 | 21.76 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| MKCA103-3 | 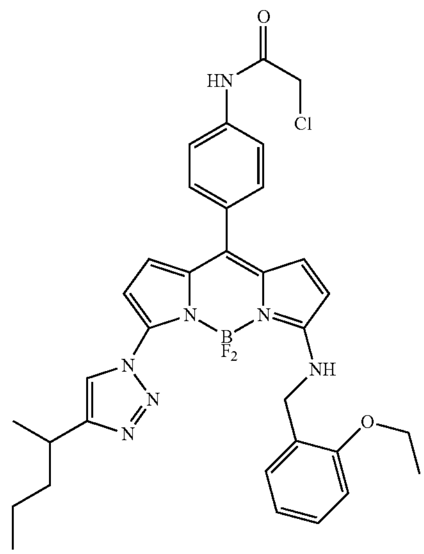 | 99% | 645.26 | 646.7 | 466 | 562 | 23.61 |
| MKCA103-4 | 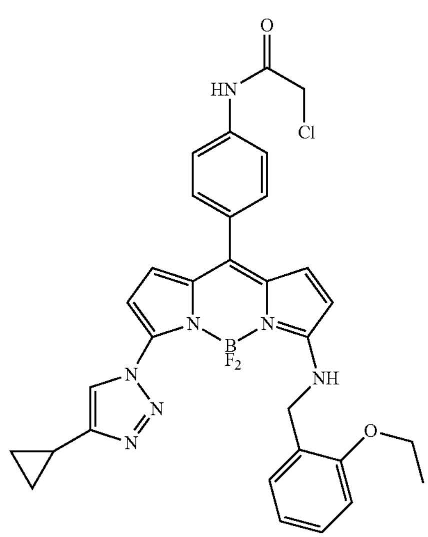 | 91% | 615.21 | 616.6 | 464 | 564 | 36.22 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| MKCA103-5 | 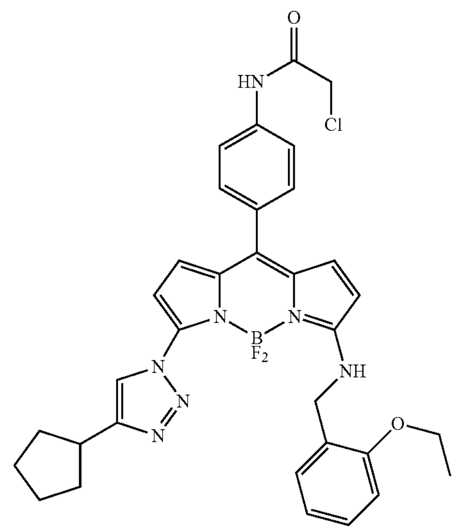 | 99% | 643.24 | 644.7 | 464 | 563 | 33.46 |
| MKCA103-8 | 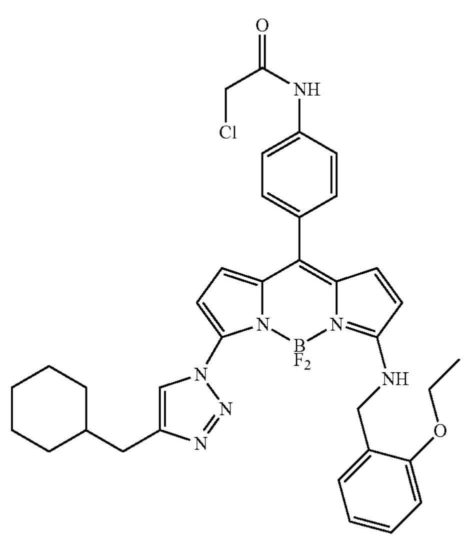 | 92% | 671.27 | 672.7 | 464 | 563 | 37.77 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA103-18 | 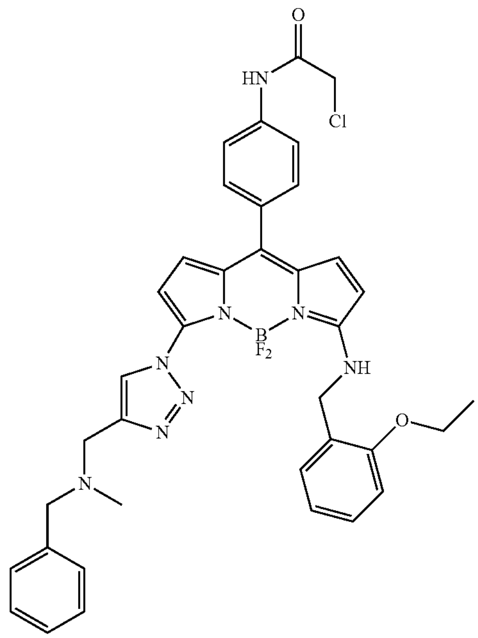 | 79% | 708.27 | 709.7 | 462 | 561 | 24.66 |
| MKCA103-19 | 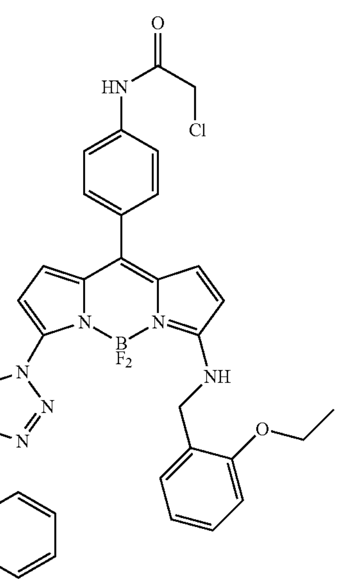 | 97% | 679.24 | 680.7 | 464 | 563 | 36.82 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA103-43 | 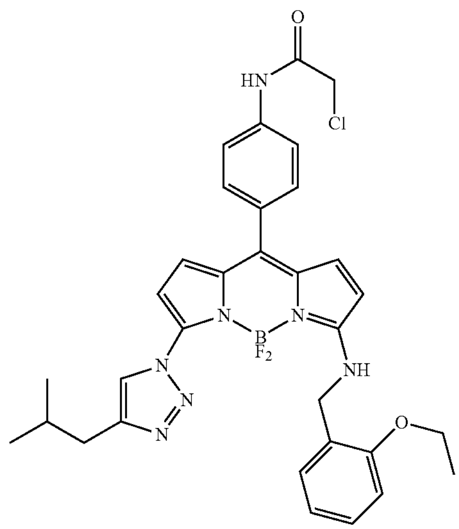 | 99% | 631.24 | 632.7 | 465 | 563 | 33.76 |
| MKCA103-48 | 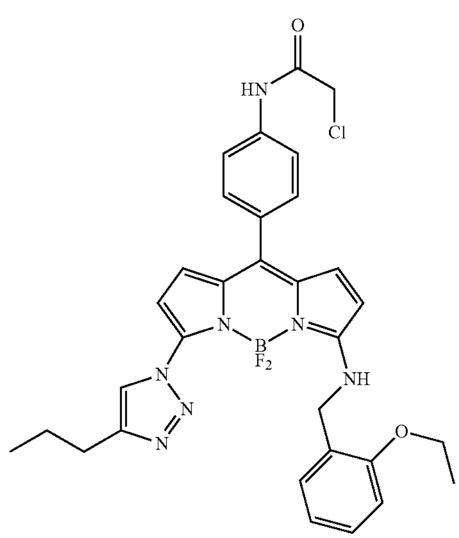 | 92% | 617.23 | 618.7 | 465 | 562 | 38.23 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA103-69 | 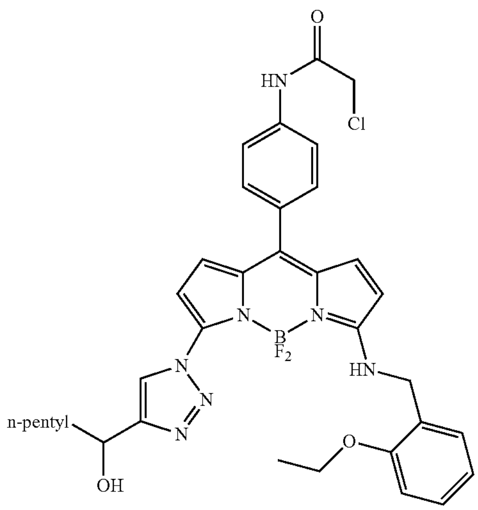 | 86% | 675.27 | 676.6 | 465 | 562 | 33.49 |
| MKCA103-70 | 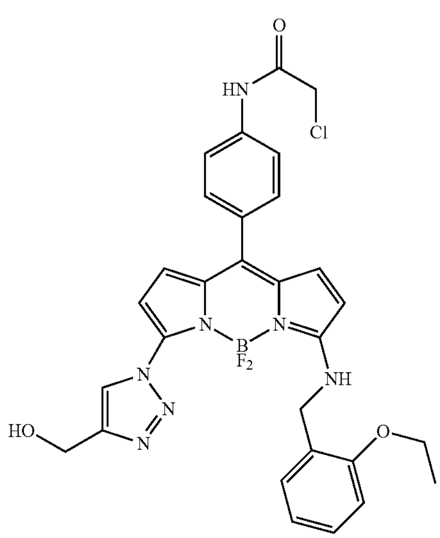 | 99% | 605.19 | 606.6 | 463 | 563 | 20.22 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA181-3 | 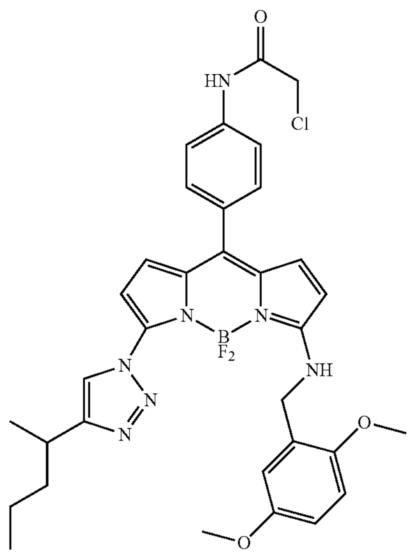 | 95% | 661.25 | 662.7 | 465 | 564 | 21.7754 |
| MKCA181-4 | 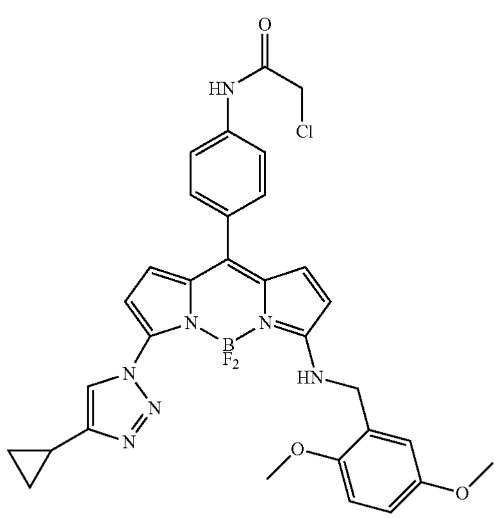 | 99% | 631.21 | 632.6 | 464 | 566 | 19.35 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA181-5 | 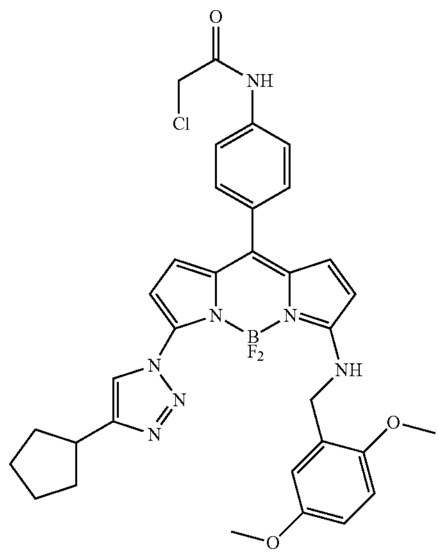 | 99% | 659.24 | 660.7 | 465 | 560 | 25.80 |
| MKCA181-8 | 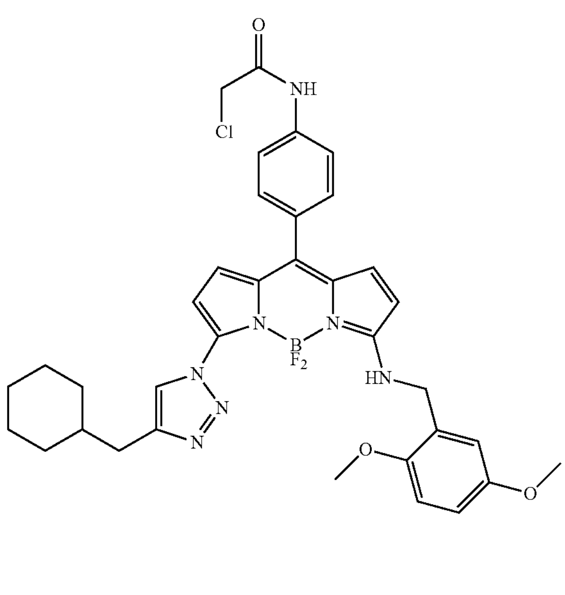 | 99% | 687.27 | 688.7 | 465 | 562 | 20.56 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA181-18 | 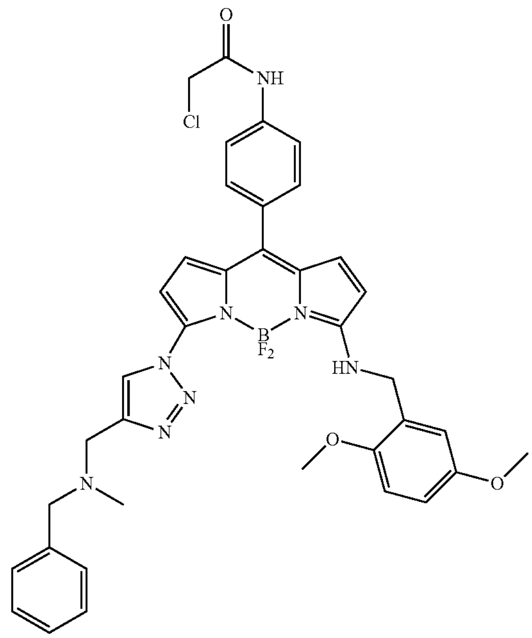 | 68% | 724.27 | 725.7 | 462 | 563 | 21.65 |
| MKCA181-19 | 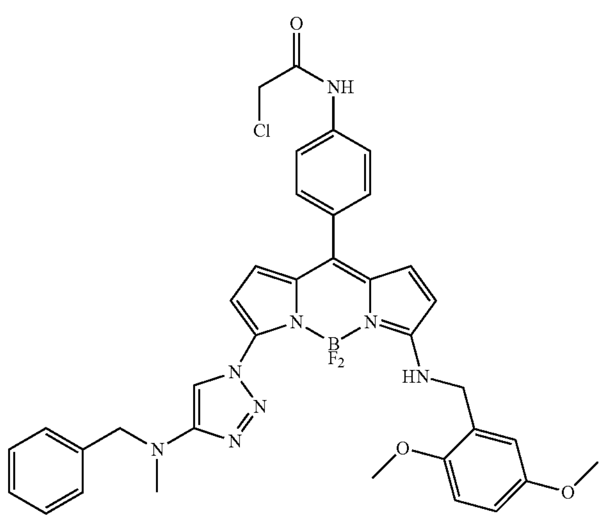 | 99% | 695.24 | 696.7 | 464 | 562 | 21.21 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA181-43 | 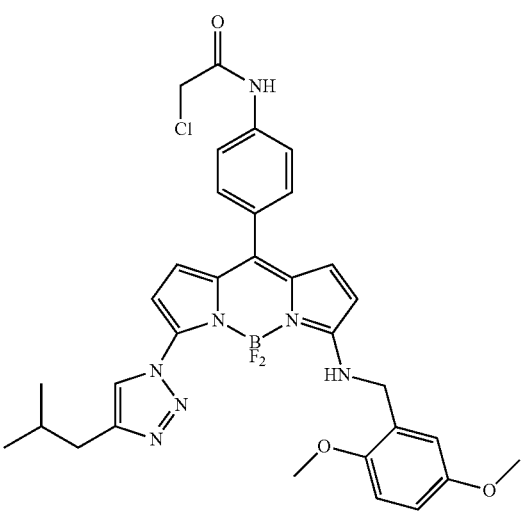 | 99% | 647.24 | 648.7 | 465 | 564 | 21.21 |
| MKCA181-48 | 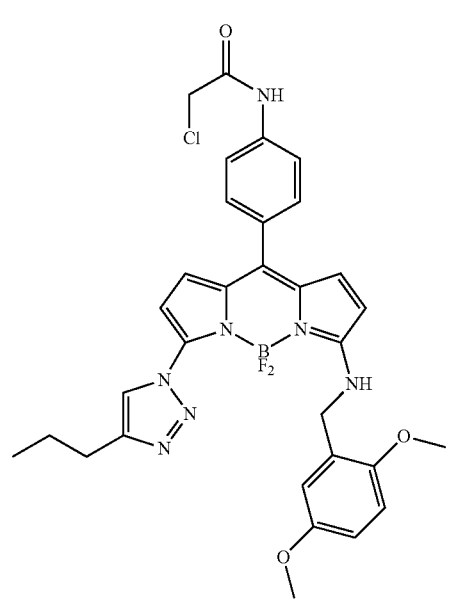 | 99% | 633.22 | 634.7 | 465 | 563 | 20.00 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA181-69 | 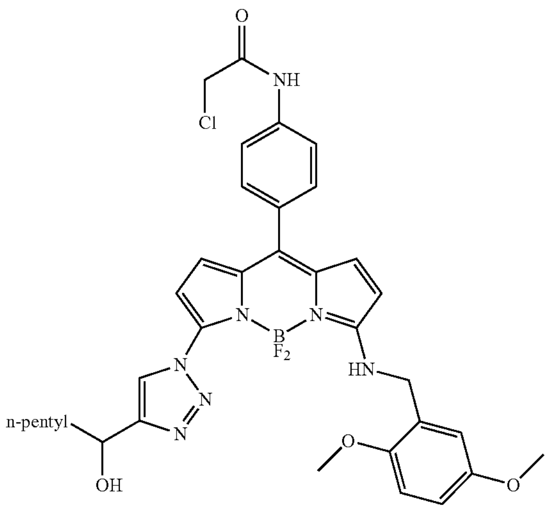 | 99% | 691.26 | 692.7 | 465 | 558 | 14.25 |
| MKCA181-70 | 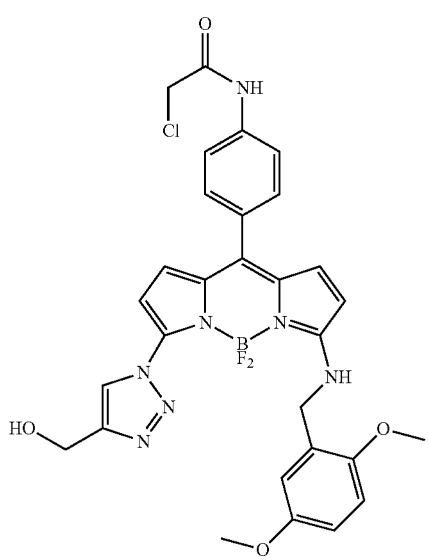 | 99% | 621.19 | 622.6 | 464 | 562 | 19.42 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| MKCA195-3 | 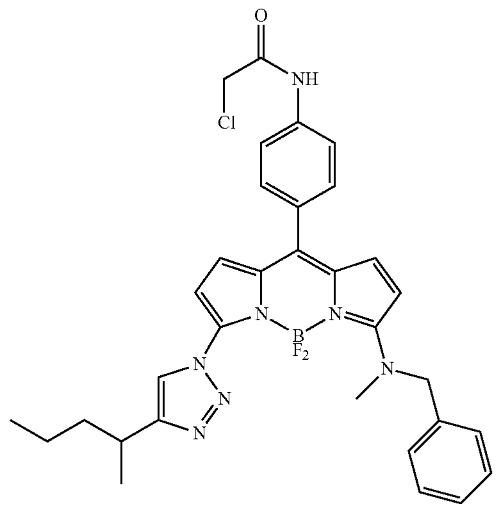 | 88% | 615.25 | 616.7 | 466 | 577 | 7.95 |
| MKCA195-4 | 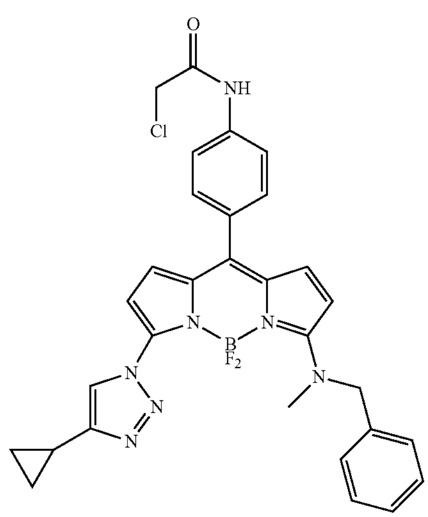 | 86% | 585.2 | 586.6 | 466 | 575 | 7.26 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA195-5 | 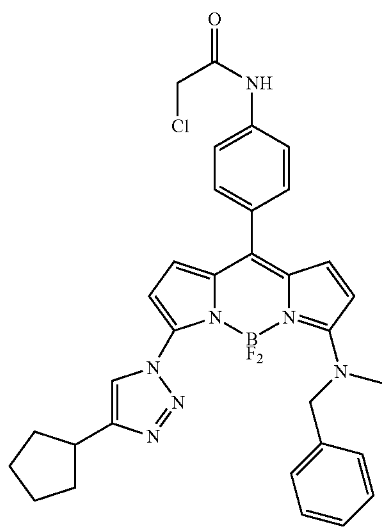 | 91% | 613.23 | 614.7 | 467 | 580 | 4.93 |
| MKCA195-8 | 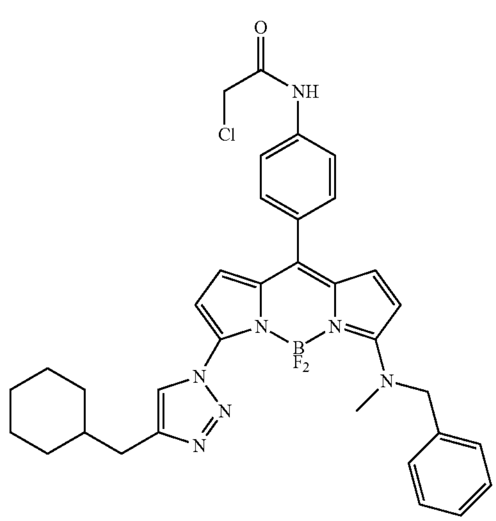 | 93% | 641.26 | 642.7 | 465 | 581 | 6.17 |

TABLE 7-continued

Chemical structures and characterization data for the MKCA compound library.

| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| MKCA195-18 | 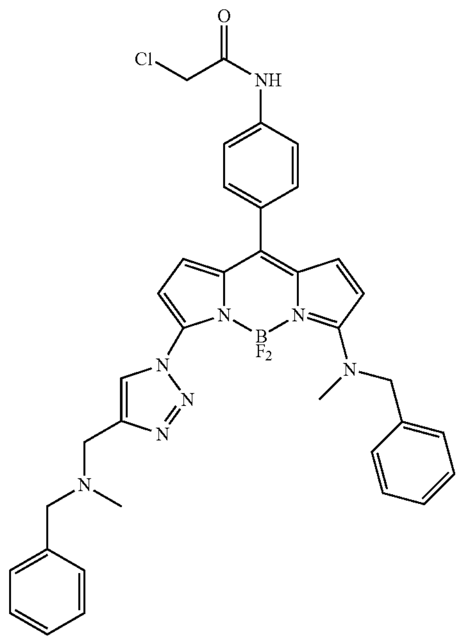 | 82% | 678.26 | 679.7 | 462 | 580 | 3.03 |
| MKCA195-19 | 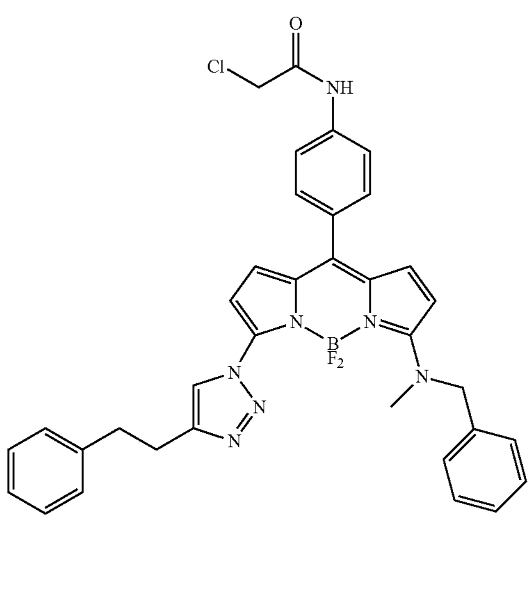 | 90% | 649.23 | 650.6 | 467 | 586 | 6.77 |

315
316
TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA195-43 | 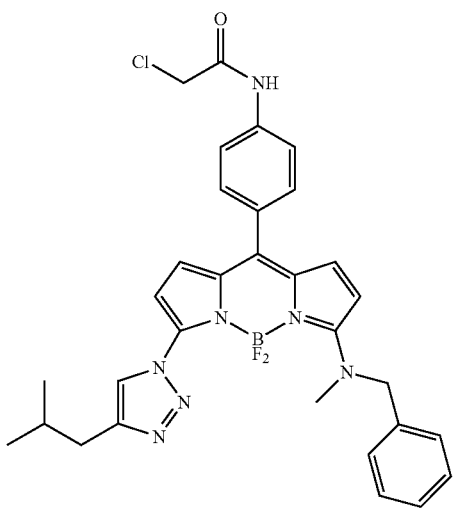 | 88.6 | 601.23 | 602.6 | 465 | 575 | 4.97 |
| MKCA195-48 | 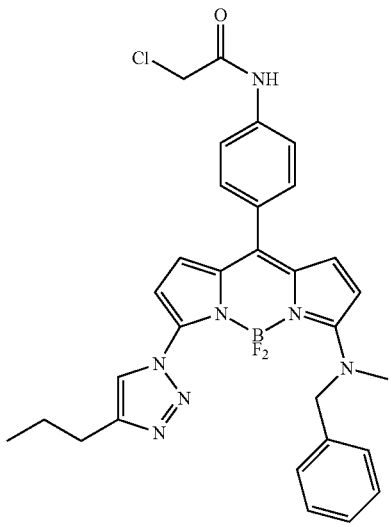 | 99% | 537.22 | 538.6 | 466 | 583 | 5.43 |

TABLE 7-continued
Chemical structures and characterization data for the MKCA compound library.
| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| MKCA195-69 | 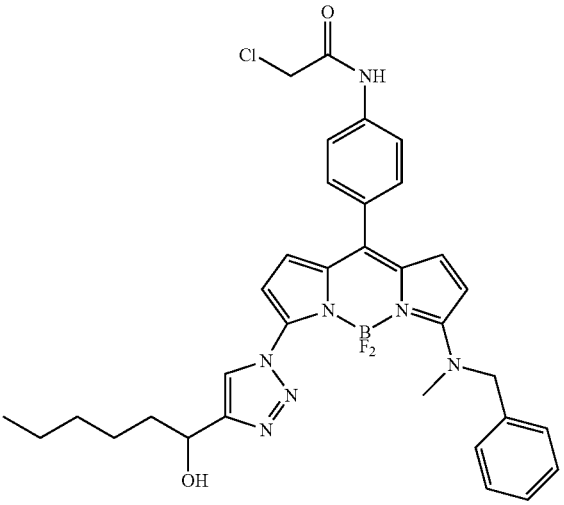 | 95% | 645.26 | 646.7 | 466 | 582 | 4.20 |
| MKCA195-70 | 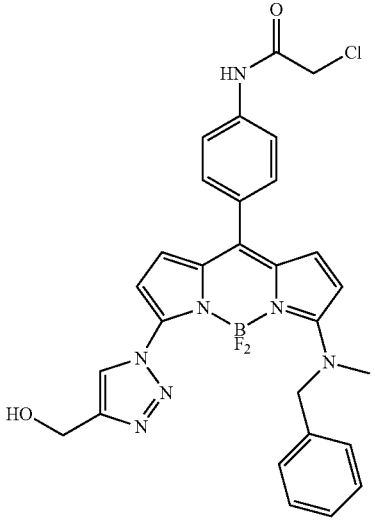 | 99% | 575.18 | 576.6 | 465 | 581 | 2.58 |
| MKCA215-3 | 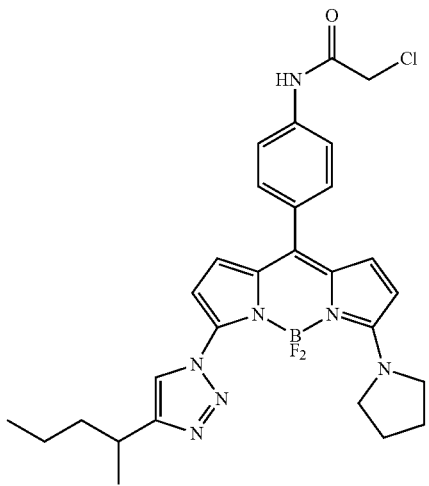 | 92% | 565.23 | 566.7 | 463 | 569 | 3.99 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA215-4 | 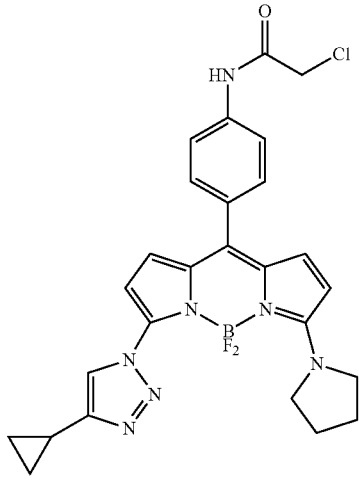 | 99% | 544.19 | 536.6 | 462 | 570 | 3.35 |
| MKCA215-5 | 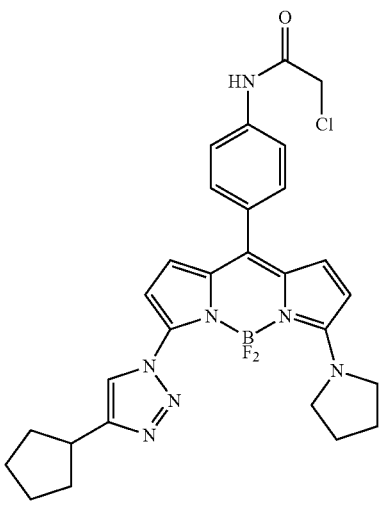 | 86% | 563.22 | 564.6 | 463 | 574 | 1.94 |
| MKCA215-8 | 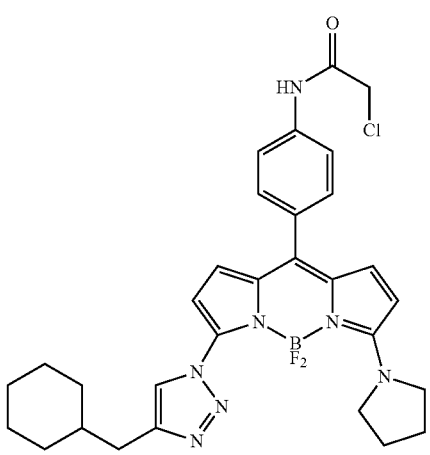 | 99% | 591.25 | 592.6 | 463 | 564 | 2.66 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA215-18 | 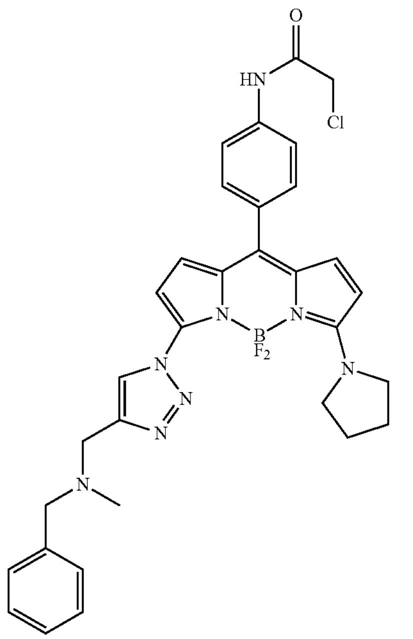 | 99% | 628.24 | 629.7 | 461 | 577 | 2.62 |
| MKCA215-19 | 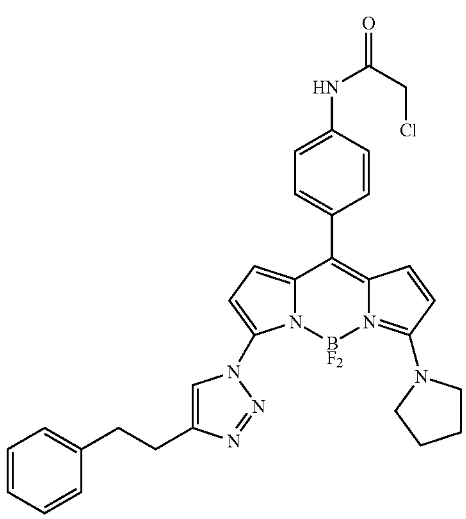 | 99% | 599.22 | 600.6 | 463 | 573 | 4.98 |

TABLE 7-continued

Chemical structures and characterization data for the MKCA compound library.

| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| MKCA215-43 | 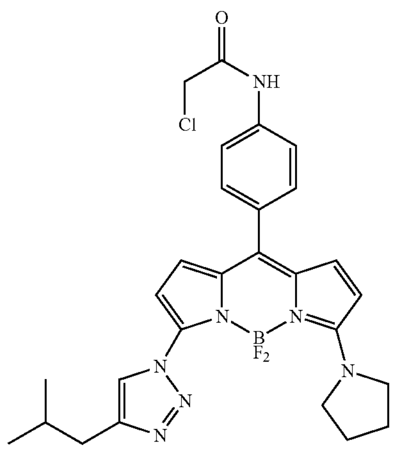 | 99% | 551.22 | 552.6 | 461 | 570 | 4.04 |
| MKCA215-48 | 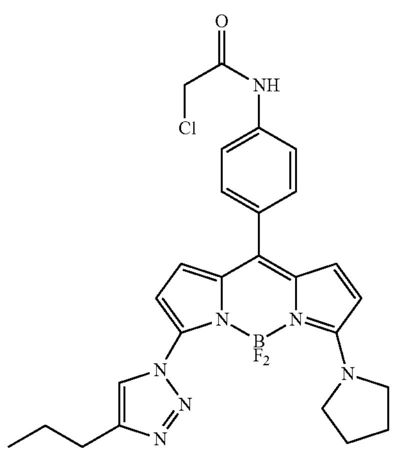 | 96% | 537.2 | 538.6 | 462 | 565 | 4.60 |
| MKCA215-69 | 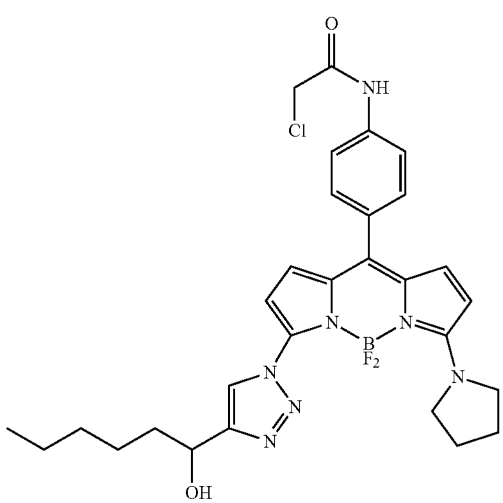 | 58% | 595.24 | 596.7 | 462 | 569 | 3.42 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
| --- | --- | --- | --- | --- | --- | --- | --- |
| MKCA215-70 | 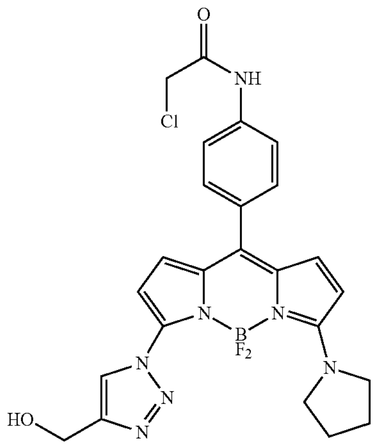 | 99% | 525.17 | 526.6 | 459 | 568 | 1.97 |
| MKCA412-3 | 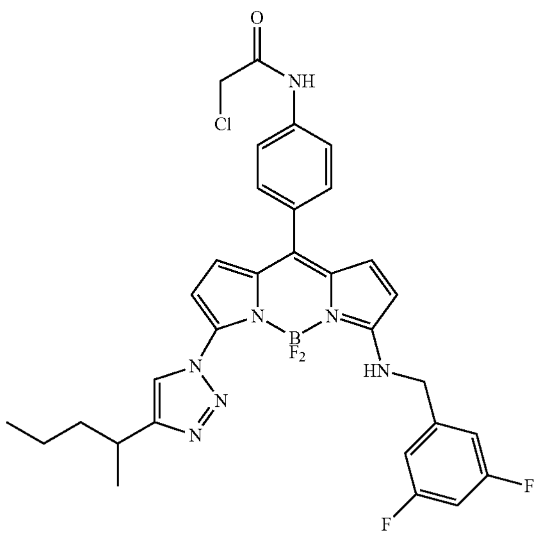 | 98% | 637.21 | 638.7 | 467 | 563 | 41.81 |
| MKCA412-4 | 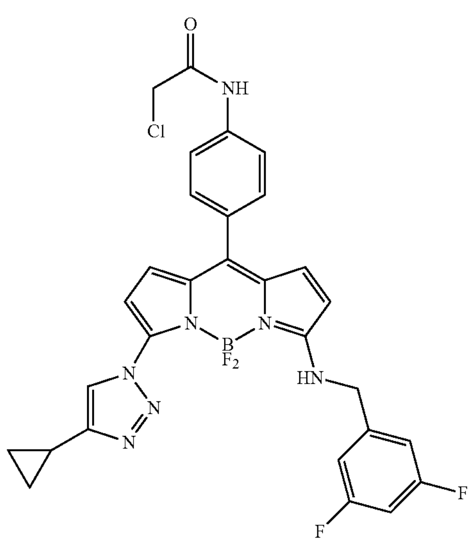 | 99% | 607.17 | 608.6 | 467 | 563 | 36.25 |

TABLE 7-continued

Chemical structures and characterization data for the MKCA compound library.

| Code | Structure | Purity (254 nm) | m/z (calc.) | m/z (exper.) | λ$_{max}$ Absorp. (nm) | λ$_{max}$ Emission (nm) | φ (%) |
|---|---|---|---|---|---|---|---|
| MKCA412-5 | 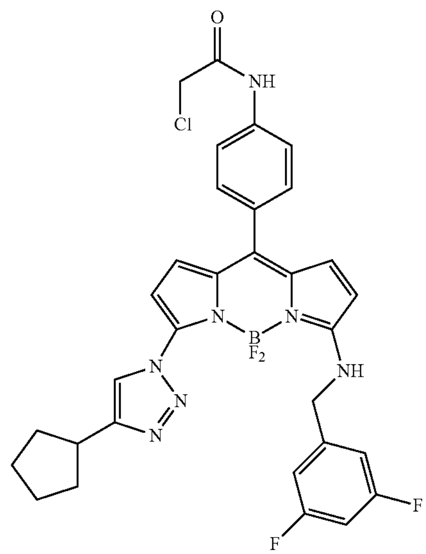 | 97% | 635.2 | 636.6 | 468 | 563 | 41.21 |
| MKCA412-8 | 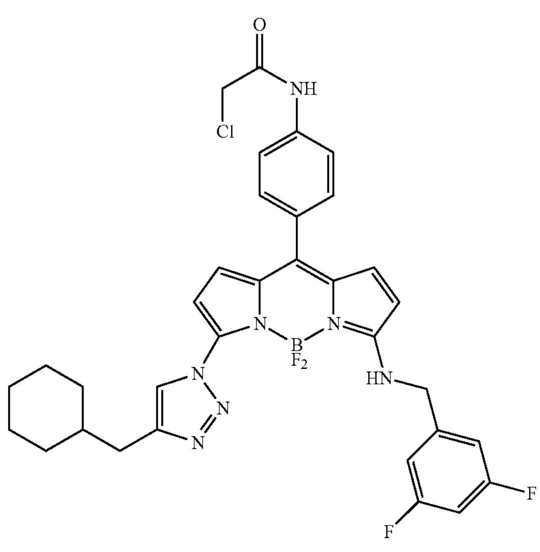 | 99% | 663.23 | 664.7 | 467 | 564 | 36.92 |

TABLE 7-continued
Chemical structures and characterization data for the MKCA compound library.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA412-18 | 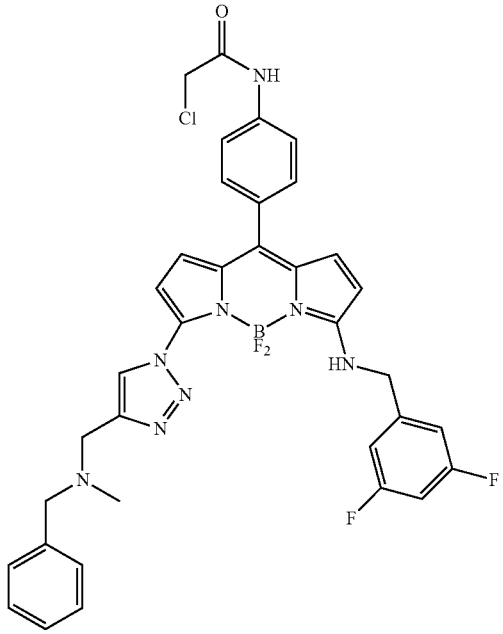 | 62% | 700.23 | 701.7 | 463 | 560 | 26.25 |
| MKCA412-19 | 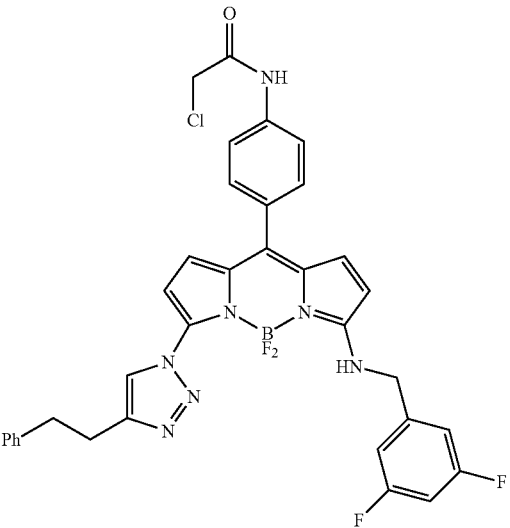 | 99% | 671.2 | 672.6 | 466 | 563 | 42.58 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA412-43 | 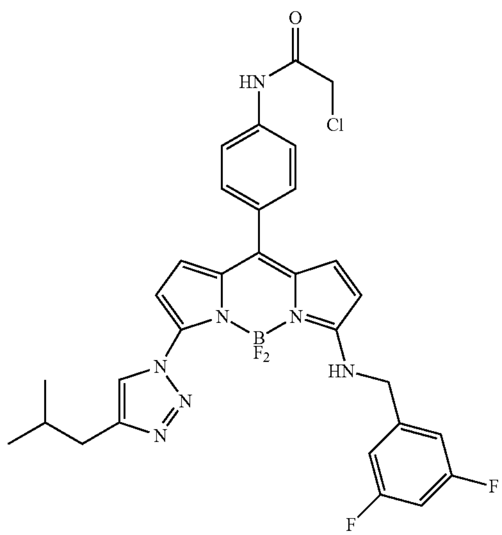 | 99% | 623.2 | 624.6 | 468 | 563 | 37.83 |
| MKCA412-48 | 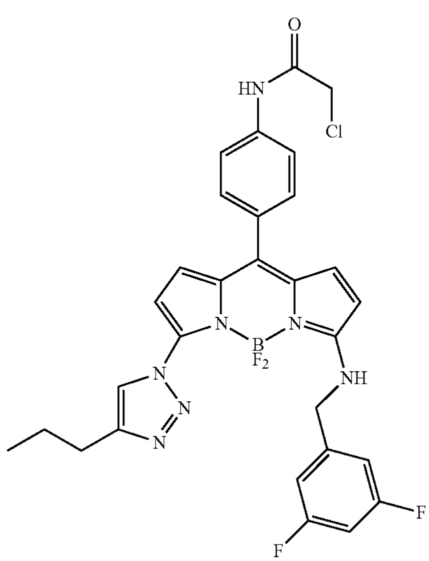 | 95% | 609.18 | 610.6 | 466 | 561 | 36.09 |

TABLE 7-continued

Chemical structures and characterization data for the MKCA compound library.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKCA412-69 | 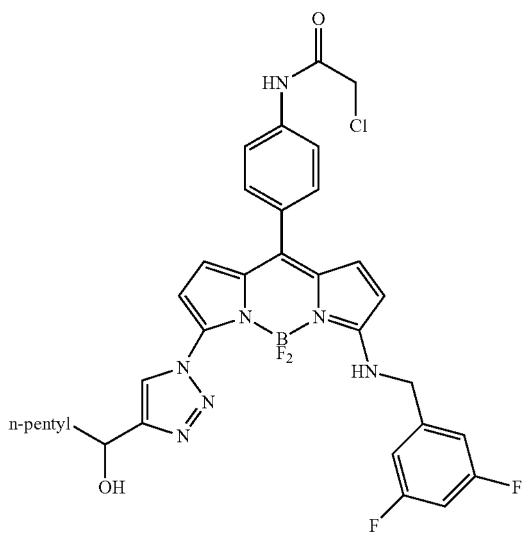 | 99% | 667.22 | 668.7 | 465 | 562 | 30.05 |
| MKCA412-70 | 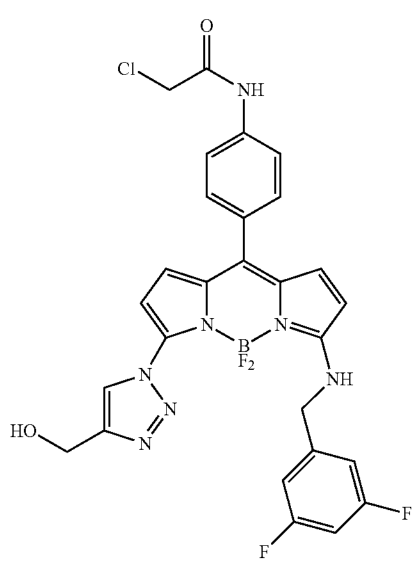 | 58% | 596.15 | 598.6 | 464 | 562 | 6.28 |

TABLE 8

Chemical structures and characterization data for the MKHA compounds.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKHA101-3 | | 99% | 597.47 | 598.2 | 468 | 560 | 0.4121 |
| MKHA103-3 | | 95% | 627.49 | 628.2 | 470 | 556 | 0.2361 |

TABLE 8-continued

Chemical structures and characterization data for the MKHA compounds.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKHA374-3 | 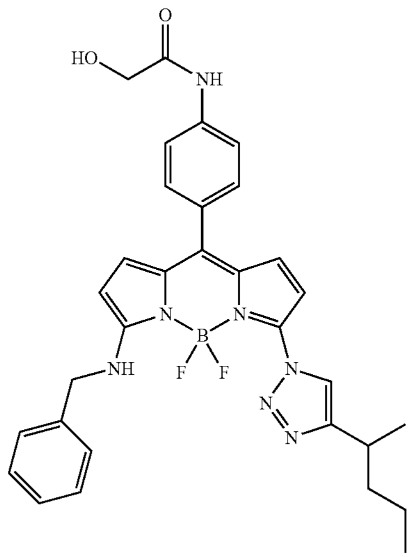 | 98% | 583.44 | 584.2 | 470 | 557 | 0.4121 |
| MKHA381-3 | 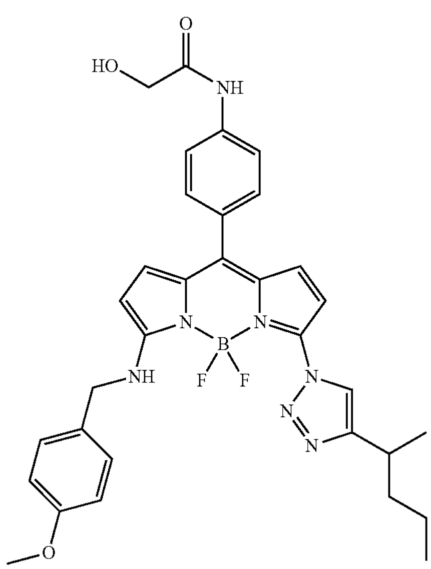 | 99% | 613.47 | 614.2 | 470 | 556 | 0.4258 |

TABLE 8-continued

Chemical structures and characterization data for the MKHA compounds.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKHA522-3 | | 99% | 639.55 | 640.4 | 470 | 559 | 0.4181 |
| MKHA101-1 | | 99% | 583.44 | 584.4 | 469 | 556 | 0.3122 |

TABLE 8-continued

Chemical structures and characterization data for the MKHA compounds.

| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKHA101-4 | 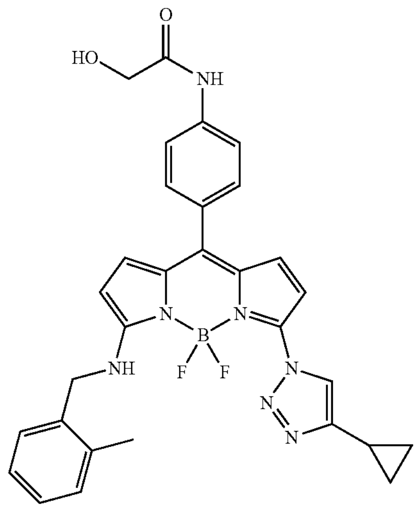 | 96% | 567.40 | 568.2 | 469 | 558 | 0.3456 |
| MKHA101-42 | 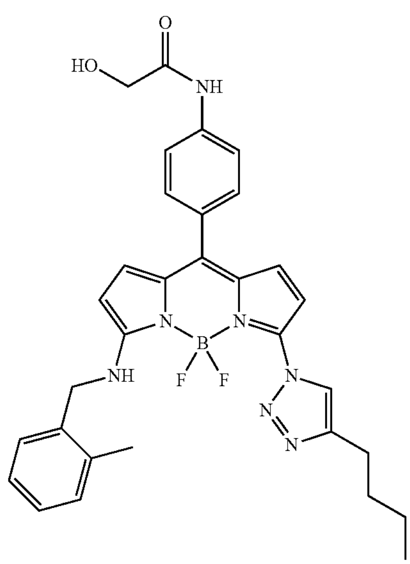 | 97% | 583.44 | 584.2 | 469 | 560 | 0.3153 |

TABLE 8-continued
Chemical structures and characterization data for the MKHA compounds.
| Code | Structure | Purity (254 nm) | m/z (calc.) | m/z (exper.) | $\lambda_{max}$ Absorp. (nm) | $\lambda_{max}$ Emission (nm) | φ (%) |
|---|---|---|---|---|---|---|---|
| MKHA101-43 | 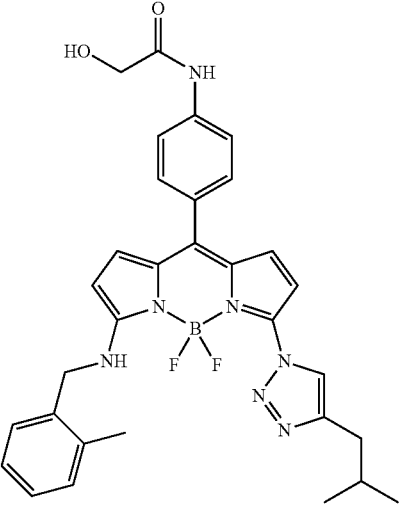 | 99% | 583.44 | 584.2 | 468 | 558 | 0.0498 |
| MKHA374-1 | 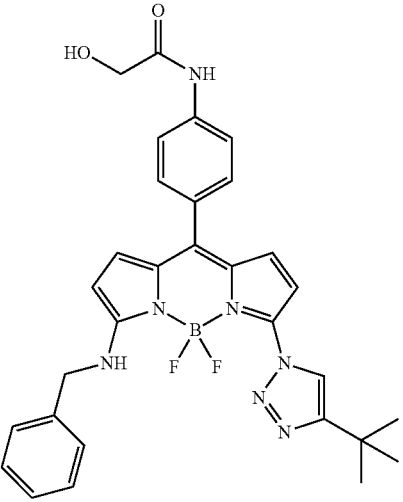 | 99% | 569.42 | 570.2 | 470 | 558 | 0.399 |
| MKHA374-4 | 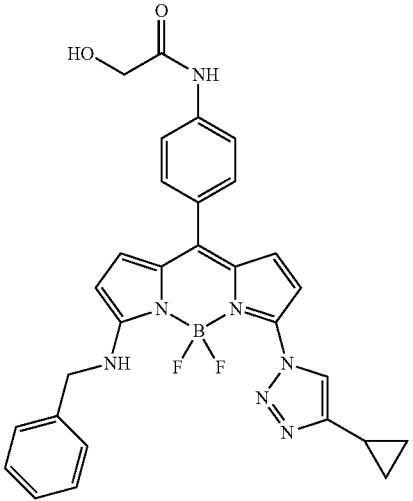 | 96% | 553.37 | 554.2 | 469 | 558 | 0.3682 |

TABLE 8-continued

Chemical structures and characterization data for the MKHA compounds.

| Code | Structure | Purity (254 nm) | m/z (calc.) | m/z (exper.) | $\lambda_{max}$ Absorp. (nm) | $\lambda_{max}$ Emission (nm) | $\phi$ (%) |
|---|---|---|---|---|---|---|---|
| MKHA374-48 | 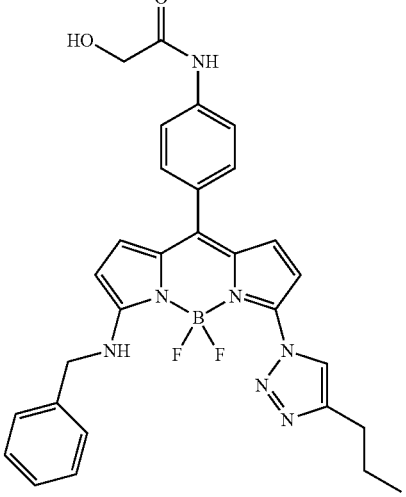 | 97% | 555.39 | 556.2 | 468 | 557 | 0.3684 |

Example 2

Figure 3:
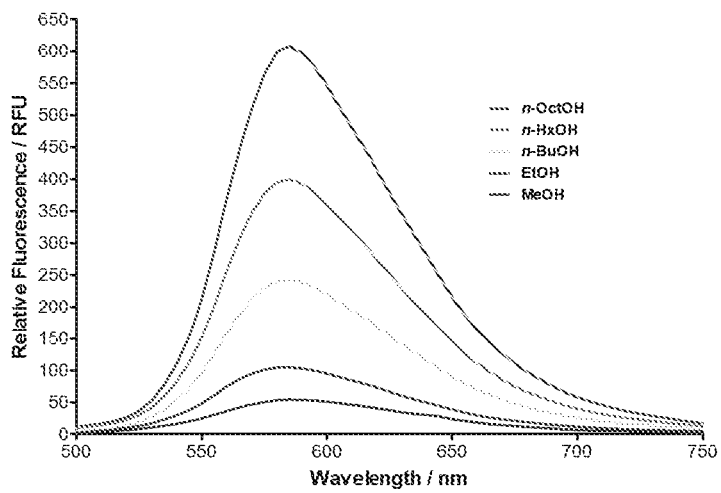
FIG. 3 shows the effect of solvent viscosity on the fluorescence intensity of BDC-9 (100 µM) at rt. Intensity of BDC-9 systematically increased in more viscous alcohols when in n-octanol and n-hexanol.

Analysis of Amino-Triazolyl BODIPY Compounds as Fluorescent Molecular Rotors The fluorescence spectra of compound (BDC-9) in different solvents of similar polarities but covering a range of viscosities were analyzed. As shown in FIG. 3, a strong correlation between fluorescence intensity and viscosity was observed. Increased solvent viscosity reduces bond rotation at positions 3 and 5 of the BODIPY core, which, without being bound to theory, minimizes non-radiative energy loss and leads to higher quantum yields (24). This result confirms the potential of amino-triazolyl BODIPYs as fluorescent molecular rotors.

Example 3

Identification of a Selective HSA Fluorescent Probe

Materials and Methods

Mixtures of BDC-9 with HSA were prepared in phosphate buffer (pH 7.3, 1% DMSO) at room temperature and fluorescence measurements were taken after incubation for 2 h unless otherwise stated.

In Vitro Fluorescence Screening

Amino-triazolyl-BODIPYs (10 μM) were screened in 10 mM HEPES buffer, pH 7.4, containing 1% DMSO. Fluorescence intensities were measured using a SpectraMax M2 platereader in 384-well plates. Excitation was provided at each compound's excitation range, and emission spectrum was obtained starting from at least 30 nm beyond the excitation wavelength. All the analytes were tested at four serial concentrations.

Figure 4:
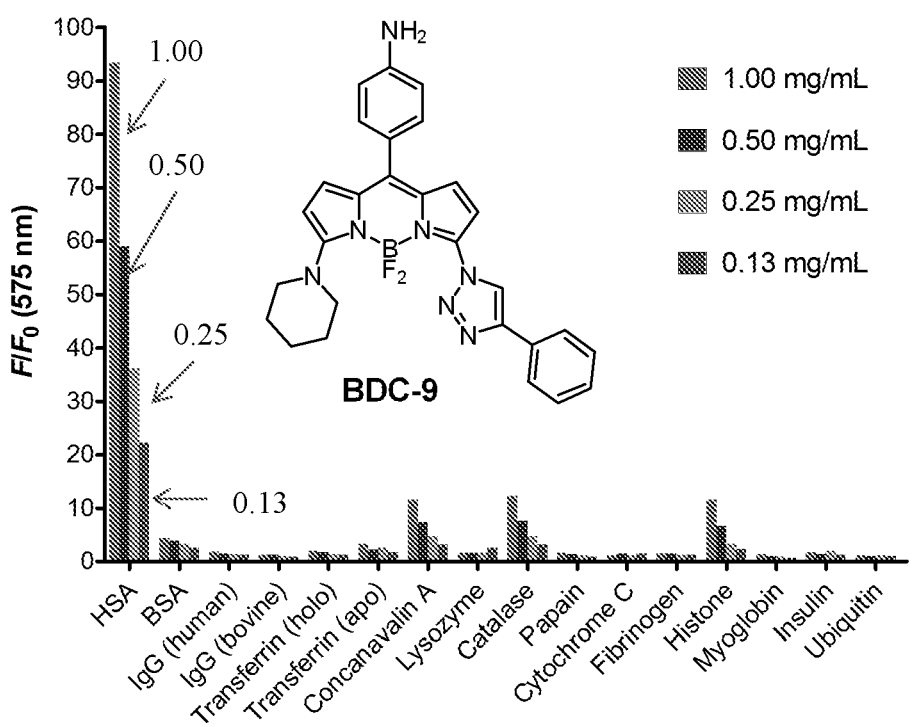
FIG. 4 shows the fluorescence response (F) of BDC-9 (10 µM) toward 16 different proteins at various concentrations (0.13, 0.25, 0.50, 1.00 mg/mL) in 10 mM HEPES buffer (pH 7.4); $\lambda_{exc.}$: 460 nm, $\lambda_{em.}$: 575 nm). $F_0$ is the fluorescence intensity of BDC-9 in HEPES buffer. Values are represented as means (n=4).

The fluorescent response of BDC, BDCAC and BDCCA was examined against 84 biologically relevant analytes that were categorized into nine different sets (i.e. pH standards, viscous solutions, genetic macromolecules, peptides, metal ions, redox molecules, nucleic acids, proteins and other metabolites). Amino-triazolyl-BODIPY compounds showed significant fluorescence increase upon incubation with certain specific proteins. As a representative example, the compound BDC-9 displayed a remarkable selectivity towards human serum albumin (HAS) when compared to other proteins and analytes (FIG. 4).

Figure 5:
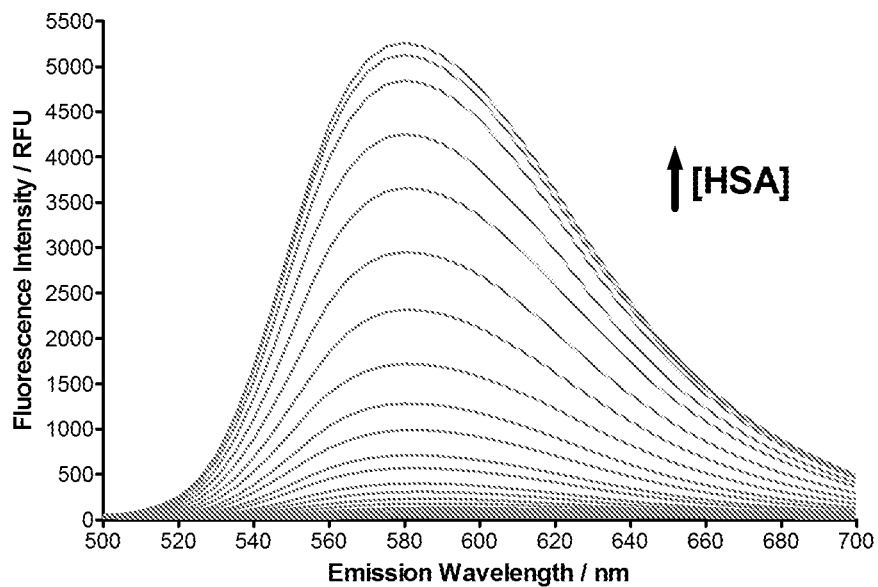
FIG. 5 shows the fluorescence spectra of BDC-9 (10 µM) upon incubation with serial dilutions of HSA (from $1.2 \times 10^{-4}$ to 4 mg/mL) in phosphate buffer, $\lambda_{exc.}$: 460 nm. Values are represented as means (n=3).
Figure 6:
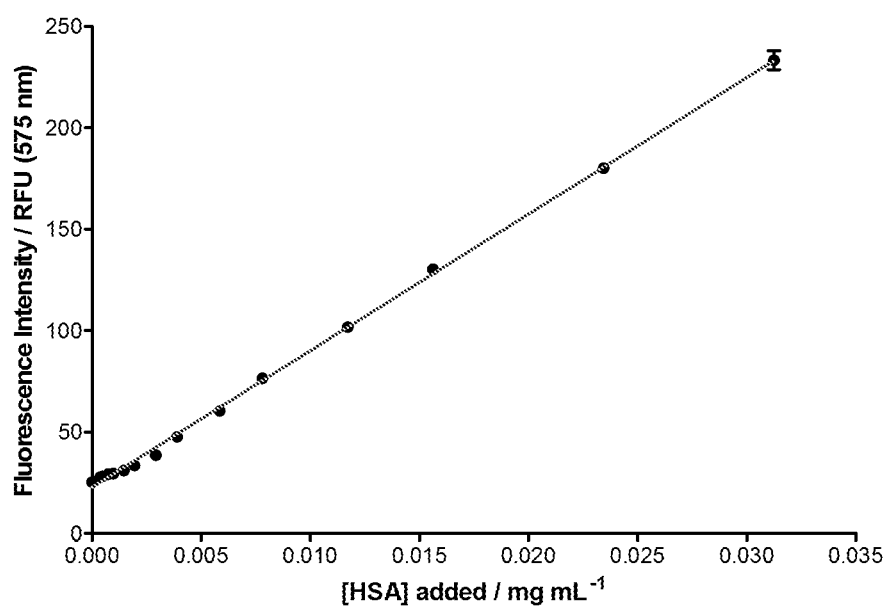
FIG. 6 shows the fluorescence emission response of BDC-9 (10 µM) upon incubation with serial dilutions of HSA; $\lambda_{exc.}$: 460 nm, $\lambda_{em.}$: 575 nm; values are represented as means and error bars as standard deviations (n=3); LOD=0.3 µg/mL; linear range=0.37 to 31 µg/mL, $R^2$=0.999.

In addition to its high selectivity, BDC-9 showed a significant 220-fold increase in fluorescence upon binding to HSA (FIG. 5). The response of BDC-9 proved to be linear within a dynamic range between 0.37 and 31 μg/mL, and the limit of detection of HSA (S/N=3) was determined as 0.3 μg/mL (FIG. 6).

Figure 7:
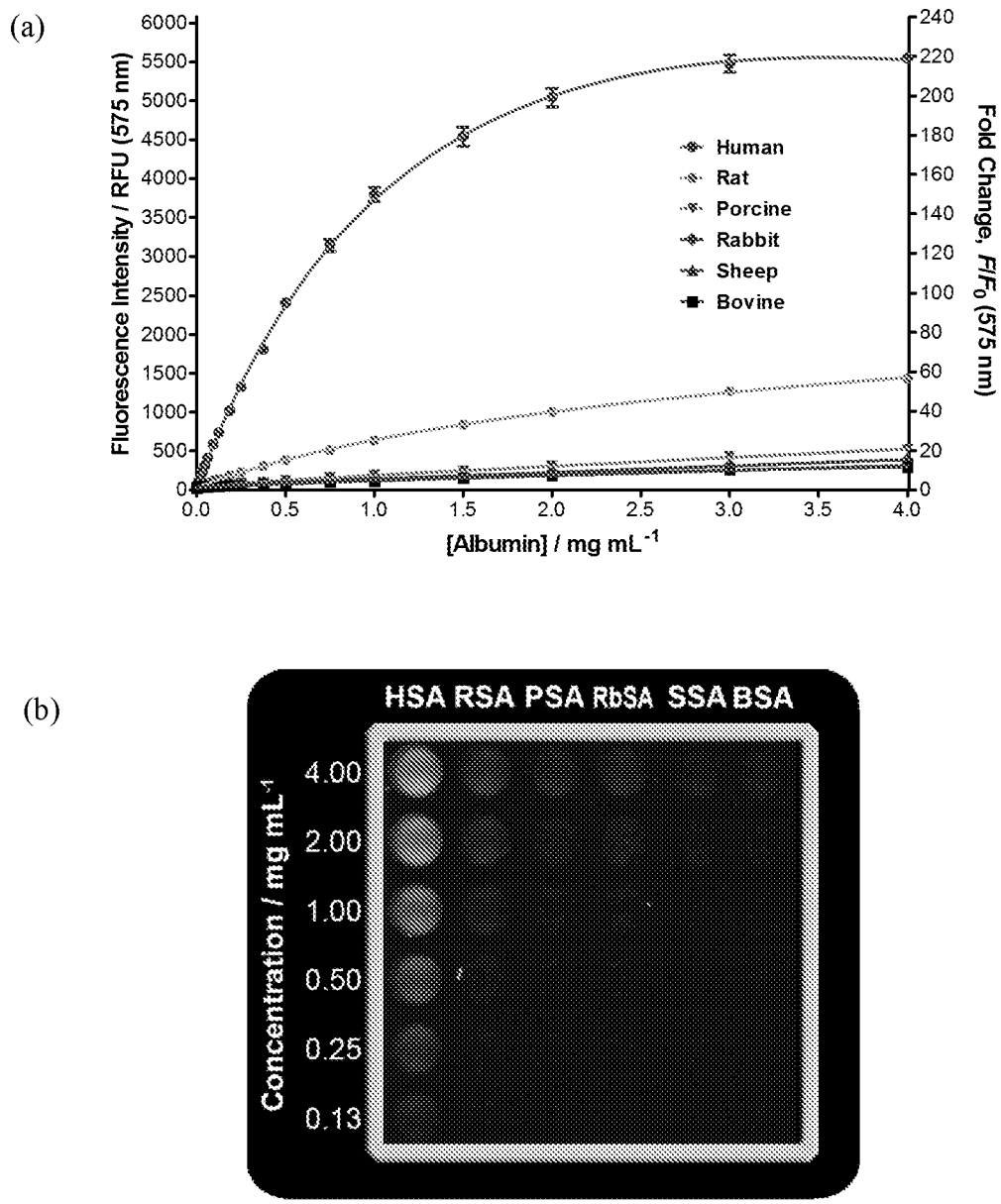
FIGS. 7a and 7b show species selectivity of BDC-9. Specifically.

The selectivity of BDC-9 towards serum albumins from different species was investigated. Serum albumins represent a family of proteins with a high degree of similarity in their primary sequence across various species (~75% homology) (34,39,40,62). Yet, some albumin ligands have been found to show species dependent binding differences, and the development of species-selective probes may be useful for structural studies of albumin binding sites (63-67). The fluorescence response of BDC-9 was evaluated against serial concentrations of serum albumins from rat (RSA), porcine (PSA), rabbit (RbSA), sheep (SSA) and bovine (BSA). As shown in FIGS. 7a-b, BDC-9 displayed a marked selectivity towards HSA with marginal response on the other species (68,69).

Example 4

Analysis of the Binding of BDC-9 at HSA

The binding properties of BDC-9 were studied. HSA consists of at least nine binding sites (34-38), amongst which fatty acid (FA) sites 1, 3 and 4 (Sudlow Site II), 5, 6 and 7 (Sudlow Site I) are known to have affinity for drug compounds (31,39-44). A recent report has demonstrated the importance of the third major drug binding site on HSA, which corresponds to Fatty Acid 1 site (FA1) (70). To verify specific binding and determine the binding site(s) of BDC-9 in HSA, competition assays using drugs binding to the respective sites (e.g. hemin (FA1 site)(71,72), dansyl-L-norvaline (FA3/4 sites) (73), propofol (FA3/4 and FA5 sites) (35), ibuprofen (FA3/4 and FA6 sites) (74) and warfarin (FA7 site) (74) were performed (75).

Figure 8:
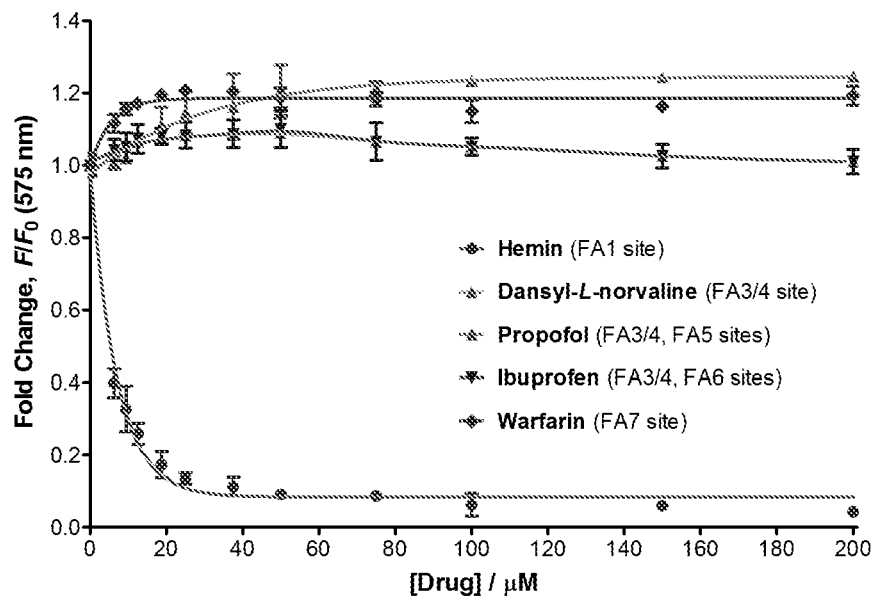
FIG. 8 shows competition with site-selective HSA-binding drugs. HSA (fatty-acid free) (0.34 mg/mL, 5 µM) was preincubated for 2 h in phosphate buffer with different concentrations of the drugs (up to 200 µM) before BDC-9 (10 µM) was added. F is the fluorescence intensity at the indicated drug concentration and $F_0$ is the fluorescence intensity with no drug added; $\lambda_{exc.}$: 460 nm, $\lambda_{em.}$: 575 nm; values are represented as means and error bars as standard deviations (n=3).

As illustrated in FIG. 8, only the competition with hemin induced a significant decrease in the fluorescent response of BDC-9 while the competition with all other drugs did not affect the fluorescence of BDC-9. These observations clearly indicate that the environmental turn-on response of BDC-9 is due to its binding to the FA1 site (heme site) of HSA. There have been several reports of fluorescent dyes binding to FA3/4 (48,49,73), FA6 (51) and FA7 (54,55,76) sites. The present invention represents the first known experimentally proven fluorescent dye binding to the FA1 site (76), in which binding is not dependent on contact with bound lipid (72). BDC-9 is therefore a valuable probe for examining the heme region on HSA.

Figure 9:
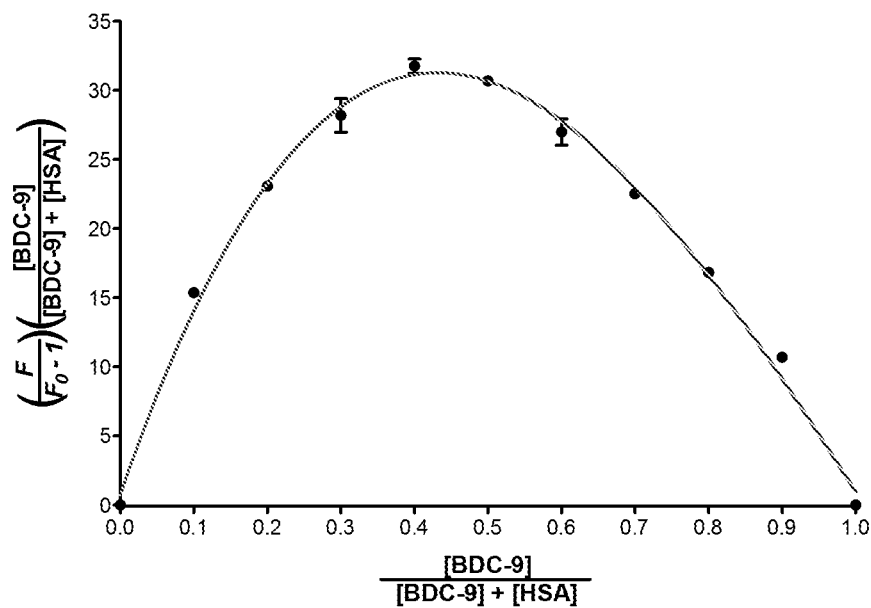
FIG. 9 shows a job plot analysis. Specifically, BDC-9 was mixed with HSA (fatty acid free) at different ratios in phosphate buffer while maintaining total concentration at 20 µM; $\lambda_{exc.}$: 460 nm, $\lambda_{em.}$: 575 nm; values are represented as means and error bars as standard deviations (n=3).

A Job plot analysis was performed to determine the stoichiometry of the complex formed by BDC-9 and HSA, and confirm the results from the site-selectivity studies. The fluorescence response of BDC-9 peaked at a 1:1 proportion of BDC-9:HSA, which indicates that BDC-9 binds mainly at one site of the protein (FIG. 9) (77,78).

Determination of Dissociation Constant for BDC-9 with HSA.

HSA (10 µM) was titrated against serial concentrations of BDC-9 (0.47 to 60 µM) and the fluorescence intensities were measured at 575 nm ($\lambda_{exc}$=460 nm). The fluorescence intensity of bound BDC-9 at each concentration was determined using the equation:

$$F_{bound} = \frac{F_{sat}(F - F_0)}{(F_{sat} - F_0)}$$

where F and $F_0$ are the fluorescence intensities of a given concentration of BDC-9 with and without HSA respectively. $F_{sat}$ is the fluorescence intensity at the same concentration of BDC-9 when fully bound.

Figure 10:
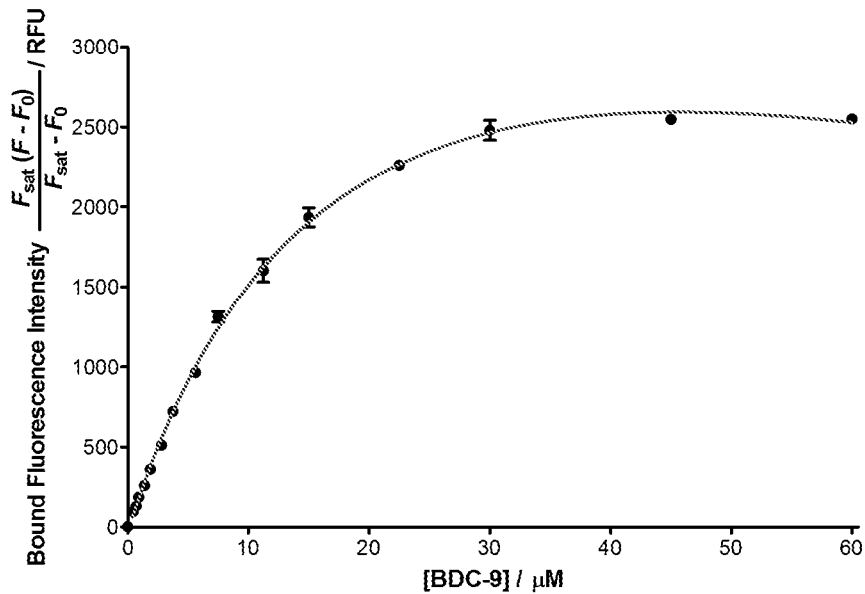
FIG. 10 is a fluorescence spectrum showing fluorescence emission of serial dilutions of BDC-9 (0, 0.47 to 60 µM) upon incubation with HSA (10 µM) in phosphate buffer; $\lambda_{exc.}$: 460 nm, $\lambda_{em.}$: 575 nm; values are represented as means and error bars as standard deviations (n=3); $K_D$=12.7±0.4 µM (one-site specific binding model).

A one-site binding model was fitted to the titration of HSA (0.67 mg/mL) with serial concentrations of BDC-9, and the dissociation constant ($K_D$) of BDC-9 was determined to be 12.7±0.4 µM (FIG. 10).

Example 5

Application of BDC-9 to Quantify HSA in Urine

Figure 11:
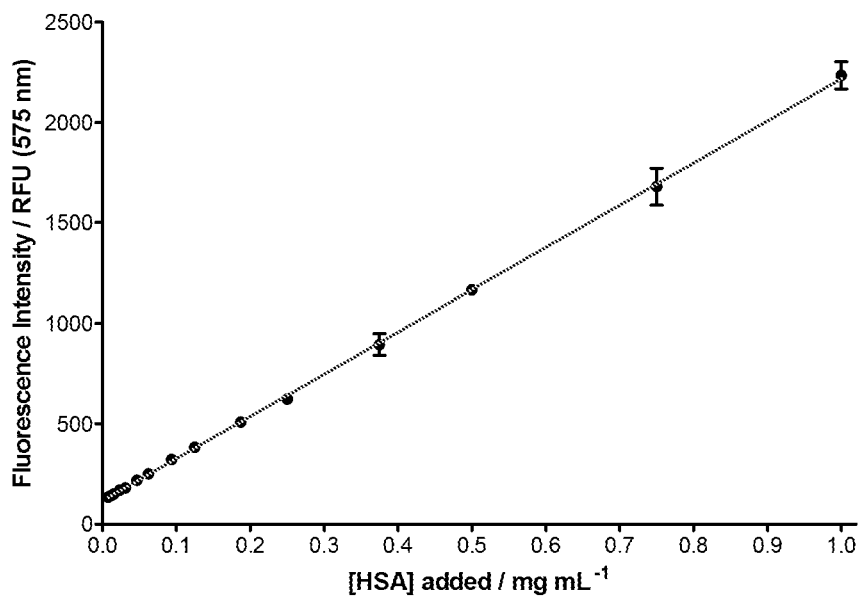
FIG. 11 shows the fluorescence response of BDC-9 in urine samples. HSA (0 to 1 mg/mL) was added to 10% urine from healthy individuals in phosphate buffer (pH=7.3). BDC-9 was added at 10 µM concentration; $\lambda_{exc.}$: 460 nm, $\lambda_{em.}$: 575 nm; values represented as means (n=3) and error bars as standard deviations; linear regression: $R^2$=0.998.

In order to examine the selectivity and sensitivity of BDC-9 in complex matrices, BDC-9 was utilized to quantify the amount of HSA in urine samples. Microalbuminuria, which involves an albumin excretion rate of 15 to 40 µg/mL (80, 81), is a well-established cardiovascular risk marker and an indication of liver and renal disease (32,33). The fluorescence response of BDC-9 was analyzed in urine that was spiked with different amounts of HSA, up to 1 mg/mL. An excellent linear correlation existed between the fluorescence response of BDC-9 and the amount of HSA in a clinically-significant range (FIG. 11), which proves the potential of BDC-9 to quantify HSA levels in urine samples.

Example 6

Discovery of MKHA and NeuO Neural Cell Probes

Figure 12:
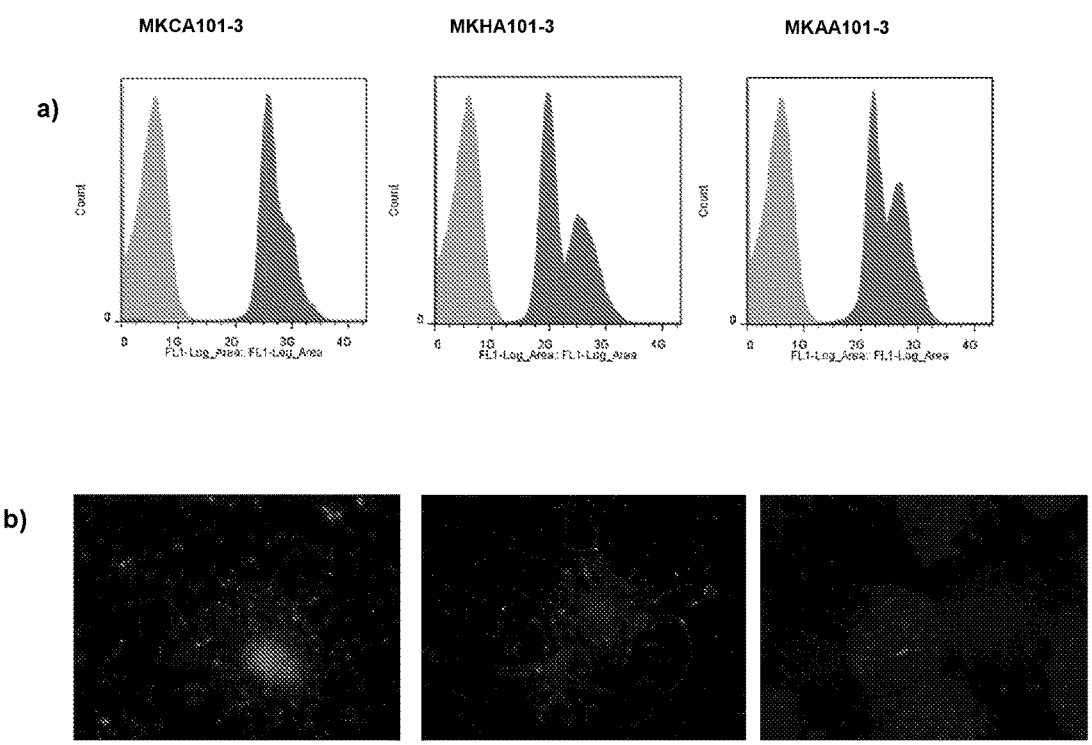
FIG. 12a shows flow cytometry profiles of MKCA101-3 (left), MKHA101-3 (middle) and MKAA101-3 (right) stained mixed primary neural cell populations showing the neuronal population segregating from the main population based on compound fluorescence (~2 G up to ~3.5 G). Unstained controls are shown in each spectrum from about 0 to about 1 G.
FIG. 12b images of neurons derived from differentiated neurospheres. MKHA101-3 shows significantly improved specificity over MKCA101-3.
Figure 13:
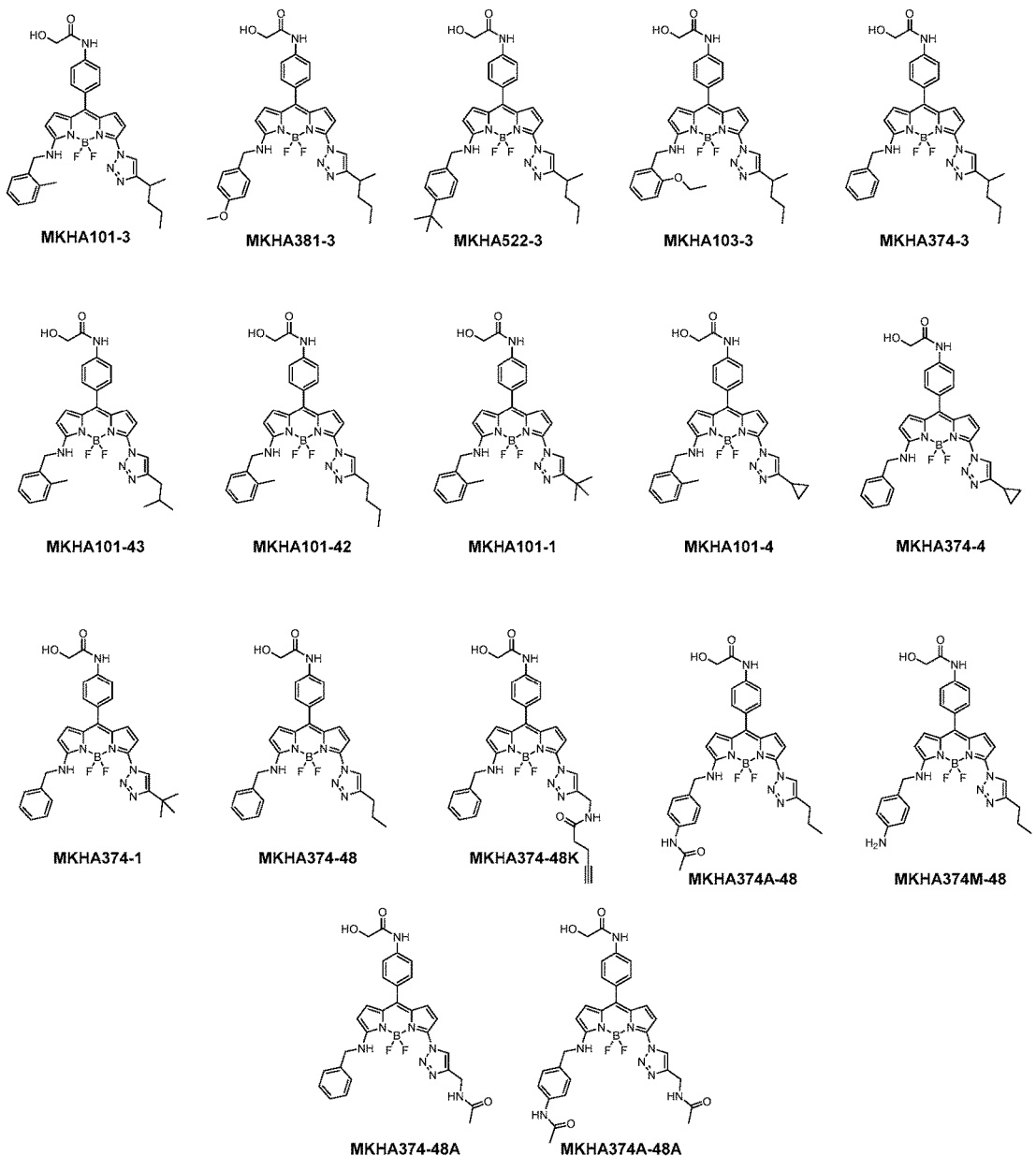
FIG. 13 shows chemical structures of MKHA101-3 and its derivatives.
Figure 14:
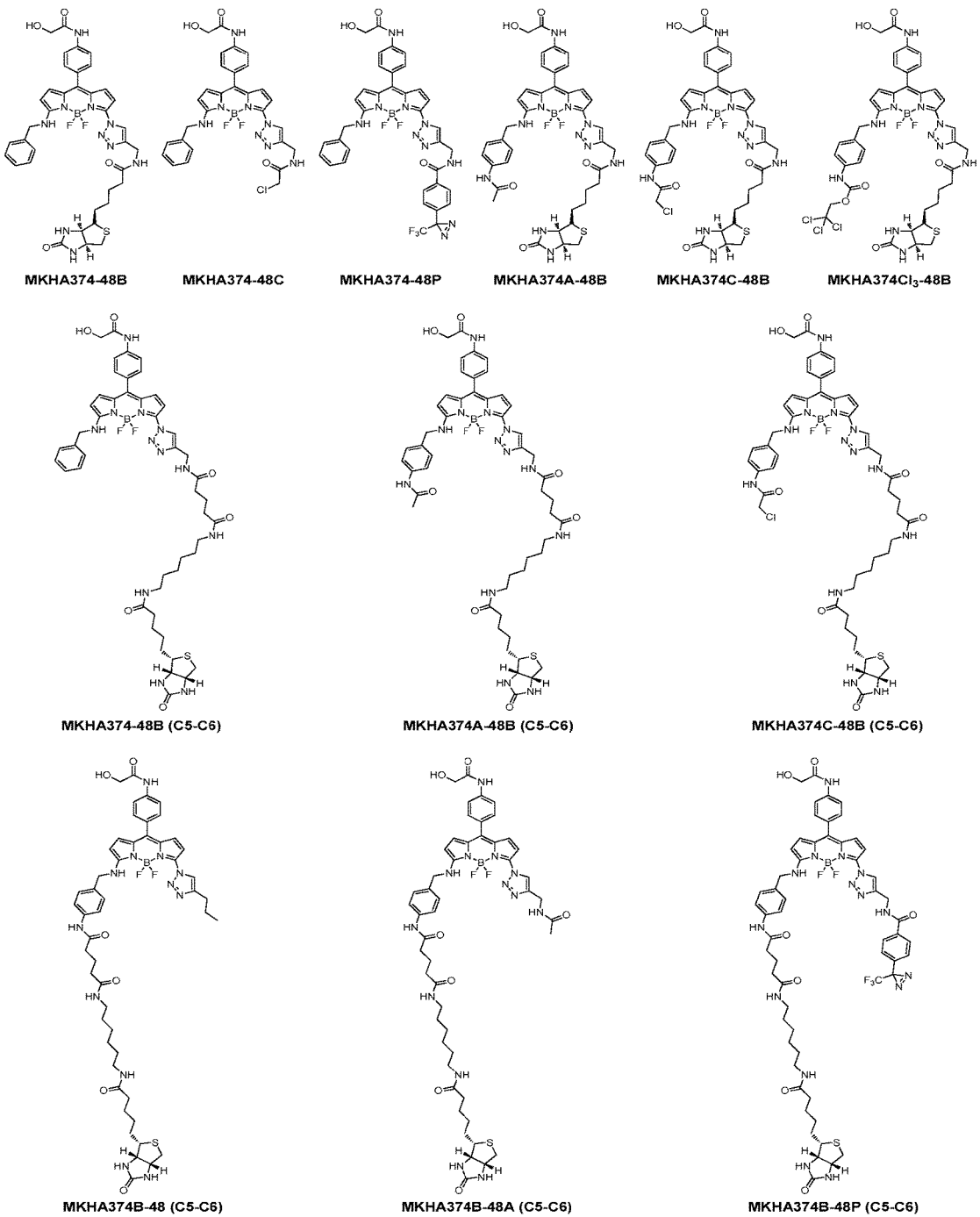
FIG. 14 shows chemical structures of MKHA374-48 affinity analogues.

In a preliminary cell-based screening of the $2^{nd}$ generation amino-triazolyl-BODIPY compounds (MK, MKAC, MKCA), MKCA compounds showed some weak response towards primary neurons. Subsequent conversion into the MKHA derivatives generally improved the fluorescence response towards primary neurons significantly (FIG. 12). Esterification to MKAA (and possibly other esters) improves permeability into intact live cells while maintaining staining specificity (FIG. 12). The acetylated MKAA undergoes rapid hydrolysis by cellular esterases after crossing the live cell membrane generates the active MKHA compound responsible for the fluorescence response. FIGS. 13 and 14 show the structures of example MKHA compounds that have been synthesized and tested for primary neuron staining.

Figure 15:
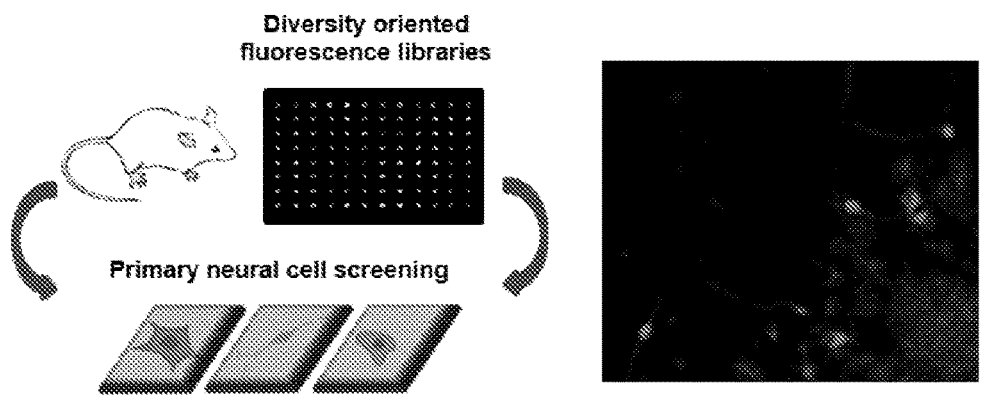
FIG. 15 shows a schematic of primary neural screening for the identification of the neuron specific probe, MKHA101-3. The image on the left shows brightly stained neurons as opposed to their other glial cell counterparts.
Figure 16:
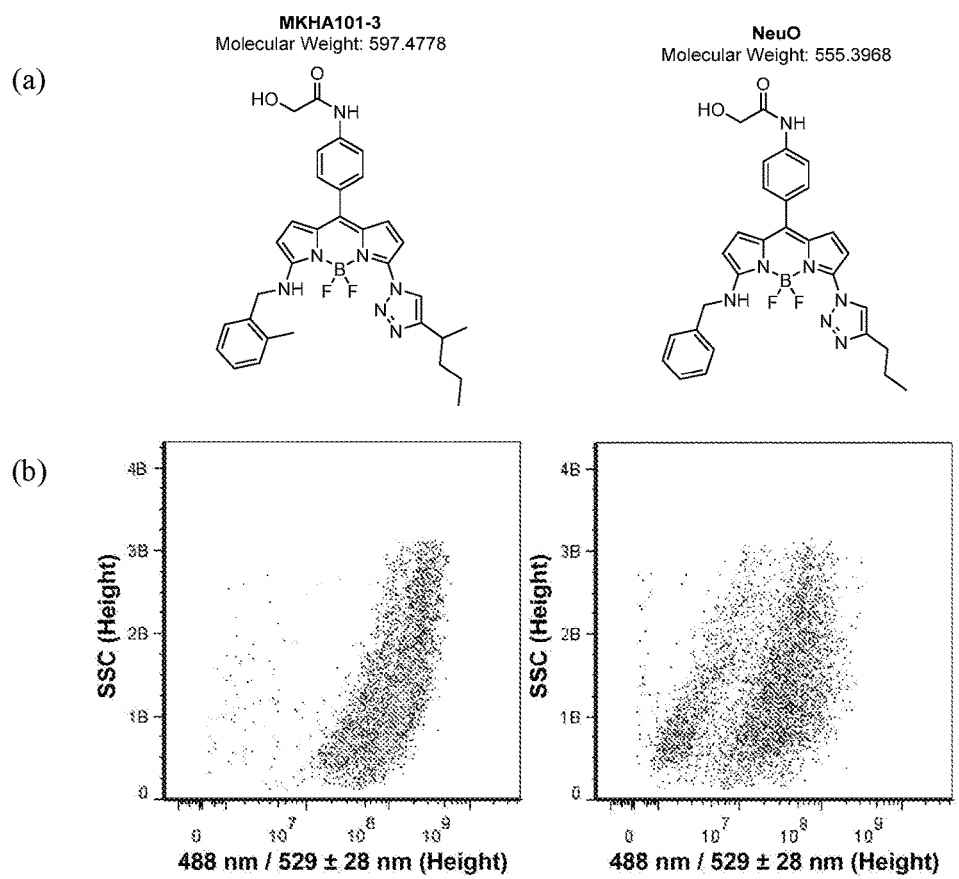
FIG. 16a shows the structures of MKHA101-3 (left) and MKHA374-48/NeuO (right).
FIG. 16b is flow cytometry profiles of MKHA101-3 (left) and NeuO (right) stained with mixed live neuron cell populations showing the neuronal population segregating from the main population based on compound fluorescence

For neuron probe discovery, a primary brain cell screening platform was utilized, which involved the use of primary neurons, astrocytes and microglia isolated by differential adhesion methods. These cells were prepared alongside one another in 384-well microplates and incubated in duplicate with 5,000 DOFL compounds at 500 nM concentrations for 1 hour at 4-5 days post-isolation (FIG. 15). Through an automatic intensity-based analysis and image-based evaluation, a primary fluorescent probe specific for neurons, MKHA101-3, was identified. Preliminary structure activity relationship (SAR) studies were performed and an improved compound, MKHA374-48, was discovered which exhibited superior selectivity towards live neurons compared to the original MKHA101-3 (FIG. 16). The compound MKHA374-48 is alternately referred to herein as NeuO (pronounced "neo") for Neuron Orange.

Example 7

NeuO is Specific for Live Neurons

Cell Imaging with MKHA101-3

Figure 17:
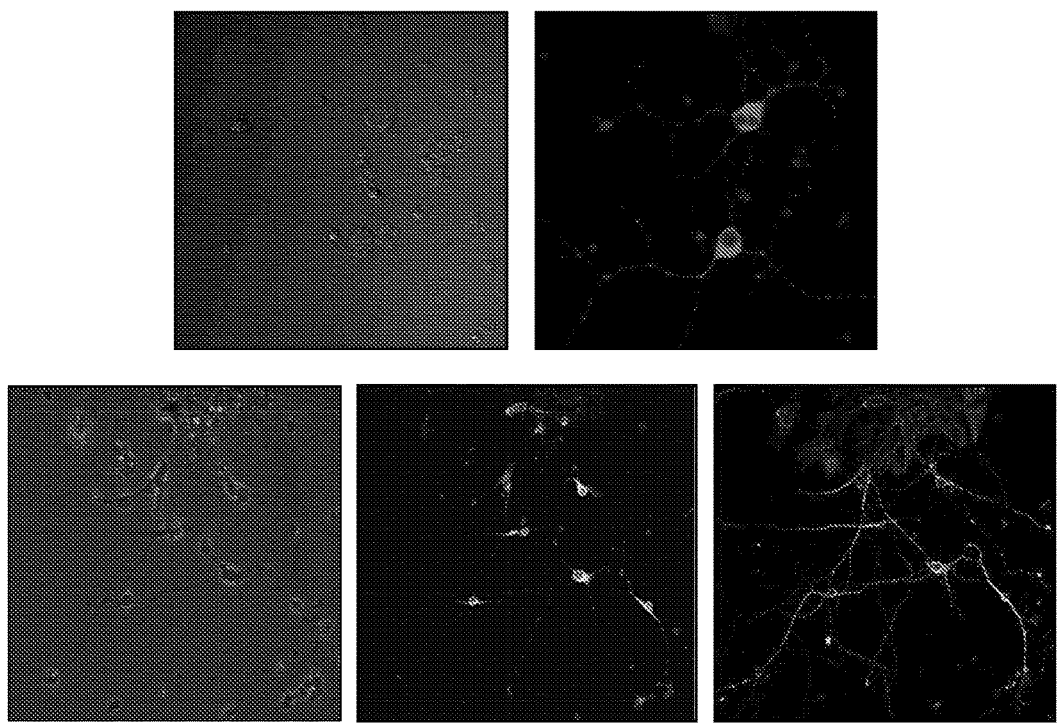
FIG. 17 shows live cell confocal images of MKHA101-3 stained neurons at 100× magnification, scale bar 20 µm and live cell compound staining and immunostaining of mixed primary neural cell cultures. Cells were stained with 500 nM of MKHA101-3 (Green) and imaged at 10× magnification before fixing with 4% PFA. They were then permeabilized with 0.1% Triton-X and immunostained with GFAP (Red) and neurons (Green).

MKHA101-3 stains the cell bodies and dendrites specifically over other neural cells. Using the heterogeneous brain cell preparations from P1-P3 mice, cells that were compound positive were also found to be β-III-tubulin positive (FIG. 17). Other cells that tested positive for the astrocyte marker, GFAP and the oligodendrocyte marker O4 were found to be compound negative thus demonstrating the specificity of MKHA101-3 compound for neurons.

Cell Imaging with NeuO

Figure 18:
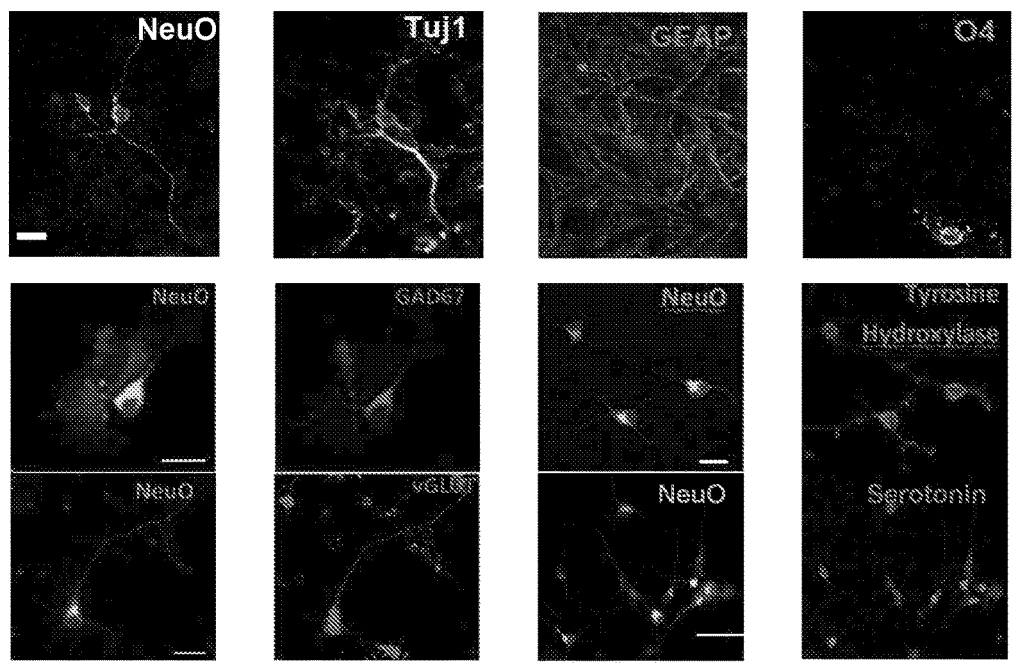
FIG. 18 shows live cell compound staining and immunostaining of mixed primary neural cell cultures. Cells were stained with 500 nM of NeuO (Green) and imaged at 10× magnification before fixing with 4% PFA. They were then permeabilized with 0.1% Triton-X and immunostained with β-III-tubulin (Tuji, Yellow), GFAP (Red) and O4).

NeuO stains the cell bodies and dendrites specifically over other neural cells. Using the heterogeneous brain cell preparations from P1-P3 mice, cells that were compound positive were also found to be β-III-tubulin (Tuji) positive (FIG. 18a). Other cells that tested positive for the astrocyte marker, GFAP and the oligodendrocyte marker, O4 were found to be compound negative thus demonstrating the specificity of our compound for neurons. NeuO appears to stain all neurons regardless of subtype (FIG. 18b).

Flow Cytometry Analysis and FACS Sorting

Figure 19:
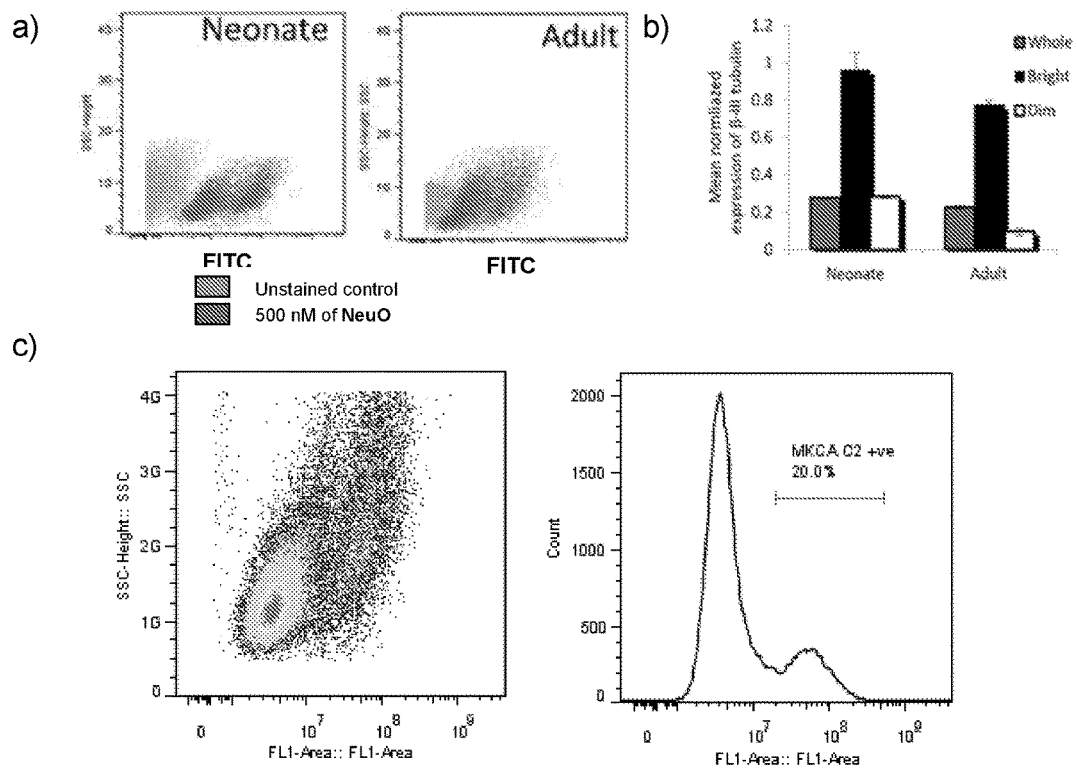
FIG. 19a shows a flow cytometry scatter profile of mixed primary neural cells from the mouse neonate and adult brain stained with 500 nM of NeuO.
FIG. 19b is a bar graph showing gene expression of 13-III-tubulin as measured from cells sorted from whole (unsorted), bright and dim fractions of neonate and adult brains.
FIG. 19c shows a flow cytometry scatter profile of mixed primary neural cells stained with 500 nM of MKHA101-3. The histogram on the right shows that compound positive cells make up 20% of the whole cell population.

Flow cytometry analysis on mixed populations of cells prepared from the brains of P1-3 mouse pups also showed a clear population of cells (10-20%) segregating from the main population (FIG. 19). To further analyze this population of compound positive cells, the two populations (Bright and Dim) were sorted out cell re-culture and RNA extraction for gene analysis.

Compound Positive Cells Isolated from FACS Show a Neuronal Morphology and are β-III-Tubulin Positive.

Figure 20:
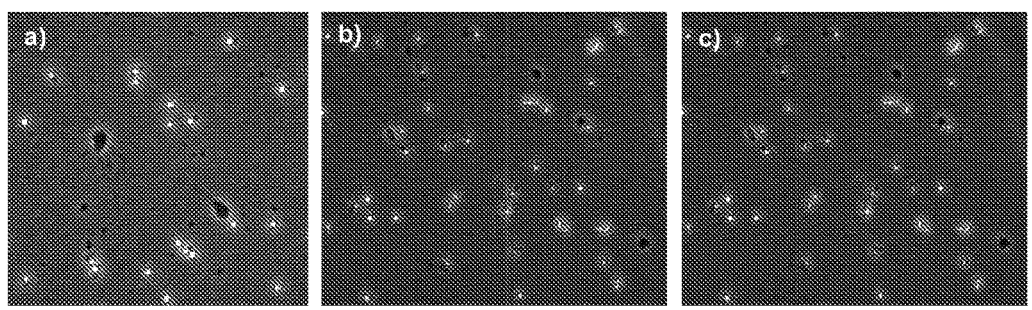
FIG. 20a shows live cells with a neuronal morphology recultured from the compound positive fraction.
FIGS. 20b and 20c show immunostained cells found to be positive for β-III-tubulin (Green), nuclei staining (Blue); Scale bar: 50 µm.

Compound bright and dim cells were sorted out and seeded for re-culture at a density of 50,000 cells/cm² in neurobasal media supplemented with B27 and FGF (10 ng/µL) on poly-D-lysine coated plates. After 5 days, cells with a neuronal morphology, characterized by the extension of dendrites were observed in the compound bright reculture fraction (FIG. 20a). These cells were subsequently immunostained for the neuronal marker, β-III-tubulin and found to be positive (FIGS. 20b and c). Compound dim reculture fractions showed few if any cell growth reminiscent of neurons.

Compound Positive Cells Show High Expression of the Neuronal Marker, β-III Tubulin.

Figure 21:
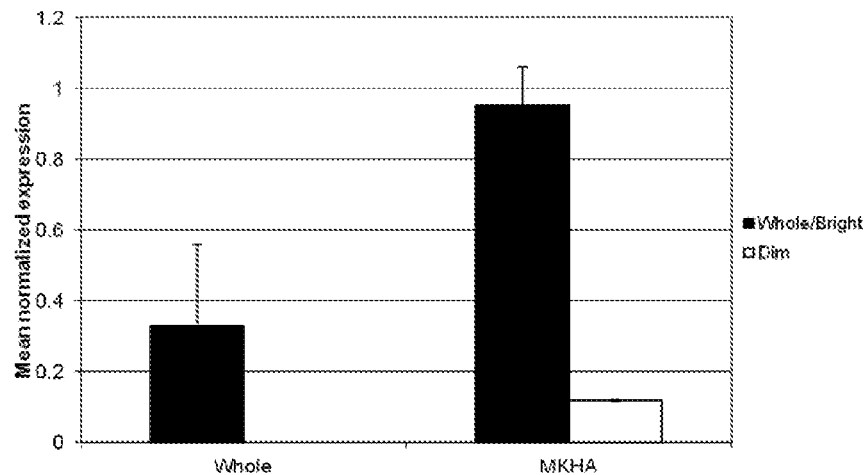
FIG. 21 is a bar graph showing the expression of β-III-tubulin in the whole (unsorted), bright and dim fractions of MKHA101-3 stained mixed primary neural cells. The bright fraction clearly shows a higher expression of β-III-tubulin compared to the whole and dim fractions.

The gene expression of the neuronal marker, β-III-tubulin, was analyzed from the RNA extracted from FACS sorted compound positive neuronal populations. Compound bright fractions consistently showed high β-III-tubulin expression (up to 10-fold higher) than compound dim fractions (FIG. 21). β-III-tubulin expression was also often up to 2-fold higher in compound bright fractions compared to unsorted fractions thus suggesting that the probe compound.

Neurons Remain Viable after Staining.

Figure 22:
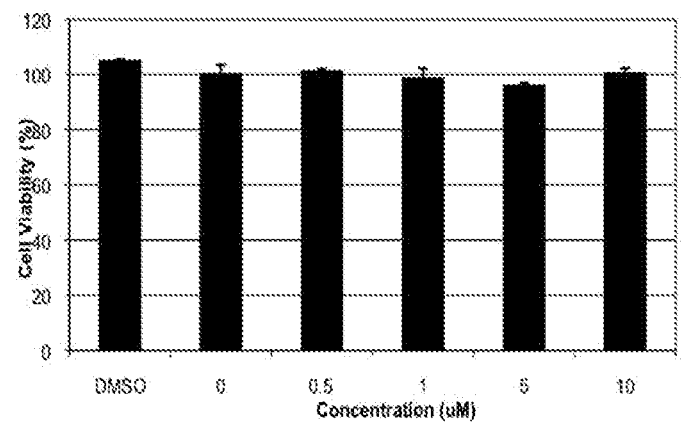
FIG. 22 is a bar graph demonstrating neuron viability. Primary neurons were isolated from P1-3 mouse pups by preferential adherence to poly-D-lysine coating. They were left to mature for 5 days before addition of compound at the stipulated concentrations for 24 h. The MTS assay (Promega) was used to assess viability according to manufacturer's instructions.

For long term tracking and downstream functional studies, it is critical that the compound is not cytotoxic towards the cells and that cells remain viable after staining. A cell cytotoxicity assay (MTS, Promega) demonstrated that 24 hour incubation with NeuO did not affect cell viability significantly at working concentrations of 500 nM or higher (FIG. 22).

NeuO can be Used for Long Term Imaging of In Vitro Neuronal Development.

Figure 23:
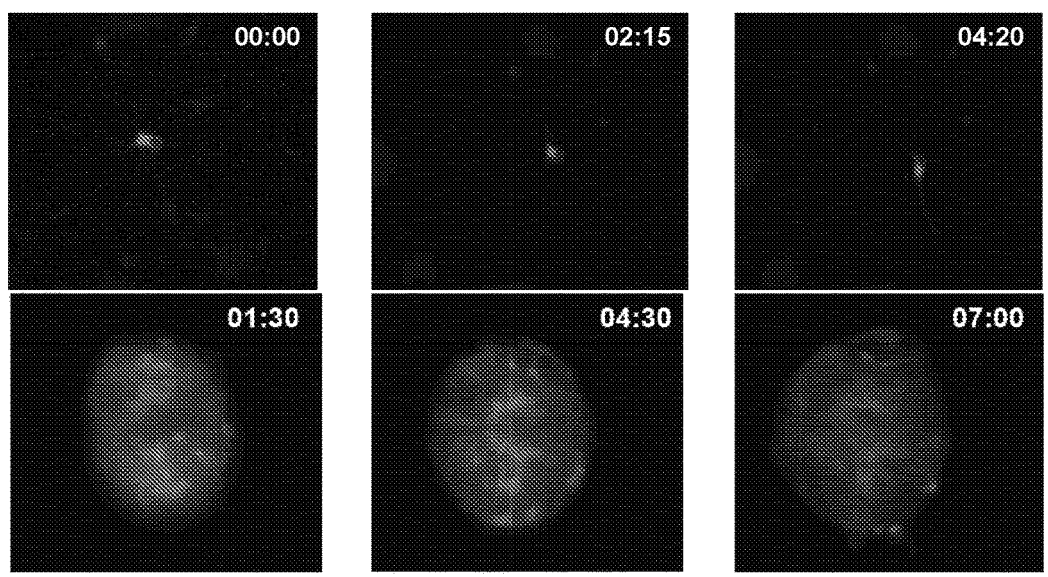
FIG. 23, in the upper panel, shows video stills of DIV1 neuron cultures, stained with 500 nM NeuO and imaged using time lapse imaging to visualize neuron dendrite formation. The lower panel of FIG. 23 shows time lapse imaging of neuronal development/-differentiation from neural progenitors. Bright NeuO stained neurons can be seen migrating from the interior of the sphere.

To test the potential of NeuO as a neuronal cell tracker, freshly harvested neurons from P1-3 mouse pups were stained and their dendrite formation was observed in vitro using time 1 imaging (FIG. 23). The survival of the cells and dye signal is critical in time lapse studies to analyze neuronal development and interaction with other neural cells.

Example 8

MKHA Compounds and Other Neuron Imaging Applications

Figure 24:
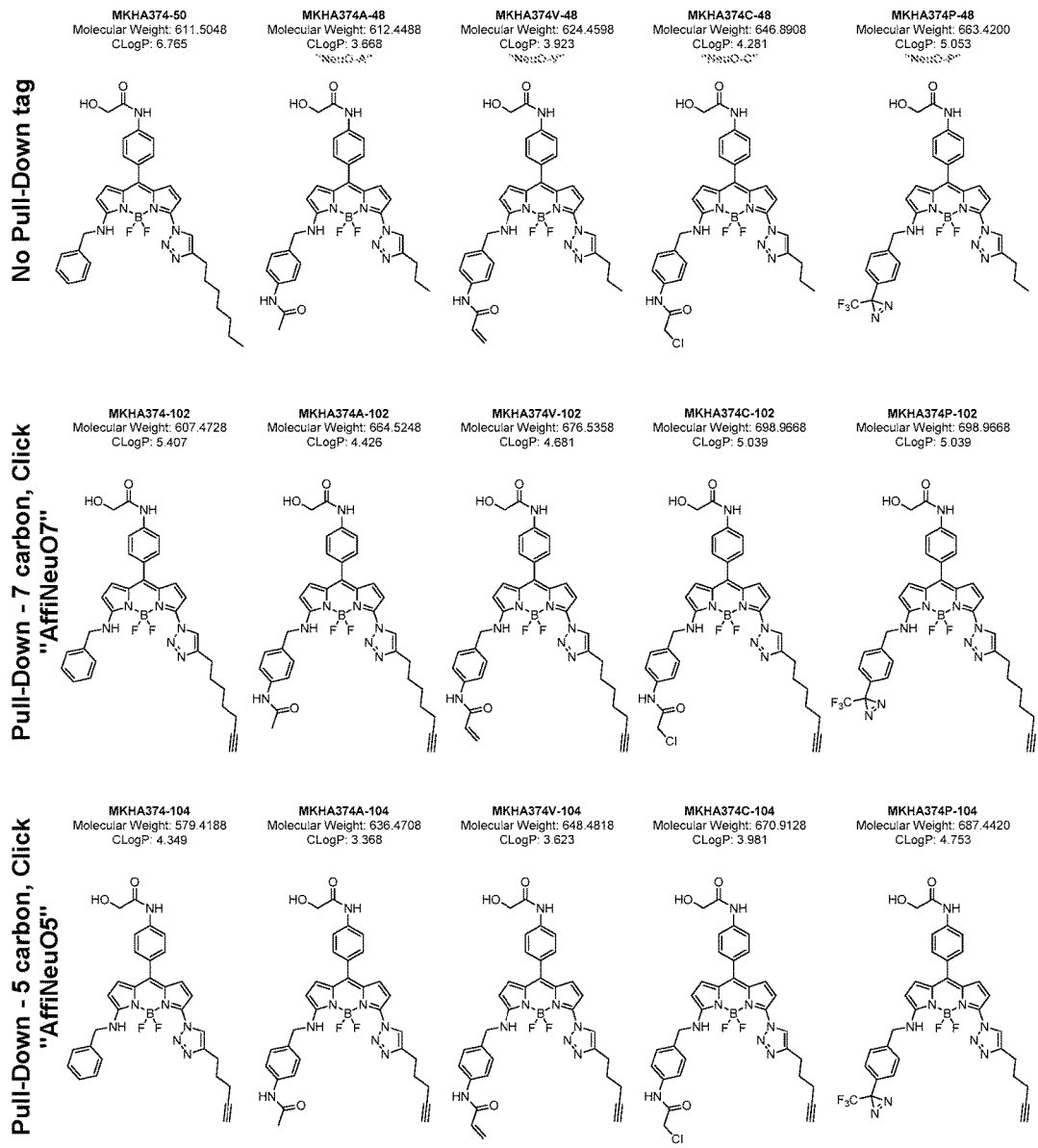
FIG. 24 depicts affinity molecules designed for covalent binding to neuronal targets and affinity enrichment.
Figure 25:
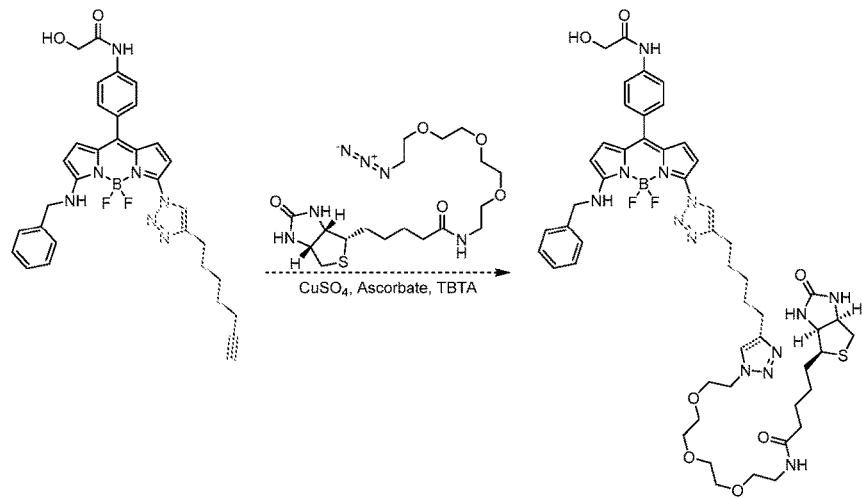
FIG. 25 depicts a representative scheme for using AffiNeuO7 and AffiNeuO5 series for affinity enrichment.
Figure 26:
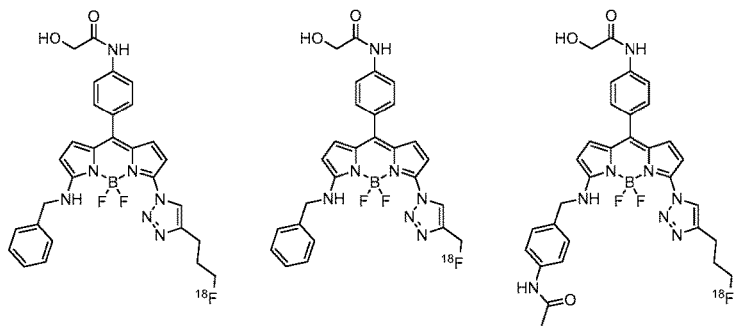
FIG. 26 depicts NeuO-PETs, which may be used in some embodiments for PET imaging.
Figure 26:
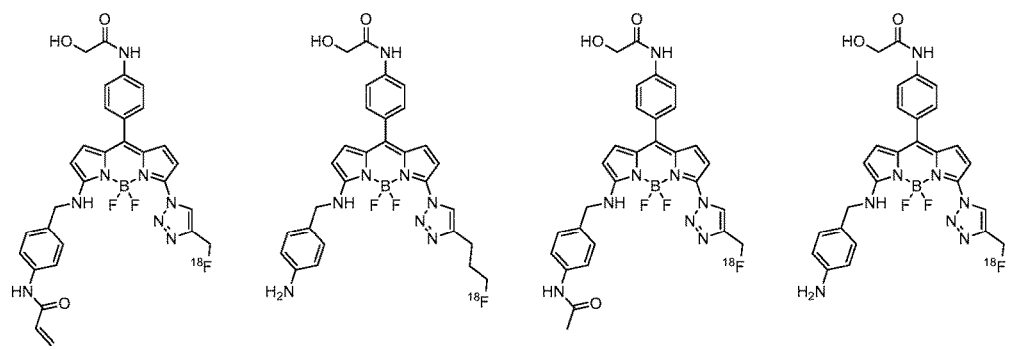
Figure 27:
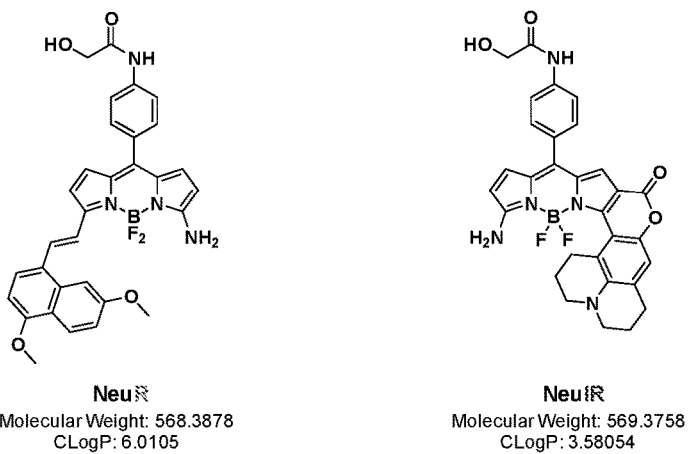
FIG. 27 depict NeuR and NeuIR red fluorescent probes for live neurons.

Based on SAR studies, additional compounds were designed and synthesized for various applications including covalent binding (FIG. 24), pull-down (FIGS. 24 and 25), PET imaging (FIG. 26) and near-infrared spectroscopy (FIG. 27). All compounds depicted in FIGS. 24-27 were found to stain live neurons.

Example 9

Figure 28:
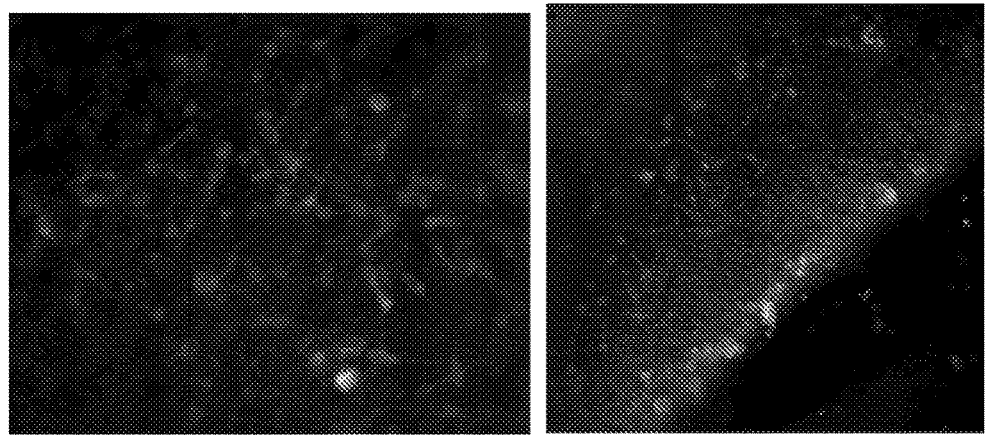
FIG. 28 shows Embryo brain slices stained with MKHA101-3 and imaged at 10× magnification. Images captured shows that the dyes specifically highlighted cells with long dendritic processes which are reminiscent of neuronal staining.

MKHA Compounds have the Potential to Label Neurons Specifically in the Live Mouse Brain To access the potential of the dyes disclosed herein for live brain slice staining, fresh embryo brain slices were stained with the compounds and imaged under a fluorescence microscope. MKHA101-3 and its derivated shows a specific cellular labeling pattern, with the dyes highlighting cells with long dendritic processes and cell bodies clustering in a manner that is consistent with a neuronal pattern (FIG. 28). This strongly suggests that the dyes can be further applied for the imaging of neurons in brain slice preparations.

REFERENCES

1. O. Buyukcakir, et al., *Org. Lett.* 11, (2009), 4644-4647.
2. C. Yu et al., *Chem.-Eur. J.* 18, (2012), 6437-6442.
3. A. Martin, et al., *Chem. Commun.* 48, (2012), 5617-5619.
4. K. Umezawa, et al., *J. Am. Chem. Soc.* 130, (2008), 1550-1551.
5. J. Bañuelos, et al., *Chem.-Eur. J.* 2011, 17, 7261-7270.
6. A. Loudet, K. Burgess, *Chem. Rev.* 2007, 107, 4891-4932.
7. G. Ulrich, R. Ziessel, A. Harriman, *Angew. Chem., Int. Ed.* 2008, 47, 1184-1201.
8. C. Bernhard, et al., *Chem. Commun.* 2010, 46, 8267-8269.
9. J. A. Hendricks, et al., *Angew. Chem., Int. Ed.* 2012, 51, 4603-4606.
10. J.-S. Lee, et al., *J. Am. Chem. Soc.* 2009, 131, 10077-10082.
11. L. D. Lavis, R. T. Raines, *ACS Chem. Biol.* 2008, 3, 142-155.
12. M. Vendrell, et al., *Chem. Commun.* 2011, 47, 8424.
13. M. Vendrell, D. Zhai, J. C. Er, Y.-T. Chang, *Chem. Rev.* 2012, 112, 4391-4420.
14. M. Meldal, C. W. Tornoe, *Chem. Rev.* 2008, 108, 2952-3015.
15. K. Sivakumar, et al., *Org. Lett.* 2004, 6, 4603-4606.
16. D. K. Scrafton, et al., *J. Org; Chem.* 2008, 73, 2871-2874.
17. J. Han, et al., *Org. Biomol. Chem.* 2009, 7, 34-36.
18. X. Qian, et al., *Chem. Commun.* 2010, 46, 6418-6436.
19. W. Qin, et al., *J. Phys. Chem. A* 2007, 111, 8588-8597.
20. B. Verbelen, et al., *Chem. Commun.* 2012, 48, 9129-9131.
21. T. Rohand, et al., *Chem. Commun.* 2006, 266-268.
22. T. Rohand, et al., *Photochem. Photobiol. Sci.* 2007, 6, 1061-1066.
23. V. Leen, et al., *Chem. Commun.* 2010, 46, 4908-4910.
24. W. Qin, et al., *J. Phys. Chem. C* 2009, 113, 11731-11740.
25. B. Temelli, C. Unaleroglu, *Tetrahedron* 2006, 62, 10130-10135.
26. L. Li, B. Nguyen, K. Burgess, *Bioorg. Med. Chem. Lett.* 2008, 18, 3112-3116.
27. L. Li, J. Han, B. Nguyen, K. Burgess, *J. Org. Chem.* 2008, 73, 1963-1970.
28. O. A. Bozdemir, et al., *J. Am. Chem. Soc.* 2010, 132, 8029-8036.
29. A. Coskun, E. Deniz, E. U. Akkaya, *Org. Lett.* 2005, 7, 5187-5189.
30. W. Qin, et al., *J Phys. Chem. A* 2008, 113, 439-447.
31. G. Fanali, et al., *Mol. Aspects Med.* 2012, 33, 209-290.
32. D. J. F. Rowe, A. Dawnay, G. F. Watts, *Ann. Clin. Biochem.* 1990, 27, 297-312.
33. C. E. Mogensen, O. Schmitz, *Med. Clin. North Am.* 1988, 72, 1465-1492.
34. S. Curry, et al., *Nat. Struct. Mol. Biol.* 1998, 5, 827-835.
35. A. A. Bhattacharya, T. Grüne, S. Curry, *J. Mol. Biol.* 2000, 303, 721-732.
36. I. Petitpas, et al., *J. Mol. Biol.* 2001, 314, 955-960.
37. I. Petitpas, et al., *Proc. Natl. Acad. Sci.* 2003, 100, 6440-6445.
38. S. Sugio, et al., *Protein Eng.* 1999, 12, 439-446.
39. S. Curry, et al., *Biochim. Biophys. Acta, Mol. Cell Biol. L.* 1999, 1441, 131-140.
40. S. Curry, *Drug Metab. Pharmacokinet.* 2009, 24, 342-357.
41. L. Zhu, et al., *J. Struct. Biol.* 2008, 162, 40-49.
42. J. R. Simard, et al, *Proc. Natl. Acad. Sci.* 2005, 102, 17958-17963.
43. G. Sudlow, D. J. Birkett, D. N. Wade, *Mol. Pharmacol.* 1976, 12, 1052-1061.
44. G. Sudlow, D. J. Birkett, D. N. Wade, *Mol. Pharmacol.* 1975, 11, 824-832.
45. F. Moreno, et al., *Photochem. Photobiol.* 1999, 70, 695-700.

46. K. Takehara, et al., *Anal. Sci.* 2009, 25, 115-120.
47. X.-t. Chen, Y. Xiang, A.-j. Tong, *Talanta* 2010, 80, 1952-1958.
48. F. Ding, W. Liu, J.-X. Diao, Y. Sun, *J. Hazard. Mater.* 2011, 186, 352-359.
49. K. K. Park, J. W. Park, A. D. Hamilton, *Org. Biomol. Chem.* 2009, 7, 4225-4232.
50. M. Banerjee, et al., *J. Photochem. Photobiol. B* 2012, 108, 23-33.
51. Y. Wang, et al., *Protein Sci.* 2011, 20, 2095-2101.
52. D. C. Wilton, *Biochem. J.* 1990, 270, 163-166.
53. B. Sengupta, P. K. Sengupta, *Biopolymers* 2003, 72, 427-434.
54. F. Moreno, et al., *Photochem. Photobiol.* 1999, 69, 8-15.
55. Y. Sun, et al., *J. Lumin.* 2012, 132, 879-886.
56. J. Rohacova, et al., *J. Phys. Chem. B* 2011, 115, 10518-10524.
57. E. Alarcon, et al., *Photochem. Photobiol. Sci* 2010, 9, 93-102.
58. Z.-d. Qi, et al., *J. Pharm. Biomed. Anal.* 2008, 46, 699-706.
59. S. Deepa, A. K. Mishra, *J. Pharm. Biomed. Anal.* 2005, 38, 556-563.
60. F.-L. Cui, J.-L. Wang, Y.-R. Cui, J.-P. Li, *Anal. Chim. Acta* 2006, 571, 175-183.
61. A.-l. Tsai, et al., *Biochim. Biophys. Acta, Gen. Subj.* 1989, 993, 74-82.
62. S. Curry, Vol. 33, 2004, pp. 29-46.
63. M. Pistolozzi, C. Bertucci, *Chirality* 2008, 20, 552-558.
64. N. E. Basken, et al., *Nucl. Med. Biol.* 2008, 35, 281-286.
65. C. J. Mathias, S. R. Bergmann, M. A. Green, *J. Nucl. Med.* 1995, 36, 1451-1455.
66. J. J. Lima, *Drug Metab. Dispos.* 1988, 16, 563-567.
67. N. E. Basken, C. J. Mathias, M. A. Green, *J. Pharm. Sci.* 2009, 98, 2170-2179.
68. A. Baldridge, et al., *ACS Comb. Sci.* 2011, 13, 214-217.
69. Y.-H. Ahn, J.-S. Lee, Y.-T. Chang, *J. Comb. Chem.* 2008, 10, 376-380.
70. F. Zsila, *Mol. Pharmaceutics* 2013, 10, 1668-1682.
71. P. Zunszain, et al., *BMC Struct. Biol.* 2003, 3, 6.
72. M. Wardell, et al., *Biochem. Biophys. Res. Commun.* 2002, 291, 813-819.
73. A. J. Ryan, et al., *J. Struct. Biol.* 2011, 174, 84-91.
74. J. Ghuman, et al., *J. Mol. Biol.* 2005, 353, 38-52.
75. G. Zhang, N. Zhao, L. Wang, *J. Lumin.* 2011, 131, 2716-2724.
76. K. Park, J. Park, A. Hamilton, *J. Fluoresc.* 2007, 17, 361-369.
77. R. Subramanyam, et al., *J. Photochem. Photobiol. B* 2009, 95, 81-88.
78. C. Y. Huang, *Meth. Enzymol.* 1982, 87, 509-525.
79. P. Job, *Ann. Chim. Anal.* 1928, 9, 113-203.
80. M. A. Kessler, et al., *Anal. Biochem.* 1997, 248, 180-182.
81. M. A. Kessler, et al., *Clin. Chem.* 1997, 43, 996-1002.
82. J. DeFelipe, *Science* 2010, 330, 1198-1201.
83. C. Kobbert, et al., *Prog. Neurobiol.* 2000, 62, 327-351.
84. M. G. Honig, R. I. Hume, *Trends Neurosci.* 1989, 12, 333-341.
85. S. M. Appleyard, *Endocrinology* 2009, 150, 5199-5201.
86. K. Duff, F. Suleman, *Brief Funct. Genomic Proteomic* 2004, 3, 47-59.
87. H. Okano, et al., *Parkinsonism Relat. D.* 2002, 9, 23-28.
88. G. J. Brewer, *J. Neurosci. Meth.* 1997, 71, 143-155.
89. S. Tolu, et al., *FASEB J.* 2010, 24, 723-730.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound having the structure of Formula (I) or a pharmaceutically acceptable salt thereof:

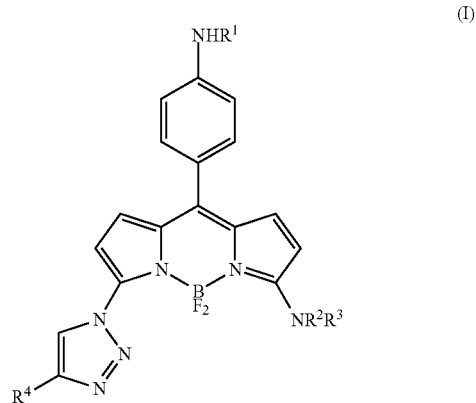

wherein:
R$^1$ is H or CO(C$_1$-C$_6$)alkyl, wherein CO(C$_1$-C$_6$)alkyl is optionally substituted at any position with 1-3 substituents selected from halogen, hydroxyl, O-acetyl, NH-acetyl, or —NH$_2$;
R$^2$ and R$^3$ are each, independently, H, (C$_1$-C$_{10}$)alkyl, (C$_6$-C$_{10}$)aryl(C$_0$-C$_6$)alkyl, (C$_3$-C$_{10}$)heteroaryl, (C$_3$-C$_8$)cycloalkyl, (C$_2$-C$_{10}$)alkynyl or (C$_2$-C$_{10}$)alkenyl;
wherein (C$_1$-C$_{10}$)alkyl, (C$_6$-C$_{10}$)aryl(C$_0$-C$_6$)alkyl, (C$_3$-C$_{10}$)heteroaryl, (C$_3$-C$_8$)cycloalkyl, (C$_2$-C$_{10}$)alkynyl and (C$_2$-C$_{10}$)alkenyl are optionally substituted at any position with 1-5 substituents selected from (C$_1$-C$_6$) alkyl, (C$_1$-C$_6$)alkoxy, NH$_2$, —NH(C$_1$-C$_6$ alkyl), —NH(CO)(C$_1$-C$_6$ alkyl), —NH(CO)(C$_1$-C$_6$ haloalkyl), —NH(CO)(C$_1$-C$_6$ alkoxy), —NH(CO) (C$_1$-C$_6$ haloalkoxy), —NH(CO)(C$_2$-C$_6$ alkenyl), —Si(C$_1$-C$_6$ alkyl), —SO$_2$(C$_1$-C$_6$ alkyl), —SH, —B(OH)$_2$, —OTosyl, —CO(C$_1$-C$_6$ alkoxyl), —COH, —COOH, —CO(C$_1$-C$_6$ alkyl) or halogen;
or R$^2$ and R$^3$ are taken together to form a ring, wherein the ring is optionally substituted with 1-5 additional substituents selected from halogen or (C$_1$-C$_6$)alkyl; and
R$^4$ is (C$_1$-C$_{10}$)alkyl, (C$_3$-C$_8$)cycloalkyl, (C$_6$-C$_{10}$)aryl, (C$_2$-C$_{10}$)alkenyl, (C$_2$-C$_{10}$)alkynyl, or (C$_3$-C$_{10}$)heteroaryl, further wherein R$^4$ is optionally substituted at any position with 1-5 substituents selected from (C$_1$-C$_{10}$) alkyl, (C$_2$-C$_{10}$)alkenyl, (C$_2$-C$_{10}$)alkynyl, (C$_3$-C$_8$)cycloalkyl, (C$_1$-C$_6$)alkoxy, (C$_6$-C$_{10}$)aryloxy, (C$_6$-C$_{10}$) aryl, amino, —NH(CO)(C$_1$-C$_6$ alkyl), —NH(CO)(C$_2$-C$_6$ alkenyl), —NH(CO)(C$_2$-C$_6$ alkynyl), —NH(CO) (C$_1$-C$_6$ haloalkyl), halo, OCF$_3$, CF$_3$, hydroxyl, or a halogen radioisotope.

2. The compound of claim 1, wherein R$^1$ is H, COCH$_3$, COCH$_2$Cl, COCH$_2$OH, COCH$_2$NH$_2$, or COCH$_2$O(CO) CH$_3$.

3. The compound of claim 2, having the structure of Formula (II):

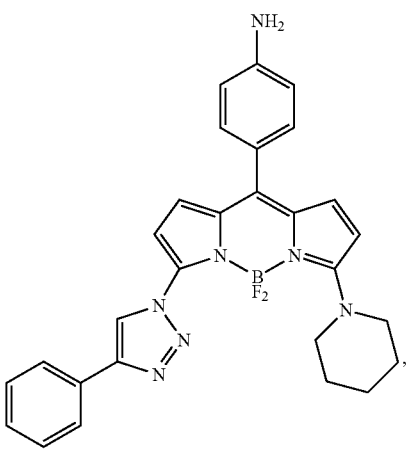

or a pharmaceutically acceptable salt thereof.

4. The compound of claim 2, having the structure of Formula (III):

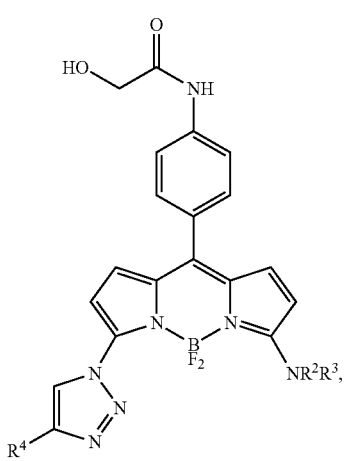

or a pharmaceutically acceptable salt thereof.

5. The compound of claim 2, having the structure of Formula (IV):

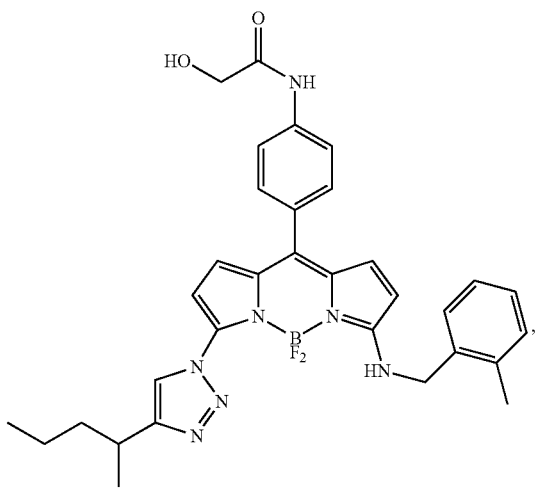

or a pharmaceutically acceptable salt thereof.

6. The compound of claim 2, having the structure of Formula (V):

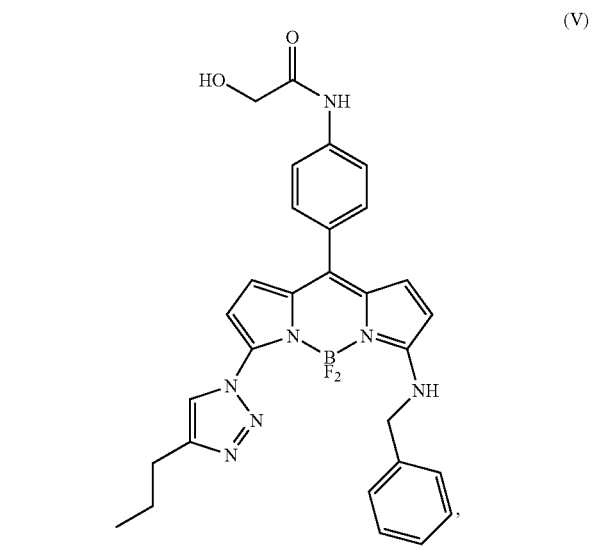

or a pharmaceutically acceptable salt thereof.

7. The compound of claim 1, wherein the compound is conjugated to a chemical reactive moiety selected from biotin, diazirine, acryloyl, haloacetyl, diaaziridine, N-hydroxysuccinimide ester, imidoester, pentafluorophenyl ester, hydroxymethyl phosphine, maleimide, pyridyldisulfide, thiosulfonate, vinylsulfone, hydrazide, alkoxyamine, aryl azide, benzophenone, isocyanate, alkyne or ketone.

8. A method for a solid phase synthesis of a compound of Formula (I) or a pharmaceutically acceptable salt thereof:

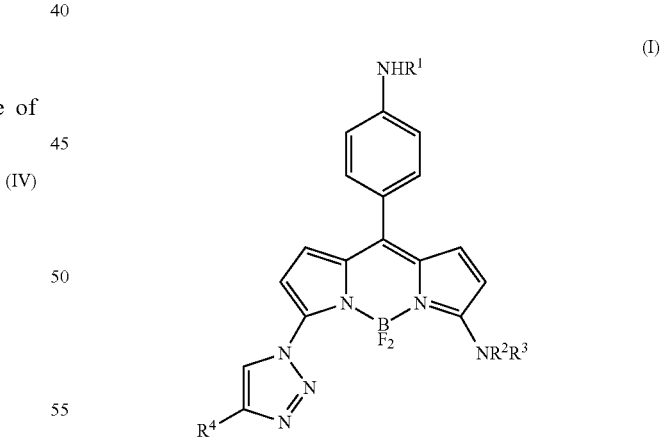

wherein:

$R^1$ is H or $CO(C_1-C_6)$alkyl, wherein $CO(C_1-C_6)$alkyl is optionally substituted at any position with 1-3 substituents selected from halogen, hydroxyl, O-acetyl, NH-acetyl, or —$NH_2$;

$R^2$ and $R^3$ are each, independently, H, $(C_1-C_{10})$alkyl, $(C_6-C_{10})$aryl$(C_0-C_6)$alkyl, $(C_3-C_{10})$heteroaryl, $(C_3-C_8)$ cycloalkyl, $(C_2-C_{10})$alkynyl or $(C_2-C_{10})$alkenyl;

wherein (C$_1$-C$_{10}$)alkyl, (C$_6$-C$_{10}$)aryl(C$_0$-C$_6$)alkyl, (C$_3$-C$_{10}$)heteroaryl, (C$_3$-C$_8$)cycloalkyl, (C$_2$-C$_{10}$)alkynyl and (C$_2$-C$_{10}$)alkenyl are optionally substituted at any position with 1-5 substituents selected from (C$_1$-C$_6$) alkyl, (C$_1$-C$_6$)alkoxy, NH$_2$, —NH(C$_1$-C$_6$ alkyl), —NH(CO)(C$_1$-C$_6$ alkyl), —NH(CO)(C$_1$-C$_6$ haloalkyl), —NH(CO)(C$_1$-C$_6$ alkoxy), —NH(CO) (C$_1$-C$_6$ haloalkoxy), —NH(CO)(C$_2$-C$_6$ alkenyl), —Si(C$_1$-C$_6$ alkyl), —SO$_2$(C$_1$-C$_6$ alkyl), —SH, —B(OH)$_2$, —OTosyl, —CO(C$_1$-C$_6$ alkoxyl), —COH, —COOH, —CO(C$_1$-C$_6$ alkyl) or halogen;

or R$^2$ and R$^3$ are taken together to form a ring, wherein the ring is optionally substituted with 1-5 additional substituents selected from halogen or (C$_1$-C$_6$)alkyl; and R$^4$ is (C$_1$-C$_{10}$)alkyl, (C$_3$-C$_8$)cycloalkyl, (C$_6$-C$_{10}$)aryl, (C$_2$-C$_{10}$)alkenyl, (C$_2$-C$_{10}$)alkynyl, or (C$_3$-C$_{10}$)heteroaryl, further wherein R$^4$ is optionally substituted at any position with 1-5 substituents selected from (C$_1$-C$_{10}$) alkyl, (C$_2$-C$_{10}$)alkenyl, (C$_2$-C$_{10}$)alkynyl, (C$_3$-C$_8$)cycloalkyl, (C$_1$-C$_6$)alkoxy, (C$_6$-C$_{10}$)aryloxy, (C$_6$-C$_{10}$) aryl, amino, —NH(CO)(C$_1$-C$_6$ alkyl), —NH(CO)(C$_2$-C$_6$ alkenyl), —NH(CO)(C$_2$-C$_6$ alkynyl), —NH(CO) (C$_1$-C$_6$ haloalkyl), halo, OCF$_3$, CF$_3$, hydroxyl, or a halogen radioisotope;

the method comprising:

(a) reacting a compound of Formula (VI):

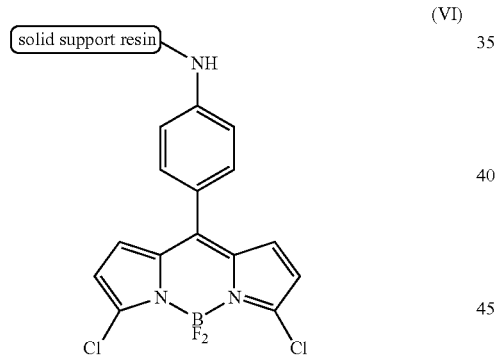

(VI)

with an azide under conditions sufficient to form a bis(azido)BODIPY compound of formula (VII):

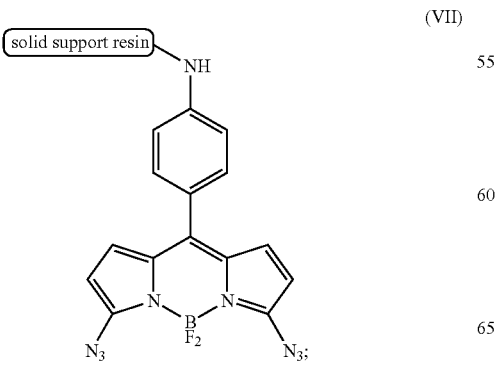

(VII)

(b) reacting the compound of Formula (VII) with an amine of the formula R$^2$R$^3$NH under conditions sufficient to form a compound of Formula (VIII):

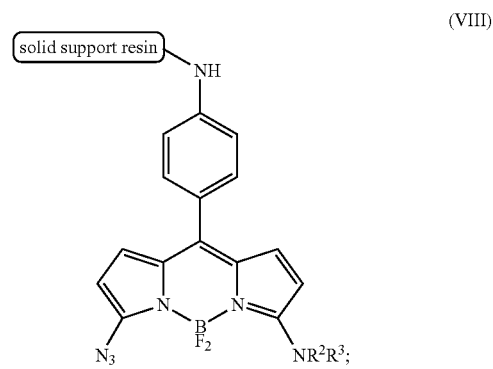

(VIII)

(c) reacting the compound of Formula (VIII) with an alkyne of the formula R$^4$—C≡CH in the presence of a copper (I) catalyst under conditions sufficient to form a compound of Formula (IX):

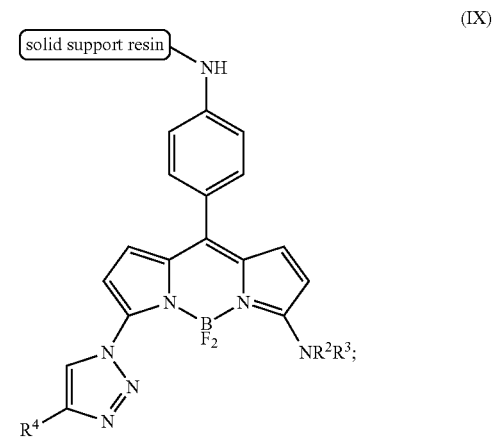

(IX)

(d) removing the solid support resin from the compound of Formula (IX) to form an unbound BODIPY compound where R$^1$ in Formula (I) is H; and (e) optionally reacting the unbound BODIPY compound of step d) with an acid chloride of the formula R$^1$COCl to form a compound of Formula (I) where R$^1$ is CO(C$_1$-C$_6$)alkyl optionally substituted with 1-3 substituents selected from halogen, O-acetyl, or N-acetyl.

9. The method of claim 8, wherein when step (e) is performed, the method comprises an additional step of treating the reaction mixture with a base under conditions sufficient to saponify an ester or amide linkage, wherein R$^1$ is CO(C$_1$-C$_6$)alkyl optionally substituted with 1-3 hydroxyl or —NH$_2$ substituents.

10. A method for a solution phase synthesis of a compound of Formula (I) or a pharmaceutically acceptable salt thereof:

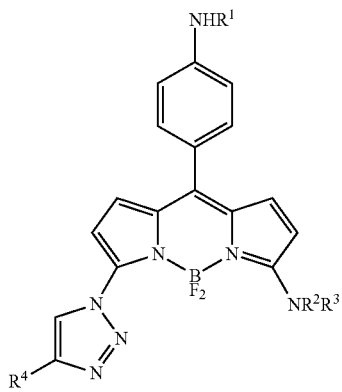

(I)

wherein:
R¹ is H or CO(C₁-C₆)alkyl, wherein CO(C₁-C₆)alkyl is optionally substituted at any position with 1-3 substituents selected from halogen, hydroxyl, O-acetyl, NH-acetyl, or —NH₂;
R² and R³ are each, independently, H, (C₁-C₁₀)alkyl, (C₆-C₁₀)aryl(C₀-C₆)alkyl, (C₃-C₁₀)heteroaryl, (C₃-C₈)cycloalkyl, (C₂-C₁₀)alkynyl or (C₂-C₁₀)alkenyl;
wherein (C₁-C₁₀)alkyl, (C₆-C₁₀)aryl(C₀-C₆)alkyl, (C₃-C₁₀)heteroaryl, (C₃-C₈)cycloalkyl, (C₂-C₁₀)alkynyl and (C₂-C₁₀)alkenyl are optionally substituted at any position with 1-5 substituents selected from (C₁-C₆) alkyl, (C₁-C₆)alkoxy, NH₂, —NH(C₁-C₆ alkyl), —NH(CO)(C₁-C₆ alkyl), —NH(CO)(C₁-C₆ haloalkyl), —NH(CO)(C₁-C₆ alkoxy), —NH(CO)(C₁-C₆ haloalkoxy), —NH(CO)(C₂-C₆ alkenyl), —Si(C₁-C₆ alkyl), —SO₂(C₁-C₆ alkyl), —SH, —B(OH)₂, —OTosyl, —CO(C₁-C₆ alkoxy), —COH, —COOH, —CO(C₁-C₆ alkyl) or halogen;
or R² and R³ are taken together to form a ring, wherein the ring is optionally substituted with 1-5 additional substituents selected from halogen or (C₁-C₆)alkyl; and
R⁴ is (C₁-C₁₀)alkyl, (C₃-C₈)cycloalkyl, (C₆-C₁₀)aryl, (C₂-C₁₀)alkenyl, (C₂-C₁₀)alkynyl, or (C₃-C₁₀)heteroaryl, further wherein R⁴ is optionally substituted at any position with 1-5 substituents selected from (C₁-C₁₀) alkyl, (C₂-C₁₀)alkenyl, (C₂-C₁₀)alkynyl, (C₃-C₈)cycloalkyl, (C₁-C₆)alkoxy, (C₆-C₁₀)aryloxy, (C₆-C₁₀) aryl, amino, —NH(CO)(C₁-C₆ alkyl), —NH(CO)(C₂-C₆ alkenyl), —NH(CO)(C₂-C₆ alkynyl), —NH(CO)(C₁-C₆ haloalkyl), halo, OCF₃, CF₃, hydroxyl, or a halogen radioisotope;
the method comprising:
(a) reacting a compound of Formula (X):

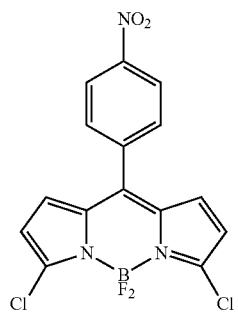

(X)

with an azide under conditions sufficient to form a bis(azido)BODIPY compound of formula (XI):

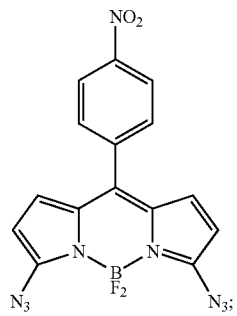

(XI)

(b) reacting the compound of Formula (XI) with an amine of the formula R²R³NH under conditions sufficient to form a compound of Formula (XII):

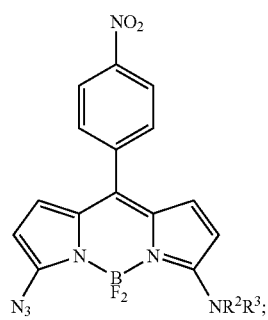

(XII)

(c) reacting the compound of Formula (XII) with an alkyne of the formula R⁴—C≡CH in the presence of a copper (I) catalyst under conditions sufficient to form a compound of Formula (XIII):

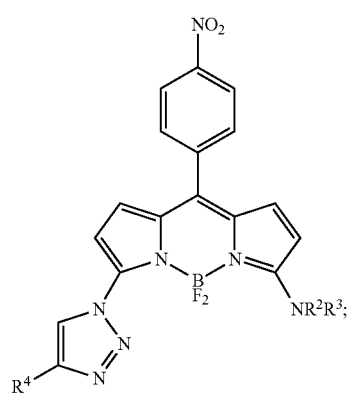

(XIII)

(d) reducing the NO₂ group in the compound of Formula (XIII) to form a BODIPY compound where R¹ in Formula (I) is H; and
(e) optionally reacting the BODIPY compound of step d) with an acid chloride of the formula R¹COCl to form a compound of Formula (I) where R¹ is CO(C₁-C₆)alkyl optionally substituted with 1-3 substituents selected from halogen, O-acetyl, or N-acetyl.

11. The method of claim 10, wherein when step (e) is performed, the method comprises an additional step of treating the reaction mixture with a base under conditions sufficient to saponify an ester or amide linkage, wherein $R^1$ is $CO(C_1-C_6)$alkyl optionally substituted with 1-3 hydroxyl or —$NH_2$ substituents.

12. A method for detecting human serum albumin (HSA) in a sample of a biological fluid, comprising:
   a) contacting a sample of biological fluid thought to contain HSA with the compound of claim 1 represented by Formula (I) or a pharmaceutically acceptable salt thereof:

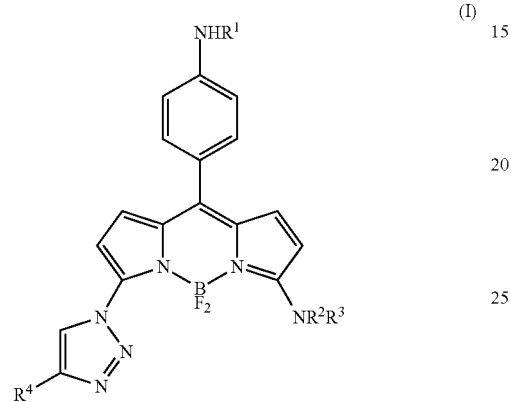

(I)

wherein:
   $R^1$ is H or $CO(C_1-C_6)$alkyl, wherein $CO(C_1-C_6)$alkyl is optionally substituted at any position with 1-3 substituents selected from halogen, hydroxyl, O-acetyl, NH-acetyl, or —$NH_2$;
   $R^2$ and $R^3$ are each, independently, H, $(C_1-C_{10})$alkyl, $(C_6-C_{10})$aryl$(C_0-C_6)$alkyl, $(C_3-C_{10})$heteroaryl, $(C_3-C_8)$cycloalkyl, $(C_2-C_{10})$alkynyl or $(C_2-C_{10})$alkenyl; wherein $(C_1-C_{10})$alkyl, $(C_6-C_{10})$aryl$(C_0-C_6)$alkyl, $(C_3-C_{10})$heteroaryl, $(C_3-C_8)$cycloalkyl, $(C_2-C_{10})$alkynyl and $(C_2-C_{10})$alkenyl are optionally substituted at any position with 1-5 substituents selected from $(C_1-C_6)$alkyl, $(C_1-C_6)$alkoxy, $NH_2$, —$NH(C_1-C_6$ alkyl), —$NH(CO)(C_1-C_6$ alkyl), —$NH(CO)(C_1-C_6$ haloalkyl), —$NH(CO)(C_1-C_6$ alkoxy), —$NH(CO)(C_1-C_6$ haloalkoxy), —$NH(CO)(C_2-C_6$ alkenyl), —$Si(C_1-C_6$ alkyl), —$SO_2(C_1-C_6$ alkyl), —$SH$, —$B(OH)_2$, —OTosyl, —$CO(C_1-C_6$ alkoxyl), —COH, —COOH, —$CO(C_1-C_6$ alkyl) or halogen;
   or $R^2$ and $R^3$ are taken together to form a ring, wherein the ring is optionally substituted with 1-5 additional substituents selected from halogen or $(C_1-C_6)$alkyl; and
   $R^4$ is $(C_1-C_{10})$alkyl, $(C_3-C_8)$cycloalkyl, $(C_6-C_{10})$aryl, $(C_2-C_{10})$alkenyl, $(C_2-C_{10})$alkynyl, or $(C_3-C_{10})$heteroaryl, further wherein $R^4$ is optionally substituted at any position with 1-5 substituents selected from $(C_1-C_{10})$alkyl, $(C_2-C_{10})$alkenyl, $(C_2-C_{10})$alkynyl, $(C_3-C_8)$cycloalkyl, $(C_1-C_6)$alkoxy, $(C_6-C_{10})$aryloxy, $(C_6-C_{10})$aryl, amino, —$NH(CO)(C_1-C_6$ alkyl), —$NH(CO)(C_2-C_6$ alkenyl), —$NH(CO)(C_2-C_6$ alkynyl), —$NH(CO)(C_1-C_6$ haloalkyl), halo, $OCF_3$, $CF_3$, hydroxyl, or a halogen radioisotope;
   to form an incubation media;
   b) incubating the incubation media of step a) under conditions sufficient to form an incubated mixture; and
   c) analyzing the mixture of step b) by fluorescence microscopy, wherein an increase in the fluorescence signal of the mixture relative to the fluorescence signal of the compound of Formula (I) not in the presence of a sample containing HSA is indicative of the presence of HSA.

13. The method of claim 12, wherein a measure of intensity of the fluorescence signal is proportional to the concentration of the HSA present in the sample.

14. The method of claim 12, wherein the compound of Formula (I) has the structure of formula (II):

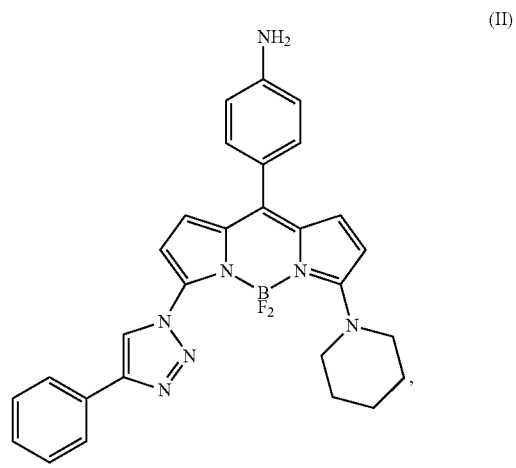

(II)

or a pharmaceutically acceptable salt thereof.

15. A method for visualizing live neurons in a cell culture, comprising:
   a) contacting a cell culture with the compound of claim 1 represented by Formula (I) or a pharmaceutically acceptable salt thereof:

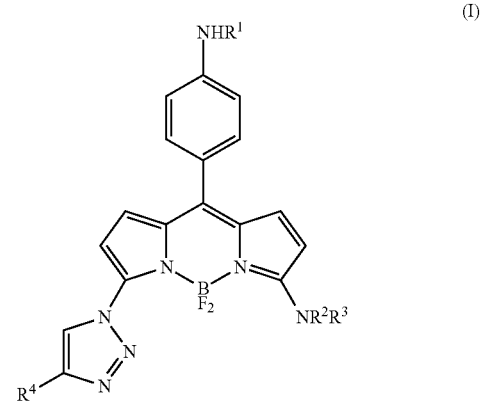

(I)

wherein:
   $R^1$ is H or $CO(C_1-C_6)$alkyl, wherein $CO(C_1-C_6)$alkyl is optionally substituted at any position with 1-3 substituents selected from halogen, hydroxyl, O-acetyl, NH-acetyl, or —$NH_2$;
   $R^2$ and $R^3$ are each, independently, H, $(C_1-C_{10})$alkyl, $(C_6-C_{10})$aryl$(C_0-C_6)$alkyl, $(C_3-C_{10})$heteroaryl, $(C_3-C_8)$cycloalkyl, $(C_2-C_{10})$alkynyl or $(C_2-C_{10})$alkenyl; wherein $(C_1-C_{10})$alkyl, $(C_6-C_{10})$aryl$(C_0-C_6)$alkyl, $(C_3-C_{10})$heteroaryl, $(C_3-C_8)$cycloalkyl, $(C_2-C_{10})$ alkynyl and (C$_2$-C$_{10}$)alkenyl are optionally substituted at any position with 1-5 substituents selected from (C$_1$-C$_6$)alkyl, (C$_1$-C$_6$)alkoxy, NH$_2$, —NH(C$_1$-C$_6$ alkyl), —NH(CO)(C$_1$-C$_6$ alkyl), —NH(CO)(C$_1$-C$_6$ haloalkyl), —NH(CO)(C$_1$-C$_6$ alkoxy), —NH(CO)(C$_1$-C$_6$ haloalkoxy), —NH(CO)(C$_2$-C$_6$ alkenyl), —Si(C$_1$-C$_6$ alkyl), —SO$_2$(C$_1$-C$_6$ alkyl), —SH, —B(OH)$_2$, —OTosyl, —CO(C$_1$-C$_6$ alkoxyl), —COH, —COOH, —CO(C$_1$-C$_6$ alkyl) or halogen;

or R$^2$ and R$^3$ are taken together to form a ring, wherein the ring is optionally substituted with 1-5 additional substituents selected from halogen or (C$_1$-C$_6$)alkyl; and R$^4$ is (C$_1$-C$_{10}$)alkyl, (C$_3$-C$_8$)cycloalkyl, (C$_6$-C$_{10}$)aryl, (C$_2$-C$_{10}$)alkenyl, (C$_2$-C$_{10}$)alkynyl, or (C$_3$-C$_{10}$)heteroaryl, further wherein R$^4$ is optionally substituted at any position with 1-5 substituents selected from (C$_1$-C$_{10}$)alkyl, (C$_2$-C$_{10}$)alkenyl, (C$_2$-C$_{10}$)alkynyl, (C$_3$-C$_8$)cycloalkyl, (C$_1$-C$_6$)alkoxy, (C$_6$-C$_{10}$)aryloxy, (C$_6$-C$_{10}$)aryl, amino, —NH(CO)(C$_1$-C$_6$ alkyl), —NH(CO)(C$_2$-C$_6$ alkenyl), —NH(CO)(C$_2$-C$_6$ alkynyl), —NH(CO)(C$_1$-C$_6$ haloalkyl), halo, OCF$_3$, CF$_3$, hydroxyl, or a halogen radioisotope;

to form an incubation media;

b) incubating the incubation media of step a) under conditions sufficient to stain the live neurons; and c) visualizing the stained live neurons of step b) with fluorescence microscopy.

16. The method of claim 15, wherein the compound of Formula (I) is a compound having the structure of Formula (XIV) or a pharmaceutically acceptable salt thereof:

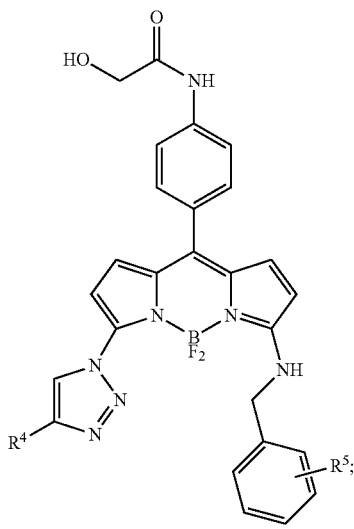

(XIV)

wherein:

R$^4$ is (C$_1$-C$_{10}$)alkyl, (C$_3$-C$_8$)cycloalkyl, (C$_6$-C$_{10}$)aryl, (C$_2$-C$_{10}$)alkenyl, (C$_2$-C$_{10}$)alkynyl, or (C$_3$-C$_{10}$)heteroaryl, further wherein R$^4$ is optionally substituted at any position with 1-5 substituents selected from (C$_1$-C$_{10}$) alkyl, (C$_2$-C$_{10}$)alkenyl, (C$_2$-C$_{10}$)alkynyl, (C$_3$-C$_8$)cycloalkyl, (C$_1$-C$_6$)alkoxy, (C$_6$-C$_{10}$)aryloxy, (C$_6$-C$_{10}$) aryl, amino, —NH(CO)(C$_1$-C$_6$ alkyl), —NH(CO)(C$_2$-C$_6$ alkenyl), —NH(CO)(C$_2$-C$_6$ alkynyl), —NH(CO)(C$_1$-C$_6$ haloalkyl), halo, OCF$_3$, CF$_3$, hydroxyl, or a halogen radioisotope; and R$^5$ is present at any position with 1-5 substituents selected from H, (C$_1$-C$_6$)alkyl, (C$_1$-C$_6$)alkoxy, NH$_2$, —NH(C$_1$-C$_6$ alkyl), —NH(CO)(C$_1$-C$_6$ alkyl), —NH(CO)(C$_1$-C$_6$ haloalkyl), —NH(CO)(C$_1$-C$_6$ alkoxy), —NH(CO)(C$_1$-C$_6$ haloalkoxy), —NH(CO)(C$_2$-C$_6$ alkenyl), —Si(C$_1$-C$_6$ alkyl), —SO$_2$(C$_1$-C$_6$ alkyl), —SH, —B(OH)$_2$, —OTosyl, —CO(C$_1$-C$_6$ alkoxyl), —COH, —COOH, —CO(C$_1$-C$_6$ alkyl) or halogen.

17. The method of claim 16, wherein the compound of Formula (I) has the structure of Formula (V):

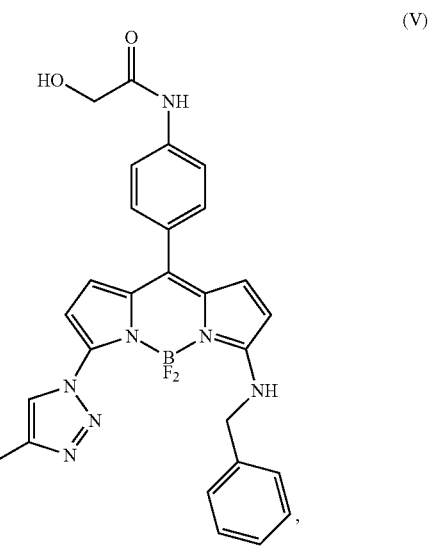

(V)

or a pharmaceutically acceptable salt thereof.

18. The compound of claim 1, having the structure of Formula (XVI):

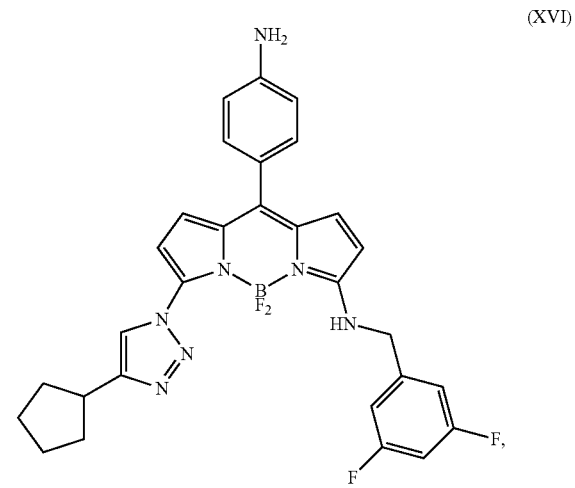

(XVI)

or a pharmaceutically acceptable salt thereof.

19. The compound of claim 1, wherein the halogen radioisotope is $^{18}$F.

* * * * *